US007220576B2

(12) United States Patent
Butt et al.

(10) Patent No.: US 7,220,576 B2
(45) Date of Patent: May 22, 2007

(54) METHODS AND COMPOSITIONS FOR PROTEIN EXPRESSION AND PURIFICATION

(75) Inventors: Tauseef R. Butt, Audubon, PA (US); Steven D. Weeks, Philadelphia, PA (US); Hiep T. Tran, West Chester, PA (US); Michael P. Malakhov, San Diego, CA (US); Oxana A. Malakhova, San Diego, CA (US)

(73) Assignee: Lifesensors, Inc., Malvern, PA (US)

( * ) Notice: Subject to any disclaimer, the term of this patent is extended or adjusted under 35 U.S.C. 154(b) by 150 days.

(21) Appl. No.: 10/389,640

(22) Filed: Mar. 14, 2003

(65) Prior Publication Data

US 2004/0018591 A1 Jan. 29, 2004

Related U.S. Application Data

(63) Continuation of application No. 10/338,411, filed on Jan. 7, 2003, now Pat. No. 7,060,461.

(60) Provisional application No. 60/346,449, filed on Jan. 7, 2002.

(51) Int. Cl.

*C12N 15/00* (2006.01)
*C12N 5/00* (2006.01)
*C12N 15/63* (2006.01)
*C12P 21/06* (2006.01)
*C07H 21/04* (2006.01)

(52) U.S. Cl. .................. 435/320.1; 435/69.1; 435/325; 435/243; 435/252.1; 435/252.33; 435/254.2; 435/348; 435/455; 536/23.1; 536/24.33; 422/61

(58) Field of Classification Search .................... 435/4, 435/6, 41, 69.1, 320.1; 536/23.1
See application file for complete search history.

(56) References Cited

U.S. PATENT DOCUMENTS 6,872,551 B2 * 3/2005 Lima et al. ................ 435/69.7
2003/0086918 A1 * 5/2003 Lima et al. .............. 424/94.63

OTHER PUBLICATIONS

Li et al. A new protease required for cell-cycle progression in yeast. Nature 398: 246-251, 1999.*
GenBank Accession No. U37458.*
Bachmair et al. In vivo half-life of a protein is a function of its amino-terminal residue. Science 234:179-186, 1986.*
pQE-30 Xa Vector. Qiagen product catalog on the world wide web.*
Varshavsky, A. Ubiquitin Fusion Technique and Its Descendants, Methods in Enzymology 327:578-593, 2000.*
Dictionary.com entry for "adjacent." pp. 1-3, http://dictionary.reference.com/search?q-adjacent.*
Saitoh, H., et al., "SUMO-1: wrestling with a new ubiquitin-related modifer", Trends Biochem. Sci. 22:374-6 (1997).
Johnson, E.S., et al., "The ubiquitin-like protein Smt3p is activated for conjugation to other proteins by an Aos1p/Uba2p heterodimer", EMBO Journal, 16: 5509-5519 (1997).
Tanaka, K., et al., "Characterization of a Fission Yeast SUMO-1 Homologue, Pmt3p, Required for Multiple Nuclear Events, Including the Control of Telomere Length and Chromosome Segregation", Molecular and Cellular Biology, 19: 8660-8672 (1999).
Li, S-J, et al, "The Yeast ULP2 (SMT4) Gene Encodes a Novel Protease Specific for the Ubiquitin-Like Smt3 Protein", Molecular and Cellular Biology 20: 2367-2377 (2000).
Ichimura, Y., et al., "A ubiquitin-line system mediates protein lipidation", Nature 408: 488-492, (2000).
Li, S-J., et al., "A new protease required for cell-cycle progression in yeast", Nature 398: 246-251, (1999).
Mossessova, E., et al., "Ulp1-SUMO Crystal Structure and Genetic Analysis Reveal Conserved Interactions and a Regulatory Element Essential for Cell Growth in Yeast", Molecular Cell, 5: 865-876 (2000).
Yeh, E.T.H., et al., "Ubiquitin-like proteins: new wines in new bottles", Gene 248: 1-14 (2000).
Baker, R.T., "Protein expression using ubiquitin fusion and cleavage", Current Opinion in Biotechnology, vol. 7: pp. 541-546, (1996).
Power, R.F., et al., "High Level Expression of a Truncated Chicken Progesterone Receptor in *Escherichia coli*", The Journal of Biological Chemistry, vol. 265: 1419-1424 (1990).
Bayer, P., et al., "Structure Determination of the Small Ubiquitin-related Modifier SUMO-1", Journal of Molecular Biology, vol. 280: pp. 275-286 (1998).
Liu, Q., et al., "The Binding Interface between an E2 (UBC9) and a Ubiquitin Homologue (UBL1)", The Journal of Biological Chemistry, vol. 274: pp. 16979-16987, (1999).
Malakhov, M.P., et al., "SUMO fusions and SUMO-specific protease for efficient expression and purification of proteins", Journal of Structural and Functional Genomics, vol. 5: pp. 75-86, (2004).

* cited by examiner

*Primary Examiner*—David Guzo
*Assistant Examiner*—Walter Schlapkohl
(74) *Attorney, Agent, or Firm*—Kathleen D. Rigaut; Dann, Dorfman, Herrell and Skillman

(57) ABSTRACT

Methods for enhancing expression levels and secretion of heterologous fusion proteins in a host cell are disclosed.

15 Claims, 87 Drawing Sheets

Scheme for Ubiquitin and Ubiquitin-Like Proteins Processing and Conjugation

Figure 3

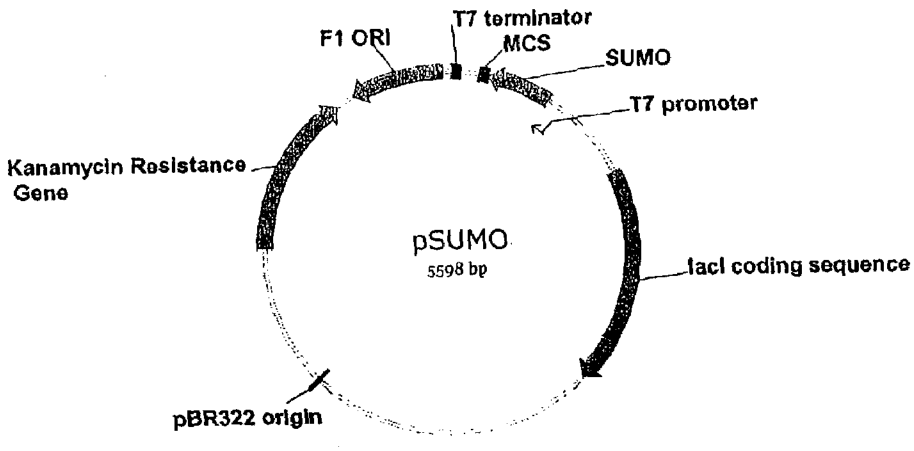

Multiple Cloning Site:

BglII (1) XbaI

1 AGATCTCGATCCCGCGAAATTAATACGACTCACTATAGGGGAATTGTGAGCGGATAACAATTCCCCTCTAGAAATAATTTTGTTTAACTTTAAGAAGGAG

NcoI

MetGlyHisHisHisHisHisHisGlySerAspSerGluValAsnGlnGluAlaLysProGluValLysProGluValLysProGluThrHis
101 ATATACCATGGGTCATCACCATCATCATCACGGGTCGGACTCAGAAGTCAATCAAGAAGCTAAGCCAGAGGTCAAGCCAGAAGTCAAGCCTGAGACTCAC

BglII

IleAsnLeuLysValSerAspGlySerSerGluIlePhePheLysIleLysLysThrThrProLeuArgArgLeuMetGluAlaPheAlaLysArgGlnGly·
201 ATCAATTTAAAGGTGTCCGATGGATCTTCAGAGATCTTCTTCAAGATCAAAAAGACCACTCCTTTAAGAAGGCTGATGGAAGCGTTCGCTAAAAGACAGG

EcoRI

·GLysGluMetAspSerLeuArgPheLeuTyrAspGlyIleArgIleGlnAlaAspGlnThrProGluAspLeuAspMetGluAspAsnAspIleIleGlu·
301 GTAAGGAAATGGACTCCTTAAGATTCTTGTACGACGGTATTAGAATTCAAGCTGATCAGACCCCTGAAGATTTGGACATGGAGGATAACGATATTATTGA

SacI SalI NotI

EagI

BsaI BamHI EcoRI HindIII XhoI

·AlaHisArgGluGlnIleGlyGly***
401 GGCTCACCGCGAACAGATTGGAGGTTGAGACCGGATCCGAATTCGAGCTCCGTCGACAAGCTTGCGGCCGCACTCGAG

↑ Hydrolase Cleavage Site

Sumo-LXR-fusion expression

Ubl-GFP co-translational cleavage
YPD, 30°C, 3.5 h induction, 100 μM $CuSO_4$

Figure 14
SUMO-GFP fusion proteins expression in Hi-Five cells
fluorescence micrographs
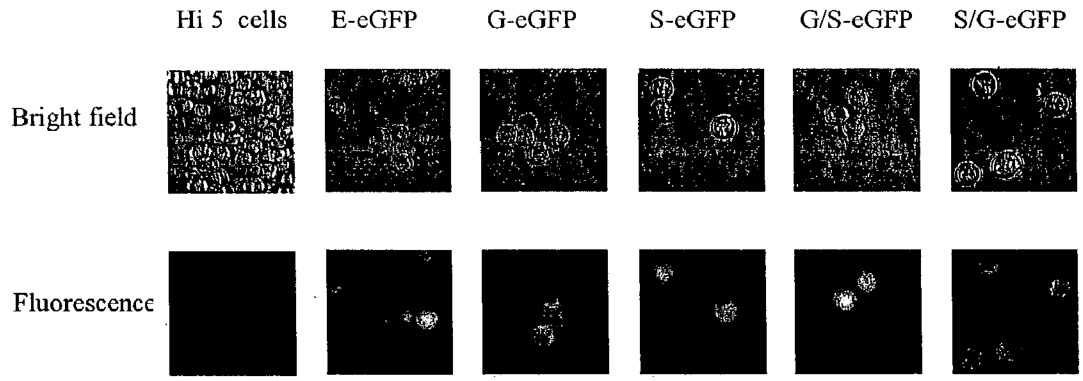
Ubiquitin-GFP fusion proteins expression in Hi-Five cells
fluorescence micrographs
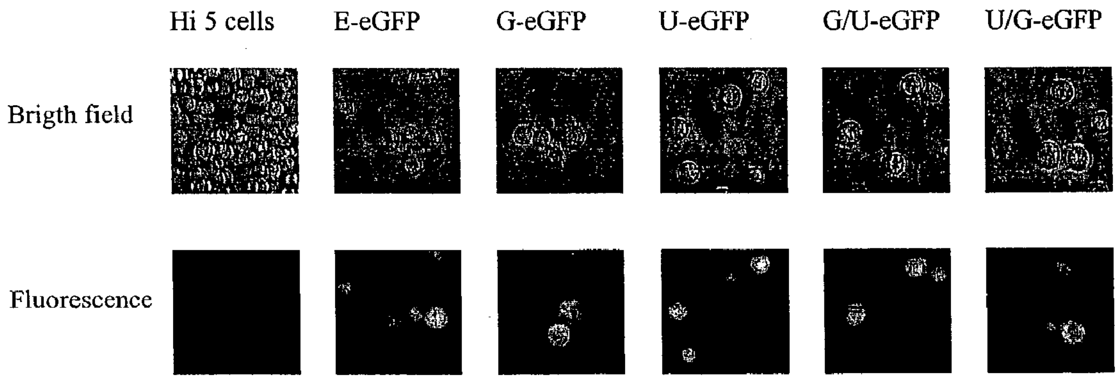

Figure 15
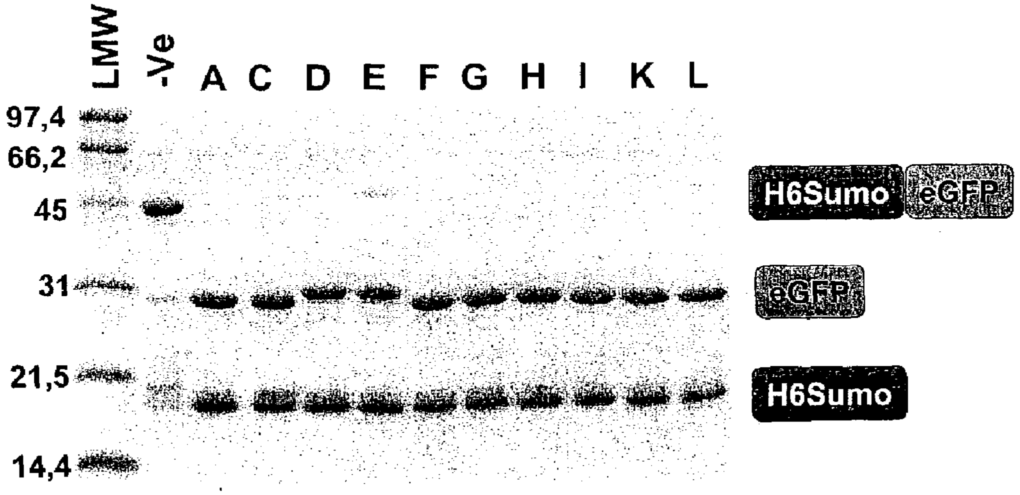
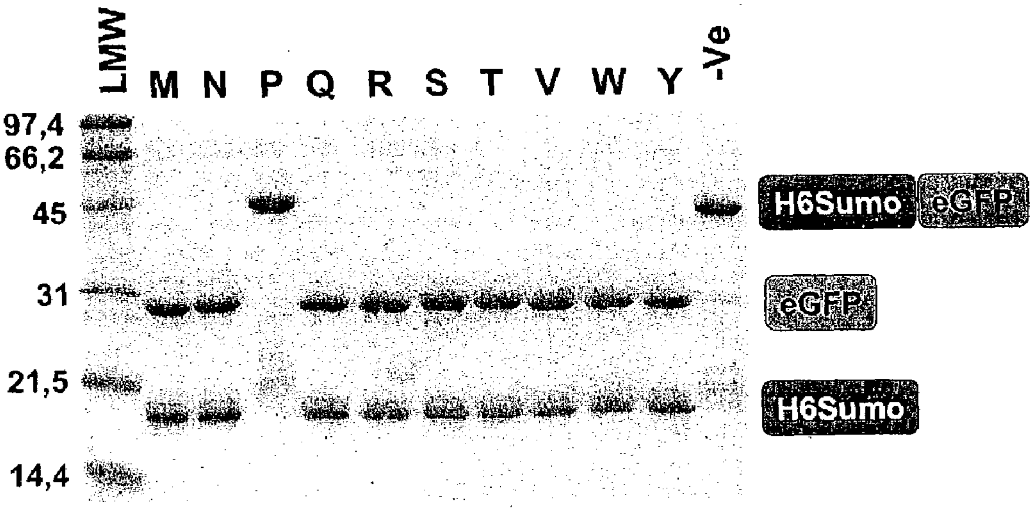

Figure 16
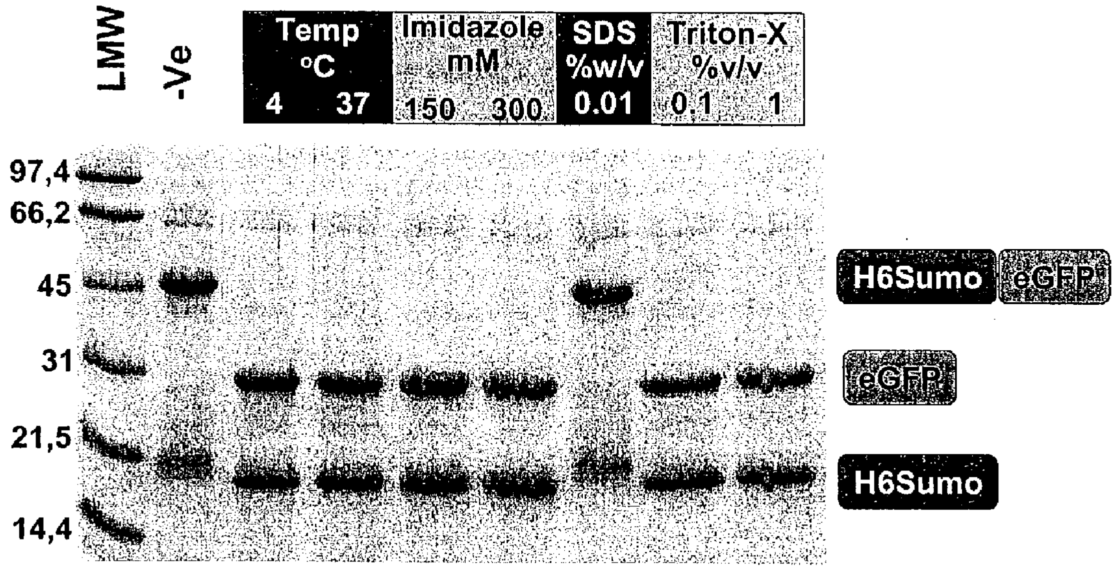
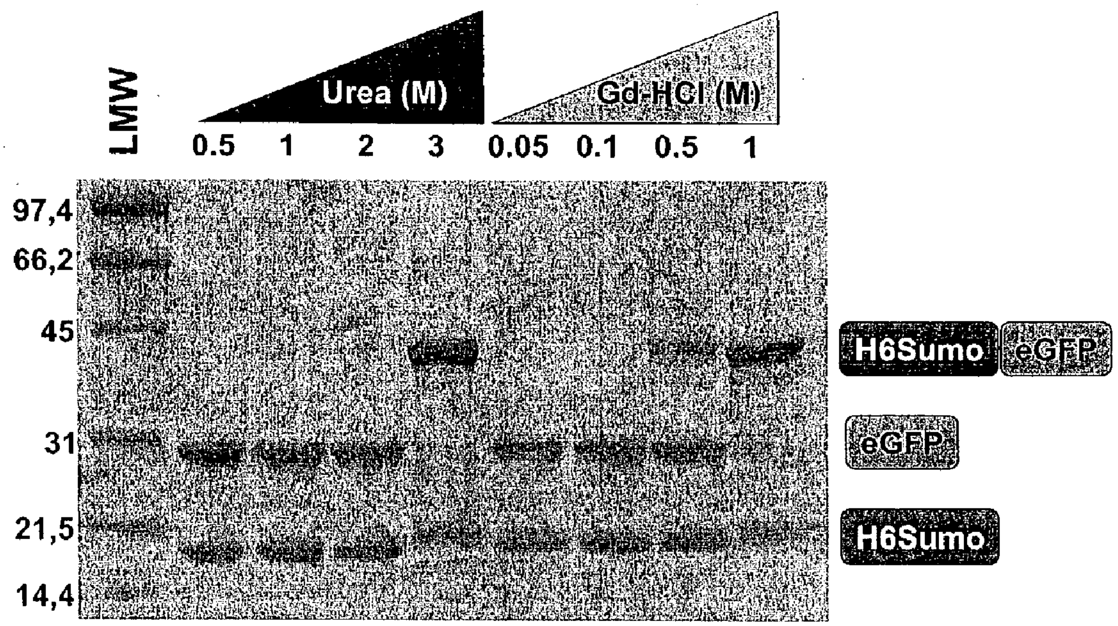

SUMO

SUMO NCBI ACCESSION# Q12306

```
      NcoI
     ~~~~~~
      M  G  H   H  H  H   H  H  G  S   D  S  E   V  N  Q
  1  CCATGGGTCA TCACCATCAT CATCACGGGT CGGACTCAGA AGTCAATCAA
     GGTACCCAGT AGTGGTAGTA GTAGTGCCCA GCCTGAGTCT TCAGTTAGTT
      E  A  K  P   E  V  K   P  E  V   K  P  E  T   H  I  N ·
 51  GAAGCTAAGC CAGAGGTCAA GCCAGAAGTC AAGCCTGAGA CTCACATCAA
     CTTCGATTCG GTCTCCAGTT CGGTCTTCAG TTCGGACTCT GAGTGTAGTT
     · L  K  V   S  D  G  S   S  E  I   F  F  K   I  K  K  T ·
101  TTTAAAGGTG TCCGATGGAT CTTCAGAGAT CTTCTTCAAG ATCAAAAAGA
     AAATTTCCAC AGGCTACCTA GAAGTCTCTA GAAGAAGTTC TAGTTTTTCT
     ·  T  P  L   R  R  L   M  E  A  F   A  K  R   Q  G  K
151  CCACTCCTTT AAGAAGGCTG ATGGAAGCGT TCGCTAAAAG ACAGGGTAAG
     GGTGAGGAAA TTCTTCCGAC TACCTTCGCA AGCGATTTTC TGTCCCATTC
      E  M  D  S   L  R  F   L  Y  D   G  I  R  I   Q  A  D ·
201  GAAATGGACT CCTTAAGATT CTTGTACGAC GGTATTAGAA TTCAAGCTGA
     CTTTACCTGA GGAATTCTAA GAACATGCTG CCATAATCTT AAGTTCGACT
     · Q  A  P   E  D  L  D   M  E  D   N  D  I   I  E  A  H ·
251  TCAGGCCCCT GAAGATTTGG ACATGGAGGA TAACGATATT ATTGAGGCTC
     AGTCCGGGGA CTTCTAAACC TGTACCTCCT ATTGCTATAA TAACTCCGAG
     ·  R  E  Q   I  G  G
301  ACCGCGAACA GATTGGAGGT
     TGGCGCTTGT CTAACCTCCA
```

GFP

GFP NCBI ACCESSION# P42212

```
      M  V  S  K  G  E  E  L  F  T
1     ATGGTGAGCA AGGGCGAGGA GCTGTTCACC
      TACCACTCGT TCCCGCTCCT CGACAAGTGG
      G  V  V  P  I  L  V  E  L  D  G  D  V  N  G  H  K ·
31    GGGGTGGTGC CCATCCTGGT CGAGCTGGAC GGCGACGTAA ACGGCCACAA
      CCCCACCACG GGTAGGACCA GCTCGACCTG CCGCTGCATT TGCCGGTGTT
      · F  S  V  S  G  E  G  E  G  D  A  T  Y  G  K  L  T ·
81    GTTCAGCGTG TCCGGCGAGG GCGAGGGCGA TGCCACCTAC GGCAAGCTGA
      CAAGTCGCAC AGGCCGCTCC CGCTCCCGCT ACGGTGGATG CCGTTCGACT
      · L  K  F  I  C  T  T  G  K  L  P  V  P  W  P  T
131   CCCTGAAGTT CATCTGCACC ACCGGCAAGC TGCCCGTGCC CTGGCCCACC
      GGGACTTCAA GTAGACGTGG TGGCCGTTCG ACGGGCACGG GACCGGGTGG
      L  V  T  T  L  T  Y  G  V  Q  C  F  S  R  Y  P  D ·
181   CTCGTGACCA CCCTGACCTA CGGCGTGCAG TGCTTCAGCC GCTACCCCGA
      GAGCACTGGT GGGACTGGAT GCCGCACGTC ACGAAGTCGG CGATGGGGCT
      · H  M  K  Q  H  D  F  F  K  S  A  M  P  E  G  Y  V ·
201   CCACATGAAG CAGCACGACT TCTTCAAGTC CGCCATGCCC GAAGGCTACG
      GGTGTACTTC GTCGTGCTGA AGAAGTTCAG GCGGTACGGG CTTCCGATGC
      · Q  E  R  T  I  F  F  K  D  D  G  N  Y  K  T  R
231   TCCAGGAGCG CACCATCTTC TTCAAGGACG ACGGCAACTA CAAGACCCGC
      AGGTCCTCGC GTGGTAGAAG AAGTTCCTGC TGCCGTTGAT GTTCTGGGCG

A  E  V  K  F  E  G  D  T  L  V  N  R  I  E  L  K ·
281   GCCGAGGTGA AGTTCGAGGG CGACACCCTG GTGAACCGCA TCGAGCTGAA
      CGGCTCCACT TCAAGCTCCC GCTGTGGGAC CACTTGGCGT AGCTCGACTT
      · G  I  D  F  K  E  D  G  N  I  L  G  H  K  L  E  Y ·
331   GGGCATCGAC TTCAAGGAGG ACGGCAACAT CCTGGGGCAC AAGCTGGAGT
      CCCGTAGCTG AAGTTCCTCC TGCCGTTGTA GGACCCCGTG TTCGACCTCA
      · N  Y  N  S  H  N  V  Y  I  M  A  D  K  Q  K  N
381   ACAACTACAA CAGCCACAAC GTCTATATCA TGGCCGACAA GCAGAAGAAC
      TGTTGATGTT GTCGGTGTTG CAGATATAGT ACCGGCTGTT CGTCTTCTTG
      G  I  K  V  N  F  K  I  R  H  N  I  E  D  G  S  V ·
431   GGCATCAAGG TGAACTTCAA GATCCGCCAC AACATCGAGG ACGGCAGCGT
      CCGTAGTTCC ACTTGAAGTT CTAGGCGGTG TTGTAGCTCC TGCCGTCGCA
      · Q  L  A  D  H  Y  Q  Q  N  T  P  I  G  D  G  P  V ·
481   GCAGCTCGCC GACCACTACC AGCAGAACAC CCCCATCGGC GACGGCCCCG
      CGTCGAGCGG CTGGTGATGG TCGTCTTGTG GGGGTAGCCG CTGCCGGGGC
      · L  L  P  D  N  H  Y  L  S  T  Q  S  A  L  S  K
531   TGCTGCTGCC CGACAACCAC TACCTGAGCA CCCAGTCCGC CCTGAGCAAA
      ACGACGACGG GCTGTTGGTG ATGGACTCGT GGGTCAGGCG GGACTCGTTT
```

Figure 24B

```
      D  P  N  E   K  R  D   H  M  V   L  L  E  F   V  T  A·
581   GACCCCAACG AGAAGCGCGA TCACATGGTC CTGCTGGAGT TCGTGACCGC
      CTGGGGTTGC TCTTCGCGCT AGTGTACCAG GACGACCTCA AGCACTGGCG
                                                  HindIII
                                                  ~~~~~~
      ·A  G  I   T  L  G  M   D  E  L   Y  K  *   *
631   CGCCGGGATC ACTCTCGGCA TGGACGAGCT GTACAAGTAA TAAGCTT
      GCGGCCCTAG TGAGAGCCGT ACCTGCTCGA CATGTTCATT ATTCGAA
```

Figure 25A

SUMO-GFP
SUMO NCBI ACCESSION# Q12306

```
    NcoI
    ~~~~~~
       M  G  H   H  H  H   H  H  G  S   D  S  E   V  N  Q
  1  CCATGGGTCA TCACCATCAT CATCACGGGT CGGACTCAGA AGTCAATCAA
     GGTACCCAGT AGTGGTAGTA GTAGTGCCCA GCCTGAGTCT TCAGTTAGTT
      E  A  K  P   E  V  K   P  E  V   K  P  E  T   H  I  N
 51  GAAGCTAAGC CAGAGGTCAA GCCAGAAGTC AAGCCTGAGA CTCACATCAA
     CTTCGATTCG GTCTCCAGTT CGGTCTTCAG TTCGGACTCT GAGTGTAGTT
     · L  K  V   S  D  G  S   S  E  I   F  F  K   I  K  K  T ·
101  TTTAAAGGTG TCCGATGGAT CTTCAGAGAT CTTCTTCAAG ATCAAAAAGA
     AAATTTCCAC AGGCTACCTA GAAGTCTCTA GAAGAAGTTC TAGTTTTTCT
     ·  T  P  L   R  R  L   M  E  A  F   A  K  R   Q  G  K
151  CCACTCCTTT AAGAAGGCTG ATGGAAGCGT TCGCTAAAAG ACAGGGTAAG
     GGTGAGGAAA TTCTTCCGAC TACCTTCGCA AGCGATTTTC TGTCCCATTC
      E  M  D  S   L  R  F   L  Y  D   G  I  R  I   Q  A  D ·
201  GAAATGGACT CCTTAAGATT CTTGTACGAC GGTATTAGAA TTCAAGCTGA
     CTTTACCTGA GGAATTCTAA GAACATGCTG CCATAATCTT AAGTTCGACT
     · Q  A  P   E  D  L  D   M  E  D   N  D  I   I  E  A  H ·
251  TCAGGCCCCT GAAGATTTGG ACATGGAGGA TAACGATATT ATTGAGGCTC
     AGTCCGGGGA CTTCTAAACC TGTACCTCCT ATTGCTATAA TAACTCCGAG
     ·  R  E  Q   I  G  G   M  V  S  K   G  E  E   L  F  T
301  ACCGCGAACA GATTGGAGGT ATGGTGAGCA AGGGCGAGGA GCTGTTCACC
     TGGCGCTTGT CTAACCTCCA TACCACTCGT TCCCGCTCCT CGACAAGTGG
      G  V  V  P   I  L  V   E  L  D   G  D  V  N   G  H  K ·
351  GGGGTGGTGC CCATCCTGGT CGAGCTGGAC GGCGACGTAA ACGGCCACAA
     CCCCACCACG GGTAGGACCA GCTCGACCTG CCGCTGCATT TGCCGGTGTT
     · F  S  V   S  G  E  G   E  G  D   A  T  Y   G  K  L  T ·
401  GTTCAGCGTG TCCGGCGAGG GCGAGGGCGA TGCCACCTAC GGCAAGCTGA
     CAAGTCGCAC AGGCCGCTCC CGCTCCCGCT ACGGTGGATG CCGTTCGACT
     ·  L  K  F   I  C  T   T  G  K  L   P  V  P   W  P  T
451  CCCTGAAGTT CATCTGCACC ACCGGCAAGC TGCCCGTGCC CTGGCCCACC
     GGGACTTCAA GTAGACGTGG TGGCCGTTCG ACGGGCACGG GACCGGGTGG
      L  V  T  T   L  T  Y   G  V  Q   C  F  S  R   Y  P  D ·
501  CTCGTGACCA CCCTGACCTA CGGCGTGCAG TGCTTCAGCC GCTACCCCGA
     GAGCACTGGT GGGACTGGAT GCCGCACGTC ACGAAGTCGG CGATGGGGCT
     · H  M  K   Q  H  D  F   F  K  S   A  M  P   E  G  Y  V ·
551  CCACATGAAG CAGCACGACT TCTTCAAGTC CGCCATGCCC GAAGGCTACG
     GGTGTACTTC GTCGTGCTGA AGAAGTTCAG GCGGTACGGG CTTCCGATGC
     ·  Q  E  R   T  I  F   F  K  D  D   G  N  Y   K  T  R
601  TCCAGGAGCG CACCATCTTC TTCAAGGACG ACGGCAACTA CAAGACCCGC
     AGGTCCTCGC GTGGTAGAAG AAGTTCCTGC TGCCGTTGAT GTTCTGGGCG
      A  E  V  K   F  E  G   D  T  L   V  N  R  I   E  L  K ·
651  GCCGAGGTGA AGTTCGAGGG CGACACCCTG GTGAACCGCA TCGAGCTGAA
     CGGCTCCACT TCAAGCTCCC GCTGTGGGAC CACTTGGCGT AGCTCGACTT
     · G  I  D   F  K  E  D   G  N  I   L  G  H   K  L  E  Y ·
701  GGGCATCGAC TTCAAGGAGG ACGGCAACAT CCTGGGGCAC AAGCTGGAGT
```

```
     CCCGTAGCTG AAGTTCCTCC TGCCGTTGTA GGACCCCGTG TTCGACCTCA
     · N  Y  N   S  H  N   V  Y  I  M   A  D  K   Q  K  N
751  ACAACTACAA CAGCCACAAC GTCTATATCA TGGCCGACAA GCAGAAGAAC
     TGTTGATGTT GTCGGTGTTG CAGATATAGT ACCGGCTGTT CGTCTTCTTG
      G  I  K  V   N  F  K   I  R  H   N  I  E  D   G  S  V ·
801  GGCATCAAGG TGAACTTCAA GATCCGCCAC AACATCGAGG ACGGCAGCGT
     CCGTAGTTCC ACTTGAAGTT CTAGGCGGTG TTGTAGCTCC TGCCGTCGCA
     · Q  L  A   D  H  Y  Q   Q  N  T   P  I  G   D  G  P  V ·
851  GCAGCTCGCC GACCACTACC AGCAGAACAC CCCCATCGGC GACGGCCCCG
     CGTCGAGCGG CTGGTGATGG TCGTCTTGTG GGGGTAGCCG CTGCCGGGGC
     · L  L  P   D  N  H   Y  L  S  T   Q  S  A   L  S  K
901  TGCTGCTGCC CGACAACCAC TACCTGAGCA CCCAGTCCGC CCTGAGCAAA
     ACGACGACGG GCTGTTGGTG ATGGACTCGT GGGTCAGGCG GGACTCGTTT
      D  P  N  E   K  R  D   H  M  V   L  L  E  F   V  T  A ·
951  GACCCCAACG AGAAGCGCGA TCACATGGTC CTGCTGGAGT TCGTGACCGC
     CTGGGGTTGC TCTTCGCGCT AGTGTACCAG GACGACCTCA AGCACTGGCG
                                                  HindIII
                                                  ~~~~~~
     · A  G  I   T  L  G  M   D  E  L   Y  K  *    *
1001 CGCCGGGATC ACTCTCGGCA TGGACGAGCT GTACAAGTAA TAAGCTT
     GCGGCCCTAG TGAGAGCCGT ACCTGCTCGA CATGTTCATT ATTCGAA
```

Ub-GFP

Ub NCBI ACCESSION# 751846A

```
     NcoI
     ~~~~~~
       M  G  H   H  H  H   H  H  G  Q   I  F  V   K  T  L
  1  CCATGGGTCA TCACCATCAT CATCACGGGC AGATCTTCGT CAAGACGTTA
     GGTACCCAGT AGTGGTAGTA GTAGTGCCCG TCTAGAAGCA GTTCTGCAAT
      T  G  K  T   I  T  L   E  V  E   P  S  D  T   I  E  N ·
 51  ACCGGTAAAA CCATAACTCT AGAAGTTGAA CCATCCGATA CCATCGAAAA
     TGGCCATTTT GGTATTGAGA TCTTCAACTT GGTAGGCTAT GGTAGCTTTT
     · V  K  A   K  I  Q  D   K  E  G   I  P  P   D  Q  Q  R ·
101  CGTTAAGGCT AAAATTCAAG ACAAGGAAGG CATTCCACCT GATCAACAAA
     GCAATTCCGA TTTTAAGTTC TGTTCCTTCC GTAAGGTGGA CTAGTTGTTT
     · L  I  F   A  G  K   Q  L  E  D   G  R  T   L  S  D
151  GATTGATCTT TGCCGGTAAG CAGCTCGAGG ACGGTAGAAC GCTGTCTGAT
     CTAACTAGAA ACGGCCATTC GTCGAGCTCC TGCCATCTTG CGACAGACTA
      Y  N  I  Q   K  E  S   T  L  H   L  V  L  R   L  R  G ·
201  TACAACATTC AGAAGGAGTC GACCTTACAT CTTGTCTTAC GCCTACGTGG
     ATGTTGTAAG TCTTCCTCAG CTGGAATGTA GAACAGAATG CGGATGCACC
     · G  M  V   S  K  G  E   E  L  F   T  G  V   V  P  I  L ·
251  AGGTATGGTG AGCAAGGGCG AGGAGCTGTT CACCGGGGTG GTGCCCATCC
     TCCATACCAC TCGTTCCCGC TCCTCGACAA GTGGCCCCAC CACGGGTAGG
     · V  E  L   D  G  D   V  N  G  H   K  F  S   V  S  G
301  TGGTCGAGCT GGACGGCGAC GTAAACGGCC ACAAGTTCAG CGTGTCCGGC
     ACCAGCTCGA CCTGCCGCTG CATTTGCCGG TGTTCAAGTC GCACAGGCCG
      E  G  E  G   D  A  T   Y  G  K   L  T  L  K   F  I  C ·
351  GAGGGCGAGG GCGATGCCAC CTACGGCAAG CTGACCCTGA AGTTCATCTG
     CTCCCGCTCC CGCTACGGTG GATGCCGTTC GACTGGGACT TCAAGTAGAC
     · T  T  G   K  L  P  V   P  W  P   T  L  V   T  T  L  T ·
401  CACCACCGGC AAGCTGCCCG TGCCCTGGCC CACCCTCGTG ACCACCCTGA
     GTGGTGGCCG TTCGACGGGC ACGGGACCGG GTGGGAGCAC TGGTGGGACT
     · Y  G  V   Q  C  F   S  R  Y  P   D  H  M   K  Q  H
451  CCTACGGCGT GCAGTGCTTC AGCCGCTACC CCGACCACAT GAAGCAGCAC
     GGATGCCGCA CGTCACGAAG TCGGCGATGG GGCTGGTGTA CTTCGTCGTG
      D  F  F  K   S  A  M   P  E  G   Y  V  Q  E   R  T  I ·
501  GACTTCTTCA AGTCCGCCAT GCCCGAAGGC TACGTCCAGG AGCGCACCAT
     CTGAAGAAGT TCAGGCGGTA CGGGCTTCCG ATGCAGGTCC TCGCGTGGTA
     · F  F  K   D  D  G  N   Y  K  T   R  A  E   V  K  F  E ·
551  CTTCTTCAAG GACGACGGCA ACTACAAGAC CCGCGCCGAG GTGAAGTTCG
     GAAGAAGTTC CTGCTGCCGT TGATGTTCTG GGCGCGGCTC CACTTCAAGC
     · G  D  T   L  V  N   R  I  E  L   K  G  I   D  F  K
601  AGGGCGACAC CCTGGTGAAC CGCATCGAGC TGAAGGGCAT CGACTTCAAG
     TCCCGCTGTG GGACCACTTG GCGTAGCTCG ACTTCCCGTA GCTGAAGTTC
      E  D  G  N   I  L  G   H  K  L   E  Y  N  Y   N  S  H ·
651  GAGGACGGCA ACATCCTGGG GCACAAGCTG GAGTACAACT ACAACAGCCA
     CTCCTGCCGT TGTAGGACCC CGTGTTCGAC CTCATGTTGA TGTTGTCGGT
     · N  V  Y   I  M  A  D   K  Q  K   N  G  I   K  V  N  F ·
701  CAACGTCTAT ATCATGGCCG ACAAGCAGAA GAACGGCATC AAGGTGAACT
     GTTGCAGATA TAGTACCGGC TGTTCGTCTT CTTGCCGTAG TTCCACTTGA
     · K  I  R   H  N  I   E  D  G  S   V  Q  L   A  D  H
751  TCAAGATCCG CCACAACATC GAGGACGGCA GCGTGCAGCT CGCCGACCAC
```

```
     AGTTCTAGGC GGTGTTGTAG CTCCTGCCGT CGCACGTCGA GCGGCTGGTG
      Y  Q  Q  N   T  P  I   G  D  G   P  V  L  L   P  D  N ·
801  TACCAGCAGA ACACCCCCAT CGGCGACGGC CCCGTGCTGC TGCCCGACAA
     ATGGTCGTCT TGTGGGGGTA GCCGCTGCCG GGGCACGACG ACGGGCTGTT
     · H  Y  L   S  T  Q  S   A  L  S   K  D  P   N  E  K  R ·
851  CCACTACCTG AGCACCCAGT CCGCCCTGAG CAAAGACCCC AACGAGAAGC
     GGTGATGGAC TCGTGGGTCA GGCGGGACTC GTTTCTGGGG TTGCTCTTCG

     ·  D  H  M   V  L  L   E  F  V  T   A  A  G   I  T  L
901  GCGATCACAT GGTCCTGCTG GAGTTCGTGA CCGCCGCCGG GATCACTCTC
     CGCTAGTGTA CCAGGACGAC CTCAAGCACT GGCGGCGGCC CTAGTGAGAG
                                  HindIII
                                  ~~~~~~~
      G  M  D  E   L  Y  K   *  *
951  GGCATGGACG AGCTGTACAA GTAATAAGCT T
     CCGTACCTGC TCGACATGTT CATTATTCGA A
```

Urm1-GFP
Urm1 NCBI ACCESSION# NP_587744

```
     NcoI
     ~~~~~~
        M  G  H   H  H  H   H  H  G  V   N  V  K   V  E  F
  1  CCATGGGTCA TCACCATCAT CATCACGGGG TAAACGTGAA AGTGGAGTTT
     GGTACCCAGT AGTGGTAGTA GTAGTGCCCC ATTTGCACTT TCACCTCAAA
      L  G  G  L   D  A  I   F  G  K   Q  R  V  H   K  I  K ·
 51  CTAGGTGGAC TTGATGCTAT TTTTGGAAAA CAAAGAGTAC ATAAAATTAA
     GATCCACCTG AACTACGATA AAAACCTTTT GTTTCTCATG TATTTTAATT
     ·M  D  K   E  D  P  V   T  V  G   D  L  I   D  H  I  V·
101  GATGGACAAA GAAGATCCTG TCACAGTGGG CGATTTGATT GACCACATTG
     CTACCTGTTT CTTCTAGGAC AGTGTCACCC GCTAAACTAA CTGGTGTAAC
     ·  S  T  M   I  N  N   P  N  D  V   S  I  F   I  E  D
151  TATCTACTAT GATCAATAAC CCTAATGACG TTAGTATCTT CATCGAAGAT
     ATAGATGATA CTAGTTATTG GGATTACTGC AATCATAGAA GTAGCTTCTA
      D  S  I  R   P  G  I   I  T  L   I  N  D  T   D  W  E ·
201  GATTCTATAA GACCCGGTAT CATCACATTA ATCAACGACA CCGACTGGGA
     CTAAGATATT CTGGGCCATA GTAGTGTAAT TAGTTGCTGT GGCTGACCCT
     ·L  E  G   E  K  D  Y   I  L  E   D  G  D   I  I  S  F·
251  GCTCGAAGGC GAAAAAGACT ACATATTGGA AGACGGTGAC ATCATCTCTT
     CGAGCTTCCG CTTTTTCTGA TGTATAACCT TCTGCCACTG TAGTAGAGAA
     ·  T  S  T   L  H  G   G  M  V  S   K  G  E   E  L  F
301  TTACTTCAAC ATTACATGGA GGTATGGTGA GCAAGGGCGA GGAGCTGTTC
     AATGAAGTTG TAATGTACCT CCATACCACT CGTTCCCGCT CCTCGACAAG
      T  G  V  V   P  I  L   V  E  L   D  G  D  V   N  G  H ·
351  ACCGGGGTGG TGCCCATCCT GGTCGAGCTG GACGGCGACG TAAACGGCCA
     TGGCCCCACC ACGGGTAGGA CCAGCTCGAC CTGCCGCTGC ATTTGCCGGT
     ·K  F  S   V  S  G  E   G  E  G   D  A  T   Y  G  K  L·
401  CAAGTTCAGC GTGTCCGGCG AGGGCGAGGG CGATGCCACC TACGGCAAGC
     GTTCAAGTCG CACAGGCCGC TCCCGCTCCC GCTACGGTGG ATGCCGTTCG
     ·  T  L  K   F  I  C   T  T  G  K   L  P  V   P  W  P
451  TGACCCTGAA GTTCATCTGC ACCACCGGCA AGCTGCCCGT GCCCTGGCCC
     ACTGGGACTT CAAGTAGACG TGGTGGCCGT TCGACGGGCA CGGGACCGGG
      T  L  V  T   T  L  T   Y  G  V   Q  C  F  S   R  Y  P ·
501  ACCCTCGTGA CCACCCTGAC CTACGGCGTG CAGTGCTTCA GCCGCTACCC
     TGGGAGCACT GGTGGGACTG GATGCCGCAC GTCACGAAGT CGGCGATGGG
     ·D  H  M   K  Q  H  D   F  F  K   S  A  M   P  E  G  Y·
551  CGACCACATG AAGCAGCACG ACTTCTTCAA GTCCGCCATG CCCGAAGGCT
     GCTGGTGTAC TTCGTCGTGC TGAAGAAGTT CAGGCGGTAC GGGCTTCCGA
     ·  V  Q  E   R  T  I   F  F  K  D   D  G  N   Y  K  T
601  ACGTCCAGGA GCGCACCATC TTCTTCAAGG ACGACGGCAA CTACAAGACC
     TGCAGGTCCT CGCGTGGTAG AAGAAGTTCC TGCTGCCGTT GATGTTCTGG
      R  A  E  V   K  F  E   G  D  T   L  V  N  R   I  E  L ·
651  CGCGCCGAGG TGAAGTTCGA GGGCGACACC CTGGTGAACC GCATCGAGCT
     GCGCGGCTCC ACTTCAAGCT CCCGCTGTGG GACCACTTGG CGTAGCTCGA
     ·K  G  I   D  F  K  E   D  G  N   I  L  G   H  K  L  E·
701  GAAGGGCATC GACTTCAAGG AGGACGGCAA CATCCTGGGG CACAAGCTGG
     CTTCCCGTAG CTGAAGTTCC TCCTGCCGTT GTAGGACCCC GTGTTCGACC
```

```
      · Y  N  Y   N  S  H   N  V  Y  I   M  A  D   K  Q  K
 751  AGTACAACTA CAACAGCCAC AACGTCTATA TCATGGCCGA CAAGCAGAAG
      TCATGTTGAT GTTGTCGGTG TTGCAGATAT AGTACCGGCT GTTCGTCTTC
       N  G  I  K   V  N  F   K  I  R   H  N  I  E   D  G  S ·
 801  AACGGCATCA AGGTGAACTT CAAGATCCGC CACAACATCG AGGACGGCAG
      TTGCCGTAGT TCCACTTGAA GTTCTAGGCG GTGTTGTAGC TCCTGCCGTC
      · V  Q  L   A  D  H  Y   Q  Q  N   T  P  I   G  D  G  P ·
 851  CGTGCAGCTC GCCGACCACT ACCAGCAGAA CACCCCCATC GGCGACGGCC
      GCACGTCGAG CGGCTGGTGA TGGTCGTCTT GTGGGGGTAG CCGCTGCCGG
      · V  L  L   P  D  N   H  Y  L  S   T  Q  S   A  L  S
 901  CCGTGCTGCT GCCCGACAAC CACTACCTGA GCACCCAGTC CGCCCTGAGC
      GGCACGACGA CGGGCTGTTG GTGATGGACT CGTGGGTCAG GCGGGACTCG
       K  D  P  N   E  K  R   D  H  M   V  L  L  E   F  V  T ·
 951  AAAGACCCCA ACGAGAAGCG CGATCACATG GTCCTGCTGG AGTTCGTGAC
      TTTCTGGGGT TGCTCTTCGC GCTAGTGTAC CAGGACGACC TCAAGCACTG
                                                     HindIII
                                                      ~~~~~~
      · A  A  G   I  T  L  G   M  D  E   L  Y  K   *  *
1001  CGCCGCCGGG ATCACTCTCG GCATGGACGA GCTGTACAAG TAATAAGCTT
      GCGGCGGCCC TAGTGAGAGC CGTACCTGCT CGACATGTTC ATTATTCGAA
```

Hub1-GFP

Hub1 NCBI ACCESSION# XM_114578

```
    NcoI
    ~~~~~~
      M  G  H   H  Y  H   H  H  G  M   I  E  V   V  V  N
  1 CCATGGGTCA TCACTATCAT CATCACGGGA TGATTGAGGT AGTTGTGAAT
    GGTACCCAGT AGTGATAGTA GTAGTGCCCT ACTAACTCCA TCAACACTTA
     D  R  L  G   K  K  V   R  V  K   C  L  A  E   D  S  V ·
 51 GACCGATTAG GCAAAAAAGT CAGAGTGAAG TGCCTTGCTG AAGATAGTGT
    CTGGCTAATC CGTTTTTTCA GTCTCACTTC ACGGAACGAC TTCTATCACA
    · G  D  F   K  K  V  L   S  L  Q   I  G  T   Q  P  N  K ·
101 AGGTGATTTC AAAAAAGTAT TGTCCTTGCA AATTGGCACC CAACCAAACA
    TCCACTAAAG TTTTTTCATA ACAGGAACGT TTAACCGTGG GTTGGTTTGT
    · I  V  L   Q  K  G   G  S  V  L   K  D  H   I  S  L
151 AAATTGTGTT GCAGAAGGGT GGAAGTGTTT TAAAAGACCA TATCTCTCTG
    TTTAACACAA CGTCTTCCCA CCTTCACAAA ATTTTCTGGT ATAGAGAGAC
     E  D  Y  E   V  H  D   Q  T  N   L  E  L  Y   Y  M  V ·
201 GAAGATTATG AGGTACATGA TCAGACAAAT TTGGAGCTGT ATTACATGGT
    CTTCTAATAC TCCATGTACT AGTCTGTTTA AACCTCGACA TAATGTACCA
    · S  K  G   E  E  L  F   T  G  V   V  P  I   L  V  E  L ·
251 GAGCAAGGGC GAGGAGCTGT TCACCGGGGT GGTGCCCATC CTGGTCGAGC
    CTCGTTCCCG CTCCTCGACA AGTGGCCCCA CCACGGGTAG GACCAGCTCG
    · D  G  D   V  N  G   H  K  F  S   V  S  G   E  G  E
301 TGGACGGCGA CGTAAACGGC CACAAGTTCA GCGTGTCCGG CGAGGGCGAG
    ACCTGCCGCT GCATTTGCCG GTGTTCAAGT CGCACAGGCC GCTCCCGCTC
     G  D  A  T   Y  G  K   L  T  L   K  F  I  C   T  T  G ·
351 GGCGATGCCA CCTACGGCAA GCTGACCCTG AAGTTCATCT GCACCACCGG
    CCGCTACGGT GGATGCCGTT CGACTGGGAC TTCAAGTAGA CGTGGTGGCC
    · K  L  P   V  P  W  P   T  L  V   T  T  L   T  Y  G  V ·
401 CAAGCTGCCC GTGCCCTGGC CCACCCTCGT GACCACCCTG ACCTACGGCG
    GTTCGACGGG CACGGGACCG GGTGGGAGCA CTGGTGGGAC TGGATGCCGC
    · Q  C  F   S  R  Y   P  D  H  M   K  Q  H   D  F  F
451 TGCAGTGCTT CAGCCGCTAC CCCGACCACA TGAAGCAGCA CGACTTCTTC
    ACGTCACGAA GTCGGCGATG GGGCTGGTGT ACTTCGTCGT GCTGAAGAAG
     K  S  A  M   P  E  G   Y  V  Q   E  R  T  I   F  F  K ·
501 AAGTCCGCCA TGCCCGAAGG CTACGTCCAG GAGCGCACCA TCTTCTTCAA
    TTCAGGCGGT ACGGGCTTCC GATGCAGGTC CTCGCGTGGT AGAAGAAGTT
    · D  D  G   N  Y  K  T   R  A  E   V  K  F   E  G  D  T ·
551 GGACGACGGC AACTACAAGA CCCGCGCCGA GGTGAAGTTC GAGGGCGACA
    CCTGCTGCCG TTGATGTTCT GGGCGCGGCT CCACTTCAAG CTCCCGCTGT
    · L  V  N   R  I  E   L  K  G  I   D  F  K   E  D  G
601 CCCTGGTGAA CCGCATCGAG CTGAAGGGCA TCGACTTCAA GGAGGACGGC
    GGGACCACTT GGCGTAGCTC GACTTCCCGT AGCTGAAGTT CCTCCTGCCG
     N  I  L  G   H  K  L   E  Y  N   Y  N  S  H   N  V  Y ·
651 AACATCCTGG GGCACAAGCT GGAGTACAAC TACAACAGCC ACAACGTCTA
    TTGTAGGACC CCGTGTTCGA CCTCATGTTG ATGTTGTCGG TGTTGCAGAT
    · I  M  A   D  K  Q  K   N  G  I   K  V  N   F  K  I  R ·
701 TATCATGGCC GACAAGCAGA AGAACGGCAT CAAGGTGAAC TTCAAGATCC
```

```
     ATAGTACCGG CTGTTCGTCT TCTTGCCGTA GTTCCACTTG AAGTTCTAGG
     · H  N  I  E  D  G  S  V  Q  L  A  D  H  Y  Q  Q
751  GCCACAACAT CGAGGACGGC AGCGTGCAGC TCGCCGACCA CTACCAGCAG
     CGGTGTTGTA GCTCCTGCCG TCGCACGTCG AGCGGCTGGT GATGGTCGTC
      N  T  P  I  G  D  G  P  V  L  L  P  D  N  H  Y  L ·
801  AACACCCCCA TCGGCGACGG CCCCGTGCTG CTGCCCGACA ACCACTACCT
     TTGTGGGGGT AGCCGCTGCC GGGGCACGAC GACGGGCTGT TGGTGATGGA
     ·S  T  Q  S  A  L  S  K  D  P  N  E  K  R  D  H  M ·
851  GAGCACCCAG TCCGCCCTGA GCAAAGACCC CAACGAGAAG CGCGATCACA
     CTCGTGGGTC AGGCGGGACT CGTTTCTGGG GTTGCTCTTC GCGCTAGTGT
     · V  L  L  E  F  V  T  A  A  G  I  T  L  G  M  D
901  TGGTCCTGCT GGAGTTCGTG ACCGCCGCCG GGATCACTCT CGGCATGGAC
     ACCAGGACGA CCTCAAGCAC TGGCGGCGGC CCTAGTGAGA GCCGTACCTG
                          HindIII
                          ~~~~~~~
      E  L  Y  K  *  *
951  GAGCTGTACA AGTAATAAGC TT
     CTCGACATGT TCATTATTCG AA
```

Rub1-GFP
Rub1 NCBI Accession# Y16890

```
    NcoI
    ~~~~~~
     M  G  H   H  H  H   H  H  G  I   V  K  X   K  T  L
  1 CCATGGGTCA TCACCATCAT CATCACGGGA TTGTTAAAGN GAAGACACTG
    GGTACCCAGT AGTGGTAGTA GTAGTGCCCT AACAATTTCN CTTCTGTGAC
     T  G  K  E  I  S  V   E  L  K   E  S  D  L   V  Y  H ·
 51 ACTGGGAAGG AGATCTCTGT TGAGCTGAAG GAATCAGATC TCGTATATCA
    TGACCCTTCC TCTAGAGACA ACTCGACTTC CTTAGTCTAG AGCATATAGT
    · I  K  E   L  L  E  E   K  E  G   I  P  P   S  Q  Q  R ·
101 CATCAAGGAA CTTTTGGAGG AAAAAGAAGG GATTCCACCA TCTCAACAAA
    GTAGTTCCTT GAAAACCTCC TTTTTCTTCC CTAAGGTGGT AGAGTTGTTT
    · L  I  F   Q  G  K   Q  I  D  D   K  L  T   V  T  D
151 GACTTATATT CCAGGGAAAA CAAATTGATG ATAAATTAAC AGTAACGGAT
    CTGAATATAA GGTCCCTTTT GTTTAACTAC TATTTAATTG TCATTGCCTA
     A  H  X  V   E  G  M   Q  L  H   L  V  L  T   L  R  G ·
201 GCACATNTAG TAGAGGGAAT GCAACTCCAC TTGGTATTAA CACTACGCGG
    CGTGTANATC ATCTCCCTTA CGTTGAGGTG AACCATAATT GTGATGCGCC
    · G  M  V   S  K  G  E   E  L  F   T  G  V   V  P  I  L ·
251 AGGTATGGTG AGCAAGGGCG AGGAGCTGTT CACCGGGGTG GTGCCCATCC
    TCCATACCAC TCGTTCCCGC TCCTCGACAA GTGGCCCCAC CACGGGTAGG
    · V  E  L   D  G  D   V  N  G  H   K  F  S   V  S  G
301 TGGTCGAGCT GGACGGCGAC GTAAACGGCC ACAAGTTCAG CGTGTCCGGC
    ACCAGCTCGA CCTGCCGCTG CATTTGCCGG TGTTCAAGTC GCACAGGCCG
     E  G  E  G   D  A  T   Y  G  K   L  T  L  K   F  I  C ·
351 GAGGGCGAGG GCGATGCCAC CTACGGCAAG CTGACCCTGA AGTTCATCTG
    CTCCCGCTCC CGCTACGGTG GATGCCGTTC GACTGGGACT TCAAGTAGAC
    · T  T  G   K  L  P  V   P  W  P   T  L  V   T  T  L  T ·
401 CACCACCGGC AAGCTGCCCG TGCCCTGGCC CACCCTCGTG ACCACCCTGA
    GTGGTGGCCG TTCGACGGGC ACGGGACCGG GTGGGAGCAC TGGTGGGACT
    · Y  G  V   Q  C  F   S  R  Y  P   D  H  M   K  Q  H
451 CCTACGGCGT GCAGTGCTTC AGCCGCTACC CCGACCACAT GAAGCAGCAC
    GGATGCCGCA CGTCACGAAG TCGGCGATGG GGCTGGTGTA CTTCGTCGTG
     D  F  F  K   S  A  M   P  E  G   Y  V  Q  E   R  T  I ·
501 GACTTCTTCA AGTCCGCCAT GCCCGAAGGC TACGTCCAGG AGCGCACCAT
    CTGAAGAAGT TCAGGCGGTA CGGGCTTCCG ATGCAGGTCC TCGCGTGGTA
    · F  F  K   D  D  G  N   Y  K  T   R  A  E   V  K  F  E ·
551 CTTCTTCAAG GACGACGGCA ACTACAAGAC CCGCGCCGAG GTGAAGTTCG
    GAAGAAGTTC CTGCTGCCGT TGATGTTCTG GGCGCGGCTC CACTTCAAGC
    · G  D  T   L  V  N   R  I  E  L   K  G  I   D  F  K
601 AGGGCGACAC CCTGGTGAAC CGCATCGAGC TGAAGGGCAT CGACTTCAAG
    TCCCGCTGTG GGACCACTTG GCGTAGCTCG ACTTCCCGTA GCTGAAGTTC
     E  D  G  N   I  L  G   H  K  L   E  Y  N  Y   N  S  H ·
651 GAGGACGGCA ACATCCTGGG GCACAAGCTG GAGTACAACT ACAACAGCCA
    CTCCTGCCGT TGTAGGACCC CGTGTTCGAC CTCATGTTGA TGTTGTCGGT
    · N  V  Y   I  M  A  D   K  Q  K   N  G  I   K  V  N  F ·
701 CAACGTCTAT ATCATGGCCG ACAAGCAGAA GAACGGCATC AAGGTGAACT
```

```
     GTTGCAGATA TAGTACCGGC TGTTCGTCTT CTTGCCGTAG TTCCACTTGA
     · K  I  R   H  N  I   E  D  G  S   V  Q  L   A  D  H
751  TCAAGATCCG CCACAACATC GAGGACGGCA GCGTGCAGCT CGCCGACCAC
     AGTTCTAGGC GGTGTTGTAG CTCCTGCCGT CGCACGTCGA GCGGCTGGTG
      Y  Q  Q  N   T  P  I   G  D  G   P  V  L  L   P  D  N ·
801  TACCAGCAGA ACACCCCCAT CGGCGACGGC CCCGTGCTGC TGCCCGACAA
     ATGGTCGTCT TGTGGGGGTA GCCGCTGCCG GGGCACGACG ACGGGCTGTT
     · H  Y  L   S  T  Q  S   A  L  S   K  D  P   N  E  K  R ·
851  CCACTACCTG AGCACCCAGT CCGCCCTGAG CAAAGACCCC AACGAGAAGC
     GGTGATGGAC TCGTGGGTCA GGCGGGACTC GTTTCTGGGG TTGCTCTTCG
     · D  H  M   V  L  L   E  F  V  T   A  A  G   I  T  L
901  GCGATCACAT GGTCCTGCTG GAGTTCGTGA CCGCCGCCGG GATCACTCTC
     CGCTAGTGTA CCAGGACGAC CTCAAGCACT GGCGGCGGCC CTAGTGAGAG

                                 HindIII
                                 ~~~~~~~
      G  M  D  E   L  Y  K   *  *
951  GGCATGGACG AGCTGTACAA GTAATAAGCT T
     CCGTACCTGC TCGACATGTT CATTATTCGA A
```

Apg8-GFP
Apg8 NCBI ACCESSION# P38182

```
      NcoI
      ~~~~
      M G H  H H H  H H G K  S T F  K S E
  1   ATGGGTCA TCACCATCAT CATCACGGGA AGTCTACATT TAAGTCTGAA
      TACCCAGT AGTGGTAGTA GTAGTGCCCT TCAGATGTAA ATTCAGACTT
     Y P F E  K R K  A E S  E R I A  D R F ·
 51  TATCCATTTG AAAAAAGGAA GGCGGAGTCG GAGAGGATTG CTGACAGGTT
     ATAGGTAAAC TTTTTTCCTT CCGCCTCAGC CTCTCCTAAC GACTGTCCAA
     · K N R  I P V I  C E K  A E K  S D I P ·
101  CAAGAATAGG ATACCTGTGA TTTGCGAAAA AGCTGAAAAG TCAGATATTC
     GTTCTTATCC TATGGACACT AAACGCTTTT TCGACTTTTC AGTCTATAAG
     · E I D  K R K  Y L V P  A D L  T V G
151  CAGAGATTGA TAAGCGTAAA TATCTAGTTC CTGCTGACCT TACCGTAGGG
     GTCTCTAACT ATTCGCATTT ATAGATCAAG GACGACTGGA ATGGCATCCC
     Q F V Y  V I R  K R I  M L P P  E K A ·
201  CAATTTGTTT ATGTTATAAG AAAGAGGATT ATGCTACCCC CTGAGAAGGC
     GTTAAACAAA TACAATATTC TTTCTCCTAA TACGATGGGG GACTCTTCCG
     · I F I  F V N D  T L P  P T A  A L M S ·
251  CATCTTCATT TTTGTCAATG ATACTTTGCC ACCTACTGCG GCGTTGATGT
     GTAGAAGTAA AAACAGTTAC TATGAAACGG TGGATGACGC CGCAACTACA
     · A I Y  Q E H  K D K D  G F L  Y V T
301  CTGCCATATA TCAAGAACAC AAGGATAAGG ACGGGTTTTT GTATGTCACT
     GACGGTATAT AGTTCTTGTG TTCCTATTCC TGCCCAAAAA CATACAGTGA
     Y S G E  N T F  G M V  S K G E  E L F ·
351  TACTCAGGAG AAAATACATT TGGTATGGTG AGCAAGGGCG AGGAGCTGTT
     ATGAGTCCTC TTTTATGTAA ACCATACCAC TCGTTCCCGC TCCTCGACAA
     · T G V  V P I L  V E L  D G D  V N G H ·
401  CACCGGGGTG GTGCCCATCC TGGTCGAGCT GGACGGCGAC GTAAACGGCC
     GTGGCCCCAC CACGGGTAGG ACCAGCTCGA CCTGCCGCTG CATTTGCCGG
     · K F S  V S G  E G E G  D A T  Y G K
451  ACAAGTTCAG CGTGTCCGGC GAGGGCGAGG GCGATGCCAC CTACGGCAAG
     TGTTCAAGTC GCACAGGCCG CTCCCGCTCC CGCTACGGTG GATGCCGTTC
     L T L K  F I C  T T G  K L P V  P W P ·
501  CTGACCCTGA AGTTCATCTG CACCACCGGC AAGCTGCCCG TGCCCTGGCC
     GACTGGGACT TCAAGTAGAC GTGGTGGCCG TTCGACGGGC ACGGGACCGG
     · T L V  T T L T  Y G V  Q C F  S R Y P ·
551  CACCCTCGTG ACCACCCTGA CCTACGGCGT GCAGTGCTTC AGCCGCTACC
     GTGGGAGCAC TGGTGGGACT GGATGCCGCA CGTCACGAAG TCGGCGATGG
     · D H M  K Q H  D F F K  S A M  P E G
601  CCGACCACAT GAAGCAGCAC GACTTCTTCA AGTCCGCCAT GCCCGAAGGC
     GGCTGGTGTA CTTCGTCGTG CTGAAGAAGT TCAGGCGGTA CGGGCTTCCG
     Y V Q E  R T I  F F K  D D G N  Y K T ·
```

```
 651  TACGTCCAGG AGCGCACCAT CTTCTTCAAG GACGACGGCA ACTACAAGAC
      ATGCAGGTCC TCGCGTGGTA GAAGAAGTTC CTGCTGCCGT TGATGTTCTG
      ·R  A  E   V  K  F  E   G  D  T   L  V  N   R  I  E  L·
 701  CCGCGCCGAG GTGAAGTTCG AGGGCGACAC CCTGGTGAAC CGCATCGAGC
      GGCGCGGCTC CACTTCAAGC TCCCGCTGTG GGACCACTTG GCGTAGCTCG
      · K  G  I   D  F  K   E  D  G  N   I  L  G   H  K  L
 751  TGAAGGGCAT CGACTTCAAG GAGGACGGCA ACATCCTGGG GCACAAGCTG
      ACTTCCCGTA GCTGAAGTTC CTCCTGCCGT TGTAGGACCC CGTGTTCGAC
       E  Y  N  Y  N  S  H   N  V  Y   I  M  A  D   K  Q  K·
 801  GAGTACAACT ACAACAGCCA CAACGTCTAT ATCATGGCCG ACAAGCAGAA
      CTCATGTTGA TGTTGTCGGT GTTGCAGATA TAGTACCGGC TGTTCGTCTT
      ·N  G  I   K  V  N  F   K  I  R   H  N  I   E  D  G  S·
 851  GAACGGCATC AAGGTGAACT TCAAGATCCG CCACAACATC GAGGACGGCA
      CTTGCCGTAG TTCCACTTGA AGTTCTAGGC GGTGTTGTAG CTCCTGCCGT
      · V  Q  L   A  D  H   Y  Q  Q  N   T  P  I   G  D  G
 901  GCGTGCAGCT CGCCGACCAC TACCAGCAGA ACACCCCCAT CGGCGACGGC
      CGCACGTCGA GCGGCTGGTG ATGGTCGTCT TGTGGGGGTA GCCGCTGCCG
       P  V  L  L   P  D  N   H  Y  L   S  T  Q  S   A  L  S·
 951  CCCGTGCTGC TGCCCGACAA CCACTACCTG AGCACCCAGT CCGCCCTGAG
      GGGCACGACG ACGGGCTGTT GGTGATGGAC TCGTGGGTCA GGCGGGACTC
      ·K  D  P   N  E  K  R   D  H  M   V  L  L   E  F  V  T·
1001  CAAAGACCCC AACGAGAAGC GCGATCACAT GGTCCTGCTG GAGTTCGTGA
      GTTTCTGGGG TTGCTCTTCG CGCTAGTGTA CCAGGACGAC CTCAAGCACT
                                                  HindIII
                                                   ~~~~~
      · A  A  G   I  T  L   G  M  D  E   L  Y  K    *  *  A
1051  CCGCCGCCGG GATCACTCTC GGCATGGACG AGCTGTACAA GTAATAAGCTT
      GGCGGCGGCC CTAGTGAGAG CCGTACCTGC TCGACATGTT CATTATTCGAA
```

Apg12-GFP
Apg12 NCBI ACCESSION# P38316

```
      NcoI
      ~~~~~~
        M  G  H   H  H  H   H  H  G  S   R  I  L   E  S  E
  1   CCATGGGTCA TCACCATCAT CATCACGGGA GTAGGATCCT AGAGAGCGAA
      GGTACCCAGT AGTGGTAGTA GTAGTGCCCT CATCCTAGGA TCTCTCGCTT
       N  E  T  E   S  D  E   S  S  I   I  S  T  N   N  G  T ·
 51   AATGAAACAG AAAGTGACGA AAGCTCCATC ATATCCACAA ATAATGGAAC
      TTACTTTGTC TTTCACTGCT TTCGAGGTAG TATAGGTGTT TATTACCTTG
      · A  M  E   R  S  R  N   N  Q  E   L  R  S   S  P  H  T ·
101   GGCAATGGAA AGATCCAGAA ATAATCAAGA ATTAAGATCA TCTCCTCATA
      CCGTTACCTT TCTAGGTCTT TATTAGTTCT TAATTCTAGT AGAGGAGTAT
      · V  Q  N   R  L  E   L  F  S  R   R  L  S   Q  L  G
151   CCGTTCAAAA TAGATTGGAA CTTTTTAGCA GGAGATTGTC TCAGCTTGGT
      GGCAAGTTTT ATCTAACCTT GAAAAATCGT CCTCTAACAG AGTCGAACCA
       L  A  S  D   I  S  V   D  Q  Q   V  E  D  S   S  S  G ·
201   TTGGCGAGTG ACATTTCTGT CGACCAGCAA GTTGAAGATT CCTCTAGTGG
      AACCGCTCAC TGTAAAGACA GCTGGTCGTT CAACTTCTAA GGAGATCACC
      · T  Y  E   Q  E  E  T   I  K  T   N  A  Q   T  S  K  Q ·
251   CACTTATGAA CAGGAAGAGA CAATCAAAAC GAATGCACAA ACAAGCAAAC
      GTGAATACTT GTCCTTCTCT GTTAGTTTTG CTTACGTGTT TGTTCGTTTG
      · K  S  H   K  D  E   K  N  I  Q   K  I  Q   I  K  F
301   AAAAAAGCCA TAAAGACGAA AAAAACATAC AAAAGATACA GATAAAATTT
      TTTTTTCGGT ATTTCTGCTT TTTTTGTATG TTTTCTATGT CTATTTTAAA
       Q  P  I  G   S  I  G   Q  L  K   P  S  V  C   K  I  S ·
351   CAGCCCATTG GTTCTATTGG GCAGTTAAAA CCATCTGTTT GTAAAATATC
      GTCGGGTAAC CAAGATAACC CGTCAATTTT GGTAGACAAA CATTTTATAG
      · M  S  Q   S  F  A  M   V  I  L   F  L  K   R  R  L  K ·
401   NATGTCACAG TCTTTTGCAA TGGTTATTTT ATTTCTTAAG AGACGGCTGA
      NTACAGTGTC AGAAAACGTT ACCAATAAAA TAAAGAATTC TCTGCCGACT
      · M  D  H   V  Y  C   Y  I  N  N   S  F  A   P  S  P
451   AAATGGACCA TGTTTATTGT TATATAAATA ATTCGTTTGC GCCAAGTCCG
      TTTACCTGGT ACAAATAACA ATATATTTAT TAAGCAAACG CGGTTCAGGC
       Q  Q  N  I   G  E  L   W  M  X   F  K  T  N   D  E  L ·
501   CAGCAAAATA TTGGTGAACT TTGGATGCNA TTCAAGACTA ATGATGAGCT
      GTCGTTTTAT AACCACTTGA AACCTACGNT AAGTTCTGAT TACTACTCGA
      · I  V  S   Y  C  A  S   V  A  F   G  M  V   S  K  G  E ·
551   TATTGTAAGT TATTGTGCAT CCGTAGCGTT TGGTATGGTG AGCAAGGGCG
      ATAACATTCA ATAACACGTA GGCATCGCAA ACCATACCAC TCGTTCCCGC
      · E  L  F   T  G  V   V  P  I  L   V  E  L   D  G  D
601   AGGAGCTGTT CACCGGGGTG GTGCCCATCC TGGTCGAGCT GGACGGCGAC
      TCCTCGACAA GTGGCCCCAC CACGGGTAGG ACCAGCTCGA CCTGCCGCTG
       V  N  G  H   K  F  S   V  S  G   E  G  E  G   D  A  T ·
651   GTAAACGGCC ACAAGTTCAG CGTGTCCGGC GAGGGCGAGG GCGATGCCAC
      CATTTGCCGG TGTTCAAGTC GCACAGGCCG CTCCCGCTCC CGCTACGGTG
      · Y  G  K   L  T  L  K   F  I  C   T  T  G   K  L  P  V ·
701   CTACGGCAAG CTGACCCTGA AGTTCATCTG CACCACCGGC AAGCTGCCCG
      GATGCCGTTC GACTGGGACT TCAAGTAGAC GTGGTGGCCG TTCGACGGGC
```

```
      · P  W  P   T  L  V   T  T  L  T   Y  G  V   Q  C  F
 751  TGCCCTGGCC CACCCTCGTG ACCACCCTGA CCTACGGCGT GCAGTGCTTC
      ACGGGACCGG GTGGGAGCAC TGGTGGGACT GGATGCCGCA CGTCACGAAG
       S  R  Y  P   D  H  M   K  Q  H   D  F  F  K   S  A  M ·
 801  AGCCGCTACC CCGACCACAT GAAGCAGCAC GACTTCTTCA AGTCCGCCAT
      TCGGCGATGG GGCTGGTGTA CTTCGTCGTG CTGAAGAAGT TCAGGCGGTA
      · P  E  G   Y  V  Q  E   R  T  I   F  F  K   D  D  G  N ·
 851  GCCCGAAGGC TACGTCCAGG AGCGCACCAT CTTCTTCAAG GACGACGGCA
      CGGGCTTCCG ATGCAGGTCC TCGCGTGGTA GAAGAAGTTC CTGCTGCCGT
      · Y  K  T   R  A  E   V  K  F  E   G  D  T   L  V  N
 901  ACTACAAGAC CCGCGCCGAG GTGAAGTTCG AGGGCGACAC CCTGGTGAAC
      TGATGTTCTG GGCGCGGCTC CACTTCAAGC TCCCGCTGTG GGACCACTTG
       R  I  E  L   K  G  I   D  F  K   E  D  G  N   I  L  G ·
 951  CGCATCGAGC TGAAGGGCAT CGACTTCAAG GAGGACGGCA ACATCCTGGG
      GCGTAGCTCG ACTTCCCGTA GCTGAAGTTC CTCCTGCCGT TGTAGGACCC
      · H  K  L   E  Y  N  Y   N  S  H   N  V  Y   I  M  A  D ·
1001  GCACAAGCTG GAGTACAACT ACAACAGCCA CAACGTCTAT ATCATGGCCG
      CGTGTTCGAC CTCATGTTGA TGTTGTCGGT GTTGCAGATA TAGTACCGGC
      · K  Q  K   N  G  I   K  V  N  F   K  I  R   H  N  I
1051  ACAAGCAGAA GAACGGCATC AAGGTGAACT TCAAGATCCG CCACAACATC
      TGTTCGTCTT CTTGCCGTAG TTCCACTTGA AGTTCTAGGC GGTGTTGTAG
       E  D  G  S   V  Q  L   A  D  H   Y  Q  Q  N   T  P  I ·
1101  GAGGACGGCA GCGTGCAGCT CGCCGACCAC TACCAGCAGA ACACCCCCAT
      CTCCTGCCGT CGCACGTCGA GCGGCTGGTG ATGGTCGTCT TGTGGGGGTA
      · G  D  G   P  V  L  L   P  D  N   H  Y  L   S  T  Q  S ·
1151  CGGCGACGGC CCCGTGCTGC TGCCCGACAA CCACTACCTG AGCACCCAGT
      GCCGCTGCCG GGGCACGACG ACGGGCTGTT GGTGATGGAC TCGTGGGTCA

      · A  L  S   K  D  P   N  E  K  R   D  H  M   V  L  L
1201  CCGCCCTGAG CAAAGACCCC AACGAGAAGC GCGATCACAT GGTCCTGCTG
      GGCGGGACTC GTTTCTGGGG TTGCTCTTCG CGCTAGTGTA CCAGGACGAC
       E  F  V  T   A  A  G   I  T  L   G  M  D  E   L  Y  K ·
1251  GAGTTCGTGA CCGCCGCCGG GATCACTCTC GGCATGGACG AGCTGTACAA
      CTCAAGCACT GGCGGCGGCC CTAGTGAGAG CCGTACCTGC TCGACATGTT
           HindIII
           ~~~~~~~
      · *  **
1301  GTAATAAGCT T
      CATTATTCGA A
```

ISG15-GFP

ISG15 NCBI ACCESSION# P05161

```
       NcoI
       ~~~~~~
         M  G  H   H  H  H   H  H  G  G   W  D  L   T  V  K
  1    CCATGGGTCA TCACCATCAT CATCACGGGG GCTGGGACCT GACGGTGAAG
       GGTACCCAGT AGTGGTAGTA GTAGTGCCCC CGACCCTGGA CTGCCACTTC
        M  L  A  G   N  E  F   Q  V  S   L  S  S  S   M  S  V ·
 51    ATGCTGGCGG GCAACGAATT CCAGGTGTCC CTGAGCAGCT CCATGTCGGT
       TACGACCGCC CGTTGCTTAA GGTCCACAGG GACTCGTCGA GGTACAGCCA
       · S  E  L   K  A  Q  I   T  Q  K   I  G  V   H  A  F  Q ·
101    GTCAGAGCTG AAGGCGCAGA TCACCCAGAA GATTGGCGTG CACGCCTTCC
       CAGTCTCGAC TTCCGCGTCT AGTGGGTCTT CTAACCGCAC GTGCGGAAGG
       · Q  R  L   A  V  H   P  S  G  V   A  L  Q   D  R  V
151    AGCAGCGTCT GGCTGTCCAC CCGAGCGGTG TGGCGCTGCA GGACAGGGTC
       TCGTCGCAGA CCGACAGGTG GGCTCGCCAC ACCGCGACGT CCTGTCCCAG
        P  L  A  S   Q  G  L   G  P  G   S  T  V  L   L  V  V ·
201    CCCCTTGCCA GCCAGGGCCT GGGCCCTGGC AGCACGGTCC TGCTGGTGGT
       GGGGAACGGT CGGTCCCGGA CCCGGGACCG TCGTGCCAGG ACGACCACCA
       · D  K  C   D  E  P  L   S  I  L   V  R  N   N  K  G  R ·
251    GGACAAATGC GACGAACCTC TGAGCATCCT GGTGAGGAAT AACAAGGGCC
       CCTGTTTACG CTGCTTGGAG ACTCGTAGGA CCACTCCTTA TTGTTCCCGG
       · S  S  T   Y  E  V   R  L  T  Q   T  V  A   H  L  K
301    GCAGCAGCAC CTACGAGGTC CGGCTGACGC AGACCGTGGC CCACCTGAAG
       CGTCGTCGTG GATGCTCCAG GCCGACTGCG TCTGGCACCG GGTGGACTTC
        Q  Q  V  S   G  L  E   G  V  Q   D  D  L  F   W  L  T ·
351    CAGCAAGTGA GCGGGCTGGA GGGTGTGCAG GACGACCTGT TCTGGCTGAC
       GTCGTTCACT CGCCCGACCT CCCACACGTC CTGCTGGACA AGACCGACTG
       · F  E  G   K  P  L  E   D  Q  L   P  L  G   E  Y  G  L ·
401    CTTCGAGGGG AAGCCCCTGG AGGACCAGCT CCCGCTGGGG GAGTACGGCC
       GAAGCTCCCC TTCGGGGACC TCCTGGTCGA GGGCGACCCC CTCATGCCGG
       · K  P  L   S  T  V   F  M  N  L   R  L  R   G  G  G
451    TCAAGCCCCT GAGCACCGTG TTCATGAATC TGCGCCTGCG GGGAGGCGGC
       AGTTCGGGGA CTCGTGGCAC AAGTACTTAG ACGCGGACGC CCCTCCGCCG
        T  E  P  G   G  M  V   S  K  G   E  E  L  F   T  G  V ·
501    ACAGAGCCTG GAGGTATGGT GAGCAAGGGC GAGGAGCTGT TCACCGGGGT
       TGTCTCGGAC CTCCATACCA CTCGTTCCCG CTCCTCGACA AGTGGCCCCA
       · V  P  I   L  V  E  L   D  G  D   V  N  G   H  K  F  S ·
551    GGTGCCCATC CTGGTCGAGC TGGACGGCGA CGTAAACGGC CACAAGTTCA
       CCACGGGTAG GACCAGCTCG ACCTGCCGCT GCATTTGCCG GTGTTCAAGT
       · V  S  G   E  G  E   G  D  A  T   Y  G  K   L  T  L
601    GCGTGTCCGG CGAGGGCGAG GGCGATGCCA CCTACGGCAA GCTGACCCTG
       CGCACAGGCC GCTCCCGCTC CCGCTACGGT GGATGCCGTT CGACTGGGAC
        K  F  I  C   T  T  G   K  L  P   V  P  W  P   T  L  V ·
651    AAGTTCATCT GCACCACCGG CAAGCTGCCC GTGCCCTGGC CCACCCTCGT
       TTCAAGTAGA CGTGGTGGCC GTTCGACGGG CACGGGACCG GGTGGGAGCA
       · T  T  L   T  Y  G  V   Q  C  F   S  R  Y   P  D  H  M ·
701    GACCACCCTG ACCTACGGCG TGCAGTGCTT CAGCCGCTAC CCCGACCACA
```

```
      CTGGTGGGAC TGGATGCCGC ACGTCACGAA GTCGGCGATG GGGCTGGTGT
       · K  Q  H   D  F  F   K  S  A  M   P  E  G   Y  V  Q
 751  TGAAGCAGCA CGACTTCTTC AAGTCCGCCA TGCCCGAAGG CTACGTCCAG
      ACTTCGTCGT GCTGAAGAAG TTCAGGCGGT ACGGGCTTCC GATGCAGGTC
       E  R  T  I   F  F  K   D  D  G   N  Y  K  T   R  A  E ·
 801  GAGCGCACCA TCTTCTTCAA GGACGACGGC AACTACAAGA CCCGCGCCGA
      CTCGCGTGGT AGAAGAAGTT CCTGCTGCCG TTGATGTTCT GGGCGCGGCT
       · V  K  F   E  G  D  T   L  V  N   R  I  E   L  K  G  I ·
 851  GGTGAAGTTC GAGGGCGACA CCCTGGTGAA CCGCATCGAG CTGAAGGGCA
      CCACTTCAAG CTCCCGCTGT GGGACCACTT GGCGTAGCTC GACTTCCCGT
       · D  F  K   E  D  G   N  I  L  G   H  K  L   E  Y  N
 901  TCGACTTCAA GGAGGACGGC AACATCCTGG GGCACAAGCT GGAGTACAAC
      AGCTGAAGTT CCTCCTGCCG TTGTAGGACC CCGTGTTCGA CCTCATGTTG
       Y  N  S  H   N  V  Y   I  M  A   D  K  Q  K   N  G  I ·
 951  TACAACAGCC ACAACGTCTA TATCATGGCC GACAAGCAGA AGAACGGCAT
      ATGTTGTCGG TGTTGCAGAT ATAGTACCGG CTGTTCGTCT TCTTGCCGTA
       · K  V  N   F  K  I  R   H  N  I   E  D  G   S  V  Q  L ·
1001  CAAGGTGAAC TTCAAGATCC GCCACAACAT CGAGGACGGC AGCGTGCAGC
      GTTCCACTTG AAGTTCTAGG CGGTGTTGTA GCTCCTGCCG TCGCACGTCG
       · A  D  H   Y  Q  Q   N  T  P  I   G  D  G   P  V  L
1051  TCGCCGACCA CTACCAGCAG AACACCCCCA TCGGCGACGG CCCCGTGCTG
      AGCGGCTGGT GATGGTCGTC TTGTGGGGGT AGCCGCTGCC GGGGCACGAC
       L  P  D  N   H  Y  L   S  T  Q   S  A  L  S   K  D  P ·
1101  CTGCCCGACA ACCACTACCT GAGCACCCAG TCCGCCCTGA GCAAAGACCC
      GACGGGCTGT TGGTGATGGA CTCGTGGGTC AGGCGGGACT CGTTTCTGGG
       · N  E  K   R  D  H  M   V  L  L   E  F  V   T  A  A  G ·
1151  CAACGAGAAG CGCGATCACA TGGTCCTGCT GGAGTTCGTG ACCGCCGCCG
      GTTGCTCTTC GCGCTAGTGT ACCAGGACGA CCTCAAGCAC TGGCGGCGGC
                                                  HindIII
                                                  ~~~~~~~
       · I  T  L   G  M  D   E  L  Y  K   *  *
1201  GGATCACTCT CGGCATGGAC GAGCTGTACA AGTAATAAGC TT
      CCTAGTGAGA GCCGTACCTG CTCGACATGT TCATTATTCG AA
```

SUMO-Protein G
Protein G NCBI Accession# X53324

```
     NcoI
     ~~~~~~
       M  G  H   H  H  H   H  H  G  S   D  S  E   V  N  Q
  1  CCATGGGTCA TCACCATCAT CATCACGGGT CGGACTCAGA AGTCAATCAA
     GGTACCCAGT AGTGGTAGTA GTAGTGCCCA GCCTGAGTCT TCAGTTAGTT
      E  A  K  P   E  V  K   P  E  V   K  P  E  T   H  I  N ·
 51  GAAGCTAAGC CAGAGGTCAA GCCAGAAGTC AAGCCTGAGA CTCACATCAA
     CTTCGATTCG GTCTCCAGTT CGGTCTTCAG TTCGGACTCT GAGTGTAGTT
     · L  K  V   S  D  G  S   S  E  I   F  F  K   I  K  K  T ·
101  TTTAAAGGTG TCCGATGGAT CTTCAGAGAT CTTCTTCAAG ATCAAAAAGA
     AAATTTCCAC AGGCTACCTA GAAGTCTCTA GAAGAAGTTC TAGTTTTTCT
     ·  T  P  L   R  R  L   M  E  A  F   A  K  R   Q  G  K
151  CCACTCCTTT AAGAAGGCTG ATGGAAGCGT TCGCTAAAAG ACAGGGTAAG
     GGTGAGGAAA TTCTTCCGAC TACCTTCGCA AGCGATTTTC TGTCCCATTC
      E  M  D  S   L  R  F   L  Y  D   G  I  R  I   Q  A  D ·
201  GAAATGGACT CCTTAAGATT CTTGTACGAC GGTATTAGAA TTCAAGCTGA
     CTTTACCTGA GGAATTCTAA GAACATGCTG CCATAATCTT AAGTTCGACT
     · Q  T  P   E  D  L  D   M  E  D   N  D  I   I  E  A  H ·
251  TCAGACCCCT GAAGATTTGG ACATGGAGGA TAACGATATT ATTGAGGCTC
     AGTCTGGGGA CTTCTAAACC TGTACCTCCT ATTGCTATAA TAACTCCGAG
     ·  R  E  Q   I  G  G   T  P  A  V   T  T  Y   K  L  V
301  ACCGCGAACA GATTGGAGGT ACGCCGGCGG TGACCACCTA TAAACTGGTG
     TGGCGCTTGT CTAACCTCCA TGCGGCCGCC ACTGGTGGAT ATTTGACCAC
      I  N  G  K   T  L  K   G  E  T   T  T  K  A   V  D  A ·
351  ATTAACGGCA AAACCCTGAA AGGCGAAACC ACCACCAAAG CGGTGGATGC
     TAATTGCCGT TTTGGGACTT TCCGCTTTGG TGGTGGTTTC GCCACCTACG
     · E  T  A   E  K  A  F   K  Q  Y   A  N  D   N  G  V  D ·
401  GGAAACCGCG GAAAAAGCGT TTAAACAGTA TGCGAACGAT AACGGCGTGG
     CCTTTGGCGC CTTTTTCGCA AATTTGTCAT ACGCTTGCTA TTGCCGCACC
     ·  G  V  W   T  Y  D   D  A  T  K   T  F  T   V  T  E
451  ATGGCGTGTG GACCTATGAT GATGCGACCA AAACCTTTAC CGTGACCGAA
     TACCGCACAC CTGGATACTA CTACGCTGGT TTTGGAAATG GCACTGGCTT
         HindIII
         ~~~~~~~
      *  *
501  TAATAAGCTT
     ATTATTCGAA
```

Figure 34A

SUMO β-GUS

β-GUS NCBI Accession# U12640

```
      M  G  H  H   H  H  H   H  G  S   D  S  E  V   N  Q  E ·
  1  ATGGGTCATC ACCATCATCA TCACGGGTCG GACTCAGAAG TCAATCAAGA
     TACCCAGTAG TGGTAGTAGT AGTGCCCAGC CTGAGTCTTC AGTTAGTTCT
     · A  K  P   E  V  K  P   E  V  K   P  E  T   H  I  N  L ·
 51  AGCTAAGCCA GAGGTCAAGC CAGAAGTCAA GCCTGAGACT CACATCAATT
     TCGATTCGGT CTCCAGTTCG GTCTTCAGTT CGGACTCTGA GTGTAGTTAA
     ·  K  V  S   D  G  S   S  E  I  F   F  K  I   K  K  T
101  TAAAGGTGTC CGATGGATCT TCAGAGATCT TCTTCAAGAT CAAAAAGACC
     ATTTCCACAG GCTACCTAGA AGTCTCTAGA AGAAGTTCTA GTTTTTCTGG
      T  P  L  R   R  L  M   E  A  F   A  K  R  Q   G  K  E ·
151  ACTCCTTTAA GAAGGCTGAT GGAAGCGTTC GCTAAAAGAC AGGGTAAGGA
     TGAGGAAATT CTTCCGACTA CCTTCGCAAG CGATTTTCTG TCCCATTCCT
     · M  D  S   L  R  F  L   Y  D  G   I  R  I   Q  A  D  Q ·
201  AATGGACTCC TTAAGATTCT TGTACGACGG TATTAGAATT CAAGCTGATC
     TTACCTGAGG AATTCTAAGA ACATGCTGCC ATAATCTTAA GTTCGACTAG
     ·  T  P  E   D  L  D   M  E  D  N   D  I  I   E  A  H
251  AGACCCCTGA AGATTTGGAC ATGGAGGATA ACGATATTAT TGAGGCTCAC
     TCTGGGGACT TCTAAACCTG TACCTCCTAT TGCTATAATA ACTCCGAGTG
      R  E  Q  I   G  G  M   E  F  M   L  R  P  V   E  T  P ·
301  CGCGAACAGA TTGGAGGTAT GGAATTCATG TTACGTCCTG TAGAAACCCC
     GCGCTTGTCT AACCTCCATA CCTTAAGTAC AATGCAGGAC ATCTTTGGGG
     · T  R  E   I  K  K  L   D  G  L   W  A  F   S  L  D  R ·
351  AACCCGTGAA ATCAAAAAAC TCGACGGCCT GTGGGCATTC AGTCTGGATC
     TTGGGCACTT TAGTTTTTTG AGCTGCCGGA CACCCGTAAG TCAGACCTAG
     ·  E  N  C   G  I  D   Q  R  W  W   E  S  A   L  Q  E
401  GCGAAAACTG TGGAATTGAT CAGCGTTGGT GGGAAAGCGC GTTACAAGAA
     CGCTTTTGAC ACCTTAACTA GTCGCAACCA CCCTTTCGCG CAATGTTCTT
      S  R  A  I   A  V  P   G  S  F   N  D  Q  F   A  D  A ·
451  AGCCGGGCAA TTGCTGTGCC AGGCAGTTTT AACGATCAGT TCGCCGATGC
     TCGGCCCGTT AACGACACGG TCCGTCAAAA TTGCTAGTCA AGCGGCTACG
     · D  I  R   N  Y  A  G   N  V  W   Y  Q  R   E  V  F  I ·
501  AGATATTCGT AATTATGCGG GCAACGTCTG GTATCAGCGC GAAGTCTTTA
     TCTATAAGCA TTAATACGCC CGTTGCAGAC CATAGTCGCG CTTCAGAAAT
     ·  P  K  G   W  A  G   Q  R  I  V   L  R  F   D  A  V
551  TACCGAAAGG TTGGGCAGGC CAGCGTATCG TGCTGCGTTT CGATGCGGTC
     ATGGCTTTCC AACCCGTCCG GTCGCATAGC ACGACGCAAA GCTACGCCAG
      T  H  Y  G   K  V  W   V  N  N   Q  E  V  M   E  H  Q ·
601  ACTCATTACG GCAAAGTGTG GGTCAATAAT CAGGAAGTGA TGGAGCATCA
     TGAGTAATGC CGTTTCACAC CCAGTTATTA GTCCTTCACT ACCTCGTAGT
     · G  G  Y   T  P  F  E   A  D  V   T  P  Y   V  I  A  G ·
651  GGGCGGCTAT ACGCCATTTG AAGCCGATGT CACGCCGTAT GTTATTGCCG
     CCCGCCGATA TGCGGTAAAC TTCGGCTACA GTGCGGCATA CAATAACGGC
     ·  K  S  V   R  I  T   V  C  V  N   N  E  L   N  W  Q
```

Figure 34B

```
 701 GGAAAAGTGT ACGTATCACC GTTTGTGTGA ACAACGAACT GAACTGGCAG
     CCTTTTCACA TGCATAGTGG CAAACACACT TGTTGCTTGA CTTGACCGTC
      T  I  P  P   G  M  V   I  T  D   E  N  G  K   K  K  Q ·
 751 ACTATCCCGC CGGGAATGGT GATTACCGAC GAAAACGGCA AGAAAAAGCA
     TGATAGGGCG GCCCTTACCA CTAATGGCTG CTTTTGCCGT TCTTTTTCGT
     · S  Y  F   H  D  F  F   N  Y  A   G  I  H   R  S  V  M ·
 801 GTCTTACTTC CATGATTTCT TTAACTATGC CGGAATCCAT CGCAGCGTAA
     CAGAATGAAG GTACTAAAGA AATTGATACG GCCTTAGGTA GCGTCGCATT
     ·  L  Y  T   T  P  N   T  W  V  D   D  I  T   V  V  T
 851 TGCTCTACAC CACGCCGAAC ACCTGGGTGG ACGATATCAC CGTGGTGACG
     ACGAGATGTG GTGCGGCTTG TGGACCCACC TGCTATAGTG GCACCACTGC
      H  V  A  Q   D  C  N   H  A  S   V  D  W  Q   V  V  A ·
 901 CATGTCGCGC AAGACTGTAA CCACGCGTCT GTTGACTGGC AGGTGGTGGC
     GTACAGCGCG TTCTGACATT GGTGCGCAGA CAACTGACCG TCCACCACCG
     · N  G  D   V  S  V  E   L  R  D   A  D  Q   Q  V  V  A ·
 951 CAATGGTGAT GTCAGCGTTG AACTGCGTGA TGCGGATCAA CAGGTGGTTG
     GTTACCACTA CAGTCGCAAC TTGACGCACT ACGCCTAGTT GTCCACCAAC
     ·  T  G  Q   G  T  S   G  T  L  Q   V  V  N   P  H  L
1001 CAACTGGACA AGGCACTAGC GGGACTTTGC AAGTGGTGAA TCCGCACCTC
     GTTGACCTGT TCCGTGATCG CCCTGAAACG TTCACCACTT AGGCGTGGAG
      W  Q  P  G   E  G  Y   L  Y  E   L  C  V  T   A  K  S ·
1051 TGGCAACCGG GTGAAGGTTA TCTCTATGAA CTGTGCGTCA CAGCCAAAAG
     ACCGTTGGCC CACTTCCAAT AGAGATACTT GACACGCAGT GTCGGTTTTC
     · Q  T  E   C  D  I  Y   P  L  R   V  G  I   R  S  V  A ·
1101 CCAGACAGAG TGTGATATCT ACCCGCTTCG CGTCGGCATC CGGTCAGTGG
     GGTCTGTCTC ACACTATAGA TGGGCGAAGC GCAGCCGTAG GCCAGTCACC
     ·  V  K  G   Q  Q  F   L  I  N  H   K  P  F   Y  F  T
1151 CAGTGAAGGG CCAACAGTTC CTGATTAACC ACAAACCGTT CTACTTTACT
     GTCACTTCCC GGTTGTCAAG GACTAATTGG TGTTTGGCAA GATGAAATGA
      G  F  G  R   H  E  D   A  D  L   R  G  K  G   F  D  N ·
1201 GGCTTTGGTC GTCATGAAGA TGCGGACTTA CGTGGCAAAG GATTCGATAA
     CCGAAACCAG CAGTACTTCT ACGCCTGAAT GCACCGTTTC CTAAGCTATT
     · V  L  M   V  H  D  H   A  L  M   D  W  I   G  A  N  S ·
1251 CGTGCTGATG GTGCACGACC ACGCATTAAT GGACTGGATT GGGGCCAACT
     GCACGACTAC CACGTGCTGG TGCGTAATTA CCTGACCTAA CCCCGGTTGA
     ·  Y  R  T   S  H  Y   P  Y  A  E   E  M  L   D  W  A
1301 CCTACCGTAC CTCGCATTAC CCTTACGCTG AAGAGATGCT CGACTGGGCA
     GGATGGCATG GAGCGTAATG GGAATGCGAC TTCTCTACGA GCTGACCCGT
      D  E  H  G   I  V  V   I  D  E   T  A  A  V   G  F  N ·
1351 GATGAACATG GCATCGTGGT GATTGATGAA ACTGCTGCTG TCGGCTTTAA
     CTACTTGTAC CGTAGCACCA CTAACTACTT TGACGACGAC AGCCGAAATT
     · L  S  L   G  I  G  F   E  A  G   N  K  P   K  E  L  Y ·
1401 CCTCTCTTTA GGCATTGGTT TCGAAGCGGG CAACAAGCCG AAAGAACTGT
     GGAGAGAAAT CCGTAACCAA AGCTTCGCCC GTTGTTCGGC TTTCTTGACA
     ·  S  E  E   A  V  N   G  E  T  Q   Q  A  H   L  Q  A
1451 ACAGCGAAGA GGCAGTCAAC GGGGAAACTC AGCAAGCGCA CTTACAGGCG
     TGTCGCTTCT CCGTCAGTTG CCCCTTTGAG TCGTTCGCGT GAATGTCCGC
      I  K  E  L   I  A  R   D  K  N   H  P  S  V   V  M  W ·
1501 ATTAAAGAGC TGATAGCGCG TGACAAAAAC CACCCAAGCG TGGTGATGTG
     TAATTTCTCG ACTATCGCGC ACTGTTTTTG GTGGGTTCGC ACCACTACAC
     · S  I  A   N  E  P  D   T  R  P   Q  V  H   G  N  I  S ·
1551 GAGTATTGCC AACGAACCGG ATACCCGTCC GCAAGTGCAC GGGAATATTT
```

```
      CTCATAACGG TTGCTTGGCC TATGGGCAGG CGTTCACGTG CCCTTATAAA
      · P L A   E A T   R K L   D  P T R   P I T
1601  CGCCACTGGC GGAAGCAACG CGTAAACTCG ACCCGACGCG TCCGATCACC
      GCGGTGACCG CCTTCGTTGC GCATTTGAGC TGGGCTGCGC AGGCTAGTGG

       C V N V   M F C   D A H   T D T I   S D L ·
1651  TGCGTCAATG TAATGTTCTG CGACGCTCAC ACCGATACCA TCAGCGATCT
      ACGCAGTTAC ATTACAAGAC GCTGCGAGTG TGGCTATGGT AGTCGCTAGA
      · F D V   L C L N   R Y Y   G W Y   V Q S G ·
1701  CTTTGATGTG CTGTGCCTGA ACCGTTATTA CGGATGGTAT GTCCAAAGCG
      GAAACTACAC GACACGGACT TGGCAATAAT GCCTACCATA CAGGTTTCGC
      · D L E   T A E   K V L E   K E L   L A W
1751  GCGATTTGGA AACGGCAGAG AAGGTACTGG AAAAAGAACT TCTGGCCTGG
      CGCTAAACCT TTGCCGTCTC TTCCATGACC TTTTTCTTGA AGACCGGACC
       Q E K L   H Q P   I I I   T E Y G   V D T ·
1801  CAGGAGAAAC TGCATCAGCC GATTATCATC ACCGAATACG GCGTGGATAC
      GTCCTCTTTG ACGTAGTCGG CTAATAGTAG TGGCTTATGC CGCACCTATG
      · L A G   L H S M   Y T D   M W S   E E Y Q ·
1851  GTTAGCCGGG CTGCACTCAA TGTACACCGA CATGTGGAGT GAAGAGTATC
      CAATCGGCCC GACGTGAGTT ACATGTGGCT GTACACCTCA CTTCTCATAG
      · C A W   L D M   Y H R V   F D R   V S A
1901  AGTGTGCATG GCTGGATATG TATCACCGCG TCTTTGATCG CGTCAGCGCC
      TCACACGTAC CGACCTATAC ATAGTGGCGC AGAAACTAGC GCAGTCGCGG
       V V G E   Q V W   N F A   D F A T   S Q G ·
1951  GTCGTCGGTG AACAGGTATG GAATTTCGCC GATTTTGCGA CCTCGCAAGG
      CAGCAGCCAC TTGTCCATAC CTTAAAGCGG CTAAAACGCT GGAGCGTTCC
      · I L R   V G G N   K K G   I F T   R D R K ·
2001  CATATTGCGC GTTGGCGGTA ACAAGAAAGG GATCTTCACT CGCGACCGCA
      GTATAACGCG CAACCGCCAT TGTTCTTTCC CTAGAAGTGA GCGCTGGCGT
      · P K S   A A F   L L Q K   R W T   G M N
2051  AACCGAAGTC GGCGGCTTTT CTGCTGCAAA AACGCTGGAC TGGCATGAAC
      TTGGCTTCAG CCGCCGAAAA GACGACGTTT TTGCGACCTG ACCGTACTTG
       F G E K   P Q Q   G G K   Q
2101  TTCGGTGAAA AACCGCAGCA GGGAGGCAAA CAA
      AAGCCACTTT TTGGCGTCGT CCCTCCGTTT GTT
```

SUMO-Liver X Receptor α
Liver X Receptor A NCBI Accession# NM_005693

G H H H H H H G S D S E V N Q E ·
1 ATGGGTCATC ACCATCATCA TCACGGGTCG GACTCAGAAG TCAATCAAGA
TACCCAGTAG TGGTAGTAGT AGTGCCCAGC CTGAGTCTTC AGTTAGTTCT
· A K P E V K P E V K P E T H I N L ·
51 AGCTAAGCCA GAGGTCAAGC CAGAAGTCAA GCCTGAGACT CACATCAATT
TCGATTCGGT CTCCAGTTCG GTCTTCAGTT CGGACTCTGA GTGTAGTTAA
· K V S D G S S E I F F K I K K T
101 TAAAGGTGTC CGATGGATCT TCAGAGATCT TCTTCAAGAT CAAAAAGACC
ATTTCCACAG GCTACCTAGA AGTCTCTAGA AGAAGTTCTA GTTTTTCTGG
T P L R R L M E A F A K R Q G K E ·
151 ACTCCTTTAA GAAGGCTGAT GGAAGCGTTC GCTAAAAGAC AGGGTAAGGA
TGAGGAAATT CTTCCGACTA CCTTCGCAAG CGATTTTCTG TCCCATTCCT
· M D S L R F L Y D G I R I Q A D Q ·
201 AATGGACTCC TTAAGATTCT TGTACGACGG TATTAGAATT CAAGCTGATC
TTACCTGAGG AATTCTAAGA ACATGCTGCC ATAATCTTAA GTTCGACTAG
· T P E D L D M E D N D I I E A H
251 AGACCCCTGA AGATTTGGAC ATGGAGGATA ACGATATTAT TGAGGCTCAC
TCTGGGGACT TCTAAACCTG TACCTCCTAT TGCTATAATA ACTCCGAGTG
R E Q I G G M S L W L G A P V P D ·
301 CGCGAACAGA TTGGAGGTAT GTCCTTGTGG CTGGGGGCCC CTGTGCCTGA
GCGCTTGTCT AACCTCCATA CAGGAACACC GACCCCCGGG GACACGGACT
· I P P D S A V E L W K P G A Q D A ·
351 CATTCCTCCT GACTCTGCGG TGGAGCTGTG GAAGCCAGGC GCACAGGATG
GTAAGGAGGA CTGAGACGCC ACCTCGACAC CTTCGGTCCG CGTGTCCTAC
· S S Q A Q G G S S C I L R E E A
401 CAAGCAGCCA GGCCCAGGGA GGCAGCAGCT GCATCCTCAG AGAGGAAGCC
GTTCGTCGGT CCGGGTCCCT CCGTCGTCGA CGTAGGAGTC TCTCCTTCGG
R M P H S A G G T A G V G L E A A ·
451 AGGATGCCCC ACTCTGCTGG GGGTACTGCA GGGGTGGGGC TGGAGGCTGC
TCCTACGGGG TGAGACGACC CCCATGACGT CCCCACCCCG ACCTCCGACG
· E P T A L L T R A E P P S E P T E ·
501 AGAGCCCACA GCCCTGCTCA CCAGGGCAGA GCCCCCTTCA GAACCCACAG
TCTCGGGTGT CGGGACGAGT GGTCCCGTCT CGGGGGAAGT CTTGGGTGTC
· I R P Q K R K K G P A P K M L G
551 AGATCCGTCC ACAAAAGCGG AAAAAGGGGC CAGCCCCCAA AATGCTGGGG
TCTAGGCAGG TGTTTTCGCC TTTTTCCCCG GTCGGGGGTT TTACGACCCC
N E L C S V C G D K A S G F H Y N ·
601 AACGAGCTAT GCAGCGTGTG TGGGGACAAG GCCTCGGGCT TCCACTACAA
TTGCTCGATA CGTCGCACAC ACCCCTGTTC CGGAGCCCGA AGGTGATGTT
· V L S C E G C K G F F R R S V I K ·
651 TGTTCTGAGC TGCGAGGGCT GCAAGGGATT CTTCCGCCGC AGCGTCATCA
ACAAGACTCG ACGCTCCCGA CGTTCCCTAA GAAGGCGGCG TCGCAGTAGT
· G A H Y I C H S G G H C P M D T
701 AGGGAGCGCA CTACATCTGC CACAGTGGCG GCCACTGCCC CATGGACACC

Figure 35B

```
     TCCCTCGCGT GATGTAGACG GTGTCACCGC CGGTGACGGG GTACCTGTGG
      Y  M  R  R  K  C  Q  E  C  R  L  R  K  C  R  Q  A ·
751  TACATGCGTC GCAAGTGCCA GGAGTGTCGG CTTCGCAAAT GCCGTCAGGC
     ATGTACGCAG CGTTCACGGT CCTCACAGCC GAAGCGTTTA CGGCAGTCCG
     · G  M  R  E  E  C  V  L  S  E  E  Q  I  R  L  K  K ·
801  TGGCATGCGG GAGGAGTGTG TCCTGTCAGA AGAACAGATC CGCCTGAAGA
     ACCGTACGCC CTCCTCACAC AGGACAGTCT TCTTGTCTAG GCGGACTTCT
     · L  K  R  Q  E  E  E  Q  A  H  A  T  S  L  P  P
851  AACTGAAGCG GCAAGAGGAG GAACAGGCTC ATGCCACATC CTTGCCCCCC
     TTGACTTCGC CGTTCTCCTC CTTGTCCGAG TACGGTGTAG GAACGGGGGG
      R  R  S  S  P  P  Q  I  L  P  Q  L  S  P  E  Q  L ·
901  AGGCGTTCCT CACCCCCCCA AATCCTGCCC CAGCTCAGCC CGGAACAACT
     TCCGCAAGGA GTGGGGGGGT TTAGGACGGG GTCGAGTCGG GCCTTGTTGA
     · G  M  I  E  K  L  V  A  A  Q  Q  Q  C  N  R  R  S ·
951  GGGCATGATC GAGAAGCTCG TCGCTGCCCA GCAACAGTGT AACCGGCGCT
     CCCGTACTAG CTCTTCGAGC AGCGACGGGT CGTTGTCACA TTGGCCGCGA
     · F  S  D  R  L  R  V  T  P  W  P  M  A  P  D  P
1001 CCTTTTCTGA CCGGCTTCGA GTCACGCCTT GGCCCATGGC ACCAGATCCC
     GGAAAAGACT GGCCGAAGCT CAGTGCGGAA CCGGGTACCG TGGTCTAGGG
      H  S  R  E  A  R  Q  Q  R  F  A  H  F  T  E  L  A ·
1051 CATAGCCGGG AGGCCCGTCA GCAGCGCTTT GCCCACTTCA CTGAGCTGGC
     GTATCGGCCC TCCGGGCAGT CGTCGCGAAA CGGGTGAAGT GACTCGACCG
     · I  V  S  V  Q  E  I  V  D  F  A  K  Q  L  P  G  F ·
1101 CATCGTCTCT GTGCAGGAGA TAGTTGACTT TGCTAAACAG CTACCCGGCT
     GTAGCAGAGA CACGTCCTCT ATCAACTGAA ACGATTTGTC GATGGGCCGA

· L  Q  L  S  R  E  D  Q  I  A  L  L  K  T  S  A
1151 TCCTGCAGCT CAGCCGGGAG GACCAGATTG CCCTGCTGAA GACCTCTGCG
     AGGACGTCGA GTCGGCCCTC CTGGTCTAAC GGGACGACTT CTGGAGACGC
      I  E  V  M  L  L  E  T  S  R  R  Y  N  P  G  S  E ·
1201 ATCGAGGTGA TGCTTCTGGA GACATCTCGG AGGTACAACC CTGGGAGTGA
     TAGCTCCACT ACGAAGACCT CTGTAGAGCC TCCATGTTGG GACCCTCACT
     · S  I  T  F  L  K  D  F  S  Y  N  R  E  D  F  A  K ·
1251 GAGTATCACC TTCCTCAAGG ATTTCAGTTA TAACCGGGAA GACTTTGCCA
     CTCATAGTGG AAGGAGTTCC TAAAGTCAAT ATTGGCCCTT CTGAAACGGT
     · A  G  L  Q  V  E  F  I  N  P  I  F  E  F  S  R
1301 AAGCAGGGCT GCAAGTGGAA TTCATCAACC CCATCTTCGA GTTCTCCAGG
     TTCGTCCCGA CGTTCACCTT AAGTAGTTGG GGTAGAAGCT CAAGAGGTCC
      A  M  N  E  L  Q  L  N  D  A  E  F  A  L  L  I  A ·
1351 GCCATGAATG AGCTGCAACT CAATGATGCC GAGTTTGCCT TGCTCATTGC
     CGGTACTTAC TCGACGTTGA GTTACTACGG CTCAAACGGA ACGAGTAACG
     · I  S  I  F  S  A  D  R  P  N  V  Q  D  Q  L  Q  V ·
1401 TATCAGCATC TTCTCTGCAG ACCGGCCCAA CGTGCAGGAC CAGCTCCAGG
     ATAGTCGTAG AAGAGACGTC TGGCCGGGTT GCACGTCCTG GTCGAGGTCC
     · E  R  L  Q  H  T  Y  V  E  A  L  H  A  Y  V  S
1451 TGGAGAGGCT GCAGCACACA TATGTGGAAG CCCTGCATGC CTACGTCTCC
     ACCTCTCCGA CGTCGTGTGT ATACACCTTC GGGACGTACG GATGCAGAGG
      I  H  H  P  H  D  R  L  M  F  P  R  M  L  M  K  L ·
1501 ATCCACCATC CCCATGACCG ACTGATGTTC CCACGGATGC TAATGAAACT
     TAGGTGGTAG GGGTACTGGC TGACTACAAG GGTGCCTACG ATTACTTTGA
     · V  S  L  R  T  L  S  S  V  H  S  E  Q  V  F  A  L ·
1551 GGTGAGCCTC CGCACCCTGA GCAGCGTCCA CTCAGAGCAA GTGTTTGCAC
```

```
      CCACTCGGAG GCCTGGGACT CGTCGCAGGT GAGTCTCGTT CACAAACGTG
      ·  R  L  Q   D  K  K   L  P  P  L   L  S  E   I  W  D
1601  TGCGTCTGCA GGACAAAAAG CTCCCACCGC TGCTCTCTGA GATCTGGGAT
      ACGCAGACGT CCTGTTTTTC GAGGGTGGCG ACGAGAGACT CTAGACCCTA
       V  H  E  *
1651  GTGCACGAAT GA
      CACGTGCTTA CT
```

SUMO Tyrosine Kinase
Tyrosin Kinase NCBI Accession# BC039039

```
     M  G  H  H   H  H  H   H  G  S   D  S  E  V   N  Q  E ·
  1  ATGGGTCATC ACCATCATCA TCACGGGTCG GACTCAGAAG TCAATCAAGA
     TACCCAGTAG TGGTAGTAGT AGTGCCCAGC CTGAGTCTTC AGTTAGTTCT
     · A  K  P   E  V  K  P   E  V  K   P  E  T   H  I  N  L ·
 51  AGCTAAGCCA GAGGTCAAGC CAGAAGTCAA GCCTGAGACT CACATCAATT
     TCGATTCGGT CTCCAGTTCG GTCTTCAGTT CGGACTCTGA GTGTAGTTAA
     · K  V  S   D  G  S   S  E  I  F   F  K  I   K  K  T
101  TAAAGGTGTC CGATGGATCT TCAGAGATCT TCTTCAAGAT CAAAAAGACC
     ATTTCCACAG GCTACCTAGA AGTCTCTAGA AGAAGTTCTA GTTTTTCTGG
     T  P  L  R   R  L  M   E  A  F   A  K  R  Q   G  K  E ·
151  ACTCCTTTAA GAAGGCTGAT GGAAGCGTTC GCTAAAAGAC AGGGTAAGGA
     TGAGGAAATT CTTCCGACTA CCTTCGCAAG CGATTTTCTG TCCCATTCCT
     · M  D  S   L  R  F  L   Y  D  G   I  R  I   Q  A  D  Q ·
201  AATGGACTCC TTAAGATTCT TGTACGACGG TATTAGAATT CAAGCTGATC
     TTACCTGAGG AATTCTAAGA ACATGCTGCC ATAATCTTAA GTTCGACTAG
     · T  P  E   D  L  D   M  E  D  N   D  I  I   E  A  H
251  AGACCCCTGA AGATTTGGAC ATGGAGGATA ACGATATTAT TGAGGCTCAC
     TCTGGGGACT TCTAAACCTG TACCTCCTAT TGCTATAATA ACTCCGAGTG
     R  E  Q  I   G  G  M   C  P  N   S  S  A  S   N  A  S ·
301  CGCGAACAGA TTGGAGGTAT GTGCCCCAAC AGCAGTGCCA GCAACGCCTC
     GCGCTTGTCT AACCTCCATA CACGGGGTTG TCGTCACGGT CGTTGCGGAG
     · G  A  A   A  P  T  L   P  A  H   P  S  T   L  T  H  P ·
351  AGGGGCTGCT GCTCCCACAC TCCCAGCCCA CCCATCCACG TTGACTCATC
     TCCCCGACGA CGAGGGTGTG AGGGTCGGGT GGGTAGGTGC AACTGAGTAG
     · Q  R  R   I  D  T   L  N  S  D   G  Y  T   P  E  P
401  CTCAGAGACG AATCGACACC CTCAACTCAG ATGGATACAC CCCTGAGCCA
     GAGTCTCTGC TTAGCTGTGG GAGTTGAGTC TACCTATGTG GGGACTCGGT
     A  R  I  T   S  P  D   K  P  R   P  M  P  M   D  T  S ·
451  GCACGCATAA CGTCCCCAGA CAAACCGCGG CCGATGCCCA TGGACACGAG
     CGTGCGTATT GCAGGGGTCT GTTTGGCGCC GGCTACGGGT ACCTGTGCTC
     · V  Y  E   S  P  Y  S   D  P  E   E  L  K   D  K  K  L ·
501  CGTGTATGAG AGCCCCTACA GCGACCCAGA GGAGCTCAAG GACAAGAAGC
     GCACATACTC TCGGGGATGT CGCTGGGTCT CCTCGAGTTC CTGTTCTTCG
     · F  L  K   R  D  N   L  L  I  A   D  I  E   L  G  C
551  TCTTCCTGAA GCGCGATAAC CTCCTCATAG CTGACATTGA ACTTGGCTGC
     AGAAGGACTT CGCGCTATTG GAGGAGTATC GACTGTAACT TGAACCGACG
     G  N  F  G   S  V  R   Q  G  V   Y  R  M  R   K  K  Q ·
601  GGCAACTTTG GCTCAGTGCG CCAGGGCGTG TACCGCATGC GCAAGAAGCA
     CCGTTGAAAC CGAGTCACGC GGTCCCGCAC ATGGCGTACG CGTTCTTCGT
     · I  D  V   A  I  K  V   L  K  Q   G  T  E   K  A  D  T ·
651  GATCGACGTG GCCATCAAGG TGCTGAAGCA GGGCACGGAG AAGGCAGACA
     CTAGCTGCAC CGGTAGTTCC ACGACTTCGT CCCGTGCCTC TTCCGTCTGT
     · E  E  M   M  R  E   A  Q  I  M   H  Q  L   D  N  P
701  CGGAAGAGAT GATGCGCGAG GCGCAGATCA TGCACCAGCT GGACAACCCC
     GCCTTCTCTA CTACGCGCTC CGCGTCTAGT ACGTGGTCGA CCTGTTGGGG
     Y  I  V  R   L  I  G   V  C  Q   A  E  A  L   M  L  V ·
751  TACATCGTGC GGCTCATTGG CGTCTGCCAG GCCGAGGCCC TCATGCTGGT
```

```
     ATGTAGCACG CCGAGTAACC GCAGACGGTC CGGCTCCGGG AGTACGACCA
     ·M  E  M   A  G  G  G   P  L  H   K  F  L   V  G  K  R·
801  CATGGAGATG GCTGGGGGCG GGCCGCTGCA CAAGTTCCTG GTCGGCAAGA
     GTACCTCTAC CGACCCCCGC CCGGCGACGT GTTCAAGGAC CAGCCGTTCT
     · E  E  I   P  V  S   N  V  A  E   L  L  H   Q  V  S
851  GGGAGGAGAT CCCTGTGAGC AATGTGGCCG AGCTGCTGCA CCAGGTGTCC
     CCCTCCTCTA GGGACACTCG TTACACCGGC TCGACGACGT GGTCCACAGG
      M  G  M  K   Y  L  E   E  K  N   F  V  H  R   D  L  A·
901  ATGGGGATGA AGTACCTGGA GGAGAAGAAC TTTGTGCACC GTGACCTGGC
     TACCCCTACT TCATGGACCT CCTCTTCTTG AAACACGTGG CACTGGACCG
     ·A  R  N   V  L  L  V   N  R  H   Y  A  K   I  S  D  F·
951  GGCCCGCAAC GTCCTGCTGG TTAACCGGCA CTACGCCAAG ATCAGCGACT
     CCGGGCGTTG CAGGACGACC AATTGGCCGT GATGCGGTTC TAGTCGCTGA
     · G  L  S   K  A  L   G  A  D  D   S  Y  Y   T  A  R
1001 TTGGCCTCTC CAAAGCACTG GGTGCCGACG ACAGCTACTA CACTGCCCGC
     AACCGGAGAG GTTTCGTGAC CCACGGCTGC TGTCGATGAT GTGACGGGCG
      S  A  G  K   W  P  L   K  W  Y   A  P  E  C   I  N  F·
1051 TCAGCAGGGA AGTGGCCGCT CAAGTGGTAC GCACCCGAAT GCATCAACTT
     AGTCGTCCCT TCACCGGCGA GTTCACCATG CGTGGGCTTA CGTAGTTGAA

     ·R  K  F   S  S  R  S   D  V  W   S  Y  G   V  T  M  W·
1101 CCGCAAGTTC TCCAGCCGCA GCGATGTCTG GAGCTATGGG GTCACCATGT
     GGCGTTCAAG AGGTCGGCGT CGCTACAGAC CTCGATACCC CAGTGGTACA
     · E  A  L   S  Y  G   Q  K  P  Y   K  K  M   K  G  P
1151 GGGAGGCCTT GTCCTACGGC CAGAAGCCCT ACAAGAAGAT GAAAGGGCCG
     CCCTCCGGAA CAGGATGCCG GTCTTCGGGA TGTTCTTCTA CTTTCCCGGC
      E  V  M  A   F  I  E   Q  G  K   R  M  E  C   P  P  E·
1201 GAGGTCATGG CCTTCATCGA GCAGGGCAAG CGGATGGAGT GCCCACCAGA
     CTCCAGTACC GGAAGTAGCT CGTCCCGTTC GCCTACCTCA CGGGTGGTCT
     ·C  P  P   E  L  Y  A   L  M  S   D  C  W   I  Y  K  W·
1251 GTGTCCACCC GAACTGTACG CACTCATGAG TGACTGCTGG ATCTACAAGT
     CACAGGTGGG CTTGACATGC GTGAGTACTC ACTGACGACC TAGATGTTCA
     · E  D  R   P  D  F   L  T  V  E   Q  R  M   R  A  C
1301 GGGAGGATCG CCCCGACTTC CTGACCGTGG AGCAGCGCAT GCGAGCCTGT
     CCCTCCTAGC GGGGCTGAAG GACTGGCACC TCGTCGCGTA CGCTCGGACA
      Y  Y  S  L   A  S  K   V  E  G   P  P  G  S   T  Q  K·
1351 TACTACAGCC TGGCCAGCAA GGTGGAAGGG CCCCCAGGCA GCACACAGAA
     ATGATGTCGG ACCGGTCGTT CCACCTTCCC GGGGGTCCGT CGTGTGTCTT
     ·A  E  A   A  C  A  *
1401 GGCTGAGGCT GCCTGTGCCT GA
     CCGACTCCGA CGGACACGGA CT
```

SUMO MAPKAPK2 Kinase

MAPKAPK2 Kinase NCBI Accession# BC036060

```
     M  G  H  H   H  H  H   H  G  S   D  S  E  V   N  Q  E ·
  1  ATGGGTCATC ACCATCATCA TCACGGGTCG GACTCAGAAG TCAATCAAGA
     TACCCAGTAG TGGTAGTAGT AGTGCCCAGC CTGAGTCTTC AGTTAGTTCT
     · A  K  P   E  V  K  P   E  V  K   P  E  T   H  I  N  L ·
 51  AGCTAAGCCA GAGGTCAAGC CAGAAGTCAA GCCTGAGACT CACATCAATT
     TCGATTCGGT CTCCAGTTCG GTCTTCAGTT CGGACTCTGA GTGTAGTTAA
     · K  V  S   D  G  S   S  E  I  F   F  K  I   K  K  T
101  TAAAGGTGTC CGATGGATCT TCAGAGATCT TCTTCAAGAT CAAAAAGACC
     ATTTCCACAG GCTACCTAGA AGTCTCTAGA AGAAGTTCTA GTTTTTCTGG
     T  P  L  R   R  L  M   E  A  F   A  K  R  Q   G  K  E ·
151  ACTCCTTTAA GAAGGCTGAT GGAAGCGTTC GCTAAAAGAC AGGGTAAGGA
     TGAGGAAATT CTTCCGACTA CCTTCGCAAG CGATTTTCTG TCCCATTCCT
     · M  D  S   L  R  F  L   Y  D  G   I  R  I   Q  A  D  Q ·
201  AATGGACTCC TTAAGATTCT TGTACGACGG TATTAGAATT CAAGCTGATC
     TTACCTGAGG AATTCTAAGA ACATGCTGCC ATAATCTTAA GTTCGACTAG
     · T  P  E   D  L  D   M  E  D  N   D  I  I   E  A  H
251  AGACCCCTGA AGATTTGGAC ATGGAGGATA ACGATATTAT TGAGGCTCAC
     TCTGGGGACT TCTAAACCTG TACCTCCTAT TGCTATAATA ACTCCGAGTG
     R  E  Q  I   G  G  M   Q  F  H   V  K  S  G   L  Q  I ·
301  CGCGAACAGA TTGGAGGTAT GCAGTTCCAC GTCAAGTCCG GCCTGCAGAT
     GCGCTTGTCT AACCTCCATA CGTCAAGGTG CAGTTCAGGC CGGACGTCTA
     · K  K  N   A  I  I  D   D  Y  K   V  T  S   Q  V  L  G ·
351  CAAGAAGAAC GCCATCATCG ATGACTACAA GGTCACCAGC CAGGTCCTGG
     GTTCTTCTTG CGGTAGTAGC TACTGATGTT CCAGTGGTCG GTCCAGGACC
     · L  G  I   N  G  K   V  L  Q  I   F  N  K   R  T  Q
401  GGCTGGGCAT CAACGGCAAA GTTTTGCAGA TCTTCAACAA GAGGACCCAG
     CCGACCCGTA GTTGCCGTTT CAAAACGTCT AGAAGTTGTT CTCCTGGGTC
     E  K  F  A   L  K  M   L  Q  D   C  P  K  A   R  R  E ·
451  GAGAAATTCG CCCTCAAAAT GCTTCAGGAC TGCCCCAAGG CCCGCAGGGA
     CTCTTTAAGC GGGAGTTTTA CGAAGTCCTG ACGGGGTTCC GGGCGTCCCT
     · V  E  L   H  W  R  A   S  Q  C   P  H  I   V  R  I  V ·
501  GGTGGAGCTG CACTGGCGGG CCTCCCAGTG CCCGCACATC GTACGGATCG
     CCACCTCGAC GTGACCGCCC GGAGGGTCAC GGGCGTGTAG CATGCCTAGC
     · D  V  Y   E  N  L   Y  A  G  R   K  C  L   L  I  V
551  TGGATGTGTA CGAGAATCTG TACGCAGGGA GGAAGTGCCT GCTGATTGTC
     ACCTACACAT GCTCTTAGAC ATGCGTCCCT CCTTCACGGA CGACTAACAG
     M  E  C  L   D  G  G   E  L  F   S  R  I  Q   D  R  G ·
601  ATGGAATGTT TGGACGGTGG AGAACTCTTT AGCCGAATCC AGGATCGAGG
     TACCTTACAA ACCTGCCACC TCTTGAGAAA TCGGCTTAGG TCCTAGCTCC
     · D  Q  A   F  T  E  R   E  A  S   E  I  M   K  S  I  G ·
651  AGACCAGGCA TTCACAGAAA GAGAAGCATC CGAAATCATG AAGAGCATCG
     TCTGGTCCGT AAGTGTCTTT CTCTTCGTAG GCTTTAGTAC TTCTCGTAGC
     · E  A  I   Q  Y  L   H  S  I  N   I  A  H   R  D  V
701  GTGAGGCCAT CCAGTATCTG CATTCAATCA ACATTGCCCA TCGGGATGTC
     CACTCCGGTA GGTCATAGAC GTAAGTTAGT TGTAACGGGT AGCCCTACAG
     K  P  E  N   L  L  Y   T  S  K   R  P  N  A   I  L  K ·
```

```
751  AAGCCTGAGA ATCTCTTATA CACCTCCAAA AGGCCCAACG CCATCCTGAA
     TTCGGACTCT TAGAGAATAT GTGGAGGTTT TCCGGGTTGC GGTAGGACTT
     ·L  T  D   F  G  F  A   K  E  T   T  S  H   N  S  L  T·
801  ACTCACTGAC TTTGGCTTTG CCAAGGAAAC CACCAGCCAC AACTCTTTGA
     TGAGTGACTG AAACCGAAAC GGTTCCTTTG GTGGTCGGTG TTGAGAAACT
     ·  T  P  C   Y  T  P   Y  Y  V  A   P  E  V   L  G  P
851  CCACTCCTTG TTATACACCG TACTATGTGG CTCCAGAAGT GCTGGGTCCA
     GGTGAGGAAC AATATGTGGC ATGATACACC GAGGTCTTCA CGACCCAGGT
      E  K  Y  D   K  S  C   D  M  W   S  L  G  V   I  M  Y·
901  GAGAAGTATG ACAAGTCCTG TGACATGTGG TCCCTGGGTG TCATCATGTA
     CTCTTCATAC TGTTCAGGAC ACTGTACACC AGGGACCCAC AGTAGTACAT
     ·I  L  L   C  G  Y  P   P  F  Y   S  N  H   G  L  A  I·
951  CATCCTGCTG TGTGGGTATC CCCCCTTCTA CTCCAACCAC GGCCTTGCCA
     GTAGGACGAC ACACCCATAG GGGGGAAGAT GAGGTTGGTG CCGGAACGGT
     ·  S  P  G   M  K  T   R  I  R  M   G  Q  Y   E  F  P
1001 TCTCTCCGGG CATGAAGACT CGCATCCGAA TGGGCCAGTA TGAATTTCCC
     AGAGAGGCCC GTACTTCTGA GCGTAGGCTT ACCCGGTCAT ACTTAAAGGG
      N  P  E  W   S  E  V   S  E  E   V  K  M  L   I  R  N·
1051 AACCCAGAAT GGTCAGAAGT ATCAGAGGAA GTGAAGATGC TCATTCGGAA
     TTGGGTCTTA CCAGTCTTCA TAGTCTCCTT CACTTCTACG AGTAAGCCTT
     ·L  L  K   T  E  P  T   Q  R  M   T  I  T   E  F  M  N·
1101 TCTGCTGAAA ACAGAGCCCA CCCAGAGAAT GACCATCACC GAGTTTATGA
     AGACGACTTT TGTCTCGGGT GGGTCTCTTA CTGGTAGTGG CTCAAATACT
     ·  H  P  W   I  M  Q   S  T  K  V   P  Q  T   P  L  H
1151 ACCACCCTTG GATCATGCAA TCAACAAAGG TCCCTCAAAC CCCACTGCAC
     TGGTGGGAAC CTAGTACGTT AGTTGTTTCC AGGGAGTTTG GGGTGACGTG
      T  S  R  V   L  K  E   D  K  E   R  W  E  D   V  K  E·
1201 ACCAGCCGGG TCCTGAAGGA GGACAAGGAG CGGTGGGAGG ATGTCAAGGA
     TGGTCGGCCC AGGACTTCCT CCTGTTCCTC GCCACCCTCC TACAGTTCCT
     ·E  M  T   S  A  L  A   T  M  R   V  D  Y   E  Q  I  K·
1251 GGAGATGACC AGTGCCTTGG CCACAATGCG CGTTGACTAC GAGCAGATCA
     CCTCTACTGG TCACGGAACC GGTGTTACGC GCAACTGATG CTCGTCTAGT

     ·  *
1301 AGTAA
     TCATT
```

SUMO β-Gal

β-Gal NCBI Accession# V00296

```
     M  G  H  H   H  H  H   H  G  S   D  S  E  V   N  Q  E ·
  1  ATGGGTCATC ACCATCATCA TCACGGGTCG GACTCAGAAG TCAATCAAGA
     TACCCAGTAG TGGTAGTAGT AGTGCCCAGC CTGAGTCTTC AGTTAGTTCT
     · A  K  P   E  V  K  P   E  V  K   P  E  T   H  I  N  L ·
 51  AGCTAAGCCA GAGGTCAAGC CAGAAGTCAA GCCTGAGACT CACATCAATT
     TCGATTCGGT CTCCAGTTCG GTCTTCAGTT CGGACTCTGA GTGTAGTTAA
     · K  V  S   D  G  S   S  E  I  F   F  K  I   K  K  T
101  TAAAGGTGTC CGATGGATCT TCAGAGATCT TCTTCAAGAT CAAAAAGACC
     ATTTCCACAG GCTACCTAGA AGTCTCTAGA AGAAGTTCTA GTTTTTCTGG
     T  P  L  R   R  L  M   E  A  F   A  K  R  Q   G  K  E ·
151  ACTCCTTTAA GAAGGCTGAT GGAAGCGTTC GCTAAAAGAC AGGGTAAGGA
     TGAGGAAATT CTTCCGACTA CCTTCGCAAG CGATTTTCTG TCCCATTCCT
     · M  D  S   L  R  F  L   Y  D  G   I  R  I   Q  A  D  Q ·
201  AATGGACTCC TTAAGATTCT TGTACGACGG TATTAGAATT CAAGCTGATC
     TTACCTGAGG AATTCTAAGA ACATGCTGCC ATAATCTTAA GTTCGACTAG
     · T  P  E   D  L  D   M  E  D  N   D  I  I   E  A  H
251  AGACCCCTGA AGATTTGGAC ATGGAGGATA ACGATATTAT TGAGGCTCAC
     TCTGGGGACT TCTAAACCTG TACCTCCTAT TGCTATAATA ACTCCGAGTG
     R  E  Q  I   G  G  M   T  M  I   T  D  S  L   A  V  V ·
301  CGCGAACAGA TTGGAGGTAT GACCATGATT ACGGATTCAC TGGCCGTCGT
     GCGCTTGTCT AACCTCCATA CTGGTACTAA TGCCTAAGTG ACCGGCAGCA
     · L  Q  R   R  D  W  E   N  P  G   V  T  Q   L  N  R  L ·
351  TTTACAACGT CGTGACTGGG AAAACCCTGG CGTTACCCAA CTTAATCGCC
     AAATGTTGCA GCACTGACCC TTTTGGGACC GCAATGGGTT GAATTAGCGG
     · A  A  H   P  P  F   A  S  W  R   N  S  E   E  A  R
401  TTGCAGCACA TCCCCCTTTC GCCAGCTGGC GTAATAGCGA AGAGGCCCGC
     AACGTCGTGT AGGGGGAAAG CGGTCGACCG CATTATCGCT TCTCCGGGCG
     T  D  R  P   S  Q  Q   L  R  S   L  N  G  E   W  R  F ·
451  ACCGATCGCC CTTCCCAACA GTTGCGCAGC CTGAATGGCG AATGGCGCTT
     TGGCTAGCGG GAAGGGTTGT CAACGCGTCG GACTTACCGC TTACCGCGAA
     · A  W  F   P  A  P  E   A  V  P   E  S  W   L  E  C  D ·
501  TGCCTGGTTT CCGGCACCAG AAGCGGTGCC GGAAAGCTGG CTGGAGTGCG
     ACGGACCAAA GGCCGTGGTC TTCGCCACGG CCTTTCGACC GACCTCACGC
     · L  P  E   A  D  T   V  V  V  P   S  N  W   Q  M  H
551  ATCTTCCTGA GGCCGATACT GTCGTCGTCC CCTCAAACTG GCAGATGCAC
     TAGAAGGACT CCGGCTATGA CAGCAGCAGG GGAGTTTGAC CGTCTACGTG
     G  Y  D  A   P  I  Y   T  N  V   T  Y  P  I   T  V  N ·
601  GGTTACGATG CGCCCATCTA CACCAACGTA ACCTATCCCA TTACGGTCAA
     CCAATGCTAC GCGGGTAGAT GTGGTTGCAT TGGATAGGGT AATGCCAGTT
     · P  P  F   V  P  T  E   N  P  T   G  C  Y   S  L  T  F ·
651  TCCGCCGTTT GTTCCCACGG AGAATCCGAC GGGTTGTTAC TCGCTCACAT
     AGGCGGCAAA CAAGGGTGCC TCTTAGGCTG CCCAACAATG AGCGAGTGTA
     · N  V  D   E  S  W   L  Q  E  G   Q  T  R   I  I  F
701  TTAATGTTGA TGAAAGCTGG CTACAGGAAG GCCAGACGCG AATTATTTTT
     AATTACAACT ACTTTCGACC GATGTCCTTC CGGTCTGCGC TTAATAAAAA
     D  G  V  N   S  A  F   H  L  W   C  N  G  R   W  V  G ·
751  GATGGCGTTA ACTCGGCGTT TCATCTGTGG TGCAACGGGC GCTGGGTCGG
     CTACCGCAAT TGAGCCGCAA AGTAGACACC ACGTTGCCCG CGACCCAGCC
```

Figure 38B

```
     ·Y  G  Q   D  S  R  L   P  S  E   F  D  L   S  A  F  L·
 801 TTACGGCCAG GACAGTCGTT TGCCGTCTGA ATTTGACCTG AGCGCATTTT
     AATGCCGGTC CTGTCAGCAA ACGGCAGACT TAAACTGGAC TCGCGTAAAA
     · R  A  G   E  N  R   L  A  V  M   V  L  R   W  S  D
 851 TACGCGCCGG AGAAAACCGC CTCGCGGTGA TGGTGCTGCG TTGGAGTGAC
     ATGCGCGGCC TCTTTTGGCG GAGCGCCACT ACCACGACGC AACCTCACTG
      G  S  Y  L   E  D  Q   D  M  W   R  M  S  G   I  F  R·
 901 GGCAGTTATC TGGAAGATCA GGATATGTGG CGGATGAGCG GCATTTTCCG
     CCGTCAATAG ACCTTCTAGT CCTATACACC GCCTACTCGC CGTAAAAGGC
     ·D  V  S   L  L  H  K   P  T  T   Q  I  S   D  F  H  V·
 951 TGACGTCTCG TTGCTGCATA AACCGACTAC ACAAATCAGC GATTTCCATG
     ACTGCAGAGC AACGACGTAT TTGGCTGATG TGTTTAGTCG CTAAAGGTAC
     · A  T  R   F  N  D   D  F  S  R   A  V  L   E  A  E
1001 TTGCCACTCG CTTTAATGAT GATTTCAGCC GCGCTGTACT GGAGGCTGAA
     AACGGTGAGC GAAATTACTA CTAAAGTCGG CGCGACATGA CCTCCGACTT
      V  Q  M  C   G  E  L   R  D  Y   L  R  V  T   V  S  L·
1051 GTTCAGATGT GCGGCGAGTT GCGTGACTAC CTACGGGTAA CAGTTTCTTT
     CAAGTCTACA CGCCGCTCAA CGCACTGATG GATGCCCATT GTCAAAGAAA
     ·W  Q  G   E  T  Q  V   A  S  G   T  A  P   F  G  G  E·
1101 ATGGCAGGGT GAAACGCAGG TCGCCAGCGG CACCGCGCCT TTCGGCGGTG
     TACCGTCCCA CTTTGCGTCC AGCGGTCGCC GTGGCGCGGA AAGCCGCCAC
     · I  I  D   E  R  G   G  Y  A  D   R  V  T   L  R  L
1151 AAATTATCGA TGAGCGTGGT GGTTATGCCG ATCGCGTCAC ACTACGTCTG
     TTTAATAGCT ACTCGCACCA CCAATACGGC TAGCGCAGTG TGATGCAGAC
      N  V  E  N   P  K  L   W  S  A   E  I  P  N   L  Y  R·
1201 AACGTCGAAA ACCCGAAACT GTGGAGCGCC GAAATCCCGA ATCTCTATCG
     TTGCAGCTTT TGGGCTTTGA CACCTCGCGG CTTTAGGGCT TAGAGATAGC
     ·A  V  V   E  L  H  T   A  D  G   T  L  I   E  A  E  A·
1251 TGCGGTGGTT GAACTGCACA CCGCCGACGG CACGCTGATT GAAGCAGAAG
     ACGCCACCAA CTTGACGTGT GGCGGCTGCC GTGCGACTAA CTTCGTCTTC
     · C  D  V   G  F  R   E  V  R  I   E  N  G   L  L  L
1301 CCTGCGATGT CGGTTTCCGC GAGGTGCGGA TTGAAAATGG TCTGCTGCTG
     GGACGCTACA GCCAAAGGCG CTCCACGCCT AACTTTTACC AGACGACGAC
      L  N  G  K   P  L  L   I  R  G   V  N  R  H   E  H  H·
1351 CTGAACGGCA AGCCGTTGCT GATTCGAGGC GTTAACCGTC ACGAGCATCA
     GACTTGCCGT TCGGCAACGA CTAAGCTCCG CAATTGGCAG TGCTCGTAGT
     ·P  L  H   G  Q  V  M   D  E  Q   T  M  V   Q  D  I  L·
1401 TCCTCTGCAT GGTCAGGTCA TGGATGAGCA GACGATGGTG CAGGATATCC
     AGGAGACGTA CCAGTCCAGT ACCTACTCGT CTGCTACCAC GTCCTATAGG
     · L  M  K   Q  N  N   F  N  A  V   R  C  S   H  Y  P
1451 TGCTGATGAA GCAGAACAAC TTTAACGCCG TGCGCTGTTC GCATTATCCG
     ACGACTACTT CGTCTTGTTG AAATTGCGGC ACGCGACAAG CGTAATAGGC
      N  H  P  L   W  Y  T   L  C  D   R  Y  G  L   Y  V  V·
1501 AACCATCCGC TGTGGTACAC GCTGTGCGAC CGCTACGGCC TGTATGTGGT
     TTGGTAGGCG ACACCATGTG CGACACGCTG GCGATGCCGG ACATACACCA
     ·D  E  A   N  I  E  T   H  G  M   V  P  M   N  R  L  T·
1551 GGATGAAGCC AATATTGAAA CCCACGGCAT GGTGCCAATG AATCGTCTGA
     CCTACTTCGG TTATAACTTT GGGTGCCGTA CCACGGTTAC TTAGCAGACT

· D  D  P   R  W  L   P  A  M  S   E  R  V   T  R  M
1601 CCGATGATCC GCGCTGGCTA CCGGCGATGA GCGAACGCGT AACGCGAATG
     GGCTACTAGG CGCGACCGAT GGCCGCTACT CGCTTGCGCA TTGCGCTTAC
```

Figure 38C

```
      V  Q  R  D  R  N  H  P  S  V  I  I  W  S  L  G  N·
1651  GTGCAGCGCG ATCGTAATCA CCCGAGTGTG ATCATCTGGT CGCTGGGGAA
      CACGTCGCGC TAGCATTAGT GGGCTCACAC TAGTAGACCA GCGACCCCTT
      ·E  S  G  H  G  A  N  H  D  A  L  Y  R  W  I  K  S·
1701  TGAATCAGGC CACGGCGCTA ATCACGACGC GCTGTATCGC TGGATCAAAT
      ACTTAGTCCG GTGCCGCGAT TAGTGCTGCG CGACATAGCG ACCTAGTTTA
      · V  D  P  S  R  P  V  Q  Y  E  G  G  G  A  D  T
1751  CTGTCGATCC TTCCCGCCCG GTGCAGTATG AAGGCGGCGG AGCCGACACC
      GACAGCTAGG AAGGGCGGGC CACGTCATAC TTCCGCCGCC TCGGCTGTGG
      T  A  T  D  I  I  C  P  M  Y  A  R  V  D  E  D  Q·
1801  ACGGCCACCG ATATTATTTG CCCGATGTAC GCGCGCGTGG ATGAAGACCA
      TGCCGGTGGC TATAATAAAC GGGCTACATG CGCGCGCACC TACTTCTGGT
      ·P  F  P  A  V  P  K  W  S  I  K  K  W  L  S  L  P·
1851  GCCCTTCCCG GCTGTGCCGA AATGGTCCAT CAAAAAATGG CTTTCGCTAC
      CGGGAAGGGC CGACACGGCT TTACCAGGTA GTTTTTTACC GAAAGCGATG
      · G  E  T  R  P  L  I  L  C  E  Y  A  H  A  M  G
1901  CTGGAGAGAC GCGCCCGCTG ATCCTTTGCG AATACGCCCA CGCGATGGGT
      GACCTCTCTG CGCGGGCGAC TAGGAAACGC TTATGCGGGT GCGCTACCCA
      N  S  L  G  G  F  A  K  Y  W  Q  A  F  R  Q  Y  P·
1951  AACAGTCTTG GCGGTTTCGC TAAATACTGG CAGGCGTTTC GTCAGTATCC
      TTGTCAGAAC CGCCAAAGCG ATTTATGACC GTCCGCAAAG CAGTCATAGG
      ·R  L  Q  G  G  F  V  W  D  W  V  D  Q  S  L  I  K·
2001  CCGTTTACAG GGCGGCTTCG TCTGGGACTG GGTGGATCAG TCGCTGATTA
      GGCAAATGTC CCGCCGAAGC AGACCCTGAC CCACCTAGTC AGCGACTAAT
      · Y  D  E  N  G  N  P  W  S  A  Y  G  G  D  F  G
2051  AATATGATGA AAACGGCAAC CCGTGGTCGG CTTACGGCGG TGATTTTGGC
      TTATACTACT TTTGCCGTTG GGCACCAGCC GAATGCCGCC ACTAAAACCG
      D  T  P  N  D  R  Q  F  C  M  N  G  L  V  F  A  D·
2101  GATACGCCGA ACGATCGCCA GTTCTGTATG AACGGTCTGG TCTTTGCCGA
      CTATGCGGCT TGCTAGCGGT CAAGACATAC TTGCCAGACC AGAAACGGCT
      ·R  T  P  H  P  A  L  T  E  A  K  H  Q  Q  Q  F  F·
2151  CCGCACGCCG CATCCAGCGC TGACGGAAGC AAAACACCAG CAGCAGTTTT
      GGCGTGCGGC GTAGGTCGCG ACTGCCTTCG TTTTGTGGTC GTCGTCAAAA
      · Q  F  R  L  S  G  Q  T  I  E  V  T  S  E  Y  L
2201  TCCAGTTCCG TTTATCCGGG CAAACCATCG AAGTGACCAG CGAATACCTG
      AGGTCAAGGC AAATAGGCCC GTTTGGTAGC TTCACTGGTC GCTTATGGAC
      F  R  H  S  D  N  E  L  L  H  W  M  V  A  L  D  G·
2251  TTCCGTCATA GCGATAACGA GCTCCTGCAC TGGATGGTGG CGCTGGATGG
      AAGGCAGTAT CGCTATTGCT CGAGGACGTG ACCTACCACC GCGACCTACC
      ·K  P  L  A  S  G  E  V  P  L  D  V  A  P  Q  G  K·
2301  TAAGCCGCTG GCAAGCGGTG AAGTGCCTCT GGATGTCGCT CCACAAGGTA
      ATTCGGCGAC CGTTCGCCAC TTCACGGAGA CCTACAGCGA GGTGTTCCAT
      · Q  L  I  E  L  P  E  L  P  Q  P  E  S  A  G  Q
2351  AACAGTTGAT TGAACTGCCT GAACTACCGC AGCCGGAGAG CGCCGGGCAA
      TTGTCAACTA ACTTGACGGA CTTGATGGCG TCGGCCTCTC GCGGCCCGTT
      L  W  L  T  V  R  V  V  Q  P  N  A  T  A  W  S  E·
2401  CTCTGGCTCA CAGTACGCGT AGTGCAACCG AACGCGACCG CATGGTCAGA
      GAGACCGAGT GTCATGCGCA TCACGTTGGC TTGCGCTGGC GTACCAGTCT

·A  G  H  I  S  A  W  Q  Q  W  R  L  A  E  N  L  S·
2451  AGCCGGGCAC ATCAGCGCCT GGCAGCAGTG GCGTCTGGCG GAAAACCTCA
      TCGGCCCGTG TAGTCGCGGA CCGTCGTCAC CGCAGACCGC CTTTTGGAGT
```

Figure 38D

```
      · V  T  L   P  A  A   S  H  A  I   P  H  L   T  T  S
2501  GTGTGACGCT CCCCGCCGCG TCCCACGCCA TCCCGCATCT GACCACCAGC
      CACACTGCGA GGGGCGGCGC AGGGTGCGGT AGGGCGTAGA CTGGTGGTCG
       E  M  D  F   C  I  E   L  G  N   K  R  W  Q   F  N  R ·
2551  GAAATGGATT TTTGCATCGA GCTGGGTAAT AAGCGTTGGC AATTTAACCG
      CTTTACCTAA AAACGTAGCT CGACCCATTA TTCGCAACCG TTAAATTGGC
      · Q  S  G   F  L  S  Q   M  W  I   G  D  K   K  Q  L  L ·
2601  CCAGTCAGGC TTTCTTTCAC AGATGTGGAT TGGCGATAAA AAACAACTGC
      GGTCAGTCCG AAAGAAAGTG TCTACACCTA ACCGCTATTT TTTGTTGACG
      · T  P  L   R  D  Q   F  T  R  A   P  L  D   N  D  I
2651  TGACGCCGCT GCGCGATCAG TTCACCCGTG CACCGCTGGA TAACGACATT
      ACTGCGGCGA CGCGCTAGTC AAGTGGGCAC GTGGCGACCT ATTGCTGTAA
       G  V  S  E   A  T  R   I  D  P   N  A  W  V   E  R  W ·
2701  GGCGTAAGTG AAGCGACCCG CATTGACCCT AACGCCTGGG TCGAACGCTG
      CCGCATTCAC TTCGCTGGGC GTAACTGGGA TTGCGGACCC AGCTTGCGAC
      · K  A  A   G  H  Y  Q   A  E  A   A  L  L   Q  C  T  A ·
2751  GAAGGCGGCG GGCCATTACC AGGCCGAAGC AGCGTTGTTG CAGTGCACGG
      CTTCCGCCGC CCGGTAATGG TCCGGCTTCG TCGCAACAAC GTCACGTGCC
      · D  T  L   A  D  A   V  L  I  T   T  A  H   A  W  Q
2801  CAGATACACT TGCTGATGCG GTGCTGATTA CGACCGCTCA CGCGTGGCAG
      GTCTATGTGA ACGACTACGC CACGACTAAT GCTGGCGAGT GCGCACCGTC
       H  Q  G  K   T  L  F   I  S  R   K  T  Y  R   I  D  G ·
2851  CATCAGGGGA AAACCTTATT TATCAGCCGG AAAACCTACC GGATTGATGG
      GTAGTCCCCT TTTGGAATAA ATAGTCGGCC TTTTGGATGG CCTAACTACC
      · S  G  Q   M  A  I  T   V  D  V   E  V  A   S  D  T  P ·
2901  TAGTGGTCAA ATGGCGATTA CCGTTGATGT TGAAGTGGCG AGCGATACAC
      ATCACCAGTT TACCGCTAAT GGCAACTACA ACTTCACCGC TCGCTATGTG
      · H  P  A   R  I  G   L  N  C  Q   L  A  Q   V  A  E
2951  CGCATCCGGC GCGGATTGGC CTGAACTGCC AGCTGGCGCA GGTAGCAGAG
      GCGTAGGCCG CGCCTAACCG GACTTGACGG TCGACCGCGT CCATCGTCTC
       R  V  N  W   L  G  L   G  P  Q   E  N  Y  P   D  R  L ·
3001  CGGGTAAACT GGCTCGGATT AGGGCCGCAA GAAAACTATC CCGACCGCCT
      GCCCATTTGA CCGAGCCTAA TCCCGGCGTT CTTTTGATAG GGCTGGCGGA
      · T  A  A   C  F  D  R   W  D  L   P  L  S   D  M  Y  T ·
3051  TACTGCCGCC TGTTTTGACC GCTGGGATCT GCCATTGTCA GACATGTATA
      ATGACGGCGG ACAAAACTGG CGACCCTAGA CGGTAACAGT CTGTACATAT
      · P  Y  V   F  P  S   E  N  G  L   R  C  G   T  R  E
3101  CCCCGTACGT CTTCCCGAGC GAAAACGGTC TGCGCTGCGG GACGCGCGAA
      GGGGCATGCA GAAGGGCTCG CTTTTGCCAG ACGCGACGCC CTGCGCGCTT
       L  N  Y  G   P  H  Q   W  R  G   D  F  Q  F   N  I  S ·
3151  TTGAATTATG GCCCACACCA GTGGCGCGGC GACTTCCAGT TCAACATCAG
      AACTTAATAC CGGGTGTGGT CACCGCGCCG CTGAAGGTCA AGTTGTAGTC
      · R  Y  S   Q  Q  Q  L   M  E  T   S  H  R   H  L  L  H ·
3201  CCGCTACAGT CAACAGCAAC TGATGGAAAC CAGCCATCGC CATCTGCTGC
      GGCGATGTCA GTTGTCGTTG ACTACCTTTG GTCGGTAGCG GTAGACGACG
      · A  E  E   G  T  W   L  N  I  D   G  F  H   M  G  I
3251  ACGCGGAAGA AGGCACATGG CTGAATATCG ACGGTTTCCA TATGGGGATT
      TGCGCCTTCT TCCGTGTACC GACTTATAGC TGCCAAAGGT ATACCCCTAA

G  G  D  D   S  W  S   P  S  V   S  A  E  F   Q  L  S ·
3301  GGTGGCGACG ACTCCTGGAG CCCGTCAGTA TCGGCGGAAT TCCAGCTGAG
      CCACCGCTGC TGAGGACCTC GGGCAGTCAT AGCCGCCTTA AGGTCGACTC
```

```
      · A  G  R   Y  H  Y  Q   L  V  W   C  Q  K   *  *
3351  CGCCGGTCGC TACCATTACC AGTTGGTCTG GTGTCAAAAA TAATAA
      GCGGCCAGCG ATGGTAATGG TCAACCAGAC CACAGTTTTT ATTATT
```

1 CGCCTTGTTA CTAGTTAGAA AAAGACATTT TTGCTGTCAG TCACTGTCAA
GCGGAACAAT GATCAATCTT TTTCTGTAAA AACGACAGTC AGTGACAGTT
51 GAGATTCTTT TGCTGGCATT TCTTCTAGAA GCAAAAAGAG CGATGCGTCT
CTCTAAGAAA ACGACCGTAA AGAAGATCTT CGTTTTTCTC GCTACGCAGA
101 TTTCCGCTGA ACCGTTCCAG CAAAAAAGAC TACCAACGCA ATATGGATTG
AAAGGCGACT TGGCAAGGTC GTTTTTTCTG ATGGTTGCGT TATACCTAAC
151 TCAGAATCAT ATAAAAGAGA AGCAAATAAC TCCTTGTCTT GTATCAATTG
AGTCTTAGTA TATTTTCTCT TCGTTTATTG AGGAACAGAA CATAGTTAAC
201 CATTATAATA TCTTCTTGTT AGTGCAATAT CATATAGAAG TCATCGAAAT
GTAATATTAT AGAAGAACAA TCACGTTATA GTATATCTTC AGTAGCTTTA

NcoI
~~~~~~~

251 AGATATTAAG AAAAACAAAC TGTACAATCC ATGGGTCATC ACCATCATCA
TCTATAATTC TTTTTGTTTG ACATGTTAGG TACCCAGTAG TGGTAGTAGT
301 TCACGGGTCG GACTCAGAAG TCAATCAAGA AGCTAAGCCA GAGGTCAAGC
AGTGCCCAGC CTGAGTCTTC AGTTAGTTCT TCGATTCGGT CTCCAGTTCG
351 CAGAAGTCAA GCCTGAGACT CACATCAATT TAAAGGTGTC CGATGGATCT
GTCTTCAGTT CGGACTCTGA GTGTAGTTAA ATTTCCACAG GCTACCTAGA
401 TCAGAGATCT TCTTCAAGAT CAAAAAGACC ACTCCTTTAA GAAGGCTGAT
AGTCTCTAGA AGAAGTTCTA GTTTTTCTGG TGAGGAAATT CTTCCGACTA
451 GGAAGCGTTC GCTAAAAGAC AGGGTAAGGA AATGGACTCC TTAAGATTCT
CCTTCGCAAG CGATTTTCTG TCCCATTCCT TTACCTGAGG AATTCTAAGA
501 TGTACGACGG TATTAGAATT CAAGCTGATC AGACCCCTGA AGATTTGGAC
ACATGCTGCC ATAATCTTAA GTTCGACTAG TCTGGGGACT TCTAAACCTG
551 ATGGAGGATA ACGATATTAT TGAGGCTCAC CGCGAACAGA TTGGAGGTAT
TACCTCCTAT TGCTATAATA ACTCCGAGTG GCGCTTGTCT AACCTCCATA
601 GGTGAGCAAG GGCGAGGAGC TGTTCACCGG GGTGGTGCCC ATCCTGGTCG
CCACTCGTTC CCGCTCCTCG ACAAGTGGCC CCACCACGGG TAGGACCAGC
651 AGCTGGACGG CGACGTAAAC GGCCACAAGT TCAGCGTGTC CGGCGAGGGC
TCGACCTGCC GCTGCATTTG CCGGTGTTCA AGTCGCACAG GCCGCTCCCG
701 GAGGGCGATG CCACCTACGG CAAGCTGACC CTGAAGTTCA TCTGCACCAC
CTCCCGCTAC GGTGGATGCC GTTCGACTGG GACTTCAAGT AGACGTGGTG
751 CGGCAAGCTG CCCGTGCCCT GGCCCACCCT CGTGACCACC CTGACCTACG
GCCGTTCGAC GGGCACGGGA CCGGGTGGGA GCACTGGTGG GACTGGATGC
801 GCGTGCAGTG CTTCAGCCGC TACCCCGACC ACATGAAGCA GCACGACTTC
CGCACGTCAC GAAGTCGGCG ATGGGGCTGG TGTACTTCGT CGTGCTGAAG
851 TTCAAGTCCG CCATGCCCGA AGGCTACGTC CAGGAGCGCA CCATCTTCTT
AAGTTCAGGC GGTACGGGCT TCCGATGCAG GTCCTCGCGT GGTAGAAGAA
901 CAAGGACGAC GGCAACTACA AGACCCGCGC CGAGGTGAAG TTCGAGGGCG
GTTCCTGCTG CCGTTGATGT TCTGGGCGCG GCTCCACTTC AAGCTCCCGC
951 ACACCCTGGT GAACCGCATC GAGCTGAAGG GCATCGACTT CAAGGAGGAC
TGTGGGACCA CTTGGCGTAG CTCGACTTCC CGTAGCTGAA GTTCCTCCTG
1001 GGCAACATCC TGGGGCACAA GCTGGAGTAC AACTACAACA GCCACAACGT
CCGTTGTAGG ACCCCGTGTT CGACCTCATG TTGATGTTGT CGGTGTTGCA
1051 CTATATCATG GCCGACAAGC AGAAGAACGG CATCAAGGTG AACTTCAAGA
GATATAGTAC CGGCTGTTCG TCTTCTTGCC GTAGTTCCAC TTGAAGTTCT
1101 TCCGCCACAA CATCGAGGAC GGCAGCGTGC AGCTCGCCGA CCACTACCAG
AGGCGGTGTT GTAGCTCCTG CCGTCGCACG TCGAGCGGCT GGTGATGGTC
1151 CAGAACACCC CCATCGGCGA CGGCCCCGTG CTGCTGCCCG ACAACCACTA
GTCTTGTGGG GGTAGCCGCT GCCGGGGCAC GACGACGGGC TGTTGGTGAT
~~~~~~~

Figure 40B

```
1201 CCTGAGCACC CAGTCCGCCC TGAGCAAAGA CCCCAACGAG AAGCGCGATC
     GGACTCGTGG GTCAGGCGGG ACTCGTTTCT GGGGTTGCTC TTCGCGCTAG
1251 ACATGGTCCT GCTGGAGTTC GTGACCGCCG CCGGGATCAC TCTCGGCATG
     TGTACCAGGA CGACCTCAAG CACTGGCGGC GGCCCTAGTG AGAGCCGTAC
                                            XhoI
                                          ~~~~~~~
1301 GACGAGCTGT ACAAGTAATA AGCTTGCGGC CGCACTCGAG GAGCTCCCTG
     CTGCTCGACA TGTTCATTAT TCGAACGCCG GCGTGAGCTC CTCGAGGGAC
1351 GCGAATTGTA CCAAGATGGC CTTTGGTGGG TTGAAGAAGG AAAAAGACAG
     CGCTTAACAT GGTTCTACCG GAAACCACCC AACTTCTTCC TTTTTCTGTC
1401 AAACGACTTA ATTACCTACT TGAAAAAAGC CTGTGAGTAA ACAGGCCCCT
     TTTGCTGAAT TAATGGATGA ACTTTTTTCG GACACTCATT TGTCCGGGGA
1451 TTTCCTTTGT CGATATCATG TAATTAGTTA TGTCACGCTT ACATTCACGC
     AAAGGAAACA GCTATAGTAC ATTAATCAAT ACAGTGCGAA TGTAAGTGCG
1501 CCTCCCCCCA CATCCGCTCT AACCGAAAAG GAAGGAGTTA GACAACCTGA
     GGAGGGGGGT GTAGGCGAGA TTGGCTTTTC CTTCCTCAAT CTGTTGGACT
1551 AGTCTAGGTC CCTATTTATT TTTTTATAGT TATGTTAGTA TTAAGAACGT
     TCAGATCCAG GGATAAATAA AAAAATATCA ATACAATCAT AATTCTTGCA
1601 TATTTATATT TCAAATTTTT CTTTTTTTTC TGTACAGACG CGTGTACGCA
     ATAAATATAA AGTTTAAAAA GAAAAAAAAG ACATGTCTGC GCACATGCGT
1651 TGTAACATTA TACTGAAAAC CTTGCTTGAG AAGGTTTTGG GACGCTCGAA
     ACATTGTAAT ATGACTTTTG GAACGAACTC TTCCAAAACC CTGCGAGCTT
1701 GGCTTTAATT TGCAAGCTTA TCGATGATAA GCTGTCAAAC ATGAGAATTC
     CCGAAATTAA ACGTTCGAAT AGCTACTATT CGACAGTTTG TACTCTTAAG
1751 GGTCGAAAAA AGAAAAGGAG AGGGCCAAGA GGGAGGGCAT TGGTGACTAT
     CCAGCTTTTT TCTTTTCCTC TCCCGGTTCT CCCTCCCGTA ACCACTGATA
1801 TGAGCACGTG AGTATACGTG ATTAAGCACA CAAAGGCAGC TTGGAGTATG
     ACTCGTGCAC TCATATGCAC TAATTCGTGT GTTTCCGTCG AACCTCATAC
1851 TCTGTTATTA ATTTCACAGG TAGTTCTGGT CCATTGGTGA AAGTTTGCGG
     AGACAATAAT TAAAGTGTCC ATCAAGACCA GGTAACCACT TTCAAACGCC
1901 CTTGCAGAGC ACAGAGGCCG CAGAATGTGC TCTAGATTCC GATGCTGACT
     GAACGTCTCG TGTCTCCGGC GTCTTACACG AGATCTAAGG CTACGACTGA
1951 TGCTGGGTAT TATATGTGTG CCCAATAGAA AGAGAACAAT TGACCCGGTT
     ACGACCCATA ATATACACAC GGGTTATCTT TCTCTTGTTA ACTGGGCCAA
2001 ATTGCAAGGA AAATTTCAAG TCTTGTAAAA GCATATAAAA ATAGTTCAGG
     TAACGTTCCT TTTAAAGTTC AGAACATTTT CGTATATTTT TATCAAGTCC
2051 CACTCCGAAA TACTTGGTTG GCGTGTTTCG TAATCAACCT AAGGAGGATG
     GTGAGGCTTT ATGAACCAAC CGCACAAAGC ATTAGTTGGA TTCCTCCTAC
2101 TTTTGGCTCT GGTCAATGAT TACGGCATTG ATATCGTCCA ACTGCATGGA
     AAAACCGAGA CCAGTTACTA ATGCCGTAAC TATAGCAGGT TGACGTACCT
2151 GATGAGTCGT GGCAAGAATA CCAAGAGTTC CTCGGTTTGC CAGTTATTAA
     CTACTCAGCA CCGTTCTTAT GGTTCTCAAG GAGCCAAACG GTCAATAATT
2201 AAGACTCGTA TTTCCAAAAG ACTGCAACAT ACTACTCAGT GCAGCTTCAC
     TTCTGAGCAT AAAGGTTTTC TGACGTTGTA TGATGAGTCA CGTCGAAGTG
2251 AGAAACCTCA TTCGTTTATT CCCTTGTTTG ATTCAGAAGC AGGTGGGACA
     TCTTTGGAGT AAGCAAATAA GGGAACAAAC TAAGTCTTCG TCCACCCTGT
2301 GGTGAACTTT TGGATTGGAA CTCGATTTCT GACTGGGTTG GAAGGCAAGA
     CCACTTGAAA ACCTAACCTT GAGCTAAAGA CTGACCCAAC CTTCCGTTCT
2351 GAGCCCCGAA AGCTTACATT TTATGTTAGC TGGTGGACTG ACGCCAGAAA
     CTCGGGGCTT TCGAATGTAA AATACAATCG ACCACCTGAC TGCGGTCTTT
2401 ATGTTGGTGA TGCGCTTAGA TTAAATGGCG TTATTGGTGT TGATGTAAGC
```

Figure 40C

```
     TACAACCACT ACGCGAATCT AATTTACCGC AATAACCACA ACTACATTCG
2451 GGAGGTGTGG AGACAAATGG TGTAAAAGAC TCTAACAAAA TAGCAAATTT
     CCTCCACACC TCTGTTTACC ACATTTTCTG AGATTGTTTT ATCGTTTAAA
2501 CGTCAAAAAT GCTAAGAAAT AGGTTATTAC TGAGTAGTAT TTATTTAAGT
     GCAGTTTTTA CGATTCTTTA TCCAATAATG ACTCATCATA AATAAATTCA
2551 ATTGTTTGTG CACTTGCCTG CAGCTTCTCA ATGATATTCG AATACGCTTT
     TAACAAACAC GTGAACGGAC GTCGAAGAGT TACTATAAGC TTATGCGAAA
2601 GAGGAGATAC AGCCTAATAT CCGACAAACT GTTTTACAGA TTTACGATCG
     CTCCTCTATG TCGGATTATA GGCTGTTTGA CAAAATGTCT AAATGCTAGC
2651 TACTTGTTAC CCATCATTGA ATTTTGAACA TCCGAACCTG GGAGTTTTCC
     ATGAACAATG GGTAGTAACT TAAAACTTGT AGGCTTGGAC CCTCAAAAGG
2701 CTGAAACAGA TAGTATATTT GAACCTGTAT AATAATATAT AGTCTAGCGC
     GACTTTGTCT ATCATATAAA CTTGGACATA TTATTATATA TCAGATCGCG
2751 TTTACGGAAG ACAATGTATG TATTTCGGTT CCTGGAGAAA CTATTGCATC
     AAATGCCTTC TGTTACATAC ATAAAGCCAA GGACCTCTTT GATAACGTAG
2801 TATTGCATAG GTAATCTTGC ACGTCGCATC CCCGGTTCAT TTTCTGCGTT
     ATAACGTATC CATTAGAACG TGCAGCGTAG GGGCCAAGTA AAAGACGCAA
2851 TCCATCTTGC ACTTCAATAG CATATCTTTG TTAACGAAGC ATCTGTGCTT
     AGGTAGAACG TGAAGTTATC GTATAGAAAC AATTGCTTCG TAGACACGAA
2901 CATTTTGTAG AACAAAAATG CAACGCGAGA GCGCTAATTT TTCAAACAAA
     GTAAAACATC TTGTTTTTAC GTTGCGCTCT CGCGATTAAA AAGTTTGTTT
2951 GAATCTGAGC TGCATTTTTA CAGAACAGAA ATGCAACGCG AAAGCGCTAT
     CTTAGACTCG ACGTAAAAAT GTCTTGTCTT TACGTTGCGC TTTCGCGATA
3001 TTTACCAACG AAGAATCTGT GCTTCATTTT TGTAAAACAA AAATGCAACG
     AAATGGTTGC TTCTTAGACA CGAAGTAAAA ACATTTTGTT TTTACGTTGC
3051 CGAGAGCGCT AATTTTTCAA ACAAAGAATC TGAGCTGCAT TTTTACAGAA
     GCTCTCGCGA TTAAAAAGTT TGTTTCTTAG ACTCGACGTA AAAATGTCTT
3101 CAGAAATGCA ACGCGAGAGC GCTATTTTAC CAACAAAGAA TCTATACTTC
     GTCTTTACGT TGCGCTCTCG CGATAAAATG GTTGTTTCTT AGATATGAAG
3151 TTTTTTGTTC TACAAAAATG CATCCCGAGA GCGCTATTTT TCTAACAAAG
     AAAAAACAAG ATGTTTTTAC GTAGGGCTCT CGCGATAAAA AGATTGTTTC
3201 CATCTTAGAT TACTTTTTTT CTCCTTTGTG CGCTCTATAA TGCAGTCTCT
     GTAGAATCTA ATGAAAAAAA GAGGAAACAC GCGAGATATT ACGTCAGAGA
3251 TGATAACTTT TTGCACTGTA GGTCCGTTAA GGTTAGAAGA AGGCTACTTT
     ACTATTGAAA AACGTGACAT CCAGGCAATT CCAATCTTCT TCCGATGAAA
3301 GGTGTCTATT TTCTCTTCCA TAAAAAAAGC CTGACTCCAC TTCCCGCGTT
     CCACAGATAA AAGAGAAGGT ATTTTTTTCG GACTGAGGTG AAGGGCGCAA
3351 TACTGATTAC TAGCGAAGCT GCGGGTGCAT TTTTTCAAGA TAAAGGCATC
     ATGACTAATG ATCGCTTCGA CGCCCACGTA AAAAAGTTCT ATTTCCGTAG
3401 CCCGATTATA TTCTATACCG ATGTGGATTG CGCATACTTT GTGAACAGAA
     GGGCTAATAT AAGATATGGC TACACCTAAC GCGTATGAAA CACTTGTCTT
3451 AGTGATAGCG TTGATGATTC TTCATTGGTC AGAAAATTAT GAACGGTTTC
     TCACTATCGC AACTACTAAG AAGTAACCAG TCTTTTAATA CTTGCCAAAG
3501 TTCTATTTTG TCTCTATATA CTACGTATAG GAAATGTTTA CATTTTCGTA
     AAGATAAAAC AGAGATATAT GATGCATATC CTTTACAAAT GTAAAAGCAT
3551 TTGTTTTCGA TTCACTCTAT GAATAGTTCT TACTACAATT TTTTTGTCTA
     AACAAAAGCT AAGTGAGATA CTTATCAAGA ATGATGTTAA AAAAACAGAT
3601 AAGAGTAATA CTAGAGATAA ACATAAAAAA TGTAGAGGTC GAGTTTAGAT
     TTCTCATTAT GATCTCTATT TGTATTTTTT ACATCTCCAG CTCAAATCTA
3651 GCAAGTTCAA GGAGCGAAAG GTGGATGGGT AGGTTATATA GGGATATAGC
     CGTTCAAGTT CCTCGCTTTC CACCTACCCA TCCAATATAT CCCTATATCG
```

Figure 40D

```
3701 ACAGAGATAT ATAGCAAAGA GATACTTTTG AGCAATGTTT GTGGAAGCGG
     TGTCTCTATA TATCGTTTCT CTATGAAAAC TCGTTACAAA CACCTTCGCC
3751 TATTCGCAAT ATTTTAGTAG CTCGTTACAG TCCGGTGCGT TTTTGGTTTT
     ATAAGCGTTA TAAAATCATC GAGCAATGTC AGGCCACGCA AAAACCAAAA
3801 TTGAAAGTGC GTCTTCAGAG CGCTTTTGGT TTTCAAAAGC GCTCTGAAGT
     AACTTTCACG CAGAAGTCTC GCGAAAACCA AAAGTTTTCG CGAGACTTCA
3851 TCCTATACTT TCTAGAGAAT AGGAACTTCG GAATAGGAAC TTCAAAGCGT
     AGGATATGAA AGATCTCTTA TCCTTGAAGC CTTATCCTTG AAGTTTCGCA
3901 TTCCGAAAAC GAGCGCTTCC GAAAATGCAA CGCGAGCTGC GCACATACAG
     AAGGCTTTTG CTCGCGAAGG CTTTTACGTT GCGCTCGACG CGTGTATGTC
3951 CTCACTGTTC ACGTCGCACC TATATCTGCG TGTTGCCTGT ATATATATAT
     GAGTGACAAG TGCAGCGTGG ATATAGACGC ACAACGGACA TATATATATA
4001 ACATGAGAAG AACGGCATAG TGCGTGTTTA TGCTTAAATG CGTACTTATA
     TGTACTCTTC TTGCCGTATC ACGCACAAAT ACGAATTTAC GCATGAATAT
4051 TGCGTCTATT TATGTAGGAT GAAAGGTAGT CTAGTACCTC CTGTGATATT
     ACGCAGATAA ATACATCCTA CTTTCCATCA GATCATGGAG GACACTATAA
4101 ATCCCATTCC ATGCGGGGTA TCGTATGCTT CCTTCAGCAC TACCCTTTAG
     TAGGGTAAGG TACGCCCCAT AGCATACGAA GGAAGTCGTG ATGGGAAATC
4151 CTGTTCTATA TGCTGCCACT CCTCAATTGG ATTAGTCTCA TCCTTCAATG
     GACAAGATAT ACGACGGTGA GGAGTTAACC TAATCAGAGT AGGAAGTTAC
4201 CTATCATTTC CTTTGATATT GGATCATATG CATAGTACCG AGAAACTAGT
     GATAGTAAAG GAAACTATAA CCTAGTATAC GTATCATGGC TCTTTGATCA
4251 GCGAAGTAGT GATCAGGTAT TGCTGTTATC TGATGAGTAT ACGTTGTCCT
     CGCTTCATCA CTAGTCCATA ACGACAATAG ACTACTCATA TGCAACAGGA
4301 GGCCACGGCA GAAGCACGCT TATCGCTCCA ATTTCCCACA ACATTAGTCA
     CCGGTGCCGT CTTCGTGCGA ATAGCGAGGT TAAAGGGTGT TGTAATCAGT
4351 ACTCCGTTAG GCCCTTCATT GAAAGAAATG AGGTCATCAA ATGTCTTCCA
     TGAGGCAATC CGGGAAGTAA CTTTCTTTAC TCCAGTAGTT TACAGAAGGT
4401 ATGTGAGATT TTGGGCCATT TTTTATAGCA AAGATTGAAT AAGGCGCATT
     TACACTCTAA AACCCGGTAA AAAATATCGT TTCTAACTTA TTCCGCGTAA
4451 TTTCTTCAAA GCTTTATTGT ACGATCTGAC TAAGTTATCT TTTAATAATT
     AAAGAAGTTT CGAAATAACA TGCTAGACTG ATTCAATAGA AAATTATTAA
4501 GGTATTCCTG TTTATTGCTT GAAGAATTGC CGGTCCTATT TACTCGTTTT
     CCATAAGGAC AAATAACGAA CTTCTTAACG GCCAGGATAA ATGAGCAAAA
4551 AGGACTGGTT CAGAATTCTT GAAGACGAAA GGGCCTCGTG ATACGCCTAT
     TCCTGACCAA GTCTTAAGAA CTTCTGCTTT CCCGGAGCAC TATGCGGATA
4601 TTTTATAGGT TAATGTCATG ATAATAATGG TTTCTTAGAC GTCAGGTGGC
     AAAATATCCA ATTACAGTAC TATTATTACC AAAGAATCTG CAGTCCACCG
4651 ACTTTTCGGG GAAATGTGCG CGGAACCCCT ATTTGTTTAT TTTTCTAAAT
     TGAAAAGCCC CTTTACACGC GCCTTGGGGA TAAACAAATA AAAAGATTTA
4701 ACATTCAAAT ATGTATCCGC TCATGAGACA ATAACCCTGA TAAATGCTTC
     TGTAAGTTTA TACATAGGCG AGTACTCTGT TATTGGGACT ATTTACGAAG
4751 AATAATATTG AAAAAGGAAG AGTATGAGTA TTCAACATTT CCGTGTCGCC
     TTATTATAAC TTTTTCCTTC TCATACTCAT AAGTTGTAAA GGCACAGCGG
4801 CTTATTCCCT TTTTTGCGGC ATTTTGCCTT CCTGTTTTTG CTCACCCAGA
     GAATAAGGGA AAAAACGCCG TAAAACGGAA GGACAAAAAC GAGTGGGTCT
4851 AACGCTGGTG AAAGTAAAAG ATGCTGAAGA TCAGTTGGGT GCACGAGTGG
     TTGCGACCAC TTTCATTTTC TACGACTTCT AGTCAACCCA CGTGCTCACC
4901 GTTACATCGA ACTGGATCTC AACAGCGGTA AGATCCTTGA GAGTTTTCGC
     CAATGTAGCT TGACCTAGAG TTGTCGCCAT TCTAGGAACT CTCAAAAGCG
4951 CCCGAAGAAC GTTTTCCAAT GATGAGCACT TTTAAAGTTC TGCTATGTGG
```

Figure 40E

```
      GGGCTTCTTG CAAAAGGTTA CTACTCGTGA AAATTTCAAG ACGATACACC
5001  CGCGGTATTA TCCCGTGTTG ACGCCGGGCA AGAGCAACTC GGTCGCCGCA
      GCGCCATAAT AGGGCACAAC TGCGGCCCGT TCTCGTTGAG CCAGCGGCGT
5051  TACACTATTC TCAGAATGAC TTGGTTGAGT ACTCACCAGT CACAGAAAAG
      ATGTGATAAG AGTCTTACTG AACCAACTCA TGAGTGGTCA GTGTCTTTTC
5101  CATCTTACGG ATGGCATGAC AGTAAGAGAA TTATGCAGTG CTGCCATAAC
      GTAGAATGCC TACCGTACTG TCATTCTCTT AATACGTCAC GACGGTATTG
5151  CATGAGTGAT AACACTGCGG CCAACTTACT TCTGACAACG ATCGGAGGAC
      GTACTCACTA TTGTGACGCC GGTTGAATGA AGACTGTTGC TAGCCTCCTG
5201  CGAAGGAGCT AACCGCTTTT TTGCACAACA TGGGGGATCA TGTAACTCGC
      GCTTCCTCGA TTGGCGAAAA AACGTGTTGT ACCCCCTAGT ACATTGAGCG
5251  CTTGATCGTT GGGAACCGGA GCTGAATGAA GCCATACCAA ACGACGAGCG
      GAACTAGCAA CCCTTGGCCT CGACTTACTT CGGTATGGTT TGCTGCTCGC
5301  TGACACCACG ATGCCTGCAG CAATGGCAAC AACGTTGCGC AAACTATTAA
      ACTGTGGTGC TACGGACGTC GTTACCGTTG TTGCAACGCG TTTGATAATT
5351  CTGGCGAACT ACTTACTCTA GCTTCCCGGC AACAATTAAT AGACTGGATG
      GACCGCTTGA TGAATGAGAT CGAAGGGCCG TTGTTAATTA TCTGACCTAC
5401  GAGGCGGATA AAGTTGCAGG ACCACTTCTG CGCTCGGCCC TTCCGGCTGG
      CTCCGCCTAT TTCAACGTCC TGGTGAAGAC GCGAGCCGGG AAGGCCGACC
                                                  BsaI
                                                ~~~~~~~
5451  CTGGTTTATT GCTGATAAAT CTGGAGCCGG TGAGCGTGGG TCTCGCGGTA
      GACCAAATAA CGACTATTTA GACCTCGGCC ACTCGCACCC AGAGCGCCAT
5501  TCATTGCAGC ACTGGGGCCA GATGGTAAGC CCTCCCGTAT CGTAGTTATC
      AGTAACGTCG TGACCCCGGT CTACCATTCG GGAGGGCATA GCATCAATAG
5551  TACACGACGG GGAGTCAGGC AACTATGGAT GAACGAAATA GACAGATCGC
      ATGTGCTGCC CCTCAGTCCG TTGATACCTA CTTGCTTTAT CTGTCTAGCG
5601  TGAGATAGGT GCCTCACTGA TTAAGCATTG GTAACTGTCA GACCAAGTTT
      ACTCTATCCA CGGAGTGACT AATTCGTAAC CATTGACAGT CTGGTTCAAA
5651  ACTCATATAT ACTTTAGATT GATTTAAAAC TTCATTTTTA ATTTAAAAGG
      TGAGTATATA TGAAATCTAA CTAAATTTTG AAGTAAAAAT TAAATTTTCC
5701  ATCTAGGTGA AGATCCTTTT TGATAATCTC ATGACCAAAA TCCCTTAACG
      TAGATCCACT TCTAGGAAAA ACTATTAGAG TACTGGTTTT AGGGAATTGC
5751  TGAGTTTTCG TTCCACTGAG CGTCAGACCC CGTAGAAAAG ATCAAAGGAT
      ACTCAAAAGC AAGGTGACTC GCAGTCTGGG GCATCTTTTC TAGTTTCCTA
5801  CTTCTTGAGA TCCTTTTTTT CTGCGCGTAA TCTGCTGCTT GCAAACAAAA
      GAAGAACTCT AGGAAAAAAA GACGCGCATT AGACGACGAA CGTTTGTTTT
5851  AAACCACCGC TACCAGCGGT GGTTTGTTTG CCGGATCAAG AGCTACCAAC
      TTTGGTGGCG ATGGTCGCCA CCAAACAAAC GGCCTAGTTC TCGATGGTTG
5901  TCTTTTTCCG AAGGTAACTG GCTTCAGCAG AGCGCAGATA CCAAATACTG
      AGAAAAAGGC TTCCATTGAC CGAAGTCGTC TCGCGTCTAT GGTTTATGAC
5951  TCCTTCTAGT GTAGCCGTAG TTAGGCCACC ACTTCAAGAA CTCTGTAGCA
      AGGAAGATCA CATCGGCATC AATCCGGTGG TGAAGTTCTT GAGACATCGT
6001  CCGCCTACAT ACCTCGCTCT GCTAATCCTG TTACCAGTGG CTGCTGCCAG
      GGCGGATGTA TGGAGCGAGA CGATTAGGAC AATGGTCACC GACGACGGTC
6051  TGGCGATAAG TCGTGTCTTA CCGGGTTGGA CTCAAGACGA TAGTTACCGG
      ACCGCTATTC AGCACAGAAT GGCCCAACCT GAGTTCTGCT ATCAATGGCC
6101  ATAAGGCGCA GCGGTCGGGC TGAACGGGGG GTTCGTGCAC ACAGCCCAGC
      TATTCCGCGT CGCCAGCCCG ACTTGCCCCC CAAGCACGTG TGTCGGGTCG
6151  TTGGAGCGAA CGACCTACAC CGAACTGAGA TACCTACAGC GTGAGCTATG
      AACCTCGCTT GCTGGATGTG GCTTGACTCT ATGGATGTCG CACTCGATAC
```

Figure 40F

```
6201  AGAAAGCGCC ACGCTTCCCG AAGGGAGAAA GGCGGACAGG TATCCGGTAA
      TCTTTCGCGG TGCGAAGGGC TTCCCTCTTT CCGCCTGTCC ATAGGCCATT
6251  GCGGCAGGGT CGGAACAGGA GAGCGCACGA GGGAGCTTCC AGGGGGAAAC
      CGCCGTCCCA GCCTTGTCCT CTCGCGTGCT CCCTCGAAGG TCCCCCTTTG
6301  GCCTGGTATC TTTATAGTCC TGTCGGGTTT CGCCACCTCT GACTTGAGCG
      CGGACCATAG AAATATCAGG ACAGCCCAAA GCGGTGGAGA CTGAACTCGC
6351  TCGATTTTTG TGATGCTCGT CAGGGGGGCG GAGCCTATGG AAAAACGCCA
      AGCTAAAAAC ACTACGAGCA GTCCCCCCGC CTCGGATACC TTTTTGCGGT
6401  GCAACGCGGC CTTTTTACGG TTCCTGGCCT TTTGCTGGCC TTTTGCTCAC
      CGTTGCGCCG GAAAAATGCC AAGGACCGGA AAACGACCGG AAAACGAGTG
6451  ATGTTCTTTC CTGCGTTATC CCCTGATTCT GTGGATAACC GTATTACCGC
      TACAAGAAAG GACGCAATAG GGGACTAAGA CACCTATTGG CATAATGGCG
6501  CTTTGAGTGA GCTGATACCG CTCGCCGCAG CCGAACGACC GAGCGCAGCG
      GAAACTCACT CGACTATGGC GAGCGGCGTC GGCTTGCTGG CTCGCGTCGC
6551  AGTCAGTGAG CGAGGAAGCG GAAGAGCGCC TGATGCGGTA TTTTCTCCTT
      TCAGTCACTC GCTCCTTCGC CTTCTCGCGG ACTACGCCAT AAAAGAGGAA
6601  ACGCATCTGT GCGGTATTTC ACACCGCATA TGGTGCACTC TCAGTACAAT
      TGCGTAGACA CGCCATAAAG TGTGGCGTAT ACCACGTGAG AGTCATGTTA
6651  CTGCTCTGAT GCCGCATAGT TAAGCCAGTA TACACTCCGC TATCGCTACG
      GACGAGACTA CGGCGTATCA ATTCGGTCAT ATGTGAGGCG ATAGCGATGC
6701  TGACTGGGTC ATGGCTGCGC CCCGACACCC GCCAACACCC GCTGACGCGC
      ACTGACCCAG TACCGACGCG GGGCTGTGGG CGGTTGTGGG CGACTGCGCG
                                                          Esp3I
                                                          ~
6751  CCTGACGGGC TTGTCTGCTC CCGGCATCCG CTTACAGACA AGCTGTGACC
      GGACTGCCCG AACAGACGAG GGCCGTAGGC GAATGTCTGT TCGACACTGG
      Esp3I
      ~~~~~
6801  GTCTCCGGGA GCTGCATGTG TCAGAGGTTT TCACCGTCAT CACCGAAACG
      CAGAGGCCCT CGACGTACAC AGTCTCCAAA AGTGGCAGTA GTGGCTTTGC
6851  CGCGAGGCAG GGATC
      GCGCTCCGTC CCTAG
```

Figure 42A

```
1    CCTTGTTACT AGTTAGAAAA AGACATTTTT GCTGTCAGTC ACTGTCAAGA
     GGAACAATGA TCAATCTTTT TCTGTAAAAA CGACAGTCAG TGACAGTTCT
51   GATTCTTTTG CTGGCATTTC TTCTAGAAGC AAAAAGAGCG ATGCGTCTTT
     CTAAGAAAAC GACCGTAAAG AAGATCTTCG TTTTTCTCGC TACGCAGAAA
101  TCCGCTGAAC CGTTCCAGCA AAAAAGACTA CCAACGCAAT ATGGATTGTC
     AGGCGACTTG GCAAGGTCGT TTTTTCTGAT GGTTGCGTTA TACCTAACAG
151  AGAATCATAT AAAAGAGAAG CAAATAACTC CTTGTCTTGT ATCAATTGCA
     TCTTAGTATA TTTTCTCTTC GTTTATTGAG GAACAGAACA TAGTTAACGT
201  TTATAATATC TTCTTGTTAG TGCAATATCA TATAGAAGTC ATCGAAATAG
     AATATTATAG AAGAACAATC ACGTTATAGT ATATCTTCAG TAGCTTTATC
                                      NcoI
                                      ~~~~~~~
251  ATATTAAGAA AAACAAACTG TACAATCCAT GGGTCATCAC CATCATCATC
     TATAATTCTT TTTGTTTGAC ATGTTAGGTA CCCAGTAGTG GTAGTAGTAG
301  ACGGGCAGAT CTTCGTCAAG ACGTTAACCG GTAAAACCAT AACTCTAGAA
     TGCCCGTCTA GAAGCAGTTC TGCAATTGGC CATTTTGGTA TTGAGATCTT
351  GTTGAACCAT CCGATACCAT CGAAAACGTT AAGGCTAAAA TTCAAGACAA
     CAACTTGGTA GGCTATGGTA GCTTTTGCAA TTCCGATTTT AAGTTCTGTT
                                                         XhoI
                                                         ~
401  GGAAGGCATT CCACCTGATC AACAAAGATT GATCTTTGCC GGTAAGCAGC
     CCTTCCGTAA GGTGGACTAG TTGTTTCTAA CTAGAAACGG CCATTCGTCG
     XhoI
     ~~~~~
451  TCGAGGACGG TAGAACGCTG TCTGATTACA ACATTCAGAA GGAGTCGACC
     AGCTCCTGCC ATCTTGCGAC AGACTAATGT TGTAAGTCTT CCTCAGCTGG
501  TTACATCTTG TCTTACGCCT ACGTGGAGGT ATGGAATTCA TGTTACGTCC
     AATGTAGAAC AGAATGCGGA TGCACCTCCA TACCTTAAGT ACAATGCAGG
551  TGTAGAAACC CCAACCCGTG AAATCAAAAA ACTCGACGGC CTGTGGGCAT
     ACATCTTTGG GGTTGGGCAC TTTAGTTTTT TGAGCTGCCG GACACCCGTA
601  TCAGTCTGGA TCGCGAAAAC TGTGGAATTG ATCAGCGTTG GTGGGAAAGC
     AGTCAGACCT AGCGCTTTTG ACACCTTAAC TAGTCGCAAC CACCCTTTCG
651  GCGTTACAAG AAAGCCGGGC AATTGCTGTG CCAGGCAGTT TTAACGATCA
     CGCAATGTTC TTTCGGCCCG TTAACGACAC GGTCCGTCAA AATTGCTAGT
701  GTTCGCCGAT GCAGATATTC GTAATTATGC GGGCAACGTC TGGTATCAGC
     CAAGCGGCTA CGTCTATAAG CATTAATACG CCCGTTGCAG ACCATAGTCG
751  GCGAAGTCTT TATACCGAAA GGTTGGGCAG GCCAGCGTAT CGTGCTGCGT
     CGCTTCAGAA ATATGGCTTT CCAACCCGTC CGGTCGCATA GCACGACGCA
801  TTCGATGCGG TCACTCATTA CGGCAAAGTG TGGGTCAATA ATCAGGAAGT
     AAGCTACGCC AGTGAGTAAT GCCGTTTCAC ACCCAGTTAT TAGTCCTTCA
851  GATGGAGCAT CAGGGCGGCT ATACGCCATT TGAAGCCGAT GTCACGCCGT
     CTACCTCGTA GTCCCGCCGA TATGCGGTAA ACTTCGGCTA CAGTGCGGCA
901  ATGTTATTGC CGGGAAAAGT GTACGTATCA CCGTTTGTGT GAACAACGAA
     TACAATAACG GCCCTTTTCA CATGCATAGT GGCAAACACA CTTGTTGCTT
951  CTGAACTGGC AGACTATCCC GCCGGGAATG GTGATTACCG ACGAAAACGG
     GACTTGACCG TCTGATAGGG CGGCCCTTAC CACTAATGGC TGCTTTTGCC
1001 CAAGAAAAAG CAGTCTTACT TCCATGATTT CTTTAACTAT GCCGGAATCC
     GTTCTTTTTC GTCAGAATGA AGGTACTAAA GAAATTGATA CGGCCTTAGG
1051 ATCGCAGCGT AATGCTCTAC ACCACGCCGA ACACCTGGGT GGACGATATC
     TAGCGTCGCA TTACGAGATG TGGTGCGGCT TGTGGACCCA CCTGCTATAG
```

Figure 42B

```
1101  ACCGTGGTGA CGCATGTCGC GCAAGACTGT AACCACGCGT CTGTTGACTG
      TGGCACCACT GCGTACAGCG CGTTCTGACA TTGGTGCGCA GACAACTGAC
1151  GCAGGTGGTG GCCAATGGTG ATGTCAGCGT TGAACTGCGT GATGCGGATC
      CGTCCACCAC CGGTTACCAC TACAGTCGCA ACTTGACGCA CTACGCCTAG
1201  AACAGGTGGT TGCAACTGGA CAAGGCACTA GCGGGACTTT GCAAGTGGTG
      TTGTCCACCA ACGTTGACCT GTTCCGTGAT CGCCCTGAAA CGTTCACCAC
1251  AATCCGCACC TCTGGCAACC GGGTGAAGGT TATCTCTATG AACTGTGCGT
      TTAGGCGTGG AGACCGTTGG CCCACTTCCA ATAGAGATAC TTGACACGCA
1301  CACAGCCAAA AGCCAGACAG AGTGTGATAT CTACCCGCTT CGCGTCGGCA
      GTGTCGGTTT TCGGTCTGTC TCACACTATA GATGGGCGAA GCGCAGCCGT
1351  TCCGGTCAGT GGCAGTGAAG GGCCAACAGT TCCTGATTAA CCACAAACCG
      AGGCCAGTCA CCGTCACTTC CCGGTTGTCA AGGACTAATT GGTGTTTGGC
1401  TTCTACTTTA CTGGCTTTGG TCGTCATGAA GATGCGGACT TACGTGGCAA
      AAGATGAAAT GACCGAAACC AGCAGTACTT CTACGCCTGA ATGCACCGTT
1451  AGGATTCGAT AACGTGCTGA TGGTGCACGA CCACGCATTA ATGGACTGGA
      TCCTAAGCTA TTGCACGACT ACCACGTGCT GGTGCGTAAT TACCTGACCT
1501  TTGGGGCCAA CTCCTACCGT ACCTCGCATT ACCCTTACGC TGAAGAGATG
      AACCCCGGTT GAGGATGGCA TGGAGCGTAA TGGGAATGCG ACTTCTCTAC
1551  CTCGACTGGG CAGATGAACA TGGCATCGTG GTGATTGATG AAACTGCTGC
      GAGCTGACCC GTCTACTTGT ACCGTAGCAC CACTAACTAC TTTGACGACG
1601  TGTCGGCTTT AACCTCTCTT TAGGCATTGG TTTCGAAGCG GGCAACAAGC
      ACAGCCGAAA TTGGAGAGAA ATCCGTAACC AAAGCTTCGC CCGTTGTTCG
1651  CGAAAGAACT GTACAGCGAA GAGGCAGTCA ACGGGGAAAC TCAGCAAGCG
      GCTTTCTTGA CATGTCGCTT CTCCGTCAGT TGCCCCTTTG AGTCGTTCGC
1701  CACTTACAGG CGATTAAAGA GCTGATAGCG CGTGACAAAA ACCACCCAAG
      GTGAATGTCC GCTAATTTCT CGACTATCGC GCACTGTTTT TGGTGGGTTC
1751  CGTGGTGATG TGGAGTATTG CCAACGAACC GGATACCCGT CCGCAAGTGC
      GCACCACTAC ACCTCATAAC GGTTGCTTGG CCTATGGGCA GGCGTTCACG
1801  ACGGGAATAT TTCGCCACTG GCGGAAGCAA CGCGTAAACT CGACCCGACG
      TGCCCTTATA AAGCGGTGAC CGCCTTCGTT GCGCATTTGA GCTGGGCTGC
1851  CGTCCGATCA CCTGCGTCAA TGTAATGTTC TGCGACGCTC ACACCGATAC
      GCAGGCTAGT GGACGCAGTT ACATTACAAG ACGCTGCGAG TGTGGCTATG
1901  CATCAGCGAT CTCTTTGATG TGCTGTGCCT GAACCGTTAT TACGGATGGT
      GTAGTCGCTA GAGAAACTAC ACGACACGGA CTTGGCAATA ATGCCTACCA
1951  ATGTCCAAAG CGGCGATTTG GAAACGGCAG AGAAGGTACT GGAAAAAGAA
      TACAGGTTTC GCCGCTAAAC CTTTGCCGTC TCTTCCATGA CCTTTTTCTT
2001  CTTCTGGCCT GGCAGGAGAA ACTGCATCAG CCGATTATCA TCACCGAATA
      GAAGACCGGA CCGTCCTCTT TGACGTAGTC GGCTAATAGT AGTGGCTTAT
2051  CGGCGTGGAT ACGTTAGCCG GGCTGCACTC AATGTACACC GACATGTGGA
      GCCGCACCTA TGCAATCGGC CCGACGTGAG TTACATGTGG CTGTACACCT
2101  GTGAAGAGTA TCAGTGTGCA TGGCTGGATA TGTATCACCG CGTCTTTGAT
      CACTTCTCAT AGTCACACGT ACCGACCTAT ACATAGTGGC GCAGAAACTA
2151  CGCGTCAGCG CCGTCGTCGG TGAACAGGTA TGGAATTTCG CCGATTTTGC
      GCGCAGTCGC GGCAGCAGCC ACTTGTCCAT ACCTTAAAGC GGCTAAAACG
2201  GACCTCGCAA GGCATATTGC GCGTTGGCGG TAACAAGAAA GGGATCTTCA
      CTGGAGCGTT CCGTATAACG CGCAACCGCC ATTGTTCTTT CCCTAGAAGT
2251  CTCGCGACCG CAAACCGAAG TCGGCGGCTT TTCTGCTGCA AAAACGCTGG
      GAGCGCTGGC GTTTGGCTTC AGCCGCCGAA AAGACGACGT TTTTGCGACC
2301  ACTGGCATGA ACTTCGGTGA AAAACCGCAG CAGGGAGGCA AACAATAAGC
      TGACCGTACT TGAAGCCACT TTTTGGCGTC GTCCCTCCGT TTGTTATTCG
                 XhoI
```

Figure 42C

```
                ~~~~~~
2351  TTGCGGCCGC ACTCGAGGAG CTCCCTGGCG AATTGTACCA AGATGGCCTT
      AACGCCGGCG TGAGCTCCTC GAGGGACCGC TTAACATGGT TCTACCGGAA
2401  TGGTGGGTTG AAGAAGGAAA AAGACAGAAA CGACTTAATT ACCTACTTGA
      ACCACCCAAC TTCTTCCTTT TTCTGTCTTT GCTGAATTAA TGGATGAACT
2451  AAAAAGCCTG TGAGTAAACA GGCCCCTTTT CCTTTGTCGA TATCATGTAA
      TTTTTCGGAC ACTCATTTGT CCGGGGAAAA GGAAACAGCT ATAGTACATT
2501  TTAGTTATGT CACGCTTACA TTCACGCCCT CCCCCCACAT CCGCTCTAAC
      AATCAATACA GTGCGAATGT AAGTGCGGGA GGGGGGTGTA GGCGAGATTG
2551  CGAAAAGGAA GGAGTTAGAC AACCTGAAGT CTAGGTCCCT ATTTATTTTT
      GCTTTTCCTT CCTCAATCTG TTGGACTTCA GATCCAGGGA TAAATAAAAA
2601  TTATAGTTAT GTTAGTATTA AGAACGTTAT TTATATTTCA AATTTTTCTT
      AATATCAATA CAATCATAAT TCTTGCAATA AATATAAAGT TTAAAAAGAA
2651  TTTTTTCTGT ACAGACGCGT GTACGCATGT AACATTATAC TGAAAACCTT
      AAAAAAGACA TGTCTGCGCA CATGCGTACA TTGTAATATG ACTTTTGGAA
2701  GCTTGAGAAG GTTTTGGGAC GCTCGAAGGC TTTAATTTGC AAGCTTATCG
      CGAACTCTTC CAAAACCCTG CGAGCTTCCG AAATTAAACG TTCGAATAGC
2751  ATGATAAGCT GTCAAACATG AGAATTCGGT CGAAAAAAGA AAAGGAGAGG
      TACTATTCGA CAGTTTGTAC TCTTAAGCCA GCTTTTTTCT TTTCCTCTCC
2801  GCCAAGAGGG AGGGCATTGG TGACTATTGA GCACGTGAGT ATACGTGATT
      CGGTTCTCCC TCCCGTAACC ACTGATAACT CGTGCACTCA TATGCACTAA
2851  AAGCACACAA AGGCAGCTTG GAGTATGTCT GTTATTAATT TCACAGGTAG
      TTCGTGTGTT TCCGTCGAAC CTCATACAGA CAATAATTAA AGTGTCCATC
2901  TTCTGGTCCA TTGGTGAAAG TTTGCGGCTT GCAGAGCACA GAGGCCGCAG
      AAGACCAGGT AACCACTTTC AAACGCCGAA CGTCTCGTGT CTCCGGCGTC
2951  AATGTGCTCT AGATTCCGAT GCTGACTTGC TGGGTATTAT ATGTGTGCCC
      TTACACGAGA TCTAAGGCTA CGACTGAACG ACCCATAATA TACACACGGG
3001  AATAGAAAGA GAACAATTGA CCCGGTTATT GCAAGGAAAA TTTCAAGTCT
      TTATCTTTCT CTTGTTAACT GGGCCAATAA CGTTCCTTTT AAAGTTCAGA
3051  TGTAAAAGCA TATAAAAATA GTTCAGGCAC TCCGAAATAC TTGGTTGGCG
      ACATTTTCGT ATATTTTTAT CAAGTCCGTG AGGCTTTATG AACCAACCGC
3101  TGTTTCGTAA TCAACCTAAG GAGGATGTTT TGGCTCTGGT CAATGATTAC
      ACAAAGCATT AGTTGGATTC CTCCTACAAA ACCGAGACCA GTTACTAATG
3151  GGCATTGATA TCGTCCAACT GCATGGAGAT GAGTCGTGGC AAGAATACCA
      CCGTAACTAT AGCAGGTTGA CGTACCTCTA CTCAGCACCG TTCTTATGGT
3201  AGAGTTCCTC GGTTTGCCAG TTATTAAAAG ACTCGTATTT CCAAAAGACT
      TCTCAAGGAG CCAAACGGTC AATAATTTTC TGAGCATAAA GGTTTTCTGA
3251  GCAACATACT ACTCAGTGCA GCTTCACAGA AACCTCATTC GTTTATTCCC
      CGTTGTATGA TGAGTCACGT CGAAGTGTCT TTGGAGTAAG CAAATAAGGG
3301  TTGTTTGATT CAGAAGCAGG TGGGACAGGT GAACTTTTGG ATTGGAACTC
      AACAAACTAA GTCTTCGTCC ACCCTGTCCA CTTGAAAACC TAACCTTGAG
3351  GATTTCTGAC TGGGTTGGAA GGCAAGAGAG CCCCGAAAGC TTACATTTTA
      CTAAAGACTG ACCCAACCTT CCGTTCTCTC GGGGCTTTCG AATGTAAAAT
3401  TGTTAGCTGG TGGACTGACG CCAGAAAATG TTGGTGATGC GCTTAGATTA
      ACAATCGACC ACCTGACTGC GGTCTTTTAC AACCACTACG CGAATCTAAT
3451  AATGGCGTTA TTGGTGTTGA TGTAAGCGGA GGTGTGGAGA CAAATGGTGT
      TTACCGCAAT AACCACAACT ACATTCGCCT CCACACCTCT GTTTACCACA
3501  AAAAGACTCT AACAAAATAG CAAATTTCGT CAAAAATGCT AAGAAATAGG
      TTTTCTGAGA TTGTTTTATC GTTTAAAGCA GTTTTTACGA TTCTTTATCC
3551  TTATTACTGA GTAGTATTTA TTTAAGTATT GTTTGTGCAC TTGCCTGCAG
      AATAATGACT CATCATAAAT AAATTCATAA CAAACACGTG AACGGACGTC
```

Figure 42D

```
3601 CTTCTCAATG ATATTCGAAT ACGCTTTGAG GAGATACAGC CTAATATCCG
     GAAGAGTTAC TATAAGCTTA TGCGAAACTC CTCTATGTCG GATTATAGGC
3651 ACAAACTGTT TTACAGATTT ACGATCGTAC TTGTTACCCA TCATTGAATT
     TGTTTGACAA AATGTCTAAA TGCTAGCATG AACAATGGGT AGTAACTTAA
3701 TTGAACATCC GAACCTGGGA GTTTTCCCTG AAACAGATAG TATATTTGAA
     AACTTGTAGG CTTGGACCCT CAAAAGGGAC TTTGTCTATC ATATAAACTT
3751 CCTGTATAAT AATATATAGT CTAGCGCTTT ACGGAAGACA ATGTATGTAT
     GGACATATTA TTATATATCA GATCGCGAAA TGCCTTCTGT TACATACATA
3801 TTCGGTTCCT GGAGAAACTA TTGCATCTAT TGCATAGGTA ATCTTGCACG
     AAGCCAAGGA CCTCTTTGAT AACGTAGATA ACGTATCCAT TAGAACGTGC
3851 TCGCATCCCC GGTTCATTTT CTGCGTTTCC ATCTTGCACT TCAATAGCAT
     AGCGTAGGGG CCAAGTAAAA GACGCAAAGG TAGAACGTGA AGTTATCGTA
3901 ATCTTTGTTA ACGAAGCATC TGTGCTTCAT TTTGTAGAAC AAAAATGCAA
     TAGAAACAAT TGCTTCGTAG ACACGAAGTA AAACATCTTG TTTTTACGTT
3951 CGCGAGAGCG CTAATTTTTC AAACAAAGAA TCTGAGCTGC ATTTTTACAG
     GCGCTCTCGC GATTAAAAAG TTTGTTTCTT AGACTCGACG TAAAAATGTC
4001 AACAGAAATG CAACGCGAAA GCGCTATTTT ACCAACGAAG AATCTGTGCT
     TTGTCTTTAC GTTGCGCTTT CGCGATAAAA TGGTTGCTTC TTAGACACGA
4051 TCATTTTTGT AAAACAAAAA TGCAACGCGA GAGCGCTAAT TTTTCAAACA
     AGTAAAAACA TTTTGTTTTT ACGTTGCGCT CTCGCGATTA AAAAGTTTGT
4101 AAGAATCTGA GCTGCATTTT TACAGAACAG AAATGCAACG CGAGAGCGCT
     TTCTTAGACT CGACGTAAAA ATGTCTTGTC TTTACGTTGC GCTCTCGCGA
4151 ATTTTACCAA CAAAGAATCT ATACTTCTTT TTTGTTCTAC AAAAATGCAT
     TAAAATGGTT GTTTCTTAGA TATGAAGAAA AAACAAGATG TTTTTACGTA
4201 CCCGAGAGCG CTATTTTTCT AACAAAGCAT CTTAGATTAC TTTTTTTCTC
     GGGCTCTCGC GATAAAAAGA TTGTTTCGTA GAATCTAATG AAAAAAAGAG
4251 CTTTGTGCGC TCTATAATGC AGTCTCTTGA TAACTTTTTG CACTGTAGGT
     GAAACACGCG AGATATTACG TCAGAGAACT ATTGAAAAAC GTGACATCCA
4301 CCGTTAAGGT TAGAAGAAGG CTACTTTGGT GTCTATTTTC TCTTCCATAA
     GGCAATTCCA ATCTTCTTCC GATGAAACCA CAGATAAAAG AGAAGGTATT
4351 AAAAAGCCTG ACTCCACTTC CCGCGTTTAC TGATTACTAG CGAAGCTGCG
     TTTTTCGGAC TGAGGTGAAG GGCGCAAATG ACTAATGATC GCTTCGACGC
4401 GGTGCATTTT TTCAAGATAA AGGCATCCCC GATTATATTC TATACCGATG
     CCACGTAAAA AAGTTCTATT TCCGTAGGGG CTAATATAAG ATATGGCTAC
4451 TGGATTGCGC ATACTTTGTG AACAGAAAGT GATAGCGTTG ATGATTCTTC
     ACCTAACGCG TATGAAACAC TTGTCTTTCA CTATCGCAAC TACTAAGAAG
4501 ATTGGTCAGA AAATTATGAA CGGTTTCTTC TATTTTGTCT CTATATACTA
     TAACCAGTCT TTTAATACTT GCCAAAGAAG ATAAAACAGA GATATATGAT
4551 CGTATAGGAA ATGTTTACAT TTTCGTATTG TTTTCGATTC ACTCTATGAA
     GCATATCCTT TACAAATGTA AAAGCATAAC AAAAGCTAAG TGAGATACTT
4601 TAGTTCTTAC TACAATTTTT TTGTCTAAAG AGTAATACTA GAGATAAACA
     ATCAAGAATG ATGTTAAAAA AACAGATTTC TCATTATGAT CTCTATTTGT
4651 TAAAAAATGT AGAGGTCGAG TTTAGATGCA AGTTCAAGGA GCGAAAGGTG
     ATTTTTTACA TCTCCAGCTC AAATCTACGT TCAAGTTCCT CGCTTTCCAC
4701 GATGGGTAGG TTATATAGGG ATATAGCACA GAGATATATA GCAAAGAGAT
     CTACCCATCC AATATATCCC TATATCGTGT CTCTATATAT CGTTTCTCTA
4751 ACTTTTGAGC AATGTTTGTG GAAGCGGTAT TCGCAATATT TTAGTAGCTC
     TGAAAACTCG TTACAAACAC CTTCGCCATA AGCGTTATAA AATCATCGAG
4801 GTTACAGTCC GGTGCGTTTT TGGTTTTTTG AAAGTGCGTC TTCAGAGCGC
     CAATGTCAGG CCACGCAAAA ACCAAAAAAC TTTCACGCAG AAGTCTCGCG
4851 TTTTGGTTTT CAAAAGCGCT CTGAAGTTCC TATACTTTCT AGAGAATAGG
```

Figure 42E

```
      AAAACCAAAA GTTTTCGCGA GACTTCAAGG ATATGAAAGA TCTCTTATCC
4901  AACTTCGGAA TAGGAACTTC AAAGCGTTTC CGAAAACGAG CGCTTCCGAA
      TTGAAGCCTT ATCCTTGAAG TTTCGCAAAG GCTTTTGCTC GCGAAGGCTT
4951  AATGCAACGC GAGCTGCGCA CATACAGCTC ACTGTTCACG TCGCACCTAT
      TTACGTTGCG CTCGACGCGT GTATGTCGAG TGACAAGTGC AGCGTGGATA
5001  ATCTGCGTGT TGCCTGTATA TATATATACA TGAGAAGAAC GGCATAGTGC
      TAGACGCACA ACGGACATAT ATATATATGT ACTCTTCTTG CCGTATCACG
5051  GTGTTTATGC TTAAATGCGT ACTTATATGC GTCTATTTAT GTAGGATGAA
      CACAAATACG AATTTACGCA TGAATATACG CAGATAAATA CATCCTACTT
5101  AGGTAGTCTA GTACCTCCTG TGATATTATC CCATTCCATG CGGGGTATCG
      TCCATCAGAT CATGGAGGAC ACTATAATAG GGTAAGGTAC GCCCCATAGC
5151  TATGCTTCCT TCAGCACTAC CCTTTAGCTG TTCTATATGC TGCCACTCCT
      ATACGAAGGA AGTCGTGATG GGAAATCGAC AAGATATACG ACGGTGAGGA
5201  CAATTGGATT AGTCTCATCC TTCAATGCTA TCATTTCCTT TGATATTGGA
      GTTAACCTAA TCAGAGTAGG AAGTTACGAT AGTAAAGGAA ACTATAACCT
5251  TCATATGCAT AGTACCGAGA AACTAGTGCG AAGTAGTGAT CAGGTATTGC
      AGTATACGTA TCATGGCTCT TTGATCACGC TTCATCACTA GTCCATAACG
5301  TGTTATCTGA TGAGTATACG TTGTCCTGGC CACGGCAGAA GCACGCTTAT
      ACAATAGACT ACTCATATGC AACAGGACCG GTGCCGTCTT CGTGCGAATA
5351  CGCTCCAATT TCCCACAACA TTAGTCAACT CCGTTAGGCC CTTCATTGAA
      GCGAGGTTAA AGGGTGTTGT AATCAGTTGA GGCAATCCGG GAAGTAACTT
5401  AGAAATGAGG TCATCAAATG TCTTCCAATG TGAGATTTTG GGCCATTTTT
      TCTTTACTCC AGTAGTTTAC AGAAGGTTAC ACTCTAAAAC CCGGTAAAAA
5451  TATAGCAAAG ATTGAATAAG GCGCATTTTT CTTCAAAGCT TTATTGTACG
      ATATCGTTTC TAACTTATTC CGCGTAAAAA GAAGTTTCGA AATAACATGC
5501  ATCTGACTAA GTTATCTTTT AATAATTGGT ATTCCTGTTT ATTGCTTGAA
      TAGACTGATT CAATAGAAAA TTATTAACCA TAAGGACAAA TAACGAACTT
5551  GAATTGCCGG TCCTATTTAC TCGTTTTAGG ACTGGTTCAG AATTCTTGAA
      CTTAACGGCC AGGATAAATG AGCAAAATCC TGACCAAGTC TTAAGAACTT
5601  GACGAAAGGG CCTCGTGATA CGCCTATTTT TATAGGTTAA TGTCATGATA
      CTGCTTTCCC GGAGCACTAT GCGGATAAAA ATATCCAATT ACAGTACTAT
5651  ATAATGGTTT CTTAGACGTC AGGTGGCACT TTTCGGGGAA ATGTGCGCGG
      TATTACCAAA GAATCTGCAG TCCACCGTGA AAAGCCCCTT TACACGCGCC
5701  AACCCCTATT TGTTTATTTT TCTAAATACA TTCAAATATG TATCCGCTCA
      TTGGGGATAA ACAAATAAAA AGATTTATGT AAGTTTATAC ATAGGCGAGT
5751  TGAGACAATA ACCCTGATAA ATGCTTCAAT AATATTGAAA AAGGAAGAGT
      ACTCTGTTAT TGGGACTATT TACGAAGTTA TTATAACTTT TTCCTTCTCA
5801  ATGAGTATTC AACATTTCCG TGTCGCCCTT ATTCCCTTTT TTGCGGCATT
      TACTCATAAG TTGTAAAGGC ACAGCGGGAA TAAGGGAAAA AACGCCGTAA
5851  TTGCCTTCCT GTTTTTGCTC ACCCAGAAAC GCTGGTGAAA GTAAAAGATG
      AACGGAAGGA CAAAAACGAG TGGGTCTTTG CGACCACTTT CATTTTCTAC
5901  CTGAAGATCA GTTGGGTGCA CGAGTGGGTT ACATCGAACT GGATCTCAAC
      GACTTCTAGT CAACCCACGT GCTCACCCAA TGTAGCTTGA CCTAGAGTTG
5951  AGCGGTAAGA TCCTTGAGAG TTTTCGCCCC GAAGAACGTT TTCCAATGAT
      TCGCCATTCT AGGAACTCTC AAAAGCGGGG CTTCTTGCAA AAGGTTACTA
6001  GAGCACTTTT AAAGTTCTGC TATGTGGCGC GGTATTATCC CGTGTTGACG
      CTCGTGAAAA TTTCAAGACG ATACACCGCG CCATAATAGG GCACAACTGC
6051  CCGGGCAAGA GCAACTCGGT CGCCGCATAC ACTATTCTCA GAATGACTTG
      GGCCCGTTCT CGTTGAGCCA GCGGCGTATG TGATAAGAGT CTTACTGAAC
6101  GTTGAGTACT CACCAGTCAC AGAAAAGCAT CTTACGGATG GCATGACAGT
      CAACTCATGA GTGGTCAGTG TCTTTTCGTA GAATGCCTAC CGTACTGTCA
```

Figure 42F

```
6151  AAGAGAATTA TGCAGTGCTG CCATAACCAT GAGTGATAAC ACTGCGGCCA
      TTCTCTTAAT ACGTCACGAC GGTATTGGTA CTCACTATTG TGACGCCGGT
6201  ACTTACTTCT GACAACGATC GGAGGACCGA AGGAGCTAAC CGCTTTTTTG
      TGAATGAAGA CTGTTGCTAG CCTCCTGGCT TCCTCGATTG GCGAAAAAAC
6251  CACAACATGG GGGATCATGT AACTCGCCTT GATCGTTGGG AACCGGAGCT
      GTGTTGTACC CCCTAGTACA TTGAGCGGAA CTAGCAACCC TTGGCCTCGA
6301  GAATGAAGCC ATACCAAACG ACGAGCGTGA CACCACGATG CCTGCAGCAA
      CTTACTTCGG TATGGTTTGC TGCTCGCACT GTGGTGCTAC GGACGTCGTT
6351  TGGCAACAAC GTTGCGCAAA CTATTAACTG GCGAACTACT TACTCTAGCT
      ACCGTTGTTG CAACGCGTTT GATAATTGAC CGCTTGATGA ATGAGATCGA
6401  TCCCGGCAAC AATTAATAGA CTGGATGGAG GCGGATAAAG TTGCAGGACC
      AGGGCCGTTG TTAATTATCT GACCTACCTC CGCCTATTTC AACGTCCTGG
6451  ACTTCTGCGC TCGGCCCTTC CGGCTGGCTG GTTTATTGCT GATAAATCTG
      TGAAGACGCG AGCCGGGAAG GCCGACCGAC CAAATAACGA CTATTTAGAC
                     BsaI
                   ~~~~~~~
6501  GAGCCGGTGA GCGTGGGTCT CGCGGTATCA TTGCAGCACT GGGGCCAGAT
      CTCGGCCACT CGCACCCAGA GCGCCATAGT AACGTCGTGA CCCCGGTCTA
6551  GGTAAGCCCT CCCGTATCGT AGTTATCTAC ACGACGGGGA GTCAGGCAAC
      CCATTCGGGA GGGCATAGCA TCAATAGATG TGCTGCCCCT CAGTCCGTTG
6601  TATGGATGAA CGAAATAGAC AGATCGCTGA GATAGGTGCC TCACTGATTA
      ATACCTACTT GCTTTATCTG TCTAGCGACT CTATCCACGG AGTGACTAAT
6651  AGCATTGGTA ACTGTCAGAC CAAGTTTACT CATATATACT TTAGATTGAT
      TCGTAACCAT TGACAGTCTG GTTCAAATGA GTATATATGA AATCTAACTA
6701  TTAAAACTTC ATTTTTAATT TAAAAGGATC TAGGTGAAGA TCCTTTTTGA
      AATTTTGAAG TAAAAATTAA ATTTTCCTAG ATCCACTTCT AGGAAAAACT
6751  TAATCTCATG ACCAAAATCC CTTAACGTGA GTTTTCGTTC CACTGAGCGT
      ATTAGAGTAC TGGTTTTAGG GAATTGCACT CAAAAGCAAG GTGACTCGCA
6801  CAGACCCCGT AGAAAAGATC AAAGGATCTT CTTGAGATCC TTTTTTTCTG
      GTCTGGGGCA TCTTTTCTAG TTTCCTAGAA GAACTCTAGG AAAAAAAGAC
6851  CGCGTAATCT GCTGCTTGCA AACAAAAAAA CCACCGCTAC CAGCGGTGGT
      GCGCATTAGA CGACGAACGT TTGTTTTTTT GGTGGCGATG GTCGCCACCA
6901  TTGTTTGCCG GATCAAGAGC TACCAACTCT TTTTCCGAAG GTAACTGGCT
      AACAAACGGC CTAGTTCTCG ATGGTTGAGA AAAAGGCTTC CATTGACCGA
6951  TCAGCAGAGC GCAGATACCA AATACTGTCC TTCTAGTGTA GCCGTAGTTA
      AGTCGTCTCG CGTCTATGGT TTATGACAGG AAGATCACAT CGGCATCAAT
7001  GGCCACCACT TCAAGAACTC TGTAGCACCG CCTACATACC TCGCTCTGCT
      CCGGTGGTGA AGTTCTTGAG ACATCGTGGC GGATGTATGG AGCGAGACGA
7051  AATCCTGTTA CCAGTGGCTG CTGCCAGTGG CGATAAGTCG TGTCTTACCG
      TTAGGACAAT GGTCACCGAC GACGGTCACC GCTATTCAGC ACAGAATGGC
7101  GGTTGGACTC AAGACGATAG TTACCGGATA AGGCGCAGCG GTCGGGCTGA
      CCAACCTGAG TTCTGCTATC AATGGCCTAT TCCGCGTCGC CAGCCCGACT
7151  ACGGGGGGTT CGTGCACACA GCCCAGCTTG GAGCGAACGA CCTACACCGA
      TGCCCCCCAA GCACGTGTGT CGGGTCGAAC CTCGCTTGCT GGATGTGGCT
7201  ACTGAGATAC CTACAGCGTG AGCTATGAGA AAGCGCCACG CTTCCCGAAG
      TGACTCTATG GATGTCGCAC TCGATACTCT TTCGCGGTGC GAAGGGCTTC
7251  GGAGAAAGGC GGACAGGTAT CCGGTAAGCG GCAGGGTCGG AACAGGAGAG
      CCTCTTTCCG CCTGTCCATA GGCCATTCGC CGTCCCAGCC TTGTCCTCTC
7301  CGCACGAGGG AGCTTCCAGG GGGAAACGCC TGGTATCTTT ATAGTCCTGT
      GCGTGCTCCC TCGAAGGTCC CCCTTTGCGG ACCATAGAAA TATCAGGACA
7351  CGGGTTTCGC CACCTCTGAC TTGAGCGTCG ATTTTTGTGA TGCTCGTCAG
```

Figure 42G

```
      GCCCAAAGCG GTGGAGACTG AACTCGCAGC TAAAAACACT ACGAGCAGTC
7401  GGGGGCGGAG CCTATGGAAA AACGCCAGCA ACGCGGCCTT TTTACGGTTC
      CCCCCGCCTC GGATACCTTT TTGCGGTCGT TGCGCCGGAA AAATGCCAAG
7451  CTGGCCTTTT GCTGGCCTTT TGCTCACATG TTCTTTCCTG CGTTATCCCC
      GACCGGAAAA CGACCGGAAA ACGAGTGTAC AAGAAAGGAC GCAATAGGGG
7501  TGATTCTGTG GATAACCGTA TTACCGCCTT TGAGTGAGCT GATACCGCTC
      ACTAAGACAC CTATTGGCAT AATGGCGGAA ACTCACTCGA CTATGGCGAG
7551  GCCGCAGCCG AACGACCGAG CGCAGCGAGT CAGTGAGCGA GGAAGCGGAA
      CGGCGTCGGC TTGCTGGCTC GCGTCGCTCA GTCACTCGCT CCTTCGCCTT
7601  GAGCGCCTGA TGCGGTATTT TCTCCTTACG CATCTGTGCG GTATTTCACA
      CTCGCGGACT ACGCCATAAA AGAGGAATGC GTAGACACGC CATAAAGTGT
7651  CCGCATATGG TGCACTCTCA GTACAATCTG CTCTGATGCC GCATAGTTAA
      GGCGTATACC ACGTGAGAGT CATGTTAGAC GAGACTACGG CGTATCAATT
7701  GCCAGTATAC ACTCCGCTAT CGCTACGTGA CTGGGTCATG GCTGCGCCCC
      CGGTCATATG TGAGGCGATA GCGATGCACT GACCCAGTAC CGACGCGGGG
7751  GACACCCGCC AACACCCGCT GACGCGCCCT GACGGGCTTG TCTGCTCCCG
      CTGTGGGCGG TTGTGGGCGA CTGCGCGGGA CTGCCCGAAC AGACGAGGGC
                                  Esp3I
                                  ~~~~~~~
7801  GCATCCGCTT ACAGACAAGC TGTGACCGTC TCCGGGAGCT GCATGTGTCA
      CGTAGGCGAA TGTCTGTTCG ACACTGGCAG AGGCCCTCGA CGTACACAGT
7851  GAGGTTTTCA CCGTCATCAC CGAAACGCGC GAGGCAGGGA TCCG
      CTCCAAAAGT GGCAGTAGTG GCTTTGCGCG CTCCGTCCCT AGGC
```

Figure 44A

```
   1  ATCATGGAGA TAATTAAAAT GATAACCATC TCGCAAATAA ATAAGTATTT
      TAGTACCTCT ATTAATTTTA CTATTGGTAG AGCGTTTATT TATTCATAAA
  51  TACTGTTTTC GTAACAGTTT TGTAATAAAA AAACCTATAA ATATTCCGGA
      ATGACAAAAG CATTGTCAAA ACATTATTTT TTTGGATATT TATAAGGCCT
 101  TTATTCATAC CGTCCCACCA TCGGGCGCGA TGGGTCATCA CCATCATCAT
      AATAAGTATG GCAGGGTGGT AGCCCGCGCT ACCCAGTAGT GGTAGTAGTA
 151  CACGGGTCGG ACTCAGAAGT CAATCAAGAA GCTAAGCCAG AGGTCAAGCC
      GTGCCCAGCC TGAGTCTTCA GTTAGTTCTT CGATTCGGTC TCCAGTTCGG
 201  AGAAGTCAAG CCTGAGACTC ACATCAATTT AAAGGTGTCC GATGGATCTT
      TCTTCAGTTC GGACTCTGAG TGTAGTTAAA TTTCCACAGG CTACCTAGAA
 251  CAGAGATCTT CTTCAAGATC AAAAAGACCA CTCCTTTAAG AAGGCTGATG
      GTCTCTAGAA GAAGTTCTAG TTTTTCTGGT GAGGAAATTC TTCCGACTAC
 301  GAAGCGTTCG CTAAAAGACA GGGTAAGGAA ATGGACTCCT TAAGATTCTT
      CTTCGCAAGC GATTTTCTGT CCCATTCCTT TACCTGAGGA ATTCTAAGAA
 351  GTACGACGGT ATTAGAATTC AAGCTGATCA GACCCCTGAA GATTTGGACA
      CATGCTGCCA TAATCTTAAG TTCGACTAGT CTGGGGACTT CTAAACCTGT
 401  TGGAGGATAA CGATATTATT GAGGCTCACC GCGAACAGAT TGGAGGTATG
      ACCTCCTATT GCTATAATAA CTCCGAGTGG CGCTTGTCTA ACCTCCATAC
 451  GTGAGCAAGG GCGAGGAGCT GTTCACCGGG GTGGTGCCCA TCCTGGTCGA
      CACTCGTTCC CGCTCCTCGA CAAGTGGCCC CACCACGGGT AGGACCAGCT
 501  GCTGGACGGC GACGTAAACG GCCACAAGTT CAGCGTGTCC GGCGAGGGCG
      CGACCTGCCG CTGCATTTGC CGGTGTTCAA GTCGCACAGG CCGCTCCCGC
 551  AGGGCGATGC CACCTACGGC AAGCTGACCC TGAAGTTCAT CTGCACCACC
      TCCCGCTACG GTGGATGCCG TTCGACTGGG ACTTCAAGTA GACGTGGTGG
 601  GGCAAGCTGC CCGTGCCCTG GCCCACCCTC GTGACCACCC TGACCTACGG
      CCGTTCGACG GGCACGGGAC CGGGTGGGAG CACTGGTGGG ACTGGATGCC
 651  CGTGCAGTGC TTCAGCCGCT ACCCCGACCA CATGAAGCAG CACGACTTCT
      GCACGTCACG AAGTCGGCGA TGGGGCTGGT GTACTTCGTC GTGCTGAAGA
 701  TCAAGTCCGC CATGCCCGAA GGCTACGTCC AGGAGCGCAC CATCTTCTTC
      AGTTCAGGCG GTACGGGCTT CCGATGCAGG TCCTCGCGTG GTAGAAGAAG
 751  AAGGACGACG GCAACTACAA GACCCGCGCC GAGGTGAAGT TCGAGGGCGA
      TTCCTGCTGC CGTTGATGTT CTGGGCGCGG CTCCACTTCA AGCTCCCGCT
 801  CACCCTGGTG AACCGCATCG AGCTGAAGGG CATCGACTTC AAGGAGGACG
      GTGGGACCAC TTGGCGTAGC TCGACTTCCC GTAGCTGAAG TTCCTCCTGC
 851  GCAACATCCT GGGGCACAAG CTGGAGTACA ACTACAACAG CCACAACGTC
      CGTTGTAGGA CCCCGTGTTC GACCTCATGT TGATGTTGTC GGTGTTGCAG
 901  TATATCATGG CCGACAAGCA GAAGAACGGC ATCAAGGTGA ACTTCAAGAT
      ATATAGTACC GGCTGTTCGT CTTCTTGCCG TAGTTCCACT TGAAGTTCTA
 951  CCGCCACAAC ATCGAGGACG GCAGCGTGCA GCTCGCCGAC CACTACCAGC
      GGCGGTGTTG TAGCTCCTGC CGTCGCACGT CGAGCGGCTG GTGATGGTCG
1001  AGAACACCCC CATCGGCGAC GGCCCCGTGC TGCTGCCCGA CAACCACTAC
      TCTTGTGGGG GTAGCCGCTG CCGGGGCACG ACGACGGGCT GTTGGTGATG
1051  CTGAGCACCC AGTCCGCCCT GAGCAAAGAC CCCAACGAGA AGCGCGATCA
      GACTCGTGGG TCAGGCGGGA CTCGTTTCTG GGGTTGCTCT TCGCGCTAGT
1101  CATGGTCCTG CTGGAGTTCG TGACCGCCGC CGGGATCACT CTCGGCATGG
      GTACCAGGAC GACCTCAAGC ACTGGCGGCG GCCCTAGTGA GAGCCGTACC
                                  Esp3I
                                 ~~~~~~~
1151  ACGAGCTGTA CAAGTAATGA GACGGAATTC AAAGGCCTAC GTCGACGAGC
      TGCTCGACAT GTTCATTACT CTGCCTTAAG TTTCCGGATG CAGCTGCTCG
```

Figure 44B

```
                                    XbaI           XhoI
                                   ~~~~~~~        ~~~~~~~
1201 TCACTAGTCG CGGCCGCTTT CGAATCTAGA GCCTGCAGTC TCGAGGCATG
     AGTGATCAGC GCCGGCGAAA GCTTAGATCT CGGACGTCAG AGCTCCGTAC
            HindIII
            ~~~~~~~
1251 CGGTACCAAG CTTGTCGAGA AGTACTAGAG GATCATAATC AGCCATACCA
     GCCATGGTTC GAACAGCTCT TCATGATCTC CTAGTATTAG TCGGTATGGT
1301 CATTTGTAGA GGTTTTACTT GCTTTAAAAA ACCTCCCACA CCTCCCCCTG
     GTAAACATCT CCAAAATGAA CGAAATTTTT TGGAGGGTGT GGAGGGGGAC
1351 AACCTGAAAC ATAAAATGAA TGCAATTGTT GTTGTTAACT TGTTTATTGC
     TTGGACTTTG TATTTTACTT ACGTTAACAA CAACAATTGA ACAAATAACG
1401 AGCTTATAAT GGTTACAAAT AAAGCAATAG CATCACAAAT TTCACAAATA
     TCGAATATTA CCAATGTTTA TTTCGTTATC GTAGTGTTTA AAGTGTTTAT
1451 AAGCATTTTT TTCACTGCAT TCTAGTTGTG GTTTGTCCAA ACTCATCAAT
     TTCGTAAAAA AAGTGACGTA AGATCAACAC CAAACAGGTT TGAGTAGTTA
1501 GTATCTTATC ATGTCTGGAT CTGATCACTG CTTGAGCCTA GGAGATCCGA
     CATAGAATAG TACAGACCTA GACTAGTGAC GAACTCGGAT CCTCTAGGCT
1551 ACCAGATAAG TGAAATCTAG TTCCAAACTA TTTTGTCATT TTTAATTTTC
     TGGTCTATTC ACTTTAGATC AAGGTTTGAT AAAACAGTAA AAATTAAAAG
1601 GTATTAGCTT ACGACGCTAC ACCCAGTTCC CATCTATTTT GTCACTCTTC
     CATAATCGAA TGCTGCGATG TGGGTCAAGG GTAGATAAAA CAGTGAGAAG
1651 CCTAAATAAT CCTTAAAAAC TCCATTTCCA CCCCTCCCAG TTCCCAACTA
     GGATTTATTA GGAATTTTTG AGGTAAAGGT GGGGAGGGTC AAGGGTTGAT
1701 TTTTGTCCGC CCACAGCGGG GCATTTTTCT TCCTGTTATG TTTTTAATCA
     AAAACAGGCG GGTGTCGCCC CGTAAAAAGA AGGACAATAC AAAAATTAGT
1751 AACATCCTGC CAACTCCATG TGACAAACCG TCATCTTCGG CTACTTTTTC
     TTGTAGGACG GTTGAGGTAC ACTGTTTGGC AGTAGAAGCC GATGAAAAAG
1801 TCTGTCACAG AATGAAAATT TTTCTGTCAT CTCTTCGTTA TTAATGTTTG
     AGACAGTGTC TTACTTTTAA AAAGACAGTA GAGAAGCAAT AATTACAAAC
1851 TAATTGACTG AATATCAACG CTTATTTGCA GCCTGAATGG CGAATGGGAC
     ATTAACTGAC TTATAGTTGC GAATAAACGT CGGACTTACC GCTTACCCTG
1901 GCGCCCTGTA GCGGCGCATT AAGCGCGGCG GGTGTGGTGG TTACGCGCAG
     CGCGGGACAT CGCCGCGTAA TTCGCGCCGC CCACACCACC AATGCGCGTC
1951 CGTGACCGCT ACACTTGCCA GCGCCCTAGC GCCCGCTCCT TTCGCTTTCT
     GCACTGGCGA TGTGAACGGT CGCGGGATCG CGGGCGAGGA AAGCGAAAGA
2001 TCCCTTCCTT TCTCGCCACG TTCGCCGGCT TTCCCCGTCA AGCTCTAAAT
     AGGGAAGGAA AGAGCGGTGC AAGCGGCCGA AAGGGGCAGT TCGAGATTTA
2051 CGGGGGCTCC CTTTAGGGTT CCGATTTAGT GCTTTACGGC ACCTCGACCC
     GCCCCCGAGG GAAATCCCAA GGCTAAATCA CGAAATGCCG TGGAGCTGGG
2101 CAAAAAACTT GATTAGGGTG ATGGTTCACG TAGTGGGCCA TCGCCCTGAT
     GTTTTTTGAA CTAATCCCAC TACCAAGTGC ATCACCCGGT AGCGGGACTA
2151 AGACGGTTTT TCGCCCTTTG ACGTTGGAGT CCACGTTCTT TAATAGTGGA
     TCTGCCAAAA AGCGGGAAAC TGCAACCTCA GGTGCAAGAA ATTATCACCT
2201 CTCTTGTTCC AAACTGGAAC AACACTCAAC CCTATCTCGG TCTATTCTTT
     GAGAACAAGG TTTGACCTTG TTGTGAGTTG GGATAGAGCC AGATAAGAAA
2251 TGATTTATAA GGGATTTTGC CGATTTCGGC CTATTGGTTA AAAAATGAGC
     ACTAAATATT CCCTAAAACG GCTAAAGCCG GATAACCAAT TTTTTACTCG
2301 TGATTTAACA AAAATTTAAC GCGAATTTTA ACAAAATATT AACGTTTACA
     ACTAAATTGT TTTTAAATTG CGCTTAAAAT TGTTTTATAA TTGCAAATGT
2351 ATTTCAGGTG GCACTTTTCG GGGAAATGTG CGCGGAACCC CTATTTGTTT
```

Figure 44C

```
     TAAAGTCCAC CGTGAAAAGC CCCTTTACAC GCGCCTTGGG GATAAACAAA
2401 ATTTTTCTAA ATACATTCAA ATATGTATCC GCTCATGAGA CAATAACCCT
     TAAAAAGATT TATGTAAGTT TATACATAGG CGAGTACTCT GTTATTGGGA
2451 GATAAATGCT TCAATAATAT TGAAAAAGGA AGAGTATGAG TATTCAACAT
     CTATTTACGA AGTTATTATA ACTTTTTCCT TCTCATACTC ATAAGTTGTA
2501 TTCCGTGTCG CCCTTATTCC CTTTTTTGCG GCATTTTGCC TTCCTGTTTT
     AAGGCACAGC GGGAATAAGG GAAAAAACGC CGTAAAACGG AAGGACAAAA
2551 TGCTCACCCA GAAACGCTGG TGAAAGTAAA AGATGCTGAA GATCAGTTGG
     ACGAGTGGGT CTTTGCGACC ACTTTCATTT TCTACGACTT CTAGTCAACC
2601 GTGCACGAGT GGGTTACATC GAACTGGATC TCAACAGCGG TAAGATCCTT
     CACGTGCTCA CCCAATGTAG CTTGACCTAG AGTTGTCGCC ATTCTAGGAA
2651 GAGAGTTTTC GCCCCGAAGA ACGTTTTCCA ATGATGAGCA CTTTTAAAGT
     CTCTCAAAAG CGGGGCTTCT TGCAAAAGGT TACTACTCGT GAAAATTTCA
2701 TCTGCTATGT GGCGCGGTAT TATCCCGTAT TGACGCCGGG CAAGAGCAAC
     AGACGATACA CCGCGCCATA ATAGGGCATA ACTGCGGCCC GTTCTCGTTG
2751 TCGGTCGCCG CATACACTAT TCTCAGAATG ACTTGGTTGA GTACTCACCA
     AGCCAGCGGC GTATGTGATA AGAGTCTTAC TGAACCAACT CATGAGTGGT
2801 GTCACAGAAA AGCATCTTAC GGATGGCATG ACAGTAAGAG AATTATGCAG
     CAGTGTCTTT TCGTAGAATG CCTACCGTAC TGTCATTCTC TTAATACGTC
2851 TGCTGCCATA ACCATGAGTG ATAACACTGC GGCCAACTTA CTTCTGACAA
     ACGACGGTAT TGGTACTCAC TATTGTGACG CCGGTTGAAT GAAGACTGTT
2901 CGATCGGAGG ACCGAAGGAG CTAACCGCTT TTTTGCACAA CATGGGGGAT
     GCTAGCCTCC TGGCTTCCTC GATTGGCGAA AAAACGTGTT GTACCCCCTA
2951 CATGTAACTC GCCTTGATCG TTGGGAACCG GAGCTGAATG AAGCCATACC
     GTACATTGAG CGGAACTAGC AACCCTTGGC CTCGACTTAC TTCGGTATGG
3001 AAACGACGAG CGTGACACCA CGATGCCTGT AGCAATGGCA ACAACGTTGC
     TTTGCTGCTC GCACTGTGGT GCTACGGACA TCGTTACCGT TGTTGCAACG
3051 GCAAACTATT AACTGGCGAA CTACTTACTC TAGCTTCCCG GCAACAATTA
     CGTTTGATAA TTGACCGCTT GATGAATGAG ATCGAAGGGC CGTTGTTAAT
3101 ATAGACTGGA TGGAGGCGGA TAAAGTTGCA GGACCACTTC TGCGCTCGGC
     TATCTGACCT ACCTCCGCCT ATTTCAACGT CCTGGTGAAG ACGCGAGCCG
3151 CCTTCCGGCT GGCTGGTTTA TTGCTGATAA ATCTGGAGCC GGTGAGCGTG
     GGAAGGCCGA CCGACCAAAT AACGACTATT TAGACCTCGG CCACTCGCAC
       BsaI
     ~~~~~~
3201 GGTCTCGCGG TATCATTGCA GCACTGGGGC CAGATGGTAA GCCCTCCCGT
     CCAGAGCGCC ATAGTAACGT CGTGACCCCG GTCTACCATT CGGGAGGGCA
3251 ATCGTAGTTA TCTACACGAC GGGGAGTCAG GCAACTATGG ATGAACGAAA
     TAGCATCAAT AGATGTGCTG CCCCTCAGTC CGTTGATACC TACTTGCTTT
3301 TAGACAGATC GCTGAGATAG GTGCCTCACT GATTAAGCAT TGGTAACTGT
     ATCTGTCTAG CGACTCTATC CACGGAGTGA CTAATTCGTA ACCATTGACA
3351 CAGACCAAGT TTACTCATAT ATACTTTAGA TTGATTTAAA ACTTCATTTT
     GTCTGGTTCA AATGAGTATA TATGAAATCT AACTAAATTT TGAAGTAAAA
3401 TAATTTAAAA GGATCTAGGT GAAGATCCTT TTTGATAATC TCATGACCAA
     ATTAAATTTT CCTAGATCCA CTTCTAGGAA AAACTATTAG AGTACTGGTT
3451 AATCCCTTAA CGTGAGTTTT CGTTCCACTG AGCGTCAGAC CCCGTAGAAA
     TTAGGGAATT GCACTCAAAA GCAAGGTGAC TCGCAGTCTG GGGCATCTTT
3501 AGATCAAAGG ATCTTCTTGA GATCCTTTTT TTCTGCGCGT AATCTGCTGC
     TCTAGTTTCC TAGAAGAACT CTAGGAAAAA AAGACGCGCA TTAGACGACG
3551 TTGCAAACAA AAAAACCACC GCTACCAGCG GTGGTTTGTT TGCCGGATCA
     AACGTTTGTT TTTTTGGTGG CGATGGTCGC CACCAAACAA ACGGCCTAGT
```

Figure 44D

```
3601 AGAGCTACCA ACTCTTTTTC CGAAGGTAAC TGGCTTCAGC AGAGCGCAGA
     TCTCGATGGT TGAGAAAAAG GCTTCCATTG ACCGAAGTCG TCTCGCGTCT
3651 TACCAAATAC TGTCCTTCTA GTGTAGCCGT AGTTAGGCCA CCACTTCAAG
     ATGGTTTATG ACAGGAAGAT CACATCGGCA TCAATCCGGT GGTGAAGTTC
3701 AACTCTGTAG CACCGCCTAC ATACCTCGCT CTGCTAATCC TGTTACCAGT
     TTGAGACATC GTGGCGGATG TATGGAGCGA GACGATTAGG ACAATGGTCA
3751 GGCTGCTGCC AGTGGCGATA AGTCGTGTCT TACCGGGTTG GACTCAAGAC
     CCGACGACGG TCACCGCTAT TCAGCACAGA ATGGCCCAAC CTGAGTTCTG
3801 GATAGTTACC GGATAAGGCG CAGCGGTCGG GCTGAACGGG GGGTTCGTGC
     CTATCAATGG CCTATTCCGC GTCGCCAGCC CGACTTGCCC CCCAAGCACG
3851 ACACAGCCCA GCTTGGAGCG AACGACCTAC ACCGAACTGA GATACCTACA
     TGTGTCGGGT CGAACCTCGC TTGCTGGATG TGGCTTGACT CTATGGATGT
3901 GCGTGAGCAT TGAGAAAGCG CCACGCTTCC CGAAGGGAGA AAGGCGGACA
     CGCACTCGTA ACTCTTTCGC GGTGCGAAGG GCTTCCCTCT TTCCGCCTGT
3951 GGTATCCGGT AAGCGGCAGG GTCGGAACAG GAGAGCGCAC GAGGGAGCTT
     CCATAGGCCA TTCGCCGTCC CAGCCTTGTC CTCTCGCGTG CTCCCTCGAA
4001 CCAGGGGGAA ACGCCTGGTA TCTTTATAGT CCTGTCGGGT TTCGCCACCT
     GGTCCCCCTT TGCGGACCAT AGAAATATCA GGACAGCCCA AAGCGGTGGA
4051 CTGACTTGAG CGTCGATTTT TGTGATGCTC GTCAGGGGGG CGGAGCCTAT
     GACTGAACTC GCAGCTAAAA ACACTACGAG CAGTCCCCCC GCCTCGGATA
4101 GGAAAAACGC CAGCAACGCG GCCTTTTTAC GGTTCCTGGC CTTTTGCTGG
     CCTTTTTGCG GTCGTTGCGC CGGAAAAATG CCAAGGACCG GAAAACGACC
4151 CCTTTTGCTC ACATGTTCTT TCCTGCGTTA TCCCCTGATT CTGTGGATAA
     GGAAAACGAG TGTACAAGAA AGGACGCAAT AGGGGACTAA GACACCTATT
4201 CCGTATTACC GCCTTTGAGT GAGCTGATAC CGCTCGCCGC AGCCGAACGA
     GGCATAATGG CGGAAACTCA CTCGACTATG GCGAGCGGCG TCGGCTTGCT
4251 CCGAGCGCAG CGAGTCAGTG AGCGAGGAAG CGGAAGAGCG CCTGATGCGG
     GGCTCGCGTC GCTCAGTCAC TCGCTCCTTC GCCTTCTCGC GGACTACGCC
4301 TATTTTCTCC TTACGCATCT GTGCGGTATT TCACACCGCA GACCAGCCGC
     ATAAAAGAGG AATGCGTAGA CACGCCATAA AGTGTGGCGT CTGGTCGGCG
4351 GTAACCTGGC AAAATCGGTT ACGGTTGAGT AATAAATGGA TGCCCTGCGT
     CATTGGACCG TTTTAGCCAA TGCCAACTCA TTATTTACCT ACGGGACGCA
4401 AAGCGGGTGT GGGCGGACAA TAAAGTCTTA AACTGAACAA AATAGATCTA
     TTCGCCCACA CCCGCCTGTT ATTTCAGAAT TTGACTTGTT TTATCTAGAT
4451 AACTATGACA ATAAAGTCTT AAACTAGACA GAATAGTTGT AAACTGAAAT
     TTGATACTGT TATTTCAGAA TTTGATCTGT CTTATCAACA TTTGACTTTA
4501 CAGTCCAGTT ATGCTGTGAA AAAGCATACT GGACTTTTGT TATGGCTAAA
     GTCAGGTCAA TACGACACTT TTTCGTATGA CCTGAAAACA ATACCGATTT
4551 GCAAACTCTT CATTTTCTGA AGTGCAAATT GCCCGTCGTA TTAAAGAGGG
     CGTTTGAGAA GTAAAAGACT TCACGTTTAA CGGGCAGCAT AATTTCTCCC
4601 GCGTGGCCAA GGGCATGGTA AAGACTATAT TCGCGGCGTT GTGACAATTT
     CGCACCGGTT CCCGTACCAT TTCTGATATA AGCGCCGCAA CACTGTTAAA
4651 ACCGAACAAC TCCGCGGCCG GGAAGCCGAT CTCGGCTTGA ACGAATTGTT
     TGGCTTGTTG AGGCGCCGGC CCTTCGGCTA GAGCCGAACT TGCTTAACAA
4701 AGGTGGCGGT ACTTGGGTCG ATATCAAAGT GCATCACTTC TTCCCGTATG
     TCCACCGCCA TGAACCCAGC TATAGTTTCA CGTAGTGAAG AAGGGCATAC
4751 CCCAACTTTG TATAGAGAGC CACTGCGGGA TCGTCACCGT AATCTGCTTG
     GGGTTGAAAC ATATCTCTCG GTGACGCCCT AGCAGTGGCA TTAGACGAAC
4801 CACGTAGATC ACATAAGCAC CAAGCGCGTT GGCCTCATGC TTGAGGAGAT
     GTGCATCTAG TGTATTCGTG GTTCGCGCAA CCGGAGTACG AACTCCTCTA
4851 TGATGAGCGC GGTGGCAATG CCCTGCCTCC GGTGCTCGCC GGAGACTGCG
```

Figure 44E

```
     ACTACTCGCG CCACCGTTAC GGGACGGAGG CCACGAGCGG CCTCTGACGC
4901 AGATCATAGA TATAGATCTC ACTACGCGGC TGCTCAAACC TGGGCAGAAC
     TCTAGTATCT ATATCTAGAG TGATGCGCCG ACGAGTTTGG ACCCGTCTTG
4951 GTAAGCCGCG AGAGCGCCAA CAACCGCTTC TTGGTCGAAG GCAGCAAGCG
     CATTCGGCGC TCTCGCGGTT GTTGGCGAAG AACCAGCTTC CGTCGTTCGC
5001 CGATGAATGT CTTACTACGG AGCAAGTTCC CGAGGTAATC GGAGTCCGGC
     GCTACTTACA GAATGATGCC TCGTTCAAGG GCTCCATTAG CCTCAGGCCG
                                  Esp3I
                                  ~~~~~~
5051 TGATGTTGGG AGTAGGTGGC TACGTCTCCG AACTCACGAC CGAAAAGATC
     ACTACAACCC TCATCCACCG ATGCAGAGGC TTGAGTGCTG GCTTTTCTAG
5101 AAGAGCAGCC CGCATGGATT TGACTTGGTC AGGGCCGAGC CTACATGTGC
     TTCTCGTCGG GCGTACCTAA ACTGAACCAG TCCCGGCTCG GATGTACACG
5151 GAATGATGCC CATACTTGAG CCACCTAACT TTGTTTTAGG GCGACTGCCC
     CTTACTACGG GTATGAACTC GGTGGATTGA AACAAAATCC CGCTGACGGG
5201 TGCTGCGTAA CATCGTTGCT GCTGCGTAAC ATCGTTGCTG CTCCATAACA
     ACGACGCATT GTAGCAACGA CGACGCATTG TAGCAACGAC GAGGTATTGT
5251 TCAAACATCG ACCCACGGCG TAACGCGCTT GCTGCTTGGA TGCCCGAGGC
     AGTTTGTAGC TGGGTGCCGC ATTGCGCGAA CGACGAACCT ACGGGCTCCG
5301 ATAGACTGTA CAAAAAAACA GTCATAACAA GCCATGAAAA CCGCCACTGC
     TATCTGACAT GTTTTTTTGT CAGTATTGTT CGGTACTTTT GGCGGTGACG
5351 GCCGTTACCA CCGCTGCGTT CGGTCAAGGT TCTGGACCAG TTGCGTGAGC
     CGGCAATGGT GGCGACGCAA GCCAGTTCCA AGACCTGGTC AACGCACTCG
5401 GCATACGCTA CTTGCATTAC AGTTTACGAA CCGAACAGGC TTATGTCAAC
     CGTATGCGAT GAACGTAATG TCAAATGCTT GGCTTGTCCG AATACAGTTG
5451 TGGGTTCGTG CCTTCATCCG TTTCCACGGT GTGCGTCACC CGGCAACCTT
     ACCCAAGCAC GGAAGTAGGC AAAGGTGCCA CACGCAGTGG GCCGTTGGAA
5501 GGGCAGCAGC GAAGTCGAGG CATTTCTGTC CTGGCTGGCG AACGAGCGCA
     CCCGTCGTCG CTTCAGCTCC GTAAAGACAG GACCGACCGC TTGCTCGCGT
                BsaI
               ~~~~~~~
5551 AGGTTTCGGT CTCCACGCAT CGTCAGGCAT TGGCGGCCTT GCTGTTCTTC
     TCCAAAGCCA GAGGTGCGTA GCAGTCCGTA ACCGCCGGAA CGACAAGAAG
5601 TACGGCAAGG TGCTGTGCAC GGATCTGCCC TGGCTTCAGG AGATCGGAAG
     ATGCCGTTCC ACGACACGTG CCTAGACGGG ACCGAAGTCC TCTAGCCTTC
5651 ACCTCGGCCG TCGCGGCGCT TGCCGGTGGT GCTGACCCCG GATGAAGTGG
     TGGAGCCGGC AGCGCCGCGA ACGGCCACCA CGACTGGGGC CTACTTCACC
5701 TTCGCATCCT CGGTTTTCTG GAAGGCGAGC ATCGTTTGTT CGCCCAGGAC
     AAGCGTAGGA GCCAAAAGAC CTTCCGCTCG TAGCAAACAA GCGGGTCCTG
5751 TCTAGCTATA GTTCTAGTGG TTGGCTACGT ATACTCCGGA ATATTAATAG
     AGATCGATAT CAAGATCACC AACCGATGCA TATGAGGCCT TATAATTATC
```

Figure 46A

```
   1 ATCCGGATAT AGTTCCTCCT TTCAGCAAAA AACCCCTCAA GACCCGTTTA
     TAGGCCTATA TCAAGGAGGA AAGTCGTTTT TTGGGGAGTT CTGGGCAAAT
  51 GAGGCCCCAA GGGGTTATGC TAGTTATTGC TCAGCGGTGG CAGCAGCCAA
     CTCCGGGGTT CCCCAATACG ATCAATAACG AGTCGCCACC GTCGTCGGTT
 101 CTCAGCTTCC TTTCGGGCTT TGTTAGCAGC CGGATCTCAG TGGTGGTGGT
     GAGTCGAAGG AAAGCCCGAA ACAATCGTCG GCCTAGAGTC ACCACCACCA
                                  HindIII
                                  ~~~~~~
 151 GGTGGTGCTC GAGTGCGGCC GCAAGCTTGT CGACGGAGCT CGAATTCGGA
     CCACCACGAG CTCACGCCGG CGTTCGAACA GCTGCCTCGA GCTTAAGCCT
        BsaI
        ~~~~~~
 201 TCCGGTCTCA ACCTCCAATC TGTTCGCGGT GAGCCTCAAT AATATCGTTA
     AGGCCAGAGT TGGAGGTTAG ACAAGCGCCA CTCGGAGTTA TTATAGCAAT
 251 TCCTCCATGT CCAAATCTTC AGGGGTCTGA TCAGCTTGAA TTCTAATACC
     AGGAGGTACA GGTTTAGAAG TCCCCAGACT AGTCGAACTT AAGATTATGG
 301 GTCGTACAAG AATCTTAAGG AGTCCATTTC CTTACCCTGT CTTTTAGCGA
     CAGCATGTTC TTAGAATTCC TCAGGTAAAG GAATGGGACA GAAAATCGCT
 351 ACGCTTCCAT CAGCCTTCTT AAAGGAGTGG TCTTTTTGAT CTTGAAGAAG
     TGCGAAGGTA GTCGGAAGAA TTTCCTCACC AGAAAAACTA GAACTTCTTC
 401 ATCTCTGAAG ATCCATCGGA CACCTTTAAA TTGATGTGAG TCTCAGGCTT
     TAGAGACTTC TAGGTAGCCT GTGGAAATTT AACTACACTC AGAGTCCGAA
 451 GACTTCTGGC TTGACCTCTG GCTTAGCTTC TTGATTGACT TCTGAGTCCG
     CTGAAGACCG AACTGGAGAC CGAATCGAAG AACTAACTGA AGACTCAGGC
                                     NcoI
                                    ~~~~~~~
 501 ACCCGTGATG ATGATGGTGA TGACCCATGG TATATCTCCT TCTTAAAGTT
     TGGGCACTAC TACTACCACT ACTGGGTACC ATATAGAGGA AGAATTTCAA
                         XbaI
                        ~~~~~~
 551 AAACAAAATT ATTTCTAGAG GGGAATTGTT ATCCGCTCAC AATTCCCCTA
     TTTGTTTTAA TAAAGATCTC CCCTTAACAA TAGGCGAGTG TTAAGGGGAT
 601 TAGTGAGTCG TATTAATTTC GCGGGATCGA GATCTCGATC CTCTACGCCG
     ATCACTCAGC ATAATTAAAG CGCCCTAGCT CTAGAGCTAG GAGATGCGGC
 651 GACGCATCGT GGCCGGCATC ACCGGCGCCA CAGGTGCGGT TGCTGGCGCC
     CTGCGTAGCA CCGGCCGTAG TGGCCGCGGT GTCCACGCCA ACGACCGCGG
 701 TATATCGCCG ACATCACCGA TGGGGAAGAT CGGGCTCGCC ACTTCGGGCT
     ATATAGCGGC TGTAGTGGCT ACCCCTTCTA GCCCGAGCGG TGAAGCCCGA
 751 CATGAGCGCT TGTTTCGGCG TGGGTATGGT GGCAGGCCCC GTGGCCGGGG
     GTACTCGCGA ACAAAGCCGC ACCCATACCA CCGTCCGGGG CACCGGCCCC
 801 GACTGTTGGG CGCCATCTCC TTGCATGCAC CATTCCTTGC GGCGGCGGTG
     CTGACAACCC GCGGTAGAGG AACGTACGTG GTAAGGAACG CCGCCGCCAC
 851 CTCAACGGCC TCAACCTACT ACTGGGCTGC TTCCTAATGC AGGAGTCGCA
     GAGTTGCCGG AGTTGGATGA TGACCCGACG AAGGATTACG TCCTCAGCGT
 901 TAAGGGAGAG CGTCGAGATC CCGGACACCA TCGAATGGCG CAAAACCTTT
     ATTCCCTCTC GCAGCTCTAG GGCCTGTGGT AGCTTACCGC GTTTTGGAAA
 951 CGCGGTATGG CATGATAGCG CCCGGAAGAG AGTCAATTCA GGGTGGTGAA
     GCGCCATACC GTACTATCGC GGGCCTTCTC TCAGTTAAGT CCCACCACTT
1001 TGTGAAACCA GTAACGTTAT ACGATGTCGC AGAGTATGCC GGTGTCTCTT
```

Figure 46B

```
     ACACTTTGGT CATTGCAATA TGCTACAGCG TCTCATACGG CCACAGAGAA
1051 ATCAGACCGT TTCCCGCGTG GTGAACCAGG CCAGCCACGT TTCTGCGAAA
     TAGTCTGGCA AAGGGCGCAC CACTTGGTCC GGTCGGTGCA AAGACGCTTT
1101 ACGCGGGAAA AAGTGGAAGC GGCGATGGCG GAGCTGAATT ACATTCCCAA
     TGCGCCCTTT TTCACCTTCG CCGCTACCGC CTCGACTTAA TGTAAGGGTT
1151 CCGCGTGGCA CAACAACTGG CGGGCAAACA GTCGTTGCTG ATTGGCGTTG
     GGCGCACCGT GTTGTTGACC GCCCGTTTGT CAGCAACGAC TAACCGCAAC
1201 CCACCTCCAG TCTGGCCCTG CACGCGCCGT CGCAAATTGT CGCGGCGATT
     GGTGGAGGTC AGACCGGGAC GTGCGCGGCA GCGTTTAACA GCGCCGCTAA
1251 AAATCTCGCG CCGATCAACT GGGTGCCAGC GTGGTGGTGT CGATGGTAGA
     TTTAGAGCGC GGCTAGTTGA CCCACGGTCG CACCACCACA GCTACCATCT
1301 ACGAAGCGGC GTCGAAGCCT GTAAAGCGGC GGTGCACAAT CTTCTCGCGC
     TGCTTCGCCG CAGCTTCGGA CATTTCGCCG CCACGTGTTA GAAGAGCGCG
1351 AACGCGTCAG TGGGCTGATC ATTAACTATC CGCTGGATGA CCAGGATGCC
     TTGCGCAGTC ACCCGACTAG TAATTGATAG GCGACCTACT GGTCCTACGG
1401 ATTGCTGTGG AAGCTGCCTG CACTAATGTT CCGGCGTTAT TTCTTGATGT
     TAACGACACC TTCGACGGAC GTGATTACAA GGCCGCAATA AAGAACTACA
1451 CTCTGACCAG ACACCCATCA ACAGTATTAT TTTCTCCCAT GAAGACGGTA
     GAGACTGGTC TGTGGGTAGT TGTCATAATA AAAGAGGGTA CTTCTGCCAT
1501 CGCGACTGGG CGTGGAGCAT CTGGTCGCAT TGGGTCACCA GCAAATCGCG
     GCGCTGACCC GCACCTCGTA GACCAGCGTA ACCCAGTGGT CGTTTAGCGC
1551 CTGTTAGCGG GCCCATTAAG TTCTGTCTCG GCGCGTCTGC GTCTGGCTGG
     GACAATCGCC CGGGTAATTC AAGACAGAGC CGCGCAGACG CAGACCGACC
1601 CTGGCATAAA TATCTCACTC GCAATCAAAT TCAGCCGATA GCGGAACGGG
     GACCGTATTT ATAGAGTGAG CGTTAGTTTA AGTCGGCTAT CGCCTTGCCC
1651 AAGGCGACTG GAGTGCCATG TCCGGTTTTC AACAAACCAT GCAAATGCTG
     TTCCGCTGAC CTCACGGTAC AGGCCAAAAG TTGTTTGGTA CGTTTACGAC
1701 AATGAGGGCA TCGTTCCCAC TGCGATGCTG GTTGCCAACG ATCAGATGGC
     TTACTCCCGT AGCAAGGGTG ACGCTACGAC CAACGGTTGC TAGTCTACCG
1751 GCTGGGCGCA ATGCGCGCCA TTACCGAGTC CGGGCTGCGC GTTGGTGCGG
     CGACCCGCGT TACGCGCGGT AATGGCTCAG GCCCGACGCG CAACCACGCC
1801 ATATCTCGGT AGTGGGATAC GACGATACCG AAGACAGCTC ATGTTATATC
     TATAGAGCCA TCACCCTATG CTGCTATGGC TTCTGTCGAG TACAATATAG
1851 CCGCCGTTAA CCACCATCAA ACAGGATTTT CGCCTGCTGG GGCAAACCAG
     GGCGGCAATT GGTGGTAGTT TGTCCTAAAA GCGGACGACC CCGTTTGGTC
1901 CGTGGACCGC TTGCTGCAAC TCTCTCAGGG CCAGGCGGTG AAGGGCAATC
     GCACCTGGCG AACGACGTTG AGAGAGTCCC GGTCCGCCAC TTCCCGTTAG
1951 AGCTGTTGCC CGTCTCACTG GTGAAAAGAA AAACCACCCT GGCGCCCAAT
     TCGACAACGG GCAGAGTGAC CACTTTTCTT TTTGGTGGGA CCGCGGGTTA
2001 ACGCAAACCG CCTCTCCCCG CGCGTTGGCC GATTCATTAA TGCAGCTGGC
     TGCGTTTGGC GGAGAGGGGC GCGCAACCGG CTAAGTAATT ACGTCGACCG
2051 ACGACAGGTT TCCCGACTGG AAAGCGGGCA GTGAGCGCAA CGCAATTAAT
     TGCTGTCCAA AGGGCTGACC TTTCGCCCGT CACTCGCGTT GCGTTAATTA
2101 GTAAGTTAGC TCACTCATTA GGCACCGGGA TCTCGACCGA TGCCCTTGAG
     CATTCAATCG AGTGAGTAAT CCGTGGCCCT AGAGCTGGCT ACGGGAACTC
2151 AGCCTTCAAC CCAGTCAGCT CCTTCCGGTG GGCGCGGGGC ATGACTATCG
     TCGGAAGTTG GGTCAGTCGA GGAAGGCCAC CCGCGCCCCG TACTGATAGC
2201 TCGCCGCACT TATGACTGTC TTCTTTATCA TGCAACTCGT AGGACAGGTG
     AGCGGCGTGA ATACTGACAG AAGAAATAGT ACGTTGAGCA TCCTGTCCAC
2251 CCGGCAGCGC TCTGGGTCAT TTTCGGCGAG GACCGCTTTC GCTGGAGCGC
     GGCCGTCGCG AGACCCAGTA AAAGCCGCTC CTGGCGAAAG CGACCTCGCG
```

Figure 46C

```
2301 GACGATGATC GGCCTGTCGC TTGCGGTATT CGGAATCTTG CACGCCCTCG
     CTGCTACTAG CCGGACAGCG AACGCCATAA GCCTTAGAAC GTGCGGGAGC
2351 CTCAAGCCTT CGTCACTGGT CCCGCCACCA AACGTTTCGG CGAGAAGCAG
     GAGTTCGGAA GCAGTGACCA GGGCGGTGGT TTGCAAAGCC GCTCTTCGTC
2401 GCCATTATCG CCGGCATGGC GGCCCCACGG GTGCGCATGA TCGTGCTCCT
     CGGTAATAGC GGCCGTACCG CCGGGGTGCC CACGCGTACT AGCACGAGGA
2451 GTCGTTGAGG ACCCGGCTAG GCTGGCGGGG TTGCCTTACT GGTTAGCAGA
     CAGCAACTCC TGGGCCGATC CGACCGCCCC AACGGAATGA CCAATCGTCT
2501 ATGAATCACC GATACGCGAG CGAACGTGAA GCGACTGCTG CTGCAAAACG
     TACTTAGTGG CTATGCGCTC GCTTGCACTT CGCTGACGAC GACGTTTTGC
2551 TCTGCGACCT GAGCAACAAC ATGAATGGTC TTCGGTTTCC GTGTTTCGTA
     AGACGCTGGA CTCGTTGTTG TACTTACCAG AAGCCAAAGG CACAAAGCAT
2601 AAGTCTGGAA ACGCGGAAGT CAGCGCCCTG CACCATTATG TTCCGGATCT
     TTCAGACCTT TGCGCCTTCA GTCGCGGGAC GTGGTAATAC AAGGCCTAGA
2651 GCATCGCAGG ATGCTGCTGG CTACCCTGTG GAACACCTAC ATCTGTATTA
     CGTAGCGTCC TACGACGACC GATGGGACAC CTTGTGGATG TAGACATAAT
2701 ACGAAGCGCT GGCATTGACC CTGAGTGATT TTTCTCTGGT CCCGCCGCAT
     TGCTTCGCGA CCGTAACTGG GACTCACTAA AAAGAGACCA GGGCGGCGTA
2751 CCATACCGCC AGTTGTTTAC CCTCACAACG TTCCAGTAAC CGGGCATGTT
     GGTATGGCGG TCAACAAATG GGAGTGTTGC AAGGTCATTG GCCCGTACAA
2801 CATCATCAGT AACCCGTATC GTGAGCATCC TCTCTCGTTT CATCGGTATC
     GTAGTAGTCA TTGGGCATAG CACTCGTAGG AGAGAGCAAA GTAGCCATAG
2851 ATTACCCCCA TGAACAGAAA TCCCCCTTAC ACGGAGGCAT CAGTGACCAA
     TAATGGGGGT ACTTGTCTTT AGGGGGAATG TGCCTCCGTA GTCACTGGTT
2901 ACAGGAAAAA ACCGCCCTTA ACATGGCCCG CTTTATCAGA AGCCAGACAT
     TGTCCTTTTT TGGCGGGAAT TGTACCGGGC GAAATAGTCT TCGGTCTGTA
2951 TAACGCTTCT GGAGAAACTC AACGAGCTGG ACGCGGATGA ACAGGCAGAC
     ATTGCGAAGA CCTCTTTGAG TTGCTCGACC TGCGCCTACT TGTCCGTCTG
3001 ATCTGTGAAT CGCTTCACGA CCACGCTGAT GAGCTTTACC GCAGCTGCCT
     TAGACACTTA GCGAAGTGCT GGTGCGACTA CTCGAAATGG CGTCGACGGA
3051 CGCGCGTTTC GGTGATGACG GTGAAAACCT CTGACACATG CAGCTCCCGG
     GCGCGCAAAG CCACTACTGC CACTTTTGGA GACTGTGTAC GTCGAGGGCC
3101 AGACGGTCAC AGCTTGTCTG TAAGCGGATG CCGGGAGCAG ACAAGCCCGT
     TCTGCCAGTG TCGAACAGAC ATTCGCCTAC GGCCCTCGTC TGTTCGGGCA
3151 CAGGGCGCGT CAGCGGGTGT TGGCGGGTGT CGGGGCGCAG CCATGACCCA
     GTCCCGCGCA GTCGCCCACA ACCGCCCACA GCCCCGCGTC GGTACTGGGT
3201 GTCACGTAGC GATAGCGGAG TGTATACTGG CTTAACTATG CGGCATCAGA
     CAGTGCATCG CTATCGCCTC ACATATGACC GAATTGATAC GCCGTAGTCT
3251 GCAGATTGTA CTGAGAGTGC ACCATATATG CGGTGTGAAA TACCGCACAG
     CGTCTAACAT GACTCTCACG TGGTATATAC GCCACACTTT ATGGCGTGTC
3301 ATGCGTAAGG AGAAAATACC GCATCAGGCG CTCTTCCGCT TCCTCGCTCA
     TACGCATTCC TCTTTTATGG CGTAGTCCGC GAGAAGGCGA AGGAGCGAGT
3351 CTGACTCGCT GCGCTCGGTC GTTCGGCTGC GGCGAGCGGT ATCAGCTCAC
     GACTGAGCGA CGCGAGCCAG CAAGCCGACG CCGCTCGCCA TAGTCGAGTG
3401 TCAAAGGCGG TAATACGGTT ATCCACAGAA TCAGGGGATA ACGCAGGAAA
     AGTTTCCGCC ATTATGCCAA TAGGTGTCTT AGTCCCCTAT TGCGTCCTTT
3451 GAACATGTGA GCAAAAGGCC AGCAAAAGGC CAGGAACCGT AAAAAGGCCG
     CTTGTACACT CGTTTTCCGG TCGTTTTCCG GTCCTTGGCA TTTTTCCGGC
3501 CGTTGCTGGC GTTTTTCCAT AGGCTCCGCC CCCCTGACGA GCATCACAAA
     GCAACGACCG CAAAAAGGTA TCCGAGGCGG GGGGACTGCT CGTAGTGTTT
3551 AATCGACGCT CAAGTCAGAG GTGGCGAAAC CCGACAGGAC TATAAAGATA
```

Figure. 46D

```
      TTAGCTGCGA GTTCAGTCTC CACCGCTTTG GGCTGTCCTG ATATTTCTAT
3601  CCAGGCGTTT CCCCCTGGAA GCTCCCTCGT GCGCTCTCCT GTTCCGACCC
      GGTCCGCAAA GGGGGACCTT CGAGGGAGCA CGCGAGAGGA CAAGGCTGGG
3651  TGCCGCTTAC CGGATACCTG TCCGCCTTTC TCCCTTCGGG AAGCGTGGCG
      ACGGCGAATG GCCTATGGAC AGGCGGAAAG AGGGAAGCCC TTCGCACCGC
3701  CTTTCTCATA GCTCACGCTG TAGGTATCTC AGTTCGGTGT AGGTCGTTCG
      GAAAGAGTAT CGAGTGCGAC ATCCATAGAG TCAAGCCACA TCCAGCAAGC
3751  CTCCAAGCTG GGCTGTGTGC ACGAACCCCC CGTTCAGCCC GACCGCTGCG
      GAGGTTCGAC CCGACACACG TGCTTGGGGG GCAAGTCGGG CTGGCGACGC
3801  CCTTATCCGG TAACTATCGT CTTGAGTCCA ACCCGGTAAG ACACGACTTA
      GGAATAGGCC ATTGATAGCA GAACTCAGGT TGGGCCATTC TGTGCTGAAT
3851  TCGCCACTGG CAGCAGCCAC TGGTAACAGG ATTAGCAGAG CGAGGTATGT
      AGCGGTGACC GTCGTCGGTG ACCATTGTCC TAATCGTCTC GCTCCATACA
3901  AGGCGGTGCT ACAGAGTTCT TGAAGTGGTG GCCTAACTAC GGCTACACTA
      TCCGCCACGA TGTCTCAAGA ACTTCACCAC CGGATTGATG CCGATGTGAT
3951  GAAGGACAGT ATTTGGTATC TGCGCTCTGC TGAAGCCAGT TACCTTCGGA
      CTTCCTGTCA TAAACCATAG ACGCGAGACG ACTTCGGTCA ATGGAAGCCT
4001  AAAAGAGTTG GTAGCTCTTG ATCCGGCAAA CAAACCACCG CTGGTAGCGG
      TTTTCTCAAC CATCGAGAAC TAGGCCGTTT GTTTGGTGGC GACCATCGCC
4051  TGGTTTTTTT GTTTGCAAGC AGCAGATTAC GCGCAGAAAA AAAGGATCTC
      ACCAAAAAAA CAAACGTTCG TCGTCTAATG CGCGTCTTTT TTTCCTAGAG
4101  AAGAAGATCC TTTGATCTTT TCTACGGGGT CTGACGCTCA GTGGAACGAA
      TTCTTCTAGG AAACTAGAAA AGATGCCCCA GACTGCGAGT CACCTTGCTT
4151  AACTCACGTT AAGGGATTTT GGTCATGAAC AATAAAACTG TCTGCTTACA
      TTGAGTGCAA TTCCCTAAAA CCAGTACTTG TTATTTTGAC AGACGAATGT
4201  TAAACAGTAA TACAAGGGGT GTTATGAGCC ATATTCAACG GGAAACGTCT
      ATTTGTCATT ATGTTCCCCA CAATACTCGG TATAAGTTGC CCTTTGCAGA
4251  TGCTCTAGGC CGCGATTAAA TTCCAACATG GATGCTGATT TATATGGGTA
      ACGAGATCCG GCGCTAATTT AAGGTTGTAC CTACGACTAA ATATACCCAT
4301  TAAATGGGCT CGCGATAATG TCGGGCAATC AGGTGCGACA ATCTATCGAT
      ATTTACCCGA GCGCTATTAC AGCCCGTTAG TCCACGCTGT TAGATAGCTA
4351  TGTATGGGAA GCCCGATGCG CCAGAGTTGT TTCTGAAACA TGGCAAAGGT
      ACATACCCTT CGGGCTACGC GGTCTCAACA AAGACTTTGT ACCGTTTCCA
4401  AGCGTTGCCA ATGATGTTAC AGATGAGATG GTCAGACTAA ACTGGCTGAC
      TCGCAACGGT TACTACAATG TCTACTCTAC CAGTCTGATT TGACCGACTG
4451  GGAATTTATG CCTCTTCCGA CCATCAAGCA TTTTATCCGT ACTCCTGATG
      CCTTAAATAC GGAGAAGGCT GGTAGTTCGT AAAATAGGCA TGAGGACTAC
4501  ATGCATGGTT ACTCACCACT GCGATCCCCG GGAAAACAGC ATTCCAGGTA
      TACGTACCAA TGAGTGGTGA CGCTAGGGGC CCTTTTGTCG TAAGGTCCAT
4551  TTAGAAGAAT ATCCTGATTC AGGTGAAAAT ATTGTTGATG CGCTGGCAGT
      AATCTTCTTA TAGGACTAAG TCCACTTTTA TAACAACTAC GCGACCGTCA
4601  GTTCCTGCGC CGGTTGCATT CGATTCCTGT TTGTAATTGT CCTTTTAACA
      CAAGGACGCG GCCAACGTAA GCTAAGGACA AACATTAACA GGAAAATTGT
4651  GCGATCGCGT ATTTCGTCTC GCTCAGGCGC AATCACGAAT GAATAACGGT
      CGCTAGCGCA TAAAGCAGAG CGAGTCCGCG TTAGTGCTTA CTTATTGCCA
4701  TTGGTTGATG CGAGTGATTT TGATGACGAG CGTAATGGCT GGCCTGTTGA
      AACCAACTAC GCTCACTAAA ACTACTGCTC GCATTACCGA CCGGACAACT
4751  ACAAGTCTGG AAAGAAATGC ATAAACTTTT GCCATTCTCA CCGGATTCAG
      TGTTCAGACC TTTCTTTACG TATTTGAAAA CGGTAAGAGT GGCCTAAGTC
4801  TCGTCACTCA TGGTGATTTC TCACTTGATA ACCTTATTTT TGACGAGGGG
      AGCAGTGAGT ACCACTAAAG AGTGAACTAT TGGAATAAAA ACTGCTCCCC
```

Figure 46E

```
4851 AAATTAATAG GTTGTATTGA TGTTGGACGA GTCGGAATCG CAGACCGATA
     TTTAATTATC CAACATAACT ACAACCTGCT CAGCCTTAGC GTCTGGCTAT
4901 CCAGGATCTT GCCATCCTAT GGAACTGCCT CGGTGAGTTT TCTCCTTCAT
     GGTCCTAGAA CGGTAGGATA CCTTGACGGA GCCACTCAAA AGAGGAAGTA
4951 TACAGAAACG GCTTTTTCAA AAATATGGTA TTGATAATCC TGATATGAAT
     ATGTCTTTGC CGAAAAAGTT TTTATACCAT AACTATTAGG ACTATACTTA
5001 AAATTGCAGT TTCATTTGAT GCTCGATGAG TTTTTCTAAG AATTAATTCA
     TTTAACGTCA AAGTAAACTA CGAGCTACTC AAAAAGATTC TTAATTAAGT
5051 TGAGCGGATA CATATTTGAA TGTATTTAGA AAAATAAACA AATAGGGGTT
     ACTCGCCTAT GTATAAACTT ACATAAATCT TTTTATTTGT TTATCCCCAA
5101 CCGCGCACAT TTCCCCGAAA AGTGCCACCT GAAATTGTAA ACGTTAATAT
     GGCGCGTGTA AAGGGGCTTT TCACGGTGGA CTTTAACATT TGCAATTATA
5151 TTTGTTAAAA TTCGCGTTAA ATTTTTGTTA AATCAGCTCA TTTTTTAACC
     AAACAATTTT AAGCGCAATT TAAAAACAAT TTAGTCGAGT AAAAAATTGG
5201 AATAGGCCGA AATCGGCAAA ATCCCTTATA AATCAAAAGA ATAGACCGAG
     TTATCCGGCT TTAGCCGTTT TAGGGAATAT TTAGTTTTCT TATCTGGCTC
5251 ATAGGGTTGA GTGTTGTTCC AGTTTGGAAC AAGAGTCCAC TATTAAAGAA
     TATCCCAACT CACAACAAGG TCAAACCTTG TTCTCAGGTG ATAATTTCTT
5301 CGTGGACTCC AACGTCAAAG GGCGAAAAAC CGTCTATCAG GGCGATGGCC
     GCACCTGAGG TTGCAGTTTC CCGCTTTTTG GCAGATAGTC CCGCTACCGG
5351 CACTACGTGA ACCATCACCC TAATCAAGTT TTTTGGGGTC GAGGTGCCGT
     GTGATGCACT TGGTAGTGGG ATTAGTTCAA AAAACCCCAG CTCCACGGCA
5401 AAAGCACTAA ATCGGAACCC TAAAGGGAGC CCCCGATTTA GAGCTTGACG
     TTTCGTGATT TAGCCTTGGG ATTTCCCTCG GGGGCTAAAT CTCGAACTGC
5451 GGGAAAGCCG GCGAACGTGG CGAGAAAGGA AGGGAAGAAA GCGAAAGGAG
     CCCTTTCGGC CGCTTGCACC GCTCTTTCCT TCCCTTCTTT CGCTTTCCTC
5501 CGGGCGCTAG GGCGCTGGCA AGTGTAGCGG TCACGCTGCG CGTAACCACC
     GCCCGCGATC CCGCGACCGT TCACATCGCC AGTGCGACGC GCATTGGTGG
5551 ACACCCGCCG CGCTTAATGC GCCGCTACAG GGCGCGTCCC ATTCGCCA
     TGTGGGCGGC GCGAATTACG CGGCGATGTC CCGCGCAGGG TAAGCGGT
```

METHODS AND COMPOSITIONS FOR PROTEIN EXPRESSION AND PURIFICATION

CROSS REFERENCE TO RELATED APPLICATION

This application is a continuation-in-part of U.S. application Ser. No. 10/338,411 filed Jan. 7, 2003, issued as U.S. Pat. No. 7,060,461, which claims priority to U.S. Provisional Application No. 60/346,449 entitled "Methods for Protein Expression and Purification" filed Jan. 7, 2002.

FIELD OF THE INVENTION

The present invention relates to the field of recombinant gene expression and purification of expressed proteins. More specifically, the invention provides materials and methods which facilitate purification of heterologous proteins from a variety of different host species.

BACKGROUND OF THE INVENTION

Several publications and patent documents are cited throughout the specification in order to describe the state of the art to which this invention pertains. Full citations for those references that are numbered can be found at the end of the specification. Each citation is incorporated herein as though set forth in full.

Functional genomic studies have been hampered by the inability to uniformly express and purify biologically active proteins in heterologous expression systems. Despite the use of identical transcriptional and translational signals in a given expression vector, expressed protein levels have been observed to vary dramatically (5, 7). For this reason, several strategies have been developed to express heterologous proteins in bacteria, yeast, mammalian and insect cells as gene-fusions.

The expression of heterologous genes in bacteria is by far the simplest and most inexpensive means available for research or commercial purposes. However, some heterologous gene products fail to attain their correct three-dimensional conformation in *E. coli* while others become sequestered in large insoluble aggregates or "inclusion bodies" when overproduced. Major denaturant-induced solubilization methods followed by removal of the denaturant under conditions that favor refolding are often required to produce a reasonable yield of the recombinant protein. Selection of ORFs for structural genomics projects has also shown that only about 20% of the genes expressed in *E. coli* render proteins that were soluble or correctly folded (36, 38). These numbers are startlingly disappointing especially given that most scientists rely on *E. coli* for initial attempts to express gene products. Several gene fusion systems such as NUS A, maltose binding protein (MBP), glutathione S transferase (GST), and thioredoxin (TRX) have been developed (17). All of these systems have certain drawbacks, ranging from inefficient expression to inconsistent cleavage from desired structure. Comprehensive data showing that a particular fusion is best for a certain family of proteins is not available.

Ubiquitin and ubiquitin like proteins (UBLs) have been described in the literature. The SUMO system has also been characterized. SUMO (small ubiquitin related modifier) is also known as Sentrin, SMT3, PIC1, GMP1 and UBL1. SUMO and the SUMO pathway are present throughout the eukaryotic kingdom and the proteins are highly conserved from yeast to humans (12, 15, 28). SUMO homologues have also been identified in *C. elegans* and plants. SUMO has 18% sequence identity with ubiquitin (28, 39). Yeast has only a single SUMO gene, which has also been termed SMT3 (23, 16). The yeast Smt3 gene is essential for viability (29). In contrast to yeast, three members of SUMO have been described in vertebrates: SUMO-1 and close homologues SUMO-2 and SUMO-3. Human SUMO-1, a 101 amino-acid polypeptide, shares 50% sequence identity with human SUMO-1/SUMO-2 (29). Yeast SUMO (SMT3) shares 47% sequence identity with mammalian SUMO-1. Although overall sequence homology between ubiquitin and SUMO is only 18%, structure determination by nuclear magnetic resonance (NMR) reveals that the two proteins share a common three dimensional structure that is characterized by a tightly packed globular fold with β-sheets wrapped around one α-helix (4). Examination of the chaperoning properties of SUMO reveals that attachment of a tightly packed globular structure to N-termini of proteins can act as nucleus for folding and protect the labile protein. All SUMO genes encode precursor proteins with a short C-terminal sequence that extends from the conserved C-terminal Gly-Gly motif. The extension sequence, 2–12 amino acids in length, is different in all cases. Cells contain potent SUMO proteases that remove the C-terminal extensions. The C-terminus of SUMO is conjugated to E amino groups of lysine residues of target proteins. The similarity of the enzymes of the sumoylation pathway to ubiquitin pathway enzymes is remarkable, given the different effects of these two protein modification pathways. Sumoylation of cellular proteins has been proposed to regulate nuclear transport, signal transduction, stress response, and cell cycle progression (29). It is very likely that SUMO chaperones translocation of proteins among various cell compartments, however, the precise mechanistic details of this function of SUMO are not known.

Other fusions promote solubility of partner proteins presumably due to their large size (e.g., NUS A). Fusion of proteins with glutathione S-transferase (GST) or maltose binding protein (MBP) has been proposed to enhance expression and yield of fusion partners. However, enhanced expression is not always observed when GST is used as GST forms dimers and can retard protein solubility. Another problem with GST or other fusion systems is that the desired protein may have to be removed from the fusion. To circumvent this problem, protease sites, such as factor X, thrombin or Tev protease sites are often engineered downstream of the fusion partner. However, incomplete cleavage and inappropriate cleavage within the fusion protein is often observed. The present invention circumvents these problems.

SUMMARY OF THE INVENTION

In accordance with the present invention compositions and methods for enhancing expression levels of a protein of interest in a host cell are provided. An exemplary method comprises i) operably linking a nucleic acid sequence encoding molecule selected from the group consisting of SUMO, RUB, HUB, APG8, APG12, URM1, and ISG15 to a nucleic acid sequence encoding said protein of interest thereby generating a construct encoding a fusion protein, ii) introducing said nucleic acid into said host cell, whereby the presence of said molecule in said fusion protein increases the expression level of said protein of interest in said host cell. In a preferred embodiment the molecule is SUMO encoded by a nucleic acid of SEQ ID NO: 2. The method optionally entails cleavage of said fusion protein and isolation of the protein of interest.

In yet another embodiment of the invention, an exemplary method for generating a protein of interest having an altered amino terminus is provided. Such a method comprises i) providing a nucleic acid sequence encoding the protein of interest; ii) altering the N-terminal amino acid coding sequence in the nucleic acid; iii) operably linking a SUMO molecule to the nucleic acid sequence; and iv) expressing the nucleic acid in a eukaryotic cell, thereby producing the protein of interest in the cell, wherein the eukaryotic cell expresses endogenous SUMO cleaving enzymes, which effect cleavage of SUMO from the sequence encoding the protein of interest, thereby producing a protein of interest having an altered amino terminus. All amino acids with the exception of proline may be added to the amino terminus using this method.

The invention also provides a method for producing a sumolated protein for tracking protein localization within a host cell. An exemplary method comprises i) providing a nucleic acid sequence encoding said protein; ii) substituting the N-terminal amino acid coding sequence in the nucleic acid for a codon which encodes proline; iii) operably linking a SUMO molecule to said nucleic acid sequence; and iv) expressing said SUMO linked protein in said host cell.

In another aspect of the invention, a method for enhancing secretion levels of a protein of interest from a host cell is provided. Such a method comprises i) operably linking a nucleic acid sequence encoding molecule selected from the group consisting of SUMO, RUB, HUB, URM1, and ISG15 to a nucleic acid sequence encoding said protein of interest thereby generating a construct encoding a fusion protein, ii) introducing said nucleic acid into said host cell, whereby the presence of said molecule in said fusion protein increases the secretion of said protein of interest from said host cell.

In yet a further aspect of the invention, kits are provided for performing the methods described above. Such kits comprise a recombinant vector containing a nucleic acid sequence encoding a UBL molecule selected from the group of SUMO, RUB, HUB, URMl, and ISGl5 operably linked to a promoter suitable for expression in the desired host cell and a multiple cloning site suitable for cloning a nucleic acid encoding the protein of interest. The recombinant vector may also contain a nucleic acid sequence encoding for a purification tag. The kits may further comprise a preparation of a protease capable of cleaving the UBL molecule from the fusion protein, an appropriate solid phase for binding the purification tag, appropriate buffers including wash and cleavage buffers, and frozen stocks of host cells. The host cells may be selected from the group of yeast cells, *E. coli*, insect cells, and mammalian cells.

BRIEF DESCRIPTION OF THE DRAWINGS

FIG. 3 is a circular map of pSUMO, an *E. coli* SUMO expression vector. The nucleic acid sequence provided (SEQ ID NO: 37) encompasses the SUMO encoding region and the multiple cloning site. The amino acid sequence provided (SEQ ID NO: 38) is 6×His tagged SUMO. Restriction enzymes are indicated above their recognition sequence. The pSUMO expression vector has been constructed in the backbone of the pET-24d expression vector (Novagen).

(FIG. 8A) and 20° C. (FIG. 8B). *E. coli* cells expressing a SUMO-fusion of MAPKAP2 kinase were induced with 0.1 (lanes 2–4), 0.25 (lanes 5–7), and 0.5 (lanes 8–10) mM IPTG. The original induction sample (I) in addition to the supernatant (S) and resuspended pellet (P) following lysis and centrifugation were analyzed by SDS-PAGE. The first lanes are BioRad low molecular weight markers.

FIG. 14 is a series of micrographs of eGFP expression in Hi-Five cells infected with different eGFP fusion baculoviruses. Pictures were taken with a Leitz Fluovert Inverted Microscope with excitation at 488 nm with Hammamatsu Orca Cooled CCD camera.

FIG. 15 contains stained SDS-polyacrylamide gels representing the in vitro Ulp1 cleavage of Ni-NTA resin purified His6SUMO-eGFP fusion proteins expressed in *E. coli*. The purified His6SUMO-eGFP fusions, containing a different amino acid at the +1 position of the Ulp1 cleavage site, were incubated at 30° C. for 3 hours with purified Ulp1 hydrolase. The lanes are marked with the single letter code of the +1 amino acid. The negative control (−Ve) is the incubation of His6SUMO-eGFP at 30° C. for 3 hours in the absence of enzyme. Low molecular weight markers (LMW) are also provided.

FIG. 16 contains a pair of stained SDS-polyacrylamide gels representing the effects of various conditions on Ulp1. Ni-NTA purified His6SUMO-GFP was incubated with Ulp1 under the indicated conditions for one hour at room temperature unless indicated otherwise. Low molecular weight markers (LMW) are also provided.

FIG. 23 is the amino acid (SEQ ID NO: 1) and nucleotide (SEQ ID NO: 2) sequences of SUMO.

FIGS. 24A and 24B are the amino acid (SEQ ID NO: 3) and nucleotide (SEQ ID NO: 4) sequences of GFP.

FIGS. 25A and 25B are the amino acid (SEQ ID NO: 5) and nucleotide (SEQ ID NO: 6) sequences of SUMO-GFP.

FIGS. 26A and 26B are the amino acid (SEQ ID NO: 7) and nucleotide (SEQ ID NO: 8) sequences of ubiquitin-GFP.

FIGS. 27A and 27B are the amino acid (SEQ ID NO: 9) and nucleotide (SEQ ID NO: 10) sequences of URM1-GFP.

FIGS. 28A and 28B are the amino acid (SEQ ID NO: 1) and nucleotide (SEQ ID NO: 12) sequences of HUB1-GFP.

FIGS. 29A and 29B are the amino acid (SEQ ID NO: 13) and nucleotide (SEQ ID NO: 14) sequences of RUB1-GFP.

FIGS. 30A and 30B are the amino acid (SEQ ID NO: 15) and nucleotide (SEQ TD NO: 16) sequences of APG8-GFP.

FIGS. 31A and 31B are the amino acid (SEQ ID NO: 17) and nucleotide (SEQ ID NO: 18) sequences of APG12-GFP.

FIGS. 32A and 32B are the amino acid (SEQ ID NO: 19) and nucleotide (SEQ ID NO: 20) sequences of ISG15-GFP.

FIG. 33 is the amino acid (SEQ ID NO: 21) and nucleotide (SEQ ID NO: 22) sequences of SUMO-Protein G.

FIGS. 34A, 34B, and 34C are the amino acid (SEQ ID NO: 23) and nucleotide (SEQ ID NO: 24) sequences of SUMO-β GUS.

FIGS. 35A, 35B, and 35C are the amino acid (SEQ ID NO: 25) and nucleotide (SEQ ID NO: 26) sequences of SUMO-LXRα.

FIGS. 36A and 36B are the amino acid (SEQ ID NO: 27) and nucleotide (SEQ ID NO: 28) sequences of SUMO-Tyrosine Kinase.

FIGS. 37A and 37B are the amino acid (SEQ ID NO: 29) and nucleotide (SEQ ID NO: 30) sequences of SUMO-MPAKAP2 Kinase.

FIGS. 38A, 38B, 38C, 38D, and 38E are the amino acid (SEQ ID NO: 31) and nucleotide (SEQ ID NO: 32) sequences of SUMO-β GAL.

FIGS. 40A, 40B, 40C, 40D, 40E and 40F are the nucleotide sequence (SEQ ID NO: 33) of YEpSUMO-eGFP. Select restriction enzyme sites are indicated.

FIGS. 42A, 42B, 42C, 42D, 42E, 42F, and 42G are the nucleotide sequence (SEQ ID NO: 34) of YEpUbGUS. Select restriction enzyme sites are indicated.

FIGS. 44A, 44B, 44C, 44D, and 44E are the nucleotide sequence (SEQ ID NO: 35) of pFastBac SUMO-eGFP. Select restriction enzyme sites are indicated.

FIGS. 46A, 46B, 46C, 46D, and 46E are the nucleotide sequence (SEQ ID NO: 36) of pSUMO (pET24d6His× SUMO). Select restriction enzyme sites are indicated.

DETAILED DESCRIPTION OF THE INVENTION

Figure 1:
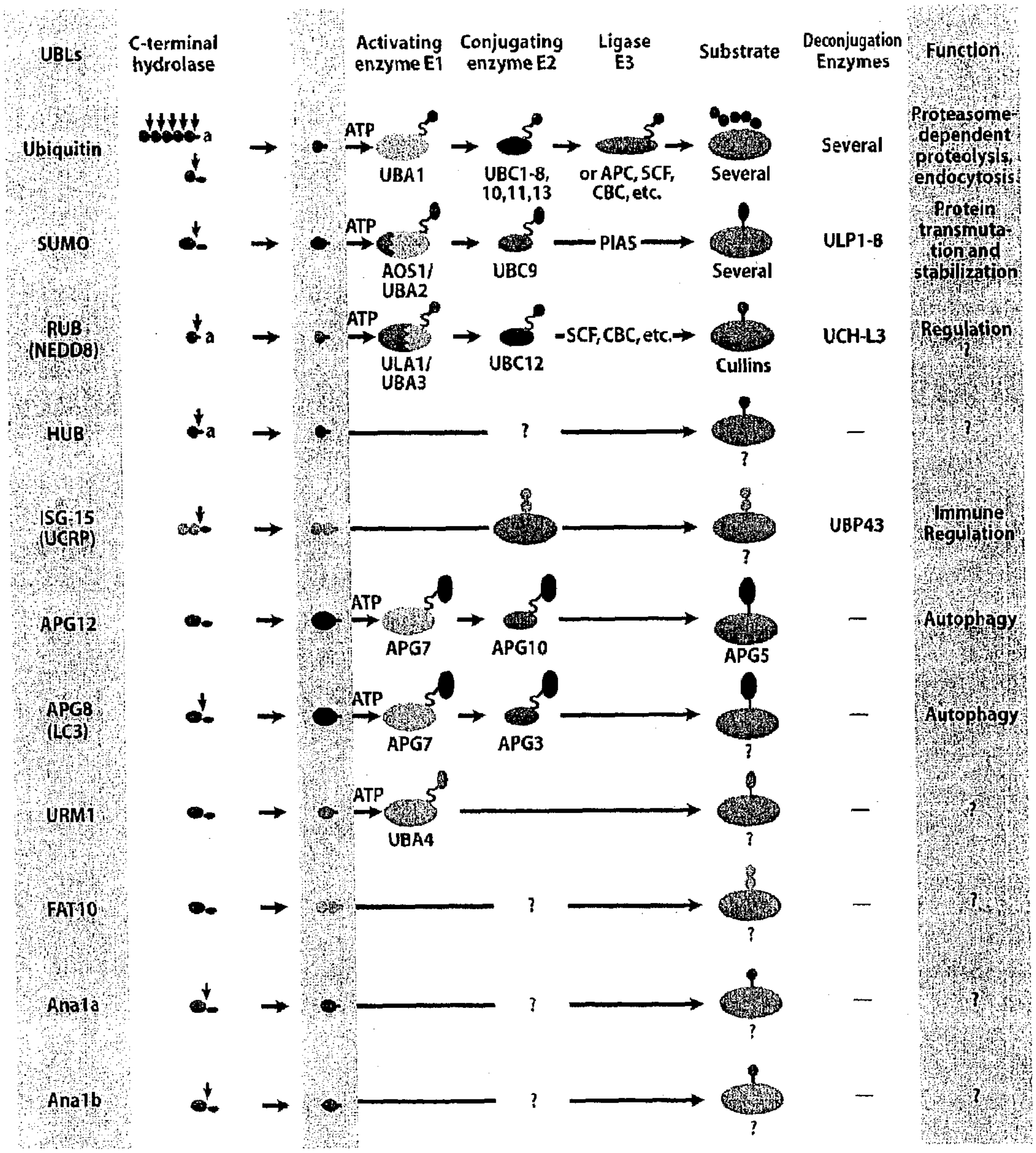
FIG. 1 is a schematic drawing illustrating the conjugation pathways for ubiquitin and ubiquitin-like proteins (UBLs). An arrow in the "C-terminal hydrolase" column indicates the cleavage of the precursor proteins. Only enzymes previously described are provided. The failure to list a particular enzyme in a particular pathway does not preclude the existence of that enzyme.

There are a number of reasons for the lack of efficient recombinant protein expression in a host, including, for example, short half life, improper folding or compartmentalization and codon bias. While the Human Genome project has successfully created a DNA "map" of the human genome, the development of protein expression technologies that function uniformly in different expression platforms and for all the protein motifs has not yet been achieved.

In accordance with the present invention, it has been discovered that that N-terminal fusion of the ubiquitin homologue SUMO or Smt3 to otherwise unexpressed or poorly expressed proteins remarkably enhances the expression levels of biologically active proteins in both prokaryotes and eukaryotes. The Ubiquitin-Like protein (UBL) family contains many proteins, including for example, SUMO, Rub1, Hub1, ISG15, Apg12, Apg8, Urm1, Ana 1a and Ana 1b (15, 28). See Table 1. The hallmark of all of these proteins, exept APG12, and URM1, is that they are synthesized as precursors and processed by a hydrolase (or proteases) to generate mature carboxy-terminal sequence. Secondly, all of the UBLs share a common structure.

In *E. coli,* fusion proteins remained intact while in yeast or insect cells fusion proteins were efficiently cleaved, except when proline was the N-terminal residue of the target protein. While any of the UBLs set forth in Table 1 may be utilized in the compositions and methods of the invention to enhance expression of heterologous fusion proteins of interest, SUMO is exemplified in the gene fusion system provided herein.

TABLE 1

Properties of Ubiquitin-like Proteins (UBLs)

| UBL (yeast) | Function | Knockout phenotype | Substrate | % UB Identity | KDa | Hydrolase | COOH Residues |
|---|---|---|---|---|---|---|---|
| UB | Translocation to proteasome for degradation. | not viable | many | 100 | 8.5 | UGH/UBPs | LRLRGG (SEQ ID NO: 39) |

TABLE 1-continued

Properties of Ubiquitin-like Proteins (UBLs)

| UBL (yeast) | Function | Knockout phenotype | Substrate | % UB Identity | KDa | Hydro-lase | COOH Residues |
|---|---|---|---|---|---|---|---|
| SUMO (SMT3) | Translocation to nucleus | not viable | Sentrins, RanGap, others | 18 | 11.6 | Aut1/Aut2 | GG |
| RUB1 (NEDD8) | Regulation of mitosis. | viable; non-essential. | cullins, cytoskelet proteins | 60 | 8.7 | not known | GG |
| HUB1 | Cell polarization during mating projections. | viable; deficient in mating. | Sph1, Hbt1 cell polarity factors | 22 | 8.2 | not known | YY |
| ISG-15 (UCRP) | Unknown | IFN, LPS hypersensi-tivity; death | many | ~30; 28 (two domains) | 15.0 | UBP43 (USP18) | LRLR GG (SEQ ID NO: 39) |
| APG12 | Autophagy | viable, defective in autophagy | Apg5 | 18 | 21.1 | not cleaved | FG |
| URM1 | Unknown | ts growth; non-essential. | unknown | 20 | 11.0 | not known | GG |
| APG8 (LC3) | Autophagy | viable; no autophago-cytosis or sporulation | phospatid yl-ethanol-amine | 18 | 13.6 | Apg4/Aut2 | FG |

The SUMO fusion system of the present invention has been successfully applied to express different molecular weight proteins such as 6 KDa Protein G domain to 110 KDa β-galactosidase in *E. coli* and eukaryotic cells. More specifically, the system allows one to: (1) enhance the expression of under-expressed proteins; (2) increase the solubility of proteins that are insoluble; (3) protect candidate proteins from degradation by intracellular proteases by fusing UBLs to their N-termini; (4) cleave the fusion protein to efficiently generate authentic proteins using naturally-present enzymes (5) generate proteins with novel amino termini; and (6) cleave all fusion proteins with remarkable efficiency irrespective of the N-terminal sequence of the fused protein, using UBL hydrolases such as SUMO hydrolase Ulp1. Because UBLs are small molecular weight proteins (~100 amino acids), they can also be used as purification tags as well. These remarkable properties of UBLs make them excellent candidates for enhancing expression and solubility of proteins. The method may also be utilized to generate novel amino termini on proteins of interest for a variety of research, diagnostic and therapeutic applications.

The ultimate fate of ubiquitinated or sumoylated proteins within a cell varies. A protein can be monoubiquitinated or polyubiquitinated. Ubiquitination of protein has multiple functions and gives rise to different fates for the protein within a cell (11). Ubiquitination primarily targets proteins to 26S proteosome for degradation (13). On the other hand, sumoylation of target proteins does not lead to degradation, but, rather, leads directly or indirectly to altered localization of proteins (15). There are about 17 deubiquitinating enzymes that cleave conjugated ubiquitin from target proteins as well as ubiquitin-ubiquitin and ubiquitin artificial-fusion proteins (1, 35). Thus far it appears that yeast has two cysteinyl proteases, called Ulp1 and Ulp2, that remove SUMO from ε-amino groups of lysine as well from the artificial linear SUMO-fusions (20, 21).

To determine if UBLs and SUMO fusion will enhance expression of recombinant proteins of different sizes and function, we have designed several UBL-GFP fusion proteins in addition to SUMO-fusion proteins and monitored their expression levels in *E. coli,* yeast and insect cells. In *E. coli,* the proteins are expressed as intact fusions, while in eukaryotes, the fusions were efficiently cleaved. A dramatic increase in the yield of proteins after fusion with SUMO and expression in *E. coli* was observed. In additional studies, SUMO-GFP protein was used as a model fusion for detailed studies in yeast and insect cells. We have designed SUMO-GFP fusion where all the N-terminal methionine residues have been replaced with the rest of the 19 amino acids. We have purified 20 sumo-GFP fusion proteins from *E. coli* and cleaved them in vitro with Ulp1. Ulp1 efficiently cleaved 19 out of the 20 possible amino acid junctions. The proline junction was not cleaved. As compared to deubiquitinating enzyme (3), Ulp1 demonstrated broad specificity and robustness in its digestion properties. Proteins having a wide range of molecular weights were cleaved efficiently by Ulp1. Similarly, in yeast, and insect cells, the fusion proteins were efficiently processed, yielding intact, biologically active proteins. In addition to enhancing protein expression levels, the SUMO-fusion approach can be used to advantage to generate desired N-termini to study novel N-terminal protein functions in the cell. Since SUMO fusion can both enhance recombinant protein yield and generate new N-termini, this technology provides an important tool for post-genomic biotechnology analyses.

The present invention also encompasses kits for use in effecting enhanced expression, secretion, purification, localization, and alteration of the amino terminus of a protein of interest. Such kits comprise a recombinant vector containing a nucleic acid sequence encoding a UBL molecule selected from the group of SUMO, RUB, HUB, URM1, and ISG15 operably linked to a promoter suitable for expression in the desired host cell and a multiple cloning site suitable for cloning a nucleic acid encoding the protein of interest in-frame with the nucleic acid sequence encoding the UBL molecule. The promoter is preferably a strong promoter and may be constitutive or regulated. Such promoters are well known in the art and include, but are not limited to, the promoters provided hereinbelow such as the ADH1, T7, and CUP1 promoters.

The recombinant vector may also contain a nucleic acid sequence encoding a purification tag in-frame with the sequence encoding the UBL molecule. Purification tags are well known in the art (see Sambrook et al., 2001, Molecular Cloning, Cold Spring Harbor Laboratory) and include, but are not limited to: polyhistidine, glutathione-S-transferase, maltose binding protein, thioredoxin, the FLAG™ epitope, and the c-myc epitope. Materials and methods for the purification of fusion proteins via purification tags are also well known in the art (see Sambrook et al., Novagen catalog, 2002, examples hereinbelow). Reagents including, but not limited to, solid supports capable of binding the purification tag, lysis buffers, wash buffers, and elution buffers may also be included in the kits.

The kits may further comprise a composition comprising a protease or proteases capable of cleaving the UBL molecule from the fusion protein, cleavage buffers, frozen stocks of host cells, and instruction manuals. The kits may also further comprise reagents for altering the nucleic acid encoding a protein of interest to generate amino termini which are different from those native to the wild-type protein. Methods for altering the nucleic acid are well known in the art and include, but are not limited to, site-directed mutagenesis and oligonucleotide-based site-directed mutagenesis (see BD Biosciences Catalog, 2001; Qiagen Catalog, 2001; Ausubel et al., eds., 1995, Current Protocols in Molecular Biology, John Wiley and Sons, Inc.).

As used herein, an "instructional material" includes a publication, a recording, a diagram, or any other medium of expression which can be used to communicate the usefulness of the composition of the invention for performing a method of the invention. The instructional material of the kit of the invention can, for example, be affixed to a container which contains a kit of the invention to be shipped together with a container which contains the kit. Alternatively, the instructional material can be shipped separately from the container with the intention that the instructional material and kit be used cooperatively by the recipient.

The materials and methods set forth below are provided to facilitate the practice of the present invention.

Figure 45:
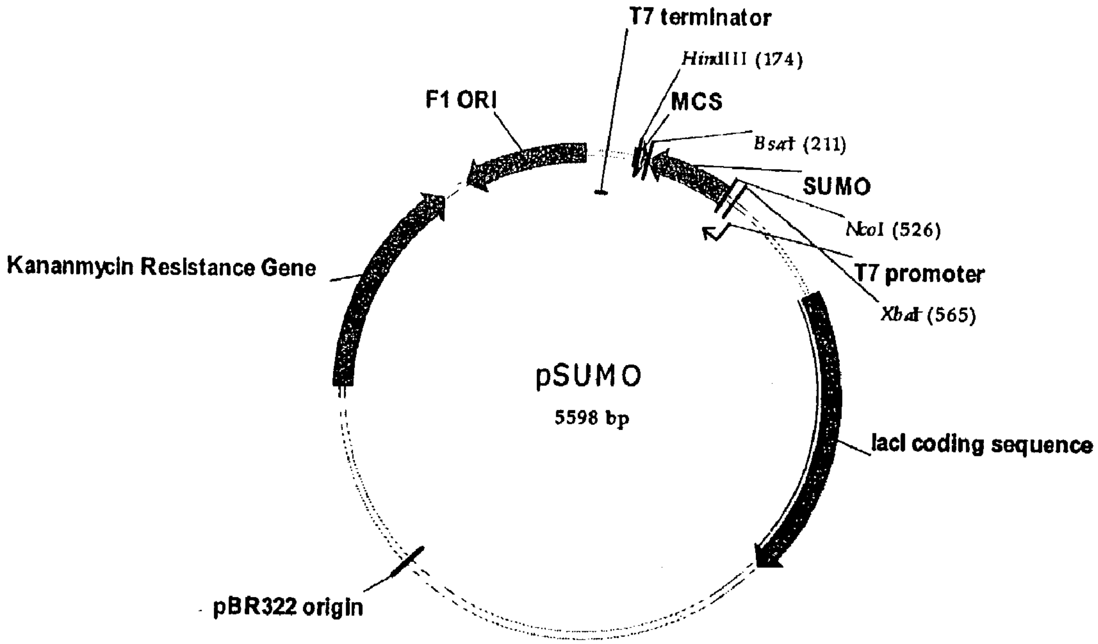
FIG. 45 is a circular map of pSUMO (pET24d6His× SUMO).

Design and Construction of *E. coli* Expression Vectors:

The original vector backbone was developed using pET 24d vector from Novagen (see FIG. 3 as well as FIGS. 45–46A–E). pET24d uses a T7 promoter system that is inducible with IPTG. The vector has a kanamycin selection marker and does not contain any translation terminator.

Figure 2:
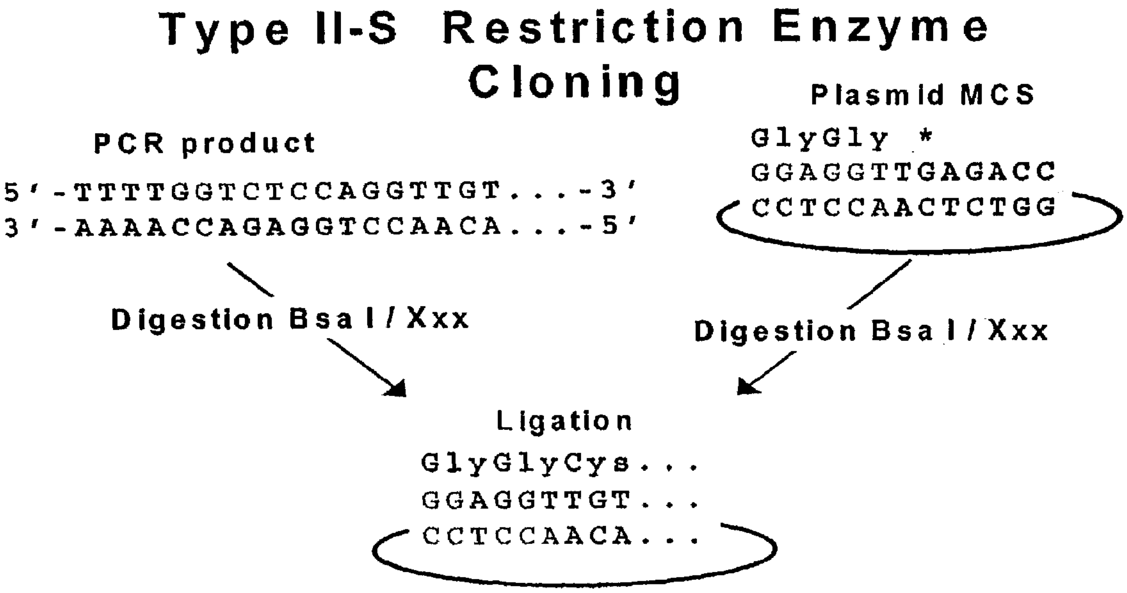
FIG. 2 is a schematic representation of the cloning strategy used to express SUMO tusion proteins. In this cloning strategy, a Bsa I site is introduced directly downstream of a SUMO sequence within a desired vector. The nucleic acid sequence encoding the protein to be expressed as a fusion with SUMO is amplified by PCR with primers that introduce a Bsa I site at the 5' end. The vector (SEQ ID NO: 62, top strand; SEQ ID NO: 63, bottom strand) and the PCR product (SEQ ID NO: 60, top strand; SEQ ID NO: 61, bottom strand) are cleaved by Bsa I and an appropriate restriction enzyme (represented by Xxx) that allows for insertion of the cleaved PCR product into the vector.

Construction of Variable His6SUMO-GFP Fusions:

A N-terminal six his-tagged SUMO (fusion vector was constructed as follows. A PCR product was generated with the primers 5 ' CCATGGGTCATCACCATCATCATCACGGGTCGGACTCAGAAGTCAATCAA- 3 ' (SEQ ID NO: 40) and 5'-GGATCCGGTCTCAACCTCCAATC TGTTCGCGGTGAG-3'(SEQ ID NO:41) using yeast Smt3 gene (16) as a template (kind gift of Erica Johnson). The FCR fragment was double digested with Nco I and Bam HI, and then ligated into pET24d, which had been similarly digested. It is important to note that the current invention utilizes a variant of the wild type yeast SUIvIO sequence. The A nucleotide at position 255 has been replaced with a G nucleotide, thus encoding an alanine instead of a threonine (SEQ ID NOS: 64 and 65). The detailed cloning strategy is provided in FIG. 2. The pET24d His6Smt3eOFP fusions, containing each of the twenty different amino acids at the +1 position of the cleavage site were generated as follows. The eGFP sequence was amplified a template, with the primers 5'-GGTCTCAAGGT NNNGTGAGCAAGGGCGAGGAGC-3'(SEQ ID NO:42) and 5'-AAGCTTATTACTTGTACAGCTCGT CCATGCC-3(SEQ ID NO: 43), where the NNN in the forward primer corresponding to the variable codon encoding one of the twenty amino acids. The PCR products were purified and double digested with Bsa I and Hind III, these were then ligated into the pET24dI-IisSUMO vector which had been similarly digested. Plasmids from clones containing the variable inserts, were sequenced to confirm the presence of the novel codon in each.

Construction of SUMO-Fusion Vectors from pSUMO:

The gene encoding the protein of interest is cloned in frame with the SUMO tag, in the pSUMO vector, by utilizing the encoded Bsa I site. Bsa I belongs to the family of Class IIS restriction enzymes, which recognize non-palindromic sequences, and cleave at a site that is separate from their recognition sequences. The latter trait gives Class IIS enzymes two useful properties. First, when a Class IIS enzyme recognition site is engineered at the end of a primer, the site is cleaved when digested. Second, overhangs created by Class IIS enzymes are template-derived and thus unique. This is in clear contrast to regular Class II restriction enzymes such as EcoRI, which creates an enzyme-defined overhang that will ligate to any EcoRI-digested end. The unique overhangs produced by Class IIS enzymes can be ligated only to their original partner.

It is often preferable to amplify the gene encoding the protein of interest via PCR prior to cloning into the pSUMO vector. The forward primer must contain the additional standard sequence:

5'-GGTCTCAAGGTNNN-3' (SEQ ID NO:44) where GGTCTC is the Bsa I site and NNN is the first codon of the gene encoding the protein of interest. Additional nucleotides are required for the primer to anneal specifically with the gene of interest during the PCR amplification. The reverse primer may contain another restriction enzyme such as Xho I to allow for directional cloning of a gene into pSUMO. Bsa I can also be employed in the reverse primer to simplify cloning steps, for example, in the following primer: 5'-GGTCTCCTCGAGTTANNN-3' (SEQ ID NO:45)

The PCR product can be digested with both Xho I and Bsa I. A digestion reaction containing just the latter enzyme generates a product that would directionally ligate into the pSUMO vector between the Bsa I and Xho I sites of the MCS.

Construction of pSUMO-Protein G Fusion *E. coli* Expression Vector:

The B2 IgG binding domain (9) from streptococcus G148 protein was synthesized by three synthetic oligonucleotides. The sequence of the gene is 5'-GT CTTAAGA CTA AGA GGT GGC ACG CCG GCG GTG ACC ACC TAT AAA CTG GTG ATT AAC GGC AAA ACC CTG AAA GGC GAA ACC ACC-3'. (SEQ ID NO:46) The 81 bps oligo sequence is 5'-GCC GTT ATC GTT CGC ATA CTG TTT AAA CGC TTT TTC CGC GGT TTC CGC ATC CAC CGC TTT GGT GGT TTC GCC TTT CAG-3'. (SEQ ID NO:47) The 86 pbs oligo sequence is 5'-CAG TAT GCG AAC GAT AAC GGC GTG GAT GGC GTG TGG ACC TAT GAT GAT GCG ACC AAA ACC TTT ACC GTG ACC GAA TAA GGT ACC CC-3' (SEQ ID NO:48). The bolded nucleotides refer to the AflII and Kpn1 sites that flank the protein G domain. ACG is the first amino acid residue of the domain. The above three oligos were annealed using the Life Technologies protocol. The annealed fragments were extended by PolI enzyme. The resultant gene was PCR amplified by the following oligo primers GI forward 5'-CTT GTC TTA AGA GGT-3' (SEQ ID NO:49) and G2 reverse primer 5'-GCT GGG TAC CTT ATT CGG TCA-3' (SEQ ID NO:50). The above protein G gene was cloned at the AflII and Kpn1 site of the human ubiquitin gene and expressed as ubiquitin-protein G fusion protein in an *E. coli* pET 22 expression vector (Novagen). The protein G sequence was in turn amplified from the ubiquitin-protein G fusion plasmid by using the primers 5'-GGTCTCAAGGTACGCCGGCGGTGACCACCT-3' (SEQ ID NO:51) and 5'-AAGCTTATTATTCGGTCACGGTAAAGGTTT-3' (SEQ ID NO:52) and inserted in pSUMO to generate pSUMO-protein G expression vector.

Construction of *E. coli* SUMO-β-galactosidase Expression Vector.

*E. coli* β-galctosidase was amplified using pfu (Stratagene) a preparation of genomic DNA from BL21(DE3) (Stratagene) as a template and the primers 5'-GGTCTCAAGGTATGACCATGATTACGGATTCACT-3' (SEQ ID NO:53) and 5'-AAGCTTATTATTATTATTTTTGACACCAGACC-3' (SEQ ID NO:54). The PCR products were purified and double digested with Bsa I and Hind III. These were then ligated into the vector pET24d6×HisSUMO, which had been similarly digested.

Construction of *E. coli* pSUMO-Liver X Receptor (LXR) Expression Vector:

The PCR products of the LXR from amino acid residue 189 to the end of the protein that spans the ligand binding domain was digested with BsaI and HindIII and ligated into the pSUMO vector, also digested with Bsa1 and HindIII.

Figure 8A:
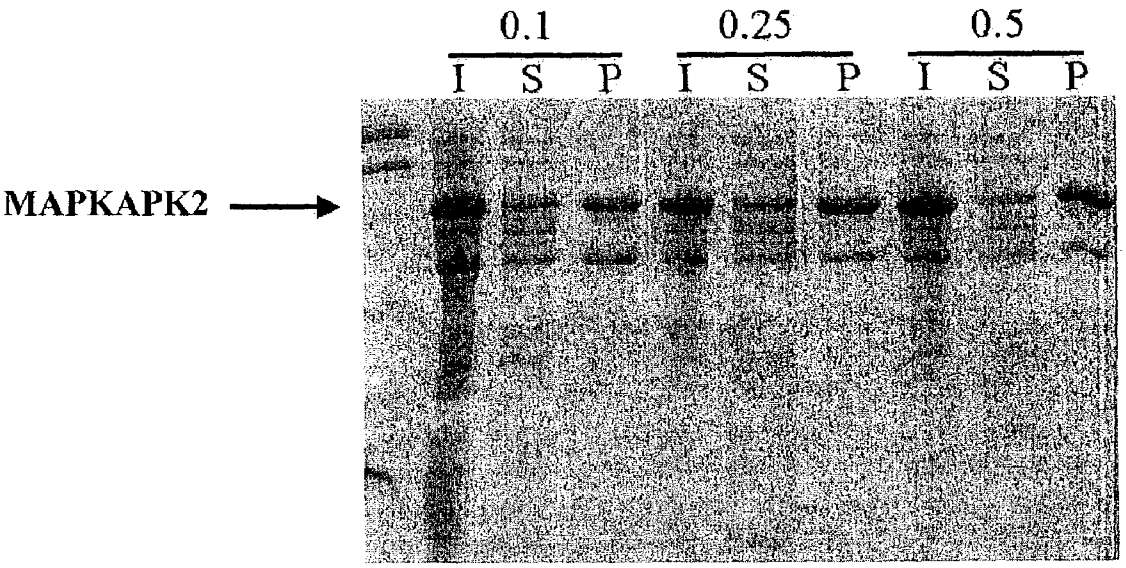
FIGS. 8A and 8B display stained SDS-polyacrylamide gels demonstrating the solubility of the SUMO-MAPKAPK2 fusion protein expressed at 37° C.
Figure 8B:
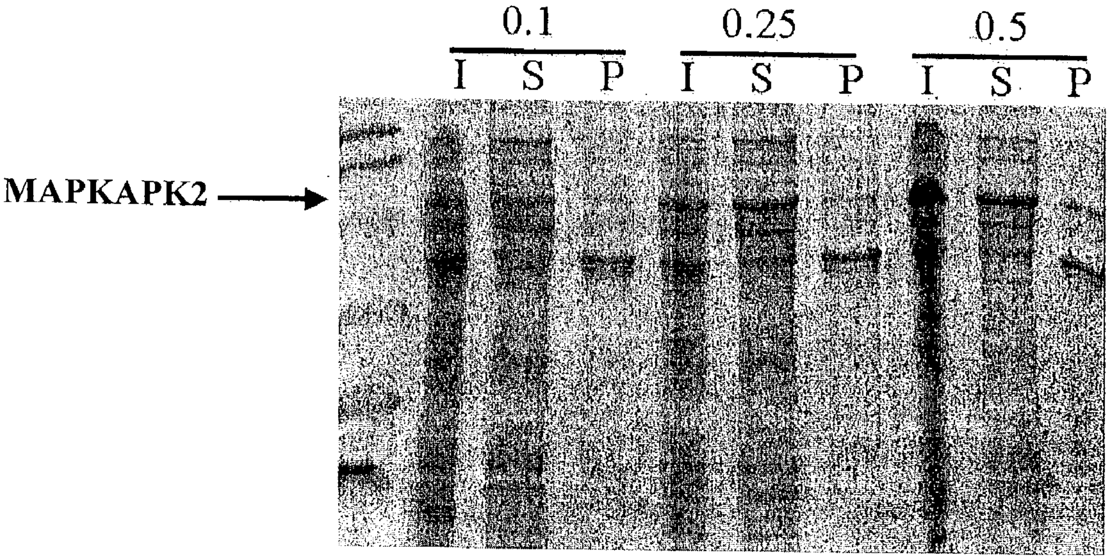

Construction of *E. coli* pSUMO-MAPKAP2 Expression Vector:

The fragment of MAPKAP2, encoded in the plasmid pMON45641, was amplified by PCR and cloned into pET24d 6HisSUMO vector by designing PCR primers that flank the sequence shown FIGS. 8A and 8B. The SUMO vector was digested with Bsa I site and Hind III. The cloning procedure yields a fusion protein, which, upon expression, purification and cleavage, generates the desired protein whose first amino acid is a glutamine (CAG).

Construction of *E. coli* pSUMO-Tyrosine Kinase Expression Vector:

For the tyrosine kinase, both, the SUMO fusion and unfused expression vectors were designed. As described above the region of kinase was cloned by PCR flanked with BsaI and Hind III sites that were cloned in to similarly digested pSUMO.

Construction of *E. coli* pSUMO-β-Glucuronidase Expression Vector:

*E. coli* β-glucuronidase was the kind gift of Ben Glick, University of Chicago) and amplified with the primers 5'-GGTCTCAAGGTATGCAGATCTTCGTCAAGACGTT-3' (SEQ ID NO:55) and 5'-AAGC TTATTATTGTTTGCCTCCCTGCTGCG-3' (SEQ ID NO:56).

Construction of *E. coli* SUMO-Hydrolase Expression Vector:

C-terminal His-tagged SUMO hydrolase/protease Ulp (403–621)p (21) (27) was expressed from pET24d in Rosetta (DE3) pLysS (Novagen). The recombinant protein was purified using Ni-NTA agarose (Qiagen) and buffer exchanged into 20 mM Tris-HCl pH 8.0, 150 mM NaCl and 5 mM β-mercaptoethanol using a PD-10 column (AP Biotech). About 2 ug of the pure protein was analyzed on gels and data shown in FIG. 6 lane Ulp1. The protein was almost 90% pure as judged by SDS-PAGE analysis.

Construction of *E. coli* UBL-GFP Fusion Vectors.

DNA sequences encoding ubiquitin (Ub), SUMO, Urm1, Hub1, Rub1, Apg8, and Apg12 were PCR-amplified using Deep-Vent polymerase (NEB) and yeast strain DNA to generate a template. Full-length human ISG15 cDNA was a kind gift of Dr. A. Haas, Medical College of Wisconsin, Milwaukee. A unique NcoI site followed by 6His sequence was introduced by PCR at the 5'-end of each Ubl cDNA. Primer sequence at the 3'-end included unique Esp3I and HindIII sites. PCR products were digested with NcoI/HindIII and inserted into respective sites of pET24d vector (Novagen) as described above. Full length GFP sequence (Clontech Cat # 60610-1) flanked by Esp3I and HindIII sites, respectively, was PCR-amplified and cloned into pCR4-TOPO-TA vector (Invitrogen). Esp3I/HindIII digested GFP-encoding gene was inserted into respective sites of pET24d-UBLl plasmids, creating final UBL-GFP expression vectors for *E. coli.* In toto, there were nine plasmid constructs coding for the following structures: 6His-Ubl-GFP. All plasmids were sequenced to confirm the expected structure.

Design and Construction of Yeast UBL-Fusion Vectors:

*Saccharomyces cerevisiae* has been used as a eukaryotic model for all the experiments involving yeast. All of the expression vectors for these studies were designed on multicopy yeast vectors that contain tryptophan or leucine as a selectable marker and 2μ as an origin of replication (22). Proteins were expressed as unfused products or as ubiquitin, SUMO or other UBL fusion proteins.

Construction of the β-Glucuronidase Yeast Expression Vectors:

To demonstrate that UBLs increase the level of secretion of the protein to the media, in addition to enhancing the level of expression, expression vectors were constructed with and without ubiquitin. We have also compared ubiquitin fusion and SUMO fusion using GFP as a model protein (see FIG. 9 and FIG. 10). pRS425-GUS plasmid was produced by cloning the XhoI-SacI fragment (containing *E. coli* β-Glucuronidase (GUS)) from plasmid pGUS1 (25, 22) into the XhoI-SacI sites of plasmid pRS425 (32). The next construction involved addition of a promoter, and resulted in the plasmid pRS425-ADH1p-GUS. The fragment XhoI-HindIII (containing the ADH1) was inserted into the XhoI-HindIII sites of the plasmid pRS425-GUS. The ADH1 promoter XhoI-HindIII fragment was cloned using polymerase chain reaction (PCR), amplifying the ADH1 promoter from the plasmid pGRIP1(37). The following primers were used to amplify the full length ADH1 promoter: ADH1-XhoI: 5'-gctcgagagcacagatgcttcgttg-3' (SEQ ID NO:57), and ADH1-HindIII: 5'-gcaaagcttggagttgattgtatgc-3' (SEQ ID NO:58). The underlining indicates the nucleotide sequence of the XhoI and HindIII restriction sites. PCR of the DNA fragment involved amplification in 30 cycles (96° C.—30 sec., 54° C.—1 min. and 72° C.—3 min.) using high replication fidelity Deep Vent Polymerase (New England Biolabs). The PCR product was then digested with XhoI and HindIII, and subsequently cloned into the XhoI-HindIII sites of pRS425-GUS. Construction of the next set of plasmids involved a change in promoter. The following two plasmids were constructed to give expression vectors containing either a methionine or proline junction between the ubiquitin and the GUS. pRS425-GPDp-Ub(Methionine)-GUS and pRS425-GPDp-Ub(Proline)-GUS were similarly constructed using both pre-constructed plasmids and PCR amplification. The final expression construct was pRS425-CUP1p-SUMO-GUS, which was the only plasmid produced with the CUP1, copper regulated promoter. This plasmid was digested with the enzymes Bg1II and NsiI, releasing the CUP1 promoter (6). The CUP1 fragment was then ligated to pRS425-GPDp-Ub-GUS, having also been digested with Bg1II-NsiI.

Construction of SUMO-N-GFP Yeast Expression Vector:

To determine what variety of N-terminal variant amino acids at the junction of SUMO and GFP can be cleaved in yeast we designed SUMO-GFP vectors in which all 20 amino acid residues were encoded at the N-terminus of GFP. Essentially all 20 SUMO-X-GFP vectors designed for *E. coli* expression were digested with Bsa I-Hind III, and the inserts were purified. The 20 inserts were cloned in Yep12 that was slightly modified. Specifically, YeEpSW was generated by digesting Yep12 with Bam HI and SacI. The CUP1 promoter region was recovered from the fragment by PCR. A polylinker was created at the 3' end of CUP1 with a variety of restriction sites including NcoI and Xho1. All 20 SUMO-GFPs (N end variants) were digested with NcoI-XhoI enzymes and cloned directly YepSW. The resultant vector YepSW-SUMO-eGFP utilizes tryptophan selection and expresses SUMO-GFP proteins under the control of the copper promoter. All vectors were sequenced to ensure correct codons at the junction of SUMO and GFP.

Construction of UBL-GFP Fusion Yeast Expression Vectors:

Construction of the UBL-GFP fusion vectors for *E. coli* has been described above. In order to make UBL yeast expression vector NcoI/XhoI fragments carrying GFP alone and all the Ubl-GFP fusions were inserted into respective sites of pYEp SW (see above) that was similarly digested with NcoI/XhoI. Insertion of UBL-GFP cassette in Yep SW (See FIGS. 39 and 40A–40F), allows copper inducible expression of Ubl-GFP fusions in yeast system.

Figure 11A:
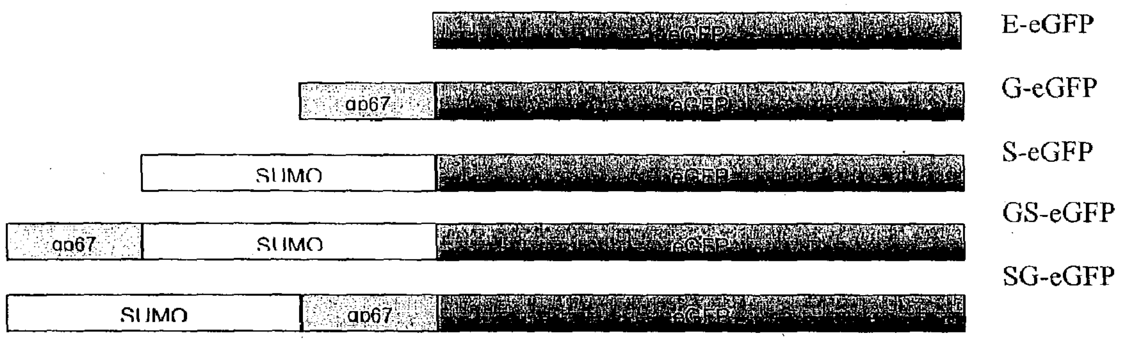
FIGS. 11A and 11B are schematic representations of the SUMO (FIG. 11A) and ubiquitin (FIG. 11B) GFP fusion proteins that also contain the gp67 secretory signal. In construct E, only unfused GFP protein is expressed. In construct G, a 7 kDa secretory sequence from gp67 was attached to the N-terminus of GFP. In constructs S and U, SUMO and ubiquitin sequences, respectively, are inserted in frame to the N-terminus of GFP. In constructs GS and GU, gp67 sequences are followed by SUMO and ubiquitin, respectively, and then GFP. In constructs SG and UG, gp67 sequences are inserted in between the C-terminus of SUMO and ubiquitin, repectively, and the N-terminus of GFP.
Figure 11B:
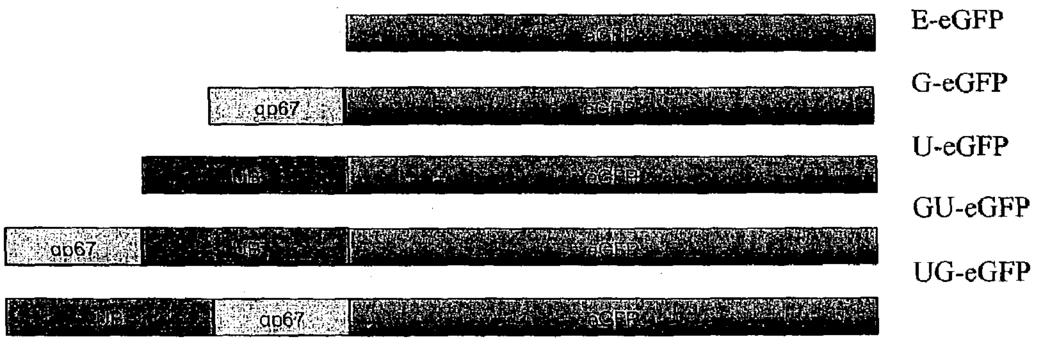

Design and Construction of Recombinant Baculovirus for SUMO and Ubiquitin GFP Fusion Expression:

To demonstrate that attachment of SUMO or ubiquitin to GFP increases its expression and enhances secretion into the media, several GFP fusion vectors were designed with different configurations of gp67 secretory signals. The basic GFP vector for expression is essentially based on *E. coli* vectors described above. Derivatives of this vector representing each candidate gene have been constructed by designing PCR primers. The construction of GFP plasmid transfer vectors for baculovirus is described. To help appreciate the rationale for the secretory signal in the context of GFP-fusion, see the diagrammatic representation shown in FIG. 11. Single letter code refers to unfused GFP (E); gp67-sec signal-GFP (G); ubiquitin-GFP (U); SUMO-GFP (S); gp67-Ub-GFP (GU); Ub-gp67-GFP (UG); gp67-SUMO-GFP (GS); and SUMO-gp67-GFP (SG).

(i) pFastbacE. A synthetic oligonucleotide containing the Esp3I site was inserted between BamHI and EcoRI cloning site of the transfer vector pFastbac1, which had been modified by removing Esp3I site from Gmr region. (ii) pFastbacG. The signal sequence of the gp67 gene derived from pACSecG2T was isolated by PCR using 2 primers (f-gp67 and r-gp67), digested with Bg1II and EcoRI in the next step, and then inserted between BamHI and EcoRI cloning sites of the transfer vector pFastbacE. (iii) pFastbacS. A full-length SUMO gene derived from pET SUMO was generated by PCR using 2 primers (f-bacsmt and r-bacsmt), digested with BsaI and EcoRI in the next step, and then inserted between BamHI and EcoRI cloning sites of the transfer vector pFastbacE. (iv) pFastbacG/S. The signal sequence of the gp67 gene in the pACSecG2T vector was generated by PCR using 2 primers (f-fusgp67 and r-fusgp67), and inserted between BamHI and EcoRI cloning sites of the transfer vector pFastbacE to create a new pFastbacG, which was used for fusion with SUMO afterward. A full-length SUMO gene derived from pET SUMO as described above (iii) was digested with BsaI and SacI and inserted between Esp3I and SacI cloning sites of the new transfer vector pFastbacG. (v) pFastbacS/G. A full-length SUMO gene derived from pET SUMO was generated by PCR using 2 primers (f-fussmt3 and r-fusgp67) and inserted between BamHI and EcoRI cloning sites of the transfer vector pFastbacE to create the new pFastbacS, used for fusion with gp67 afterward. The signal sequence of the gp67 gene derived from pACSecG2T as described above (ii) was digested with BsaI and SacI, and then inserted between the Esp3I and SacI cloning sites of the new transfer vector pFastbacS.

Preparation of Baculovirus Stocks and Cell Growth.

Transfer vector constructs based on the pFastbac 1 shuttle plasmid (Invitrogen, Inc.) were transposed in DH10Bac *E. coli* competent cells to transfer the respective e-GFP fusion sequences into recombinant virus DNA by site-specific integration. After alkaline lysis of transformed (white colonies) of *E. coli* cells, which contain recombinant virus (bacmid) DNA, and extraction of the recombinant bacmid DNA, the bacmid DNA was used to transfect *Spodoptera frugiperda* (Sf9) insect cells, in which virus replication occurs. The virus was then amplified to produce passage 2 (for long-term storage) and passage 3 virus (for working) stocks by infection of fresh Sf9 cell cultures and used directly to infect cells for fusion protein expression. Virus infectivity (pfu/ml) was determined by titration in Sf9 cells using the BacPAK™ Rapid Titer Kit (BD Sciences Clontech, Inc.). A 50 ml culture of Hi-Five cells at concentration of 1×106 cells/ml, was infected with recombinant virus at MOI=5 in Express Five media (serum free media). The cells were grown in 100 ml spinner flask at 27° C. Every 24 hours, cell viability was determined by trypan blue and cell counting. 5 ml of the suspension culture was removed at 24 hour intervals, centrifuged at 500×g at 4° C. in 10 minutes. The supernatant was transferred into a fresh tube to monitor any protein that may have been secreted into the media (see below).

Analysis of Proteins from Insect Cell Compartments:

Cell pellets (from above step) were gently washed in 1 ml PBS and recentrifuged at 500×g at 4° C. for 10 minutes. All supernatant and pellets are stored at −80° C. The presence of recombinant protein in cells and media was ascertained by SDS-PAGE and Western blotting of supernatant and cell pellets. The total intracellular protein was extracted by M-PER extraction buffer (Pierce), a neutral buffer for protein extraction. The cell pellet was mixed with rapid pipetting and incubated for 1 hour on an orbital shaker. The suspension was centrifuged at 500×g at 4° C. for 10 minutes to remove debris. The supernatant contained extracted cellular proteins that were either analyzed by PAGE or stored at −80° C. To analyze the proteins present in the media, the following procedure was adopted. Trichloroacetic acid was added to 5 ml media to a final concentration of 20%. The suspension was mixed well and left on ice for three hours, and then centrifuged 500×g at 4° C. for 10 minutes. The white pellet was washed with 80% ethyl alcohol twice, and then dried. The pellet was suspended in 1 ml of M-PER buffer for PAGE to compare the distribution of control (unfused) and SUMO-fused proteins inside and outside the cell.

Methods for Analysis of Yeast Expressed Fusion Proteins:

Yeast cultures were grown in synthetic or rich media. Standard yeast and *E. coli* media were prepared as described (31). The yeast strain Y4727: Mata his3-Δ200 leu2-Δ0 lys2-Δ0 met5-Δ0 trp1-Δ63 ura3-Δ0 was used as a host (gift from Dr. Jeff Boeke) or BJ 1991. Yeast transformation was performed according to published procedures (8). Yeast transformants with autonomously replicating plasmids were maintained in yeast selective media. The *E. coli* β-Galactosidase and β-Glucuronidase proteins were expressed under the regulation of either the alcohol dehydrogenase (ADH), or Glyceraldehyde-Phosphate-Dehydrogenase (GPD) promoter or copper metallothioneine (CUP1) promoter in 2 μm multicopy plasmids with the LEU2 selective marker.

Yeast cells were transformed with appropriate expression vectors, and single colonies were grown in synthetic media minus the selectable marker. For each protein, at least two single colonies were independently analyzed for protein expression. Cells were grown in 5 ml culture overnight and, in the morning, the culture was diluted to an O.D. at 600 nm of 0.5. If the gene was under the control of copper inducible promoter, copper sulfate was added to 100 μM and the culture was allowed to grow for at least three hours. Cells were pelleted at 2000×g for 5 minutes, washed with 10 mM Tris-EDTA buffer pH 7.5. If enzymatic assays were performed, cells were disrupted in assay buffer with glass beads, 2× times the volume of the pellet. Cells were centrifuged and the supernatant was recovered for enzymatic or protein analysis. Alternatively, if the level and the type of protein was analyzed by SDS-PAGE, cell pellet was suspended in SDS-PAGE buffer and boiled for 5 mins. The suspension was centrifuged, and 10–20 ul aliquots were run on 12% SDS-PAGE.

Measurement of β-GUS Activity from Yeast:

β-Glucuronidase (GUS) is a 65 kDa protein that is a useful marker for protein trafficking. We have used GUS to determine the role of N-terminal ubiquitin on secretion of GUS in yeast. Yeast cells were transformed with various GUS vectors, grown overnight in selective liquid media at 30° C., and diluted in the liquid selective media to 0.1 OD600 (OD culture). Yeast cells were incubated in the presence of inducer in shaker at 30° C. After 4 hours of incubation, 100 μl of 2× "Z" Sarcosine-ONPG buffer (120 mM Na2HPO4, 80 mM NaH2PO4, 20 mM KCl, 2 mM MgSO4, 100 mM β-mercaptoethanol, pH 7.0, 0.4% lauroyl sarcosine) was added. (The 2× "Z" Sarcosine-buffer is freshly prepared or stored at −20° C. prior use.) We used a fluorometric assay with 4-methylumbelliferyl β-D-glucuronide as the substrate for β-GUS assay. After incubation at 37° C. for 1 hour (t incubation), the reaction was stopped by adding 100 μl of quenching solution, 0.5 M $Na_2CO_3$. The GUS activity was determined by reading the plates in a fluorometric plate reader. For calorimetric reactions, relative activity was calculated as following: (1000×OD reaction)/(t incubation×OD culture).

*E. coli* Growth, Compartmentalization and Protein Expression.

Protein expression studies were carried out in the Rosetta bacterial strain (Novagen). This strain is derived from the lambda DE3 lysogen strain and carries a chromosomal copy of the IPTG inducible T7 RNA polymerase along with tRNAs on a pACYC based plasmid. Cultures were grown in LB as well as minimal media and at growth temperatures of 37° C. and 20° C. with 100 ug/mL ampicillin and 30 ug/mL chloramphenicol. The culture was diluted 50 fold and grown to mid log (OD at 600 nm=0.5–0.7), at which time the culture was induced with 1 mM IPTG. Induction was allowed to proceed for 4–5 hrs. Upon completion of induction, cells were centrifuged and resuspended in a buffer containing 20% sucrose. To analyze protein induction in total cells, SDS-PAGE buffer was added and the protein was analyzed following SDS-PAGE and staining with Coomassie blue.

Separation of Soluble and Insoluble Fractions.

*E. coli* were harvested by mild centrifugation and washed once with PBS buffer. Cells were resuspended in 4 ml of PBS and ruptured by several pulses of sonication. Unbroken cells were removed by mild centrifugation (5 min at 1500× g) and supernatants were sonicated again to ensure complete cell lysis. An aliquot (5 μl) was mixed with 2% SDS to ensure that no viscosity is detected owing to lysis of unbroken cells. After ensuring that no unbroken cells remained in the lysate, insoluble material consisting of cell walls, inclusion bodies and membrane fragments was sedimented by centrifugation (18,000×g for 10 min). The supernatant was considered "Soluble fraction".

The pellets were washed from any remaining soluble proteins, lipids and peptidoglycan as follows. Pellets were resuspended in 600 μl of PBS and to the suspensions 600 μl of solution containing 3 M urea and 1% Tri ton X100 was added. The suspension was briefly vortexed and insoluble material was collected by centrifugation as above. The PBS/Urea/Triton wash was repeated two more times to ensure complete removal of soluble proteins. The washed pellets, designated as "insoluble fraction," consisted primarily of inclusion bodies formed by over expressed proteins. Approximately 10 μg of protein from each fraction was resolved on 12% SDS-PAGE minigels and stained with Coomassie Brilliant Blue.

Fluorescence (GFP Activity) Assessment.

GFP fluorescence was measured in soluble fractions (approx. 0.1 mg of soluble protein in a final volume of 40 μl) using Fluoroscan Accent FL fluorometer (LabSystems) with Excitation 485 nm/Emission 510 nm filter set with the exposure set to 40 sec. The data are presented in Arbitrary Units (AU).

Western Blotting.

Twenty μg of total yeast protein per lane were resolved on 12% SDS-PAGE minigel and electro-blotted to nitrocellulose membranes by standard methods. Membranes were blocked with 5% milk in TTBS buffer and incubated with rabbit anti-GFP antibodies (Clontech, cat no. 8367) at 1:100 dilution overnight at 4° C. Secondary HRP-conjugated antibodies were from Amersham. Identical gels were run in parallel and stained with Coomassie to ensure equal loading of the samples.

The various 6HisxSUMO-GFP (16) fusions were expressed in Rosetta (DE3) pLysS (Novagen) using the procedures recommended by the manufacturer. Expression levels in the absence and presence of the fusion proteins was compared by SDS-PAGE analysis. The recombinant proteins were purified using Ni-NTA agarose; (Qiagen) using procedures recommended by the manufacturer.

Cleavage of Proteins

For studies in *E. coli*, an organism that does not possess SUMO or ubiquitin cleaving enzymes, each cleavage reaction contained 100 ul of purified fusion protein, 99 ul of the buffer 20 mM Tris-HCl pH 8.0, 150 mM NaCl, 5 mM β-mercaptoethanol, and 1 ul of enzyme. The reactions were incubated for 3 hours at 30° C., and stopped by addition of 6× Laemmli SDS-page loading buffer followed by boiling at 95° C. for 5 minutes. The products of the cleavage reaction were analyzed by SDS-PAGE.

The following examples are provided to illustrate various embodiments of the present invention. They are not intended to limit the invention in any way.

EXAMPLE I

Attachment of C-Terminus of UBLs to N-Terminus of GFP Enhances the Expression and Solubility of the Protein in *E. coli*.

Figure 4A:
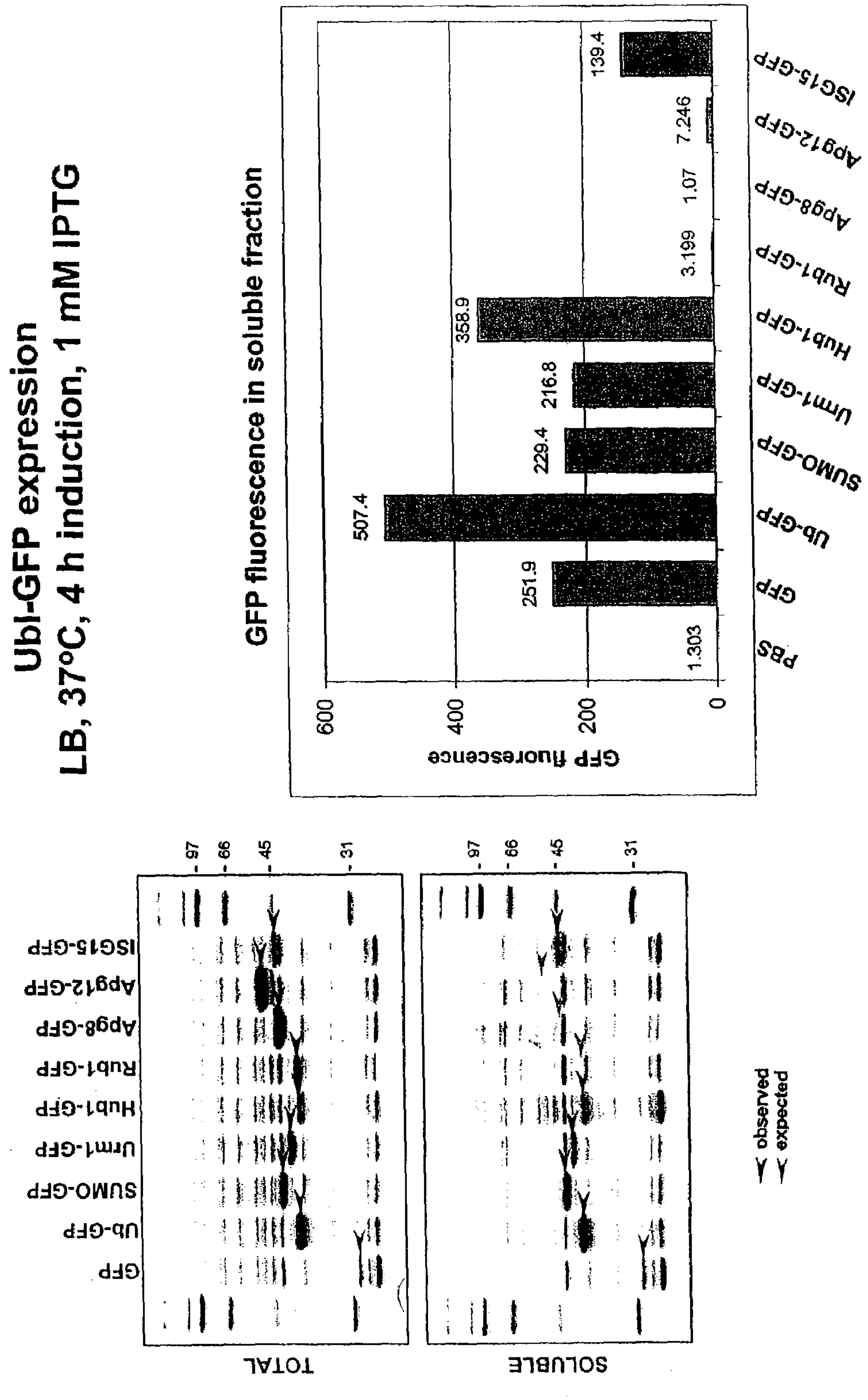
FIGS. 4A and 4B show Coomassie stained gels and graphic data that demonstrate that the attachment of the carboxy-terminus of UBLs to the amino-terminus of target proteins increases expression and/or enhances solubility of the protein in *E. coli.* Green fluorescence protein (GFP) and UBL-GFP fusions encoded in pET24d *E. coli* expression vectors were expressed in the *E. coli* Rosetta pLysS strain (Novagen). Expression was induced either at 37° C. with 1 mM IPTG for four hours either in LB medium (FIG. 4A) or in minimal media with 1 mM IPTG at 26° C. overnight (FIG. 4B). Left panels are Coomassie stained SDS-polyacrylamide gels of total cellular protein (top) and soluble proteins (bottom). The first lanes of each gel are molecular weight markers. Dark arrow indicates observed GFP species and light arrow indicates size of expected GFP species. Right panel is quantitative representation in Arbitrary Units (AU) of GFP fluorescence present in soluble fractions as measured in a Fluorscan Ascent FL fluorometer (LabSystems).

The design and construction of all the UBL *E. coli* expression vectors has been described above. The DNA sequences, accession numbers of the UBL-GFP fusion proteins, and translation frames are shown FIGS. 25–32. FIG. 4A shows the 37° C. expression pattern of GFP, Ub-GFP, SUMO-GFP, Urm1-GFP, Hub1-GFP, Rub1-GFP, Apg8-GFP, Apg12-GFP, ISG15-GFP. Un-fused GFP is generally poorly expressed in *E. coli*. The data show that all of the UBLs enhance the expression level of GFP to varying degrees. However, the greatest amount of induction was observed with Ub, SUMO, Urm1, Apg8 and Apg12. Induced cells were broken by sonication and soluble proteins were analyzed on SDS-polyacrylamide gels. The stained gel shows (FIG. 4A, Soluble Panel) that ubiquitin, SUMO, Urm1, Hub1 and ISG15 were able to solublize the GFP while Rub1, Apg8 and Apg12 fusion proteins were not soluble, however, fusion to these proteins did enhance the level of expression several fold. To determine if the fusion proteins were folded correctly, we determined the fluorescence properties of proteins in the soluble fraction. FIG. 4A also shows GFP fluorescence in approximately 0.1 mg of soluble protein in a final volume of 40 ul using Fluoroscan Accent FL fluorometer (LabSystems) with Excitation 485 nm/Emission 510 nm filter set with the exposure set to 40 sec. The data are presented in Arbitrary Units (AU) and show that Ub, SUMO, Urm1, Hub1 and ISG15 produced GFP protein that was able to fluoresce and, thus, was folded correctly. Fusions of GFP with Rub1, Apg8 and Apg12 were induced in large amounts but were not soluble and did not show any fluorescence.

In addition, it is shown that ISG15 plays a role in immune response (24). Thus presentation of ISG15 as a fusion protein is a viable tool for novel vaccine candidates. Similarly, Apg8 and Apg12 translocate protein to compartments in the cell for autophagy (30).

Similar experiments were performed with all the UBL-GFP fusion proteins, but the induction was performed at 26° C. overnight. The data shown in FIG. 4B confirms the finding in FIG. 4A. Almost all of the UBLs except Hub1 showed dramatically enhanced expression of GFP after fusion. In the case of SUMO, the level of expression was increased about 20 fold. Analysis of soluble fraction showed that Ub, SUMO, Urm and ISG15 were able to solubilize fused GFP (see FIG. 4B, Soluble panel). Functional analysis of fusion GFP was performed by fluorescence from the soluble fraction. This data confirms the observation made in FIG. 4A. Combining all the data from the induction studies demonstrates that fusion of all the UBLs to GFP enhances expression level from 2–40 fold. In addition, Ub, SUMO, Urm1, Hub1 and ISG15 also increase the solubility of the GFP. These UBLs are therefore capable of producing correctly folded proteins in *E. coli.*

Figure 5:
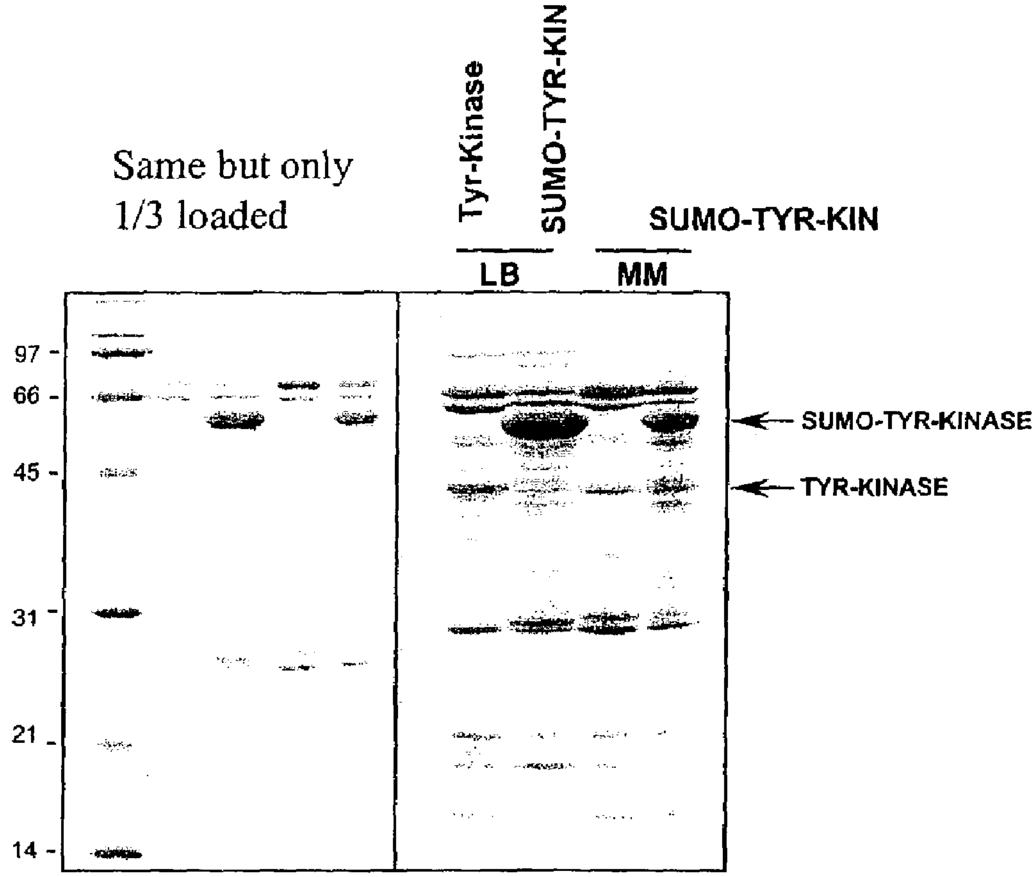
FIG. 5 is a Coomassie stained SDS-polyacrylamide gel demonstrating the expression and purification of a human tyrosine kinase as a SUMO fusion protein in *E. coli.* Tyrosine kinase and the fusion protein SUMO-tyrosine kinase were expressed in the Rossetta pLysS strain (Novagen) of *E. coli* in LB or minimal media (MM). The right panel shows the Ni-NTA resin purified proteins from the transformed *E. coli* cells. The left panel has the same lane arrangement as the right panel, but ⅓ of the amount protein was loaded on the SDS-polyacrylamide gel. Numbers indicate molecular weight standards in the first lane.
Figure 6:
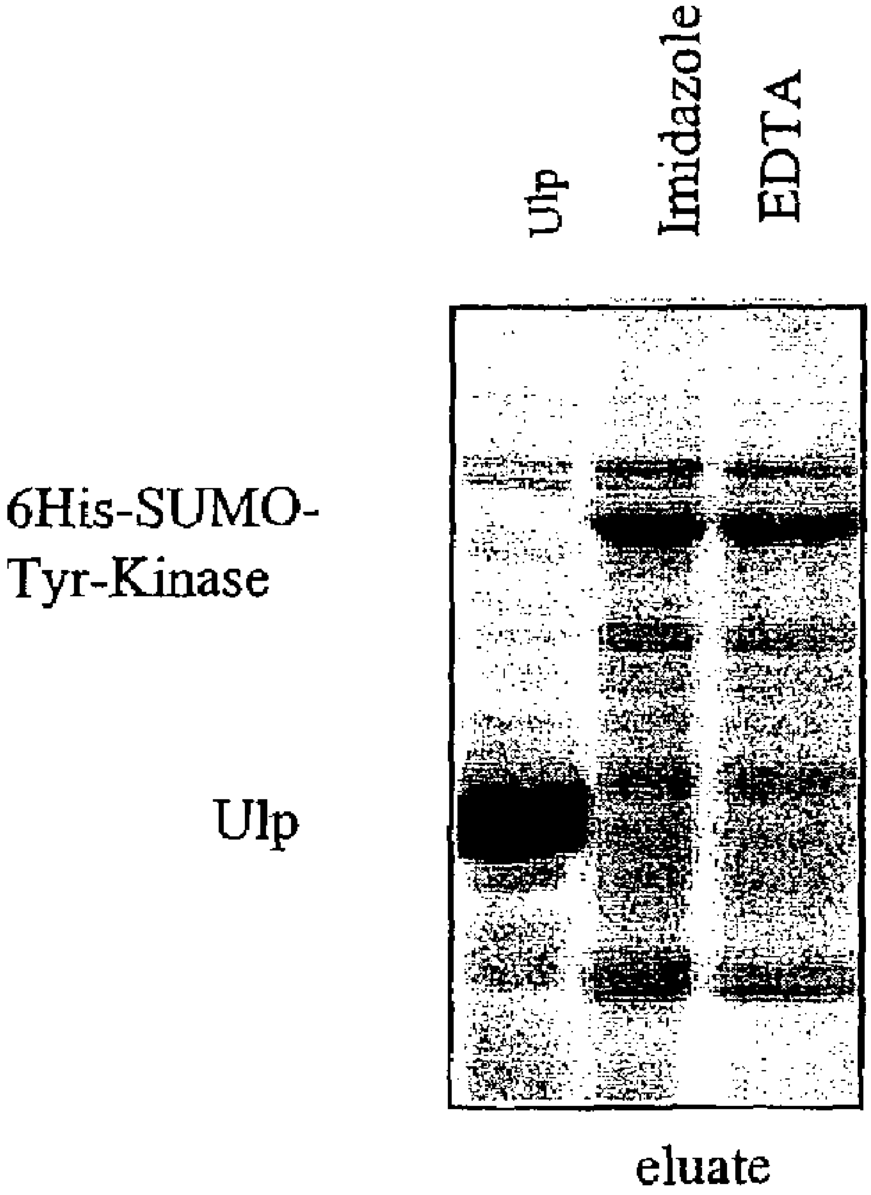
FIG. 6 shows a Coomassie stained SDS-polyacrylamide gel representing purified SUMO hydrolase from *E. coli* and the partial purification and elution of SUMO-tyrosine kinase fusion protein. *E. coli* cells were transformed with a vector expressing either SUMO hydrolase Ulp1 or SUMO-tyrosine kinase and cultured in minimal media. Proteins were subsequently purified by Ni-NTA resin. SUMO-tyrosine kinase was further purified by elution with either 100 mM EDTA or 250 mM imidazole. The gel shows that the current methods yield approximately 90% pure Ulp1 protein.

To gain more insight into the role of UBLs in enhancement of expression and solubility, we have tested the SUMO-fusion systems with other proteins as well. Serine threonine kinases, tyrosine kinase and human nuclear receptor have proven difficult to express in *E. coli*. Researchers have opted to use tissue culture systems to express soluble kinases of receptors. FIG. 5 shows expression 6His-SUMO-Tyr-Kinase and unfused Tyr-Kinase in *E. coli* using LB or minimal medium (MM), and purified on Ni-NTA resin as described previously. The small fraction of resin was boiled with 1×SDS-PAGE sample buffer and aliquots were resolved on the 12% SDS-PAGE. Equal amounts of *E. coli* culture were taken for SUMO-Tyr-kinase and unfused Tyr-kinase and purification was performed under identical conditions. The stained gel in FIG. 5 shows that SUMO fusion increases the yield of the kinase at least 20 fold, in cells grown in LB media. FIG. 6 also shows the pattern of the SUMO-Try kinase that was eluted from Ni-NTA by 100 mM EDTA or 250 mM imidazole. These data further demonstrate that SUMO fusion enhances the expression of difficult to express protein such as Tyr-kinase, and that the expressed fusion protein is soluble.

Figure 7:
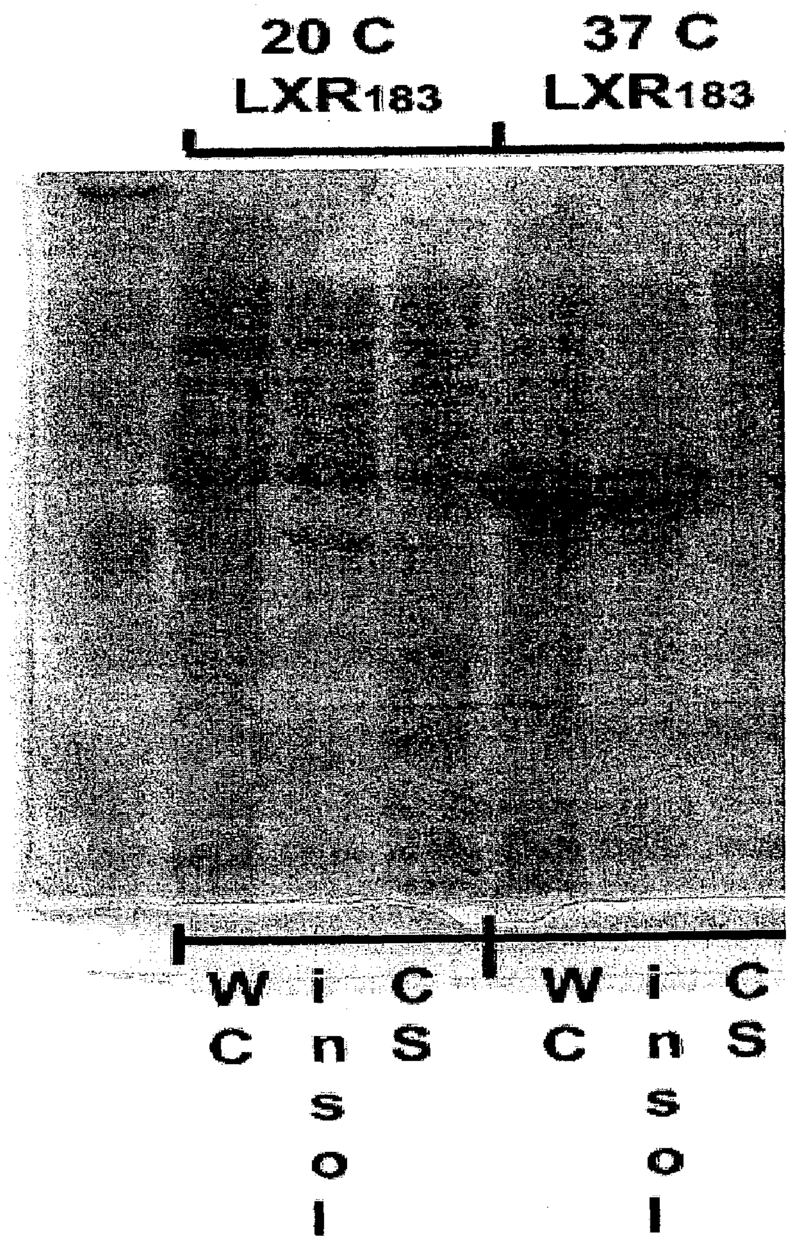
FIG. 7 is a stained SDS-polyacrylamide gel of the expression of the liver X receptor (LXR) ligand binding domain as a fusion protein with SUMO. *E. coli* cells were transformed with a SUMO-LXR expression vector. The cells were subsequently induced with 1 mM IPTG at 20° C. overnight or 37° C. for 3 hours. 10 µg of total protein (WC), soluble protein (CS), and insoluble protein (Insol) from each induction were loaded per well of a 12% SDS-polyacrylamide gel.

Human nuclear receptor proteins, such as steroid receptors, contain ligand-binding domains. These proteins have proven hard to express in soluble form in *E. coli.* We have used human liver X receptor (LXR) ligand binding domain to demonstrate that SUMO fusion promotes solubility of the protein in *E. coli.* The ligand-binding domain of LXR was expressed as SUMO fusion in Rosetta plysS cell at 20° C. or 37° C. and the pattern of soluble and insoluble protein was analyzed. FIG. 7 shows the stained SDS-polyacrylamide gel demonstrating that about 40% of the LXR protein was solublized by SUMO fusion, see lane CS in 20° C. box in FIG. 7 (predominant band in 40 kDa range). If the cells were induced at 37° C., hardly any SUMO-LXR was soluble although the level of protein induction had increased dramatically. Further proof that SUMO promotes solubility of previously insoluble proteins was gained by expressing MAPKAP2 kinase as a SUMO-fusion in *E. coli.* FIGS. 8A and 8B shows induction kinetics in *E. coli* cells expressing kinase at 20° C. and 37° C. Numbers at the top of the gel, 0.1, 0.25 and 0.5 refer to the mM concentration of inducer IPTG, in the culture. The original induced culture (I), supernatant from lysed cells (S) and resuspended pellet (P) were analyzed on 12% SDS-PAGE. The data clearly demonstrate that 90% of the SUMO kinase is soluble when the cells are induced at 20° C. with 0.25 mM IPTG. Although induction at 37° C. allows greater degree of expression, more than 50% of the kinase is still insoluble under these conditions. Cleavage of SUMO-MAPKKAP2 kinase by SUMO hydrolase is described in Example III. Also see FIG. 18.

Overall, these results show that in bacteria, fusion of UBLs to GFP increases the level of expression from 2–40 fold. Some of the UBLs such as Ub, SUMO, Urm1, Hub1, and ISG15 solublize otherwise insoluble proteins. In particular, SUMO has been demonstrated to increase solubility of kinases and LXR α under controlled temperature induction from 50–95% of the total expressed protein.

EXAMPLE II

Sumo-Fusion Expression in Yeast and Insect Cells

Fusions of C-Terminal UBLs to the N-Terminus of GFPs are Cleaved in Yeast

Figure 4B:
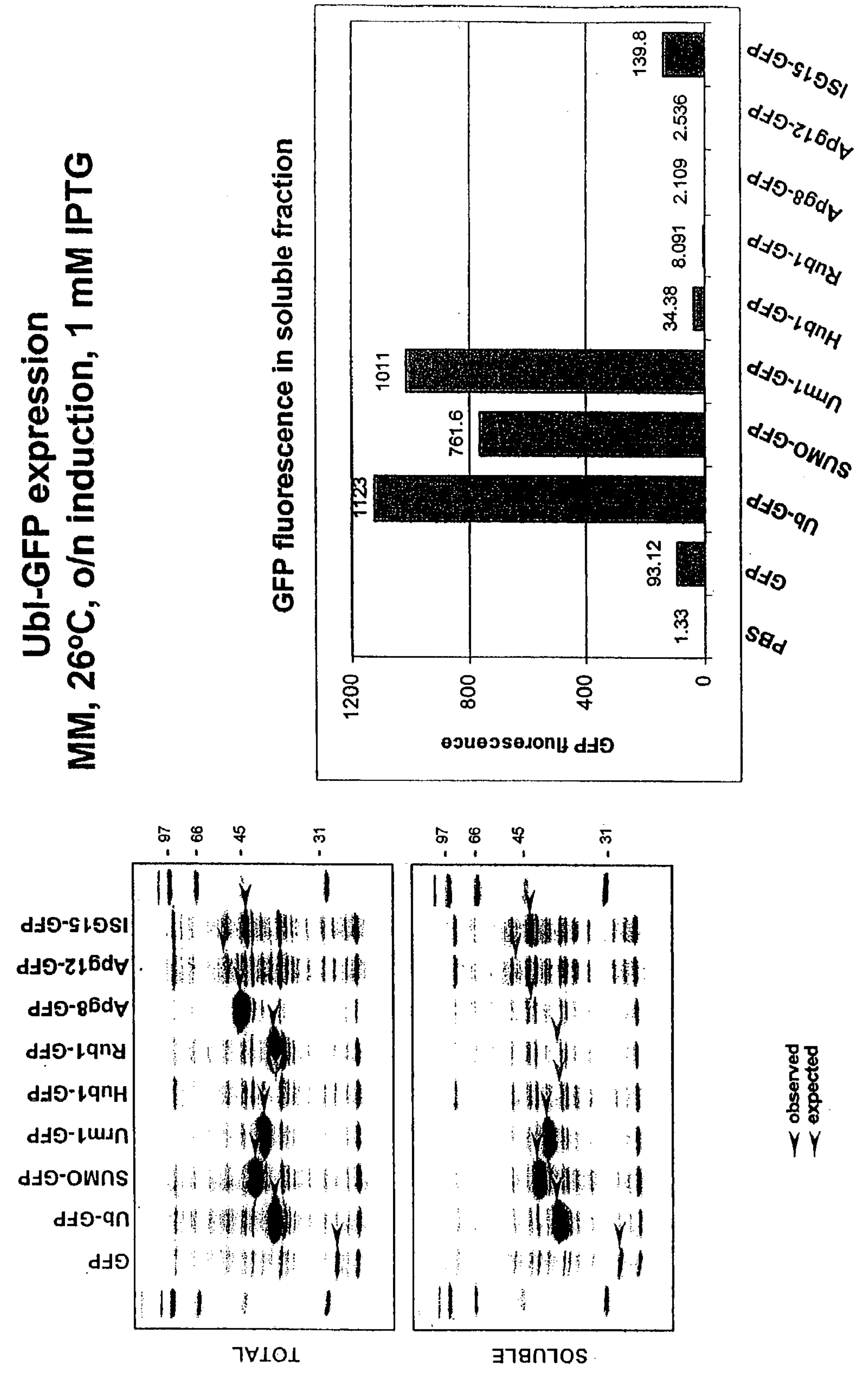
Figure 9:
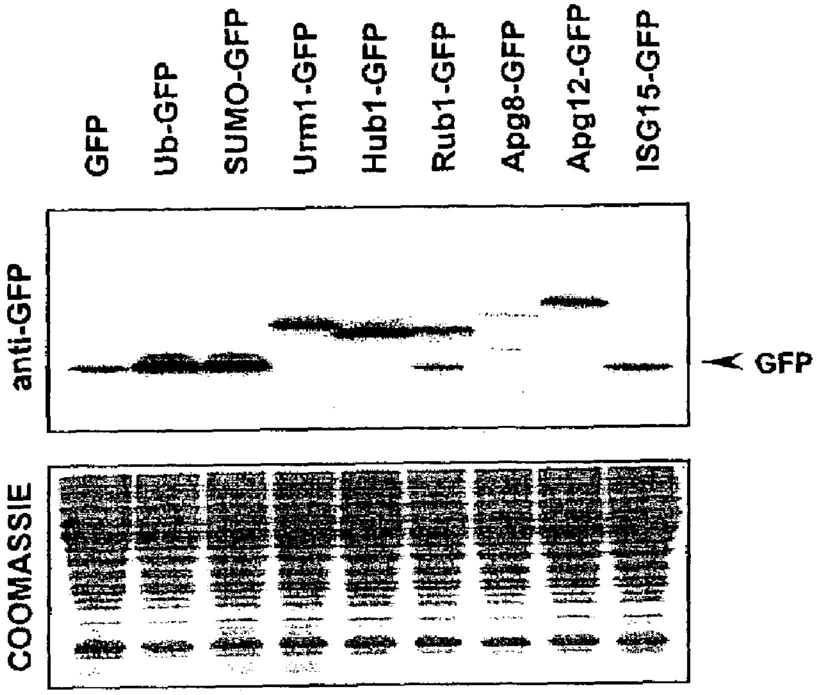
FIG. 9 is a Western blot (top panel) of UBL-GFP fusion proteins expressed in yeast cells demonstrating that UBL-GFP fusion proteins are co-translationally cleaved in yeast. Yeast strain BJ1991 was transformed with a vector expressing Ub-GFP, SUMO-GFP, Urm1-GFP, Hub1-GFP, Rub1-GFP, Apg8-GFP, Apg12-GFP or ISG15-GFP under the control of a copper sulfate regulated promoter. Total cell extracts were prepared by boiling the cells in SDS-PAGE buffer and briefly sonicating the sample to reduce viscosity. 20 μg of the total yeast proteins were resolved on 12% SDS-PAGE minigels and analyzed by Western blot with a rabbit polyclonal antibody against GFP and a secondary HRP-conjugated antibody. The arrow indicates the size of unfused GFP. An identical gel (bottom panel) was run in parallel and stained with Coomassie to ensure equal loading of the proteins from all samples.
Figure 10:
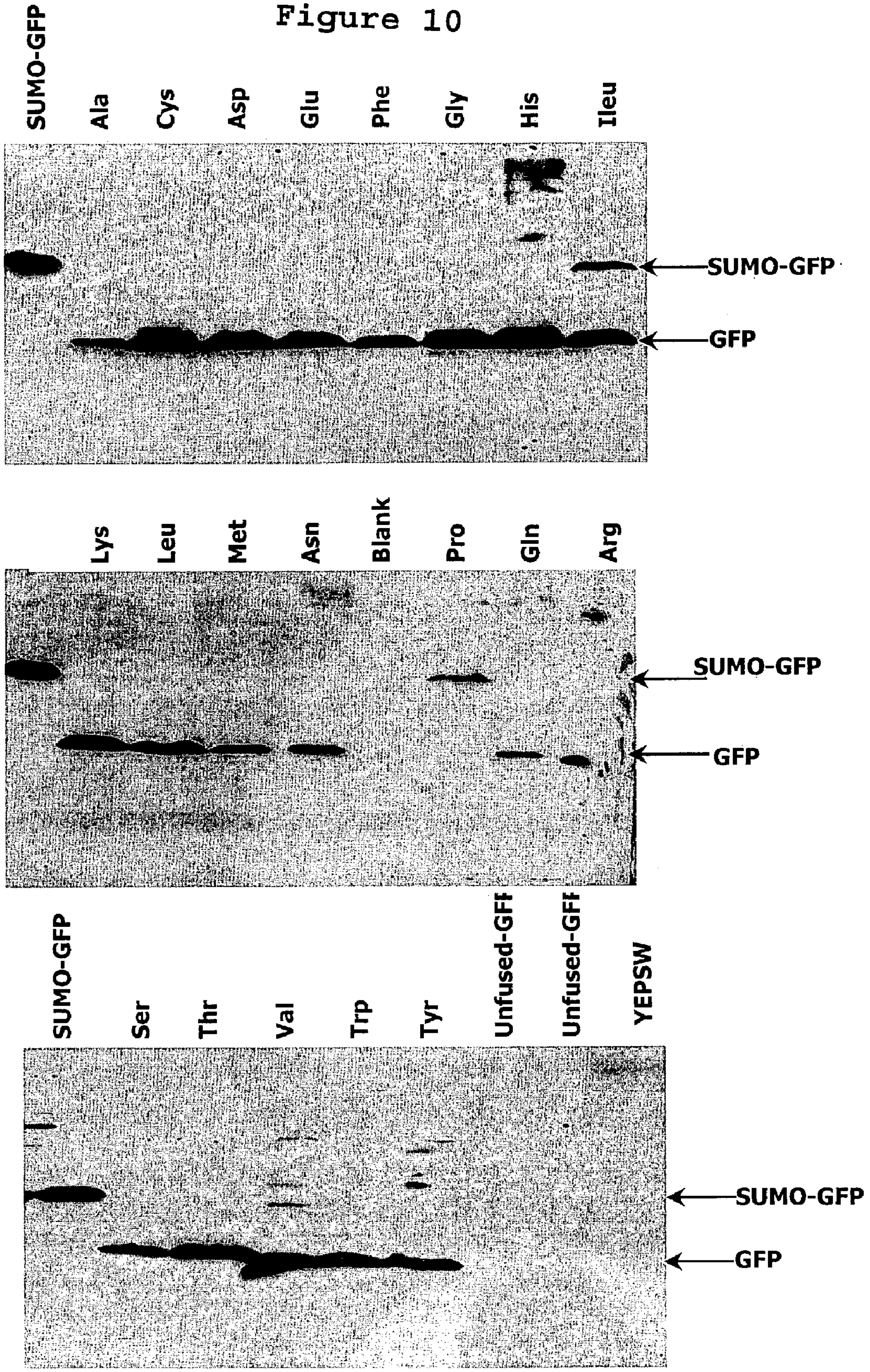
FIG. 10 is a series of Western blots that indicate SUMO-GFP Fusions are co-translationally cleaved in yeast generating novel amino termini. In addition to methionine as the first amino acid of GFP following the C-terminal Gly-Gly sequence of SUMO, we have engineered the remaining 19 amino acids as the amino-terminal residue of GFP in yeast SUMO-(X)20-GFP expression vectors. All expression vectors containing the 20 amino-terminal variants of GFP fusion proteins were expressed in yeast under the control of copper inducible promoter. Yeast lysates were separated by SDS-PAGE and analyzed by Western blot with antibodies against GFP. The "unfused-GFP" lanes represent the expression of GFP alone with no SUMO fusion. The "SUMO-GFP" lanes are bacterially expressed SUMO-GFP.

To further assess the utility of UBL fusion in eukaryotic cells we expressed all of the UBL-GFP fusions previously described in FIG. 4 in yeast. *S. cerevisiae* BJ1991 strain was transformed with either YEp-GFP or YEp-UBL-GFP fusion constructs using standard procedures. Positive clones were grown in YPD medium and induced with 100 μM $CuSO_4$ at cell density OD600=0.2 for 3.5 hours. Total cell extracts were prepared by boiling the yeast cells in SDS-PAGE buffer. Twenty ug of proteins were analyzed on 12% SDS gels. A replica gel was stained in Coomassie blue and another gel was blotted and probed with antibodies against GFP. Data in FIG. 9 shows that Ub-GFP, SUMO-GFP and ISG15-GFP fusions were efficiently cleaved in yeast, while Rub1-GFP fusion was partially cleaved. Apg8-GFP fusion was cleaved into two fragments. It is noteworthy that all the UBL-GFP fusions were designed with methionine as the first amino terminus. GFP fusion with Urm1, Hub1 and Apg12 expressed well, but were not cleaved in yeast. There was a modest increase in expression of GFP following fusion with Ub, SUMO, ISG15 and cleavage in yeast. Generally we have observed 10–20 fold increase in the level of protein expression following fusion to UBL in prokaryotes and eukaryotes (see FIGS. 4B, 10 and 11). The reason for the modest increase in GFP fusion following cleavage is that the cells were grown in induction media containing 100 μM copper sulfate in rich YPD media. Rich media contains many copper binding sites, and less free copper is available to induce the gene. A nearly 100-fold increase in GFP production has been observed with a variety of N-terminal fusions when cells were induced with 100 μM copper sulfate in synthetic media. See FIG. 10.

Generation of New Amino Termini:

The identity of the N-terminus of a protein has been proposed to control its half-life (the N-end Rule) (35). Many important biopharmaceuticals such as growth factors, chemokines, and other cellular proteins, require desired N-termini for therapeutic activity. It has not been possible to generate desired N-termini, as nature initiates translation from methionine, but the SUMO system offers a novel way to accomplish this.

To demonstrate that all N-termini of GFP in SUMO-GFP fusions were efficiently cleaved when expressed in yeast, a comprehensive study of SUMO-GFP with 20 N-termini was carried out. Multi-copy yeast expression plasmids were designed as described above. Plasmids were transformed in yeast strain BJ 1991, four single colonies were selected, and the levels and cleavage patterns of two of the strains were analyzed by SDS-PAGE and western blotting. Data from Western blots of a single colony is presented in FIG. 10. These results are in agreement with our in vitro studies of purified SUMO-X-GFPs (from *E. coli*) and its cleavage pattern of SUMO hydrolase. All of the SUMO-GFP fusions were cleaved efficiently except those containing proline at the junction (see FIG. 10, middle panel lane "Pro"). It is also interesting to note that SUMO-Ileu-GFP was partially cleaved during the phase of copper induction. All of the genes are under the control of copper inducible promoter. It is possible that SUMO-Ileu-GFP is resistant to cleavage due to the non-polar nature of the residue at the +1 active site of SUMO hydrolase. In this respect SUMO-Val-GFP was also partially resistant to cleavage in vivo (see lower most panel lane labeled "Val"). It is clear from these results that SUMO-Pro-GFP fusion was completely resistant to cleavage by yeast SUMO hydrolases as no GFP was observed (see lane "pro" in middle panel of FIG. 10). This data is consistent with our previous observations. See FIG. 15. Another important aspect of these findings is that fusion of SUMO with various N-termini of GFP appears to increase the expression of almost all the proteins, although to various degrees. For example Cys-GFP, Gly-GFP and His-GFP accumulated in greater amounts as compared to other N-terminal GFPs. A direct comparison of the increase in the level of GFP following fusion to SUMO can be made by comparing the level of un-fused GFP (see last lanes of lower most panel in FIG. 10). Although 20 ug of yeast proteins were loaded on SDS-PAGE the GFP signal was not detected. To ensure that we were not dealing with mutation or any artifact, we loaded a protein sample from another single colony that was induced in under similar conditions and the sample was loaded next to the previous GFP. No signal was detected, suggesting that unfused GFP is made in very small amounts that cannot be detected under the present experimental conditions, (i.e., a four hour induction with copper sulfate). These studies show that fusion with SUMO leads to a dramatic increase in the amount of protein expressed in yeast. All of the N-terminal fusions are cleaved by endogenous SUMO hydrolases except when the N-terminal residue is proline. Thus for enhanced expression of a protein in eukaryotes permanent attachment of SUMO is not required as significant (~100 fold) increased accumulation of the protein was observed even after the cleavage of SUMO. At the same time, SUMO-pro-fusions are also useful as 6×His-SUMO can be used to purify the protein from yeast, and the SUMO moiety can be removed with 10 times greater amounts of the SUMO hydrolase (see example III).

Previous studies have shown that attachment of ubiquitin to the N-termini of proteins in yeast enhances expression, and protein fusions containing all amino acid at the N-terminal residue, except proline, are efficiently cleaved in yeast (2, 10, 34). However, these technologies have several drawbacks. Firstly, none of the deubiquitinating enzymes (DUBs) have been shown to efficiently cleave ubiquitin fusion proteins of varying sizes and structures (3,1), despite the fact that they were discovered more than 15 years ago (35, 19, 3). Secondly, and perhaps more importantly, ubiquitin predominantly functions as a signal for proteolysis (14). Therefore, for physiological reasons and for the lack of robust cleavage of artificial ubiquitin-fusions by DUBs, the ubiquitin gene fusion system has not been successfully developed for commercial applications. We have observed that the SUMO system appears to perform in a manner that is remarkably superior to that of ubiquitin, as SUMO and other UBL fusions enhance protein expression and solubility in prokaryotes. In addition, many of the UBLs increase expression of GFP, following the cleavage of UBL in yeast. Unlike the ubiquitin-fusion system, which may direct the protein to the ubiquitin proteosome pathway, the current cleavage of fusion-protein in yeast is the result of C-terminal fusion with SUMO, and proteins generated with novel N-termini are not subject to degradation by the ubiquitin-proteosome pathway. This is one of the reasons that large amount of GFP has accumulated in yeast after cleavage of the SUMO fusion (see FIG. 10).

N-Terminal Attachment of Ubiquitin Promotes Protein Secretion:

To date, a role for ubiquitin in the secretion of proteins has not been determined. We have assessed whether N-terminal fusion of ubiquitin to a protein promotes its secretion in yeast. Several yeast expression vectors that express *E. coli* β-glucoronidase (GUS) were designed. All of the yeast GUS expression vectors described in Table 2 are engineered under the control of the strong glycolytic GPD promoter that expresses constitutively. Some of the constructs were also expressed under the control of a copper regulated metallothionein promoter (CUP1) as well. CUP1 promoter driven synthesis of the SUMO-GUS constructs was induced by addition of 100 μM copper sulfate and incubation of 3 hours. To determine the level of GUS from media, cells were harvested by centrifugation at 2000×g for 10 mins. Supernatant was collected and equal amounts of aliquots were assayed for enzymatic activity or western blot analysis as described above. For the comparative study, all strains were treated identically and grown at the same time to equal O.D, and the assays were performed at the same time. To examine intracellular enzymatic activity, the cells were harvested by centrifugation and washed with Tris EDTA buffer, pH 7.5. The cell pellets were suspended in sarcosine buffer and ruptured with glass beads at 4° C., three times by vigorously vortexing. Supernatant was collected for assay of the enzymatic activity. The amount of protein secretion was determined by estimating relative activity of the enzyme in the media. The data is shown in Table 2.

TABLE 2

Ubiquitin-GUS Expression and Secretion in Yeast
GUS activity was measured as described. It was not possible to measure specific units of GUS in the media as yeast grown in synthetic media. Yeast secretes little protein and current methods of protein estimation, BioRad kit cannot estimate the protein, the data was presented as + where one + is equal to 2 units of GUS as described in invention.
− Sign means no GUS activity was detected.

| Vector (pRS425) | Promoter | Signal Sequence | GUS Activity Inside Cell | GUS Activity In Supernatant |
|---|---|---|---|---|
| ADH1-GUS1 | ADH1 | — | +++ | − |
| GPD-α-factor-GUS1 | GPD | α-factor | ++ | |
| GPD-Ub-GUS1 | GPD | Ubiquitin | ++++ | ++++ |
| GPD-Ub-α-factor-GUS1 | GPD | Ubiquitin-α-factor | ++++ | − |
| GPD-α-factor-Ub (pro)-GUS1 | GPD | α-factor-Ubiquitin(pro) | ++ | − |
| GPD-α-factor-Ub (met)-GUS1 | GPD | α-factor-Ubiquitin(met) | ++ | − |
| CUP1-Ub-GUS1 | CUP1 | Ubiquitin | ++++ | ++ |

The following conclusions are drawn from this study.

Figure 13A:
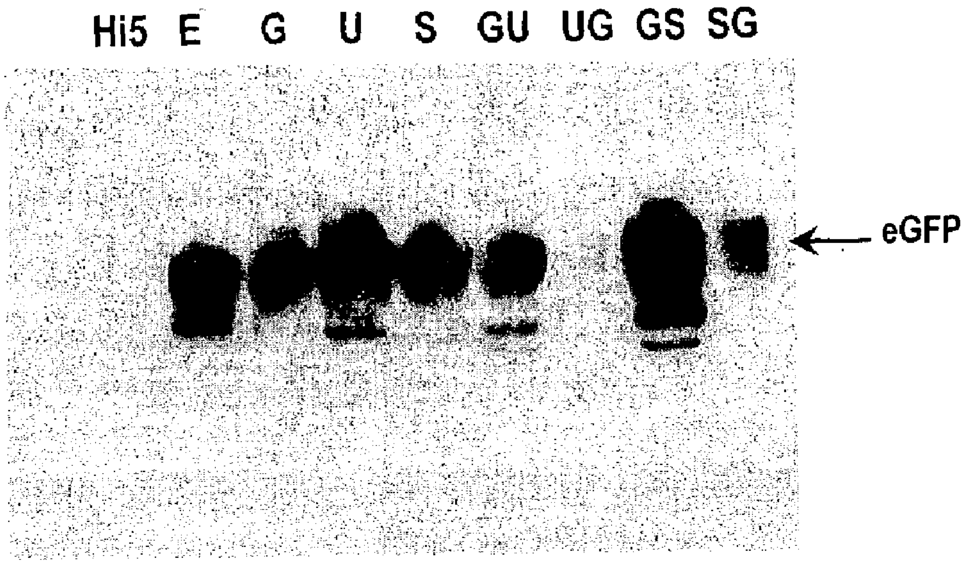
FIGS. 13A, 13B, and 13C are Western blots demonstrating expression of SUMO and ubiquitin fusion proteins in insect cells. Hi-five insect cells were infected with recombinant baculovirus encoding for SUMO or ubiquitin fusion proteins. At 48 hours post-infection, equal amounts of cell lysates (FIGS. 13A and 13C) and media (FIG. 13B) were separated by SDS-PAGE and analyzed by Western blot with antibodies against GFP. The lanes are: Hi5 is Hi Five cells, E is eGFP, G is gp67-eGFP, U is ubiquitin-eGFP, S is SUMO-eGFP, GU is gp67-ubiquitin-eGFP, UG is ubiquitin-gp67-eGFP, GS is gp67-SUMO-eGFP, SG is SUMO-gp67-eGFP, and S-P is SUMO-proline-GFP.

1) Fusion of ubiquitin to GUS leads to a several fold increase when yeast extracts were analyzed by enzymatic assays.
2) Insertion of proline at the junction of ubiquitin and GUS did not allow cleavage of the ubiquitin-GUS fusion protein.
3) The attachment of alpha factor secretory sequences to the N-terminus of ubiquitin-fusion did not have show any appreciable increase in secretion of the protein into the media.
4) Presence of alpha factor sequences between ubiquitin and GUS did not lead to any increase in extracellular level of GUS activity.
5) Greatest amount of secretion was observed with ubiquitin-Met-GUS. These observations suggest that endogenous secretory sequences of GUS in the context of ubiquitin promote the best secretion for GUS. To this end the current data from yeast correlates very well with the ubiquitin-GFP protein secretion in insect cells (see FIG. 13).

Fusion of SUMO and Ubiquitin to the N-Terminus of GFP Promotes Enhanced Expression and Secretion in Insect Cells.

Figure 12A:
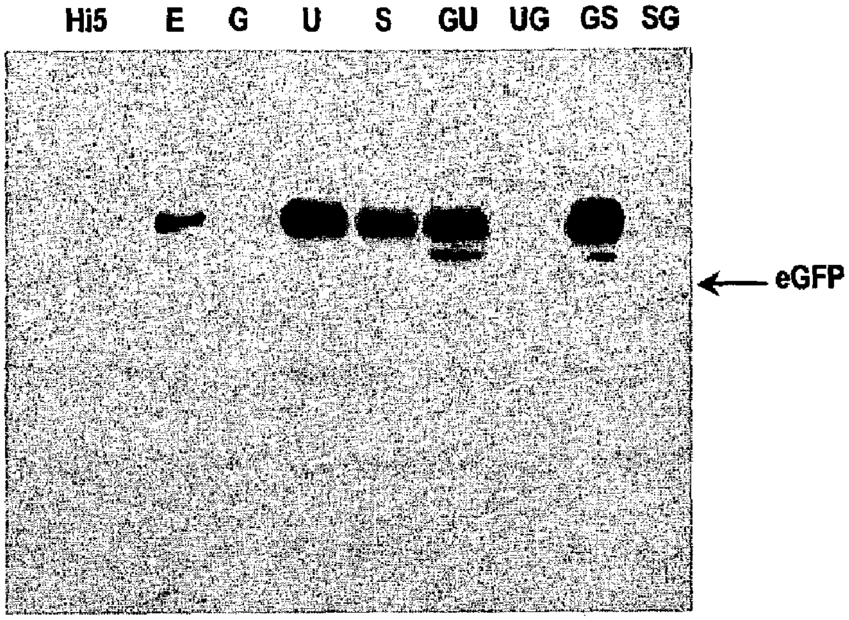
FIGS. 12A and 12B are Western blots demonstrating expression of SUMO and ubiquitin fusion proteins in insect cells. Hi-five insect cells were infected with recombinant baculovirus encoding for SUMO or ubiquitin fusion proteins. At 24 hours post-infection, equal amounts of cell lysates (FIG. 12A) and media (FIG. 12B) were separated by SDS-PAGE and analyzed by Western blot with antibodies against GFP. Lane markers: Hi5 is Hi Five cells, E is eGFP, G is gp67-eGFP, U is ubiquitin-eGFP, S is SUMO-eGFP, GU is gp67-ubiquitin-eGFP, UG is ubiquitin-gp67-eGFP, GS is gp67-SUMO-eGFP, SG is SUMO-gp67-eGFP, and eGFP is a positive control.
Figure 12B:
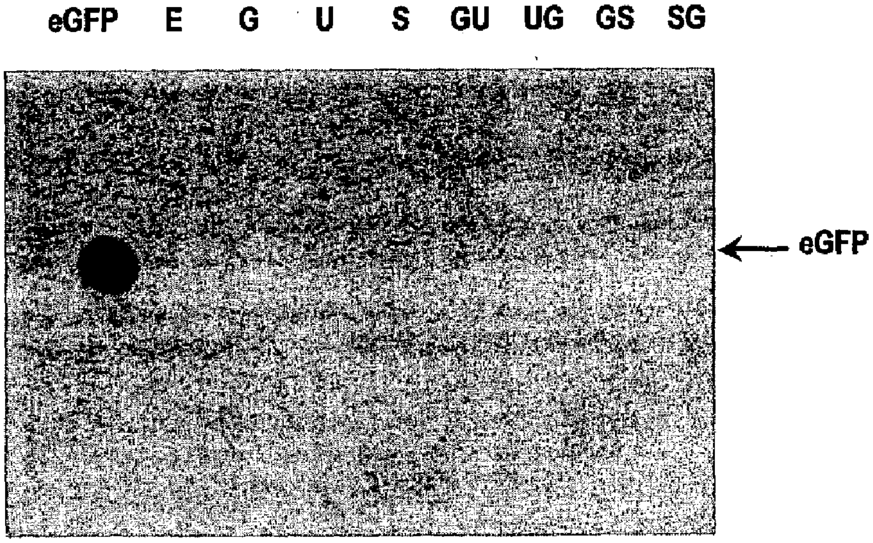

The role of SUMO in enhanced expression and secretion of proteins in cultured cells has also been studied in insect cells. Baculovirus vectors expressing SUMO-GFP constructs and appropriate controls have been described above. See FIG. 11A for the orientation gp67 secretory signals in the SUMO-GFP constructs. Data from a 24 hour infection is shown in FIG. 12. Panel A shows intracellular protein analysis by Western blots. It is clear that fusion with ubiquitin and SUMO promotes a large increase in the amount of protein (compare lane E with lane U and S). Insertion of gp67 signal sequences to the N-terminus of SUMO leads to further increase in the amount of protein in insect cells (compare unfused GFP lane E with gp67-SUMO-GFP lane GS). On the other hand attachment of gp67 signal sequence to the N-terminus of GFP (lane G, UG or SG) did not increase the level of protein expression, to the contrary there was diminution of signal when gp67 was attached to N-terminus of GFP (lane G) or between SUMO and GFP (lane SG). We estimate that in the level of expression in the context of gp67-SUMO-GFP is 20× fold higher as compared to unfused GFP (lane E) or 40× fold higher as compared to gp67-GFP (lane G). No unfused GFP was secreted by any of the constructs at 24 hour post infection, as shown in blot in FIG. 12 panel B. These results show that fusion with SUMO leads to a dramatic increase in expression of GFP in insect cells. Additionally, both SUMO-GFP and gp67-SUMO-GFP were efficiently cleaved by endogenous SUMO hydrolases.

Similar experiments were performed with cells 48 hours post infection. The data in FIGS. 13A and B show that the pattern of intracellular expression was similar to the one seen in 24 hours of infection; however, large amounts of ubiquitin and SUMO-GFP protein were secreted at 48 hour post infection. Examination of the blots from media and intracellular protein show that reasonable expression of unfused GFP was observed inside the cell, but hardly any protein was secreted in the media (compare lane E of panel A and panel B in FIG. 13). Attachment of gp67 to the N-terminus of SUMO-GFP leads to the greatest amount of protein secreted into the media (see lane GS in panel B). Another important finding is that attachment of ubiquitin without any signal sequences shows very high secretion of GFP in the media. This result is completely consistent with our finding that attachment of ubiquitin to the N-terminus of GUS promotes the greatest amount of secretion of GUS into the yeast media.

Figure 13B:
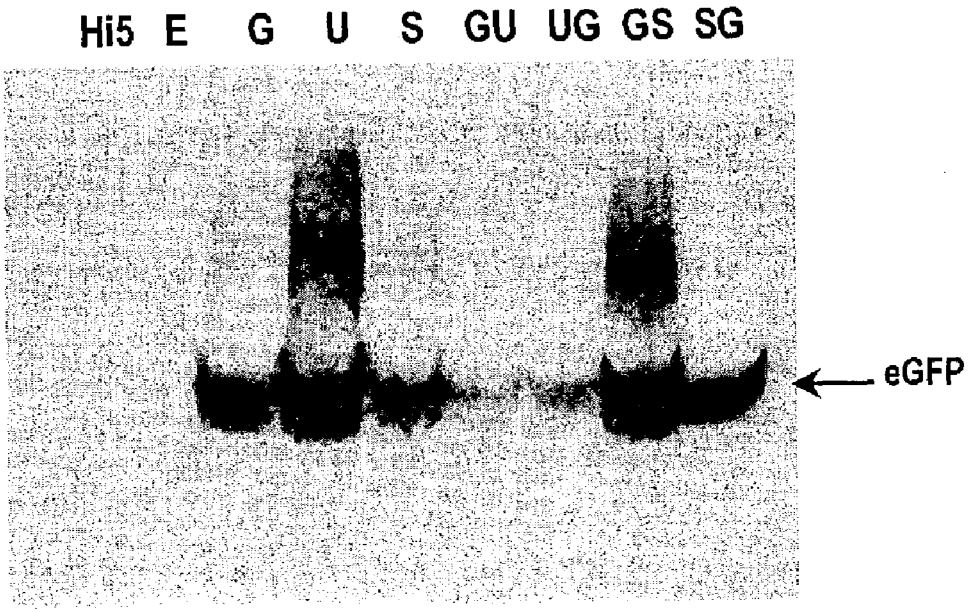
Figure 13C:
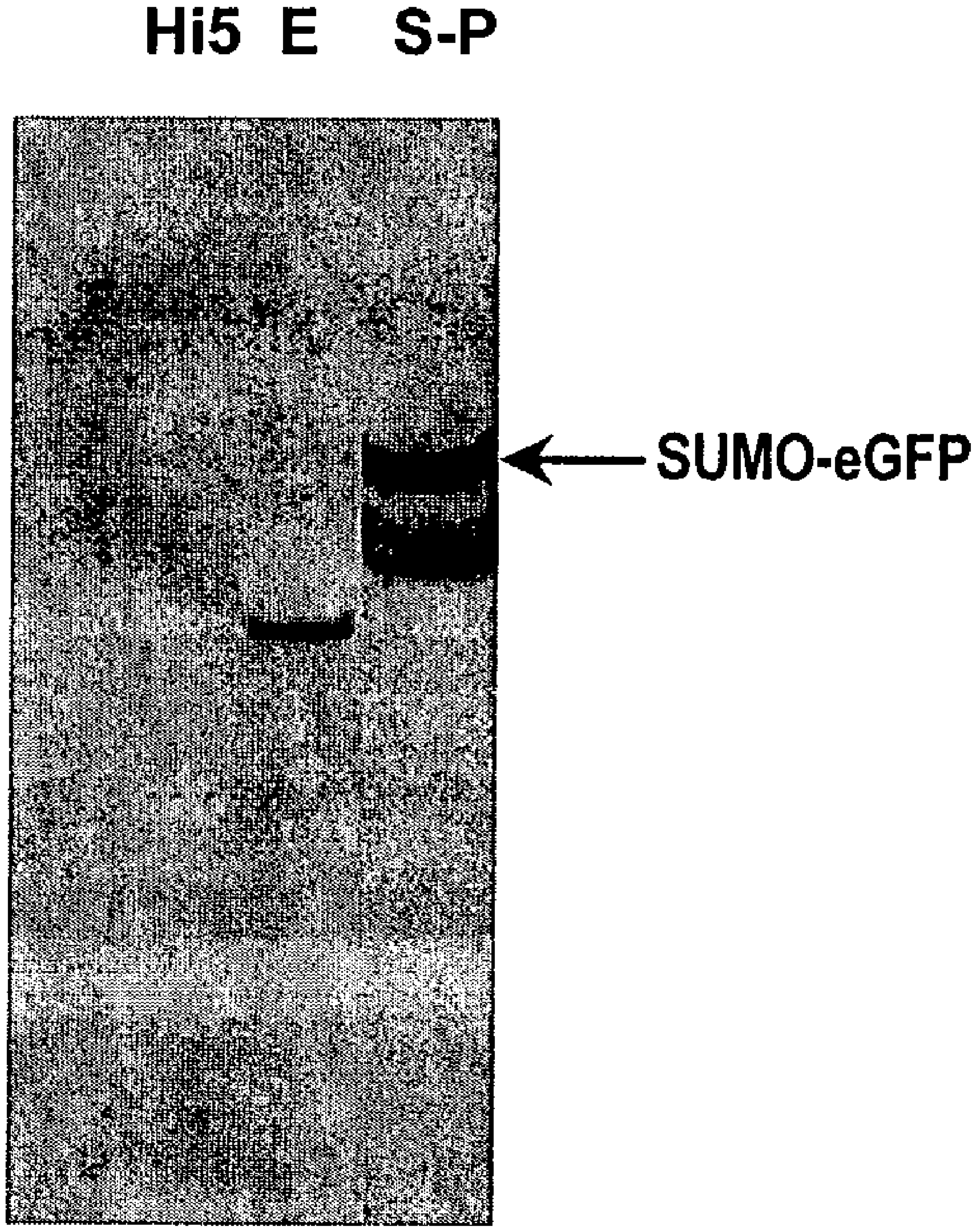

We have also discovered that SUMO-Pro-GFP fusion was not cleaved by endogenous SUMO hydrolases in insect cells (FIG. 13C). Although some non-specific degradation of SUMO-Pro-GFP was observed in these experiments (see lane S-P in FIG. 13C), we conclude that unlike SUMO-GFP, SUMO-Pro-GFP is not cleaved in insect cells. This observation is also consistent with the finding in yeast that SUMO-Pro-GFP is not cleaved in cells while other N-terminal GFP fusions are processed in yeast.

Further confirmation of these observations was obtained by fluorescence imaging of the cells expressing GFP fusion proteins. FIG. 14 shows that cells expressing GFP and fusion GFP fluoresce intensely. The fluorescence imaging was the strongest and most widely diffused in cell expressing gp67-SUMO-GFP and Ub-GFP. These cells show the largest amount of GFP secreted into the media (FIG. 13 panel B). It appears that secretory signal attachment directly the to N-terminus of GFP produces less GFP in the media and inside the cells. This observation is borne out by low fluorescence intensity and granulated pigmented fluorescence (see panel G-eGFP, S/G-eGFP and U/G-eGFP). These data have led to the following conclusions:

1) The increase in the amount of SUMO-fusion protein expression in insect cells was several-fold higher (20–40 fold) than that of unfused protein, as determined by and Western blot analysis.
2) All of the SUMO-GFP constructs that contain methionine at the +1 position were cleaved except SUMO-Proline-GUS. This aspect of the SUMO-fusion technology allows us to express proteins that are stably sumoylated.
3) Attachment of ubiquitin to the N-terminus of GFP led to dramatic enhancement in secretion of the protein in the media. Ubiquitin promotes secretion of proteins that may or may not have endogenous secretory signal. Thus, N-terminal ubiquitination may be utilized as a tool to enhance secretetion of proteins in eukaryotic cells.
4) N-terminal SUMO also promotes secretion of protein in insect cells.

EXAMPLE III

SUMO Protease ULP1 Cleaves a Variety of SUMO-Fusion Proteins:

Properties and Applications in Protein and Peptide Expression and Purification

Yeast cells contain two SUMO proteases, Ulp1 and Ulp2, which cleave sumoylated proteins in the cell. At least eight SUMO hydrolases have been identified in mammalian systems. The yeast SUMO hydrolase Ulp1 catalyzes two reactions. It processes full length SUMO into its mature form and it also de-conjugates SUMO from side chain lysines of target proteins. Examples I and II establish our findings that attachment of SUMO to the N-terminus of under-expressed proteins dramatically enhances their expression in *E. coli*, yeast and insect cells. To broaden the application of SUMO fusion technology as a tool for expression of proteins and peptides of different sizes and structures, the ability of Ulp1 to cleave a variety of proteins and peptides has been examined. Purified recombinant SUMO-GFPs were efficiently cleaved when any amino acid except Proline is present in the +1 position of the cleavage site. Similar properties of SUMO hydrolase Ulp1 were observed when Sumo-tyrosine kinase, Sumo-protein G, Sumo-β-GUS, and SUMO MAPKAP2 kinase were used as substrates. The in vitro activity of the enzyme showed that it was active under broad ranges of pH, temperature, and salt and imidazole concentration. These findings suggest that the Ulp1 is much more robust in cleavage of the SUMO-fusion proteins as compared to its counterpart, ubiquitin-fusion hydrolase. Broad specificity and highly efficient cleavage properties of the Ulp1 indicate that SUMO-fusion technology can be used as a universal tag to purify a variety of proteins and peptides, which are readily cleaved to render highly pure proteins.

The following materials and methods are provided to facilitate the practice of Example III.

Affinity Purification and Cleavage of SUMO Fusion Proteins with SUMO Hydrolase.

The following table lists the solutions required for the affinity purification and cleavage procedures:

| Solution | Components |
|---|---|
| Lysis buffer | 25 mM Tris pH 8.0; 50 mM NaCl |
| Wash Buffer | 25 mM imidazole; 50 mM Tris pH 8.0; 250 mM NaCl; (optional) 5–10 mM β-mercaptoethanol (protein dependent) |
| Elution Buffer | 300 mM imidazole; 50 mM Tris pH 8.0; 250 mM NaCl; (optional) 5–10 mM β-mercaptoethanol (protein dependent) |
| SUMO hydrolase (Ulp1) Cleavage Buffer | 50 mM Tris pH 8.0; 250 mM NaCl; 5 mM β-mercaptoethanol (protein dependent) |

From typical 250 ml cultures, the samples are pelleted by centrifugation, and supernatants are removed by decanting. Generally, from 250 ml of culture, 1.0–1.5 grams of wet cells are produced. Pelleted cells are then resuspended in 5–10 ml of lysis buffer. RNase and DNase are added to final concentration of 10 ug/ml lysis solution. Samples are kept on ice throughout the sonication procedure. Using an appropriate tip, the samples are sonicated 3–5 times for 10 second pulses at 50% duty cycle. Sonicates are incubated on ice for 30 minutes; if the samples are viscous after this time, the sonication procedure is repeated. Lysed samples (in lysis solution) are loaded onto 1-ml columns. The columns are washed with 5 to 10 volumes of wash buffer (wash fractions are saved until the procedure is complete). Columns are developed with 2.5 ml of elution buffer, and SUMO hydrolase cleavage is performed by one of two methods: 1) cleavage is performed in elution buffer, with SUMO hydrolase added at 50 ul/250 ml buffer, samples incubated at room temperature for 2 hr or overnight at 4° C., and cleavage monitored by gel electrophoresis; 2) imidazole is first removed by dialysis, gel filtration, or desalting, samples are then resuspended in SUMO hydrolase cleavage buffer, SUMO hydrolase is added at 50 ||l/2.5 ml buffer, and samples are incubated at room temperature for 2 hr or at 4° C. overnight, with cleavage monitored by gel electrophoresis. Units of SUMO hydrolase are defined as the amount of enzyme that cleaves 1 ug of pure SUMO-Met-GFP (up to 95%) in 50 mM Tris-HCl pH 8.0, 0.5 mM DTT, 150 mM NaCl at room temperature in 60 minutes.

After cleavage, protein can be stored at 4° C., or subjected to purification.

Flow Chart of Affinity Purification and Cleavage Options

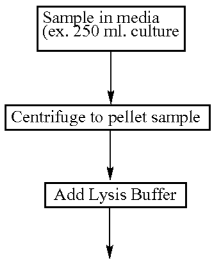

-continued

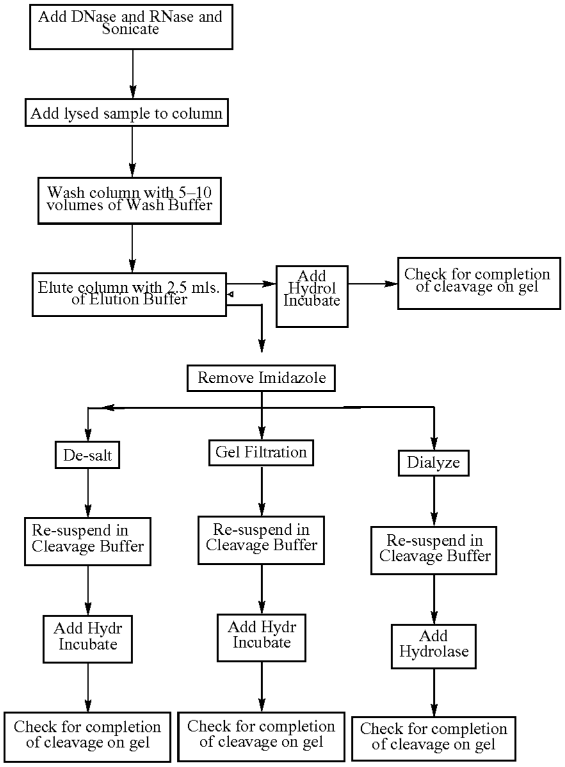

The expression and purification of carboxy terminus of Ulp1p is described above.

In Vitro Cleavage Experiments

The various His6smt3XeGFP fusions were expressed in Rosetta (DE3) pLysS (Novagen). The recombinant proteins were purified using Ni-NTA agarose (Qiagen). The comparative in vitro cleavage reactions were carried out by first normalizing the amount of the various fusions in each reaction. This was done by measuring the fluorescence properties of the purified fusion proteins using the fluorimeter Fluoriskan II (Lab Systems) and then diluting the more concentrated samples with the Ni-NTA agarose elution buffer (20 mM Tris-HCl pH 8.0, 150 mM NaCl 300 mM Imidazole and 5 mM beta-mercaptoethanol), such that their fluorescence values equaled that of the lowest yielder. Each cleavage reaction contained 100 ul of protein, 99 ul of the buffer 20 mM Tris-HCl pH 8.0, 150 mM NaCl and 5 mM beta-mercaptoethanol and 1 ul of enzyme. The reactions were incubated for 3 hours at 30° C. after which they were stopped by addition of 6× Laemmli SDS-page loading buffer followed by boiling at 95° C. for 5 minutes. The products of the cleavage reaction were analyzed by SDS-PAGE.

Proline cleavage experiments were carried out in a fashion similar to those described above. The purified His6smt3PeGFP was buffer exchanged into 20 mM Tris-HCl pH 8.0, 150 mM NaCl and 5 mM beta-mercaptoethanol using a PD-10 column. A 10 fold increase in the amount of Ulp1 were added to each reaction. Digestions were incubated for 3 hours at 30° C. All reactions were stopped by addition of Laemmli loading buffer and analyzed by SDS-page.

FIG. 15 shows the stained SDS-PAGE analysis of all the SUMO-X-GFPs and their digestion by SUMO hydrolase. The findings clearly show that Ulp1 hydrolase was able to cleave all the SUMO-GFP fusions except proline. These finding are similar to the observations made in yeast (FIG. 10) and in insect cells (FIG. 13).

Conjugation of ubiquitin and SUMO to its target proteins is a highly regulated and dynamic process. Several deubiquitinating enzymes (DUBs) have been identified in yeast and other eukaryotic cells (1). Yeast genetics studies show that many of these enzymes are not essential suggesting that an overlapping function is performed by most of these enzymes. DUBs have been most extensively studied and shown to cleave linear ubiquitin fusions as well isopepetide bonds (3, 35). Much less is known about the enzymes that remove SUMO from isopeptide bonds or artificial SUMO-fusion proteins. Hochstrasser and Li have shown that Ulp1 and Ulp2 remove Smt3 and SUMO 1 from proteins and play a role in progression through the G2/M phase and recovery of cells from checkpoint arrest, respectively (20, 21). Ulp1 and Ulp2 cleave C-terminus of SUMO (–GGATY; SEQ ID NO: 59) to mature form (–GG) and de-conjugate Smt3 from the side chains of lysines (20, 21). The sequence similarity of two enzymes is restricted to a 200-amino acid sequence called ULP that contains the catalytically active region. The three-dimensional structure of the ULP domain from Ulp1 has been determined in a complex form with SUMO (Smt3) precursor (27). These studies show that conserved surfaces of SUMO determine the processing and de-conjugation of SUMO. Database searches of the human genome and recent findings suggest that there are at least 7 human ULPs with the size ranging from 238 to 1112 amino acid residues (18, 33, 39). It is intriguing to note that SUMO Ulps are not related to DUBs, suggesting that SUMO Ulps evolved separately from DUBs. The findings that ULP structure is distantly related to adenovirus processing protease, intracellular pathogen *Chlammydia trachomatis* and other proposed bacterial cystiene protease core domains suggest that this sequence evolved in prokaryotes (20, 21). Detailed properties of the SUMO proteases are provided in described in Table 3.

TABLE 3

SUMO Hydrolases/Proteases

| Enzyme | Properties (MW) | Reference |
|---|---|---|
| UB1-specific Protease ULP1 | 72 KDa. 6 21 residues Cleaves linear fusion and SUMO isopeptides bonds. | Li and Hochstrasser, 1999 (REF 20) |
| ULP2 (Yeast) | 117 KDa, 1034 residues Cleaves linear fusions and SUMO isopeptide structures. | Li and Hochstrasser, 2000 (REF 21) |
| SUMO-I C-Terminal | 30 Kda Cleaves linear fusions and SUMO isopeptide structures | Suzuki, et al, 1999 (REF 33) |
| SUMO-I specific Protease SUSP I (Human) | 126 KDa 1112 residues Specific for SUMO-1 fusion but not Smt3 fusion. Does not cleave isopeptide bond. | Kim, et al, 2000 (REF 18) |
| Sentrin specific Proteases (SENP) SENP1 SENP2 SENP3 SENP4 SENP5 SENP6 SENP7 | All of the SENP enzymes have conserved C-terminal region with core catalytic cysteine. The smallest SENP7 is 238 residues and the largest SENP6 is 1112 residues. | Yeh, et al, 2000 (REF 39) |

Ulp1 has proven extremely robust in cleaving a variety of SUMO-fusion proteins expressed in *E. coli* as described in the present example. We have designed SUMO-GFP fusions in which the N-terminal methionine has been replaced with rest of the 19 amino acids. Attachment of 6×His to N-terminus of SUMO afforded easy purification of the 20 SUMO-GFP fusions from *E. coli*. The enzyme was active under broad ranges of pH, temperature, salts and imidazole concentration and was very effective in cleaving variety of proteins from SUMO fusion that includes BPTI a 6.49 KDa, Protein G a 7 KDa, β-Glucuronidase (GUS) and 110 KDa β-Galactosidase (GAL) genes. These findings suggest that the Ulp1 is much more robust in cleavage of the SUMO-fusion proteins as compared to its counterpart ubiquitin-fusion hydrolase.

SUMO Protease/Hydrolase is a Robust Enzyme:

Effects of Temperature and Additives

Figure 17:
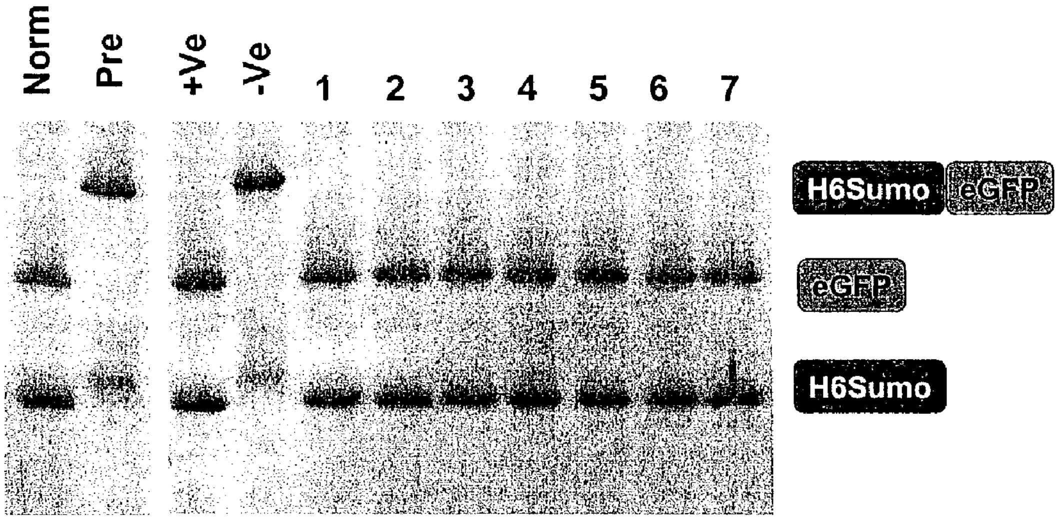
FIG. 17 is a stained SDS-polyacrylamide gel representing the effects of various protease inhibitors on Ulp1. Ni-NTA purified His6SUMO-GFP was incubated with Ulp1 and 10 mM of various protease inhibitors for 1 hour at room temperature. Lane markers: Norm is addition of Ulp1 and N-ethymaleimide (NEM) to the substrate at the same time, Pre is the incubation of Ulp1 with NEM prior to the addition of substrate, +Ve is the absence of any inhibitor, −Ve is in the absence of Ulp1, lane 1 is with E-64, lane 2 is with EDTA, lane 3 is with leupeptin, lane 4 is with NEM, lane 5 is with pepstatin, lane 6 is with TLCK. Low molecular weight markers (LMW) are also provided.

The effects of various additives/conditions and temperature upon the in vitro cleavage reaction were determined as follows: His6smt3MeGFP was expressed from pET24d in Rosetta (DE3) pLysS (Novagen). The recombinant protein was purified as before using Ni-NTA agarose (Qiagen) and then buffer exchanged into 20 mM Tris-HCl pH 8.0, 150 mM NaCl and 5 mM β-mercaptoethanol using a PD-10 column (AP Biotech). Cleavage reactions were performed with 100 ug of the purified protein, 0.5 ul of enzyme, the appropriate amount of a stock solution of additive to generate the final concentrations listed in Table 4, plus the exchange buffer up to a final volume of 200 ul. Reactions were incubated for 1 hour at 37° C. except for those at 4° C. were incubated for 3 hours. The data in FIG. 16 shows that Ulp1 was extremely active at 37° C. as well as at 4° C. Generally, His tagged proteins are purified on nickel columns and eluted with imidazole. We have discovered that the enzyme was remarkably active at 0–300 mM imidazole concentration. The enzyme was highly active at 0.01% SDS and up to 1% triton X 100. See Table 4. Similarly, chaotropic agents such as urea and did not effect the activity of the enzyme up to 2 M. Ulp1 showed 50% activity at 0.5M concentration of guanadinium hydrochloride (FIG. 16 and Table 4). A variety of reagents, including cysteine protease inhibitors, EDTA, PMSF. Pepstatin, Leupeptin, TLCK had no effect on the enzymatic activity (FIG. 17 and Table 4). N-ethymaleimide was active only if incubated with the enzyme prior to addition of the substrate. All the data shown in Table 2 demonstrate that this enzyme is extremely robust and thus constitutes a superior reagent for cleaving fusion proteins under variety of conditions.

TABLE 4

The Effect of Different Conditions on the Ulp1 Hydrolase Activity

| Conditions/ Additions | Effect |
|---|---|
| Environmental: | |
| Temperature | Ulp1 is active over a broad range of temperatures, cleaving from 4 to 37° C. |
| Salts: | |
| Imidazole | Ulp1 shows similar activity in the range of 0 to 300 mM |
| Detergents: | |
| SDS | 0.01% SDS blocks activity |
| Triton-X | Ulp1 shows similar activity on the range of 0 to 0.1% |

TABLE 4-continued

The Effect of Different Conditions on the Ulp1 Hydrolase Activity

| Conditions/ Additions | Effect |
|---|---|
| Chaotrophs | |
| Urea | Ulp1 shows complete activity up to and including a 2 M concentration |
| Gdm HCl | Ulp1 shows 50% activity in 0.5 M but is completely inactive in 1 M concentrations |
| Protease inhibitors: | |
| E-64 | Cysteine protease inhibitor; no affect |
| EDTA | Metalloprotease inhibitor; no affect |
| PMSF | Serine protease inhibitor; no affect |
| Pepstatin | Aspartate protease inhibitor; no affect |
| Leupeptin | Inhibits serine and cysteine proteases with trypsin-like specificity; no affect |
| TLCK-HCl | Inhibits serine and cysteine proteases with chymotrypsin-like specificity; no affect |
| N-ethylmaleimide | Cysteine protease inhibitor; on effective if enzyme is preincubated with inhibitor before addition of substrate |

Figure 18:
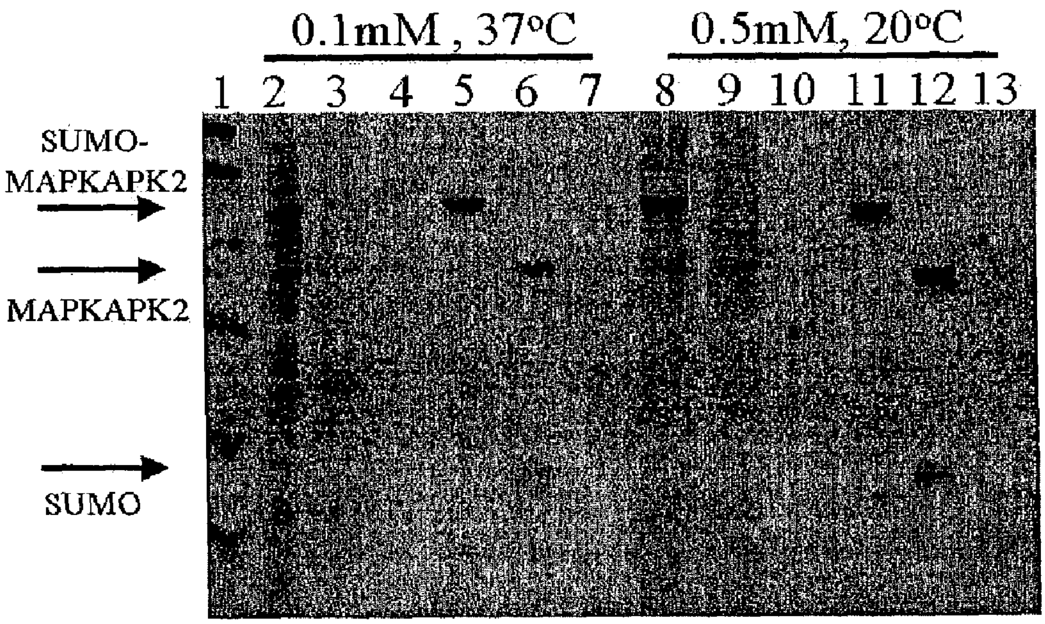
FIG. 18 is a stained SDS-polyacrylamide gel showing purification and cleavage of MAPKAP2. *E. coli* transformed with the expression vector for SUMO-MAPKAP2 where either grown at 37° C. and induced with 0.1 mM IPTG (lanes 2–7) or at 20° C. and induced with 0.5 mM IPTG (lanes 8–13). Cell lysates were Ni-NTA purified and separated by SDS-PAGE. Lane 1: BioRad low molecular weight marker; lanes 2 and 8: soluble fraction of cell lysates; lanes 3 and 9: flow through from Ni-NTA column; lanes 4 and 10: 15 mM imidazole wash of Ni-NTA column; lanes 5 and 11: 300 mm imidazole elution of Ni-NTA column; lanes 6 and 12: supernatant of 2 hour incubation of elution with SUMO hydrolase at 30° C.; and lanes 7 and 13: pellet of hydrolase incubation.

Robust Properties of SUMO Hydrolase: Cleavage of Different Size Fusion Proteins Under Broad pH Range:

FIG. 18 shows purification of a 40 kDa MAPKAP2 kinase that was difficult to express unless fused to SUMO. We have shown in Example I (FIG. 8) that this kinase was expressed in a highly soluble form (95%) as fusion to SUMO. FIG. 18 shows that whether purfied from cells expressing at 37° C. or 20° C., the SUMO fusion was efficiently cleaved under the conditions described.

Figure 19:
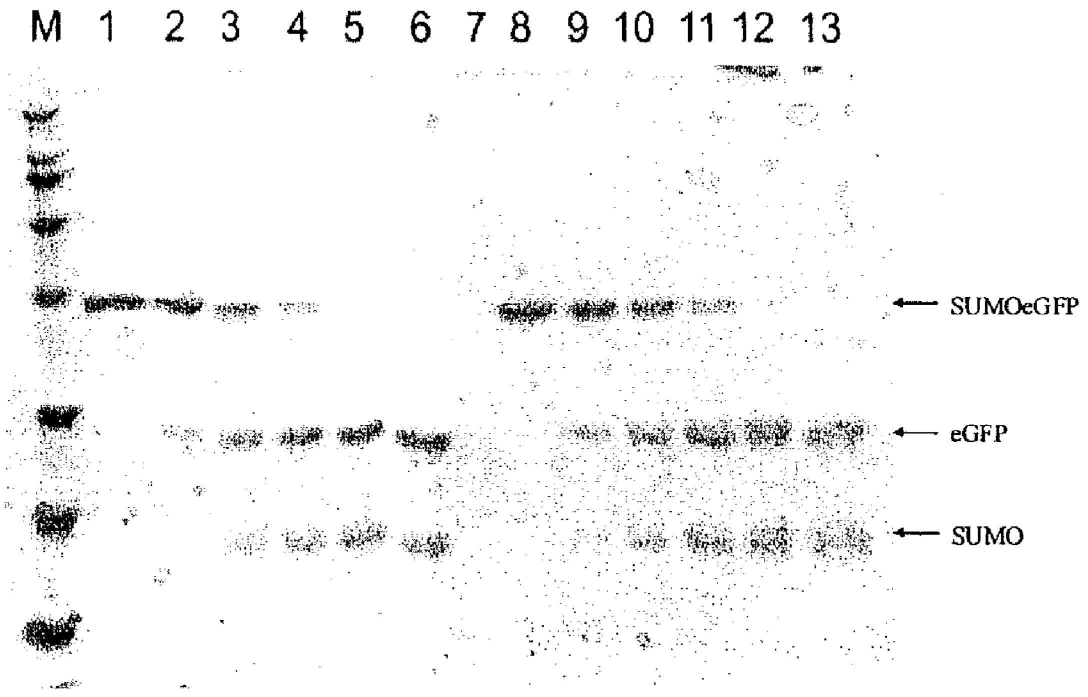
FIG. 19 is a stained SDS-polyacrylamide gel showing SUMO hydrolase function at pH 7.5 and 8.0. Purified SUMO-GFP was cleaved using 1/50 diluted purified stock of SUMO hydrolase in sodium phosphate buffer pH 7.5 (lanes 1–6) and 8.0 (lanes 8–13) at room temperature for the following length of times: lanes 1 and 8: 0 minutes, lanes 2 and 9: 1 min, lanes 3 and 10: 2.5 min, lanes 4 and 11: 5 min, lanes 5 and 12: 10 min, and lanes 6 and 13: 20 min. Lane 7 is blank and M is molecular weight markers.

The SUMO hydrolase also functions under broad pH range. FIG. 19 shows kinetics of cleavage at pH 7.5 and 8.0. The data shows that purified SUMO-GFP was completely digested at room temperature. We have also performed experiments from pH 5.5 to 10. The data (not shown) support the notion that this enzyme is active over broad range of pH.

Figure 20:
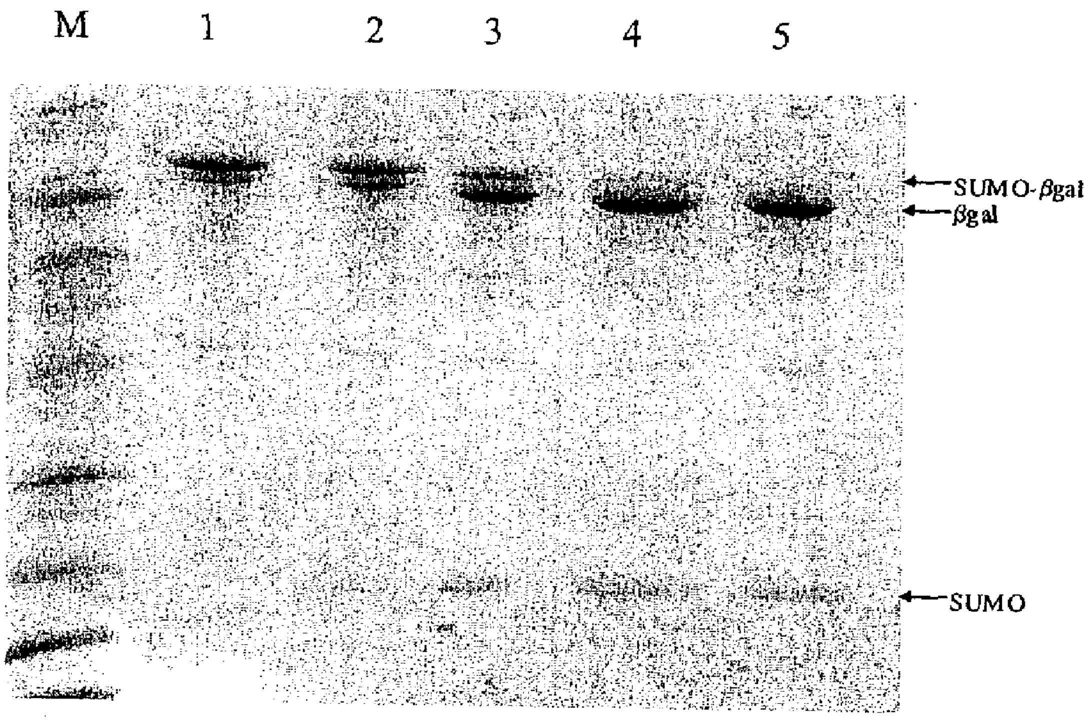
FIG. 20 is a stained SDS-polyacrylamide gel indicating SUMO hydrolase cleaves SUMO-β-Galactosidase. Purified SUMO hydrolase was incubated with *E. coli* produced SUMO-β-Galactosidase at room temperature for 0 minutes (lane 1), 2.5 min (lane 2), 5 min (lane 3), 10 min (lane 4), and 20 min (lane 5). Molecular weight markers are provided in lane M.

As discussed above, for broad utility of the system it is important that the enzyme be able to cleave fusion proteins of different sizes and structures in vitro. FIG. 20 shows the digestion pattern of SUMO-β-galactosidase (β-Gal) a 110 KDa protein. β-Gal enzyme is composed of tetrameric subunits. The digestion pattern demonstrates that in 20 minutes, SUMO hydrolase was able to cleave 100% of the protein.

Figure 21:
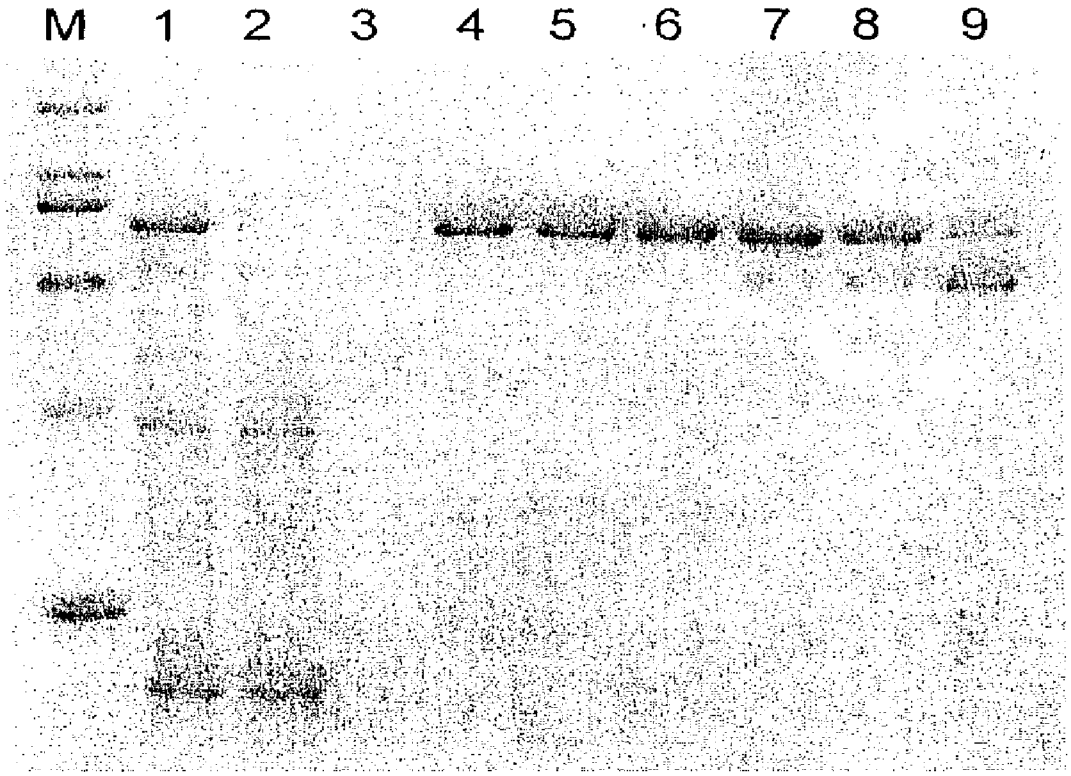
FIG. 21 is a stained SDS-polyacrylamide gel showing the cleavage of SUMO-GUS by SUMO Hydrolase in the presence of urea. Ni-NTA purified SUMO-β-GUS was incubated with 1/50 dilution of purified stock of SUMO hydrolase for 1 hour in increasing concentrations of urea at pH 8.0. Lane markers: M is broad range molecular weight marker; lane 1 is SUMO-GUS from soluble *E. coli* fraction; lane 2: flow through from nickel column; lane 3: wash; lane 4: elution; lanes 5–9: SUMO-GUS and hydrolase with various denaturants, specifically, lane 5: none; lane 6: 1 mM DTT; lane 7: 0.5 M Urea; lane 8: 1.0M Urea; lane 9: 2.0M Urea.

Among dozens of proteins expressed as SUMO fusions in our lab, only one, β-GUS, proved partially resistant to cleavage by the hydrolase. Configurations of artificial SUMO fusion are bound to occur wherein the structure of the protein will hinder the ability of the enzyme to recognize and bind the cleavage site of the fusion protein. This problem has been solved by adding small concentrations of urea, which does not inhibit the hydrolase, but results in cleavage the fusion that was previously resistant. FIG. 21 shows the digestion pattern of purified β-GUS and SUMO hydrolase before and after addition of urea. Lane 6 and 9 contain the same amount of SUMO hydrolase to which 2M urea was added during the incubation. Addition of urea allowed complete cleavage of 65 KDa β-GUS in 20 min at room temperature. This data further proves that the SUMO hydrolase cleaves broad spectrum of fusion protein efficiently. Additives such as urea can be added to aid complete cleavage of these structures that are resistant to hydrolase action.

Figure 22:
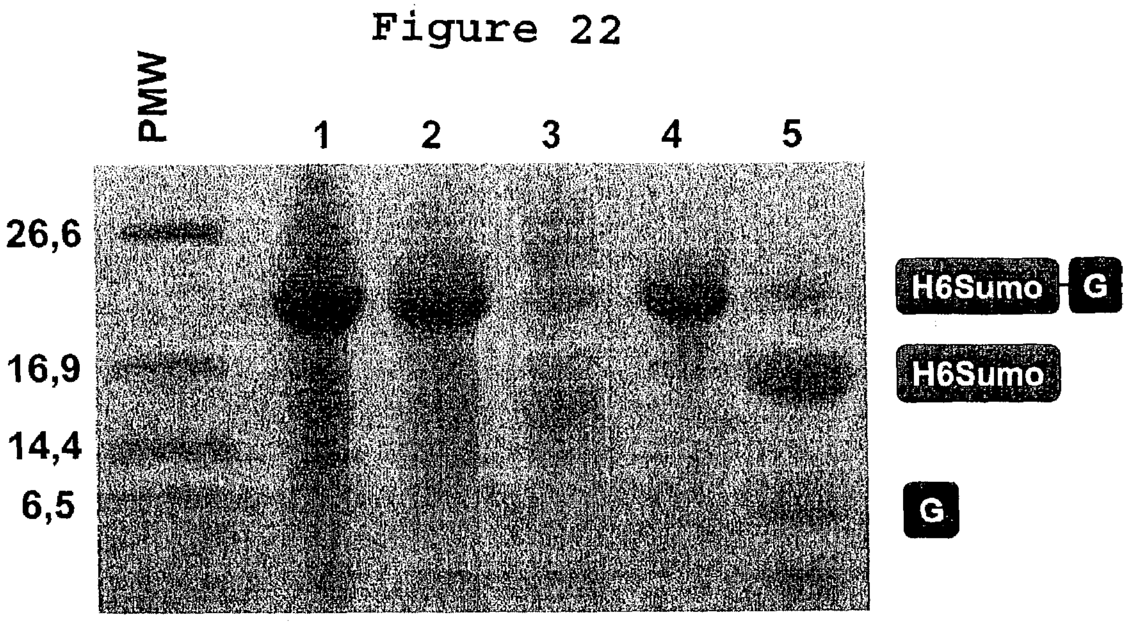
FIG. 22 is a stained SDS-polyacrylamide gel demonstrating the rapid isolation of a SUMO fusion protein. *E. coli* cells expressing a single IgG binding domain from Protein G fused to His6Smt3 were lysed with guanidinium chloride lysis buffer. Cell lysate supernatants were purified over Ni-NTA and eluted in a native buffer that allows for cleavage by Ulp1. Lane markers: PMW is molecular weight markers; lane 1 is cellular proteins prior to treatment with guanidinium chloride, lane 2 is guanidinium chloride cell lysates, lane 3 is flow through from Ni-NTA column, lane 4 is elution, and lane 5 is Ulp1 cleavage of elution.
Figure 39:
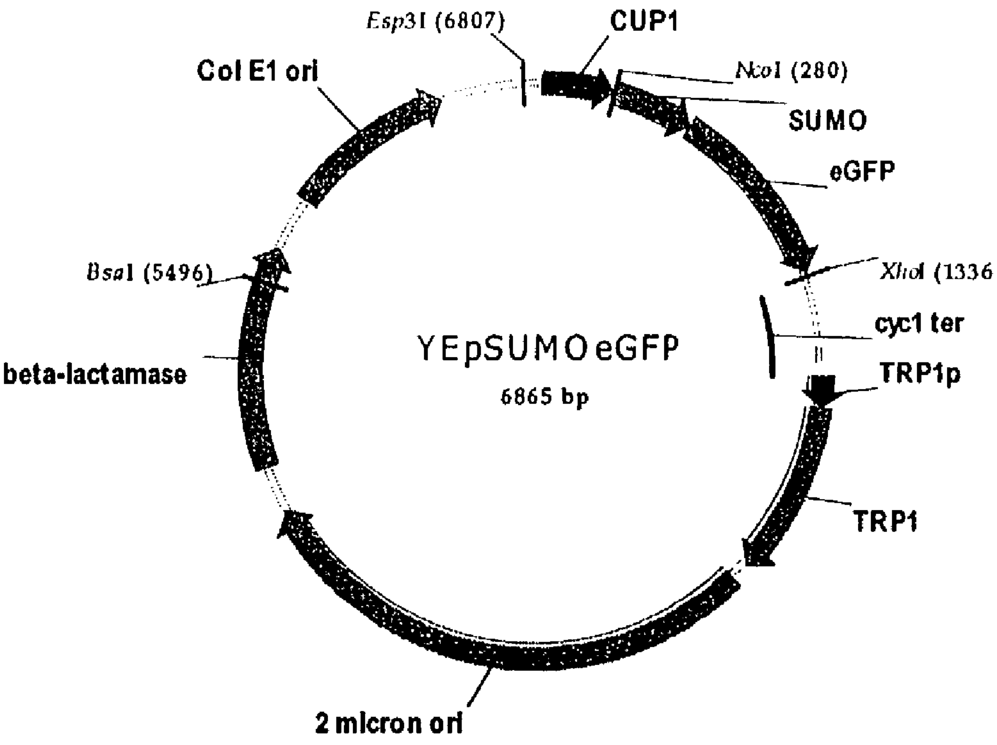
FIG. 39 is a circular map of YEpSUMO-eGFP.
Figure 41:
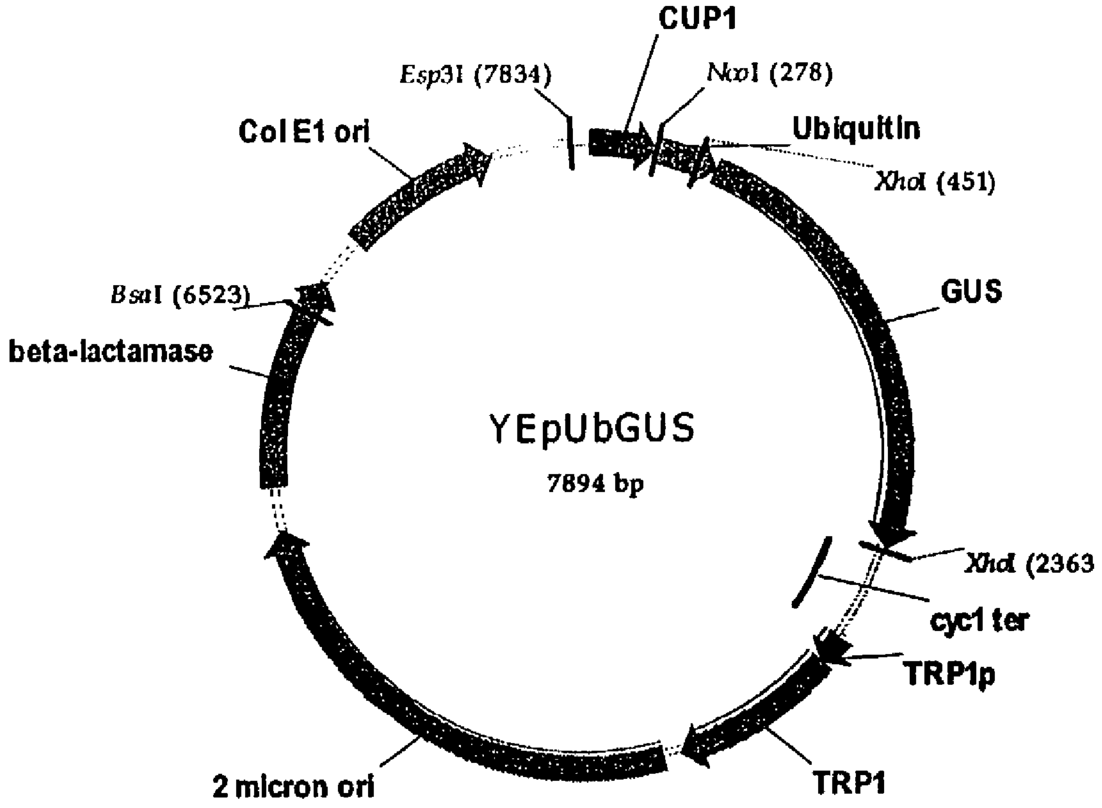
FIG. 41 is a circular map of YEpUbGUS.
Figure 43:
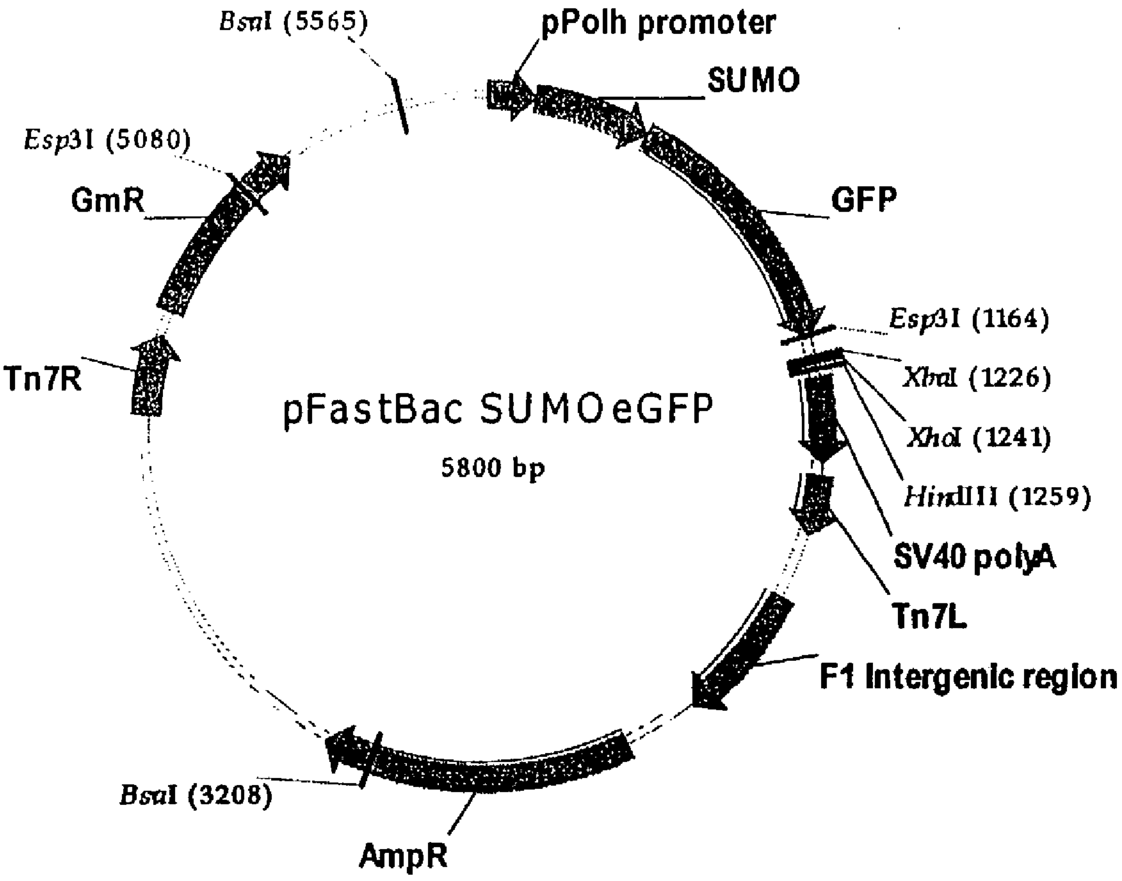
FIG. 43 is a circular map of pFastBac SUMO-eGFP.

High Throughput Protein Purification of Fusion Proteins: Rapid Peptide Miniprep We have discovered that, due to the rapid folding properties of SUMO, the fused protein can also be rapidly re-natured after treatment of the crude protein mix with chaotropic agents such as guanidinium hydrochloride or urea. We have developed a simple and rapid procedure to purify SUMO-fused proteins that are expressed in prokaryotes and eukaryotes. This method was tested with SUMO-protein G fusion expressed in *E. coli.* Cells expressing 6×His-SUMO-G protein fusion were harvested and frozen until required for protein purification. Three times the weight per volume lysis buffer (6 M Guanidinium Chloride, 20 mM Tris-HCl, 150 mM NaCl, pH 8.0) was added to the cell pellet rapidly lyse the cells. The supernatant was loaded onto a pre-equilibrated column containing Ni-NTA agarose (Qiagen), the flow through was collected for analysis. The column was then washed, first with 2 column volumes (CV) of Lysis buffer, followed by 3 CV of wash buffer (20 mM Tris-HCl, 150 mM NaCl 15 mM Imidazole pH 8.0). The fusion protein was then eluted using 2 CV of elution buffer (20 mM Tris-HCl, 150 mM NaCl 300 mM Imidazole pH 8.0). The purified product is present in a native buffer that allows for cleavage and release of the peptide from the Sumo fusion using Ulp1. See FIG. 22. This data demonstrates that it is possible to rapidly purify the fusion protein and cleave it from the resin with Ulp1. It is possible that proteins of higher molecular weights may not rapidly re-nature and be amenable to cleavage by Ulp1. However, since the Ulp1 requires three-dimensional SUMO be intact the purification and cleavage properties are more dependent on the refolding of SUMO. Similar to DNA mini-preps, rapid mini preps for the expression and purification analysis of the fused proteins may be readily employed. Table 5 summarizes the data showing the dramatic enhancement of protein production observed when utilizing the compositions and methods of the present invention. The sequences and vectors utilized in the practice of the invention are shown in FIGS. 23–46.

TABLE 5

| Fusion with SUMO Enhances Protein Expression | |
|---|---|
| *E. coli* Expression of UBLs | All of the fusion have Met N-Termini |
| SUMO-GFP | 40 fold |
| Ub-GFP | 40 fold |
| Urm1-GFP | 50 fold |
| Hub1-GFP | 2 fold |
| Rub1-GFP | 50 fold |
| Apg8-GFP | 40 fold |
| Apg12-GFP | 20 fold |
| ISG15-GFP | 3–5 fold |
| Yeast | Met and Various N-Termini |
| Various UBLs expressed in rich media. | Copper induction not observed in rich media, however, Ub, SUMO, ISG15 fusions were processed and GFP induced 3–5 fold. |
| All of the twenty N-terminal variants were expressed in yeast as SUMO-X-GFP fusions. GFP was processed in all cases, except when N-terminal residue was proline. | Dramatic induction of GFP following fusion with SUMO. At least 50–100 fold induction as compared to unfused GFP expression. Under current loading conditions (20 ug) GFP was not detectable. |

TABLE 5-continued

| Fusion with SUMO Enhances Protein Expression | |
|---|---|
| Insect Cells | Met as N-termini |
| SUMO-GFP | 10 fold compared to GFP |
| gp67-SUMO-GFP | 30 fold compared to gp-GFP |
| gp67-SUMO-GFP | 50 fold compared to SUMO-gp67-GFP |
| Secretion SUMO-GFP | At least 50 fold compared to GFP |
| Secretion Ub-GFP | At least 50 fold compared to GFP |

REFERENCES

1. Amerik, A. Y., S. J. Li, and M. Hochstrasser. 2000. Analysis of the deubiquitinating enzymes of the yeast *Saccharomyces cerevisiae*. Biol Chem 381:981–92.
2. Bachmair, A., D. Finley, and A. Varshavsky. 1986. In vivo half-life of a protein is a function of its amino-terminal residue. Science 234:179–86.
3. Baker, R. T. 1996. Protein expression using ubiquitin fusion and cleavage. Curr Opin Biotechnol 7:541–6.
4. Bayer, P., A. Arndt, S. Metzger, R. Mahajan, F. Melchior, R. Jaenicke, and J. Becker. 1998. Structure determination of the small ubiquitin-related modifier SUMO-1. J Mol Biol 280:275–86.
5. Butt, T. R., S. Jonnalagadda, B. P. Monia, E. J. Sternberg, J. A. Marsh, J. M. Stadel, D. J. Ecker, and S. T. Crooke. 1989. Ubiquitin fusion augments the yield of cloned gene products in *Escherichia coli.* Proc Natl Acad Sci USA 86:2540–4.
6. Butt, T. R., E. J. Sternberg, J. A. Gorman, P. Clark, D. Hamer, M. Rosenberg, and S. T. Crooke. 1984. Copper metallothionein of yeast, structure of the gene, and regulation of expression. Proc Natl Acad Sci USA 81:3332–6.
7. Ecker, D. J., J. M. Stadel, T. R. Butt, J. A. Marsh, B. P. Monia, D. A. Powers, J. A. Gorman, P. E. Clark, F. Warren, A. Shatzman, and et al. 1989. Increasing gene expression in yeast by fusion to ubiquitin. J Biol Chem 264:7715–9.
8. Gietz, D., A. St. Jean, R. A. Woods, and R. H. Schiestl. 1992. Improved method for high efficiency transformation of intact yeast cells. Nucleic Acids Res 20:1425.
9. Goward, C. R., J. P. Murphy, T. Atkinson, and D. A. Barstow. 1990. Expression and purification of a truncated recombinant streptococcal protein G. Biochem J 267: 171–7.
10. Graumann, K., J. L. Wittliff, W. Raffelsberger, L. Miles, A. Jungbauer, and T. R. Butt. 1996. Structural and functional analysis of N-terminal point mutants of the human estrogen receptor. J Steroid Biochem Mol Biol 57:293–300.
11. Hicke, L. 1997. Ubiquitin-dependent internalization and down-regulation of plasma membrane proteins. Faseb J 11:1215–26.
12. Hochstrasser, M. 2000. Evolution and function of ubiquitin-like protein-conjugation systems. Nat Cell Biol 2:E153–7.
13. Hochstrasser, M. 1995. Ubiquitin, proteasomes, and the regulation of intracellular protein degradation. Curr Opin Cell Biol 7:215–23.
14. Hochstrasser, M. 1996. Ubiquitin-dependent protein degradation. Annu Rev Genet 30:405–39.

15. Jentsch, S., and G. Pyrowolakis. 2000. Ubiquitin and its kin: how close are the family ties? Trends Cell Biol 10:335–42._00001785_00001785.

16. Johnson, E. S., I. Schwienhorst, R. J. Dohmen, and G. Blobel. 1997. The ubiquitin-like protein Smt3p is activated for conjugation to other proteins by an Aos1p/Uba2p heterodimer. Embo J 16:5509–19.

17. Kapust, R. B., and D. S. Waugh. 1999. *Escherichia coli* maltose-binding protein is uncommonly effective at promoting the solubility of polypeptides to which it is fused. Protein Sci 8:1668–74.

18. Kim, K. I., S. H. Baek, Y. J. Jeon, S. Nishimori, T. Suzuki, S. Uchida, N. Shimbara, H. Saitoh, K. Tanaka, and C. H. Chung. 2000. A new SUMO-1-specific protease, SUSP1, that is highly expressed in reproductive organs. J Biol Chem 275:14102–6.

19. LaBean, T. H., S. A. Kauffman, and T. R. Butt. 1995. Libraries of random-sequence polypeptides produced with high yield as carboxy-terminal fusions with ubiquitin. Mol Divers 1:29–38.

20. Li, S. J., and M. Hochstrasser. 1999. A new protease required for cell-cycle progression in yeast. Nature 398: 246–51.

21. Li, S. J., and M. Hochstrasser. 2000. The yeast ULP2 (SMT4) gene encodes a novel protease specific for the ubiquitin-like Smt3 protein. Mol Cell Biol 20:2367–77.

22. Lyttle, C. R., P. Damian-Matsumura, H. Juul, and T. R. Butt. 1992. Human estrogen receptor regulation in a yeast model system and studies on receptor agonists and antagonists. J Steroid Biochem Mol Biol 42:677–85.

23. Mahajan, R., L. Gerace, and F. Melchior. 1998. Molecular characterization of the SUMO-1 modification of RanGAP1 and its role in nuclear envelope association. J Cell Biol 140:259–70.

24. Malakhova, O., M. Malakhov, C. Hetherington, and D. E. Zhang. 2002. Lipopolysaccharide activates the expression of ISG15-specific protease UBP43 via interferon regulatory factor 3. J Biol Chem 277:14703–11.

25. Marathe, S. V., and J. E. McEwen. 1995. Vectors with the gus reporter gene for identifying and quantitating promoter regions in *Saccharomyces cerevisiae*. Gene 154: 105–7.

26. Matunis, M. J., J. Wu, and G. Blobel. 1998. SUMO-1 modification and its role in targeting the Ran GTPase-activating protein, RanGAP1, to the nuclear pore complex. J Cell Biol 140:499–509.

27. Mossessova, E., and C. D. Lima. 2000. Ulp1-SUMO crystal structure and genetic analysis reveal conserved interactions and a regulatory element essential for cell growth in yeast. Mol Cell 5:865–76.

28. Muller, S., C. Hoege, G. Pyrowolakis, and S. Jentsch. 2001. SUMO, ubiquitin's mysterious cousin. Nat Rev Mol Cell Biol 2:202–10.

29. Muller, S., M. J. Matunis, and A. Dejean. 1998. Conjugation with the ubiquitin-related modifier SUMO-1 regulates the partitioning of PML within the nucleus. Embo J 17:61–70.

30. Ohsumi, Y. 2001. Molecular dissection of autophagy: two ubiquitin-like systems. Nat Rev Mol Cell Biol 2:211–6.

31. Sherman, F., G. Fink, and J. Hicks. 1986. Methods in yeast genetics. Cold Spring Harbor Laboratory, Cold Spring Harbor, N.Y.

32. Sikorski, R. S., and P. Hieter. 1989. A system of shuttle vectors and yeast host strains designed for efficient manipulation of DNA in *Saccharomyces cerevisiae.* Genetics 122:19–27.

33. Suzuki, T., A. Ichiyama, H. Saitoh, T. Kawakami, M. Omata, C. H. Chung, M. Kimura, N. Shimbara, and K. Tanaka. 1999. A new 30-kDa ubiquitin-related SUMO-1 hydrolase from bovine brain. J Biol Chem 274:31131–4.

34. Varshavsky, A. 1996. The N-end rule: functions, mysteries, uses. Proc Natl Acad Sci USA 93:12142–9.

35. Varshavsky, A. 2000. Ubiquitin fusion technique and its descendants. Methods Enzymol 327:578–93.

36. Waldo, G. S., B. M. Standish, J. Bereudzen, and T. C. Terwilliger. 1999. Rapid protein-folding assay using green fluorescent protein. Nat Biotechnol 17:691–5.

37. Walfish, P. G., T. Yoganathan, Y. F. Yang, H. Hong, T. R. Butt, and M. R. Stallcup. 1997. Yeast hormone response element assays detect and characterize GRIP1 coactivator-dependent activation of transcription by thyroid and retinoid nuclear receptors. Proc Natl Acad Sci USA 94:3697–702.

38. Wright, L. C., J. Seybold, A. Robichaud, I. M. Adcock, and P. J. Barnes. 1998. Phosphodiesterase expression in human epithelial cells. Am J Physiol 275:L694–700.

39. Yeh, E. T., L. Gong, and T. Kamitani. 2000. Ubiquitin-like proteins: new wines in new bottles. Gene 248:1–14.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A kit comprising a recombinant vector containing a nucleic acid sequence encoding small ubiquitin related modifier (SUMO) operably linked to a promoter and a multiple cloning site; wherein said multiple cloning site allows for inserting a nucleic acid encoding a protein of interest in-frame and immediately 3' to the nucleic acid sequence encoding the Gly-Gly cleavage site of SUMO.

2. The kit of claim 1, wherein said kit further comprises host cells.

3. The kit of claim 2, wherein said host cells are selected from the group of yeast cells, *E. coli*, insect cells, and mammalian cells.

4. The kit of claim 1, wherein said kit further comprises reagents for oligonucleotide-based site-directed mutagenesis for altering the nucleic acid encoding said protein of interest such that the altered nucleic acid encodes said protein of interest with an altered amino terminus.

5. The kit of claim 4, wherein said reagents comprise primers for performing oligonucleotide-based site-directed mutagenesis.

6. A kit for purification of a protein from a host cell comprising:

i) a recombinant vector comprising:

a) a nucleic acid sequence encoding SUMO;

b) a promoter;

c) a nucleic acid sequence encoding for a purification tag; and d) a multiple cloning site;

wherein said promoter is operably linked to said nucleic acid sequence encoding SUMO, wherein said nucleic acid sequence encoding a purification tag is in-frame and operably linked to the nucleic acid sequence encoding SUMO, and wherein said multiple cloning site allows for inserting a nucleic acid encoding a protein of interest in-frame and immediately 3' to the nucleic acid sequence encoding the Gly-Gly cleavage site of SUMO, and ii) a composition comprising a protease which specifically cleaves SUMO after the Gly-Gly cleavage site.

7. The kit of claim 6, wherein said kit further comprises host cells.

8. The kit of claim 7 wherein said host cells are selected from the group of yeast cells, *E. coli*, insect cells, and mammalian cells.

9. The kit of claim 6 further comprising:

i) a solid support for binding the purification tag, ii) lysis buffers, iii) wash buffers, iv) elution buffers, v) cleavage buffers, and vi) instruction material.

10. The kit of claim 1, wherein said SUMO is SEQ ID NO: 65.

11. The kit of claim 6, wherein said SUMO is SEQ ID NO: 65.

12. The kit of claim 1, wherein said multiple cloning site comprises a Bsa I site.

13. The kit of claim 6, wherein said multiple cloning site comprises a Bsa I site.

14. The kit of claim 1, wherein said multiple.cloning site is nucleotides 426–478 of SEQ ID NO: 37.

15. The kit of claim 6, wherein said multiple cloning site is nucleotides 426–478 of SEQ ID NO: 37.

* * * * *

SEQUENCE LISTING

```
<160> NUMBER OF SEQ ID NOS: 65

<210> SEQ ID NO 1
<211> LENGTH: 106
<212> TYPE: PRT
<213> ORGANISM: Artificial Sequence
<220> FEATURE:
<223> OTHER INFORMATION: Synthetic Sequence

<400> SEQUENCE: 1

Met Gly His His His His His His Gly Ser Asp Ser Glu Val Asn Gln
1               5                   10                  15

Glu Ala Lys Pro Glu Val Lys Pro Glu Val Lys Pro Glu Thr His Ile
```

-continued

```
            20                  25                  30

Asn Leu Lys Val Ser Asp Gly Ser Ser Glu Ile Phe Phe Lys Ile Lys
        35                  40                  45

Lys Thr Thr Pro Leu Arg Arg Leu Met Glu Ala Phe Ala Lys Arg Gln
    50                  55                  60

Gly Lys Glu Met Asp Ser Leu Arg Phe Leu Tyr Asp Gly Ile Arg Ile
65                  70                  75                  80

Gln Ala Asp Gln Ala Pro Glu Asp Leu Asp Met Glu Asp Asn Asp Ile
                85                  90                  95

Ile Glu Ala His Arg Glu Gln Ile Gly Gly
            100                 105

<210> SEQ ID NO 2
<211> LENGTH: 320
<212> TYPE: DNA
<213> ORGANISM: Artificial Sequence
<220> FEATURE:
<223> OTHER INFORMATION: Synthetic Sequence

<400> SEQUENCE: 2
ccatgggtca tcaccatcat catcacgggt cggactcaga agtcaatcaa gaagctaagc     60
cagaggtcaa gccagaagtc aagcctgaga ctcacatcaa tttaaaggtg tccgatggat    120
cttcagagat cttcttcaag atcaaaaaga ccactccttt aagaaggctg atggaagcgt    180
tcgctaaaag acagggtaag gaaatggact ccttaagatt cttgtacgac ggtattagaa    240
ttcaagctga tcaggcccct gaagatttgg acatggagga taacgatatt attgaggctc    300
accgcgaaca gattggaggt                                                320

<210> SEQ ID NO 3
<211> LENGTH: 239
<212> TYPE: PRT
<213> ORGANISM: Artificial Sequence
<220> FEATURE:
<223> OTHER INFORMATION: Synthetic Sequence

<400> SEQUENCE: 3

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160
```

-continued

```
Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 4
<211> LENGTH: 727
<212> TYPE: DNA
<213> ORGANISM: Artificial Sequence
<220> FEATURE:
<223> OTHER INFORMATION: Synthetic Sequence

<400> SEQUENCE: 4
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720
taagctt                                                               727

<210> SEQ ID NO 5
<211> LENGTH: 345
<212> TYPE: PRT
<213> ORGANISM: Artificial Sequence
<220> FEATURE:
<223> OTHER INFORMATION: Synthetic Sequence

<400> SEQUENCE: 5

Met Gly His His His His His His Gly Ser Asp Ser Glu Val Asn Gln
1               5                   10                  15

Glu Ala Lys Pro Glu Val Lys Pro Glu Val Lys Pro Glu Thr His Ile
            20                  25                  30

Asn Leu Lys Val Ser Asp Gly Ser Ser Glu Ile Phe Phe Lys Ile Lys
        35                  40                  45

Lys Thr Thr Pro Leu Arg Arg Leu Met Glu Ala Phe Ala Lys Arg Gln
    50                  55                  60

Gly Lys Glu Met Asp Ser Leu Arg Phe Leu Tyr Asp Gly Ile Arg Ile
65                  70                  75                  80

Gln Ala Asp Gln Ala Pro Glu Asp Leu Asp Met Glu Asp Asn Asp Ile
                85                  90                  95
```

-continued

```
Ile Glu Ala His Arg Glu Gln Ile Gly Gly Met Val Ser Lys Gly Glu
            100                 105                 110

Glu Leu Phe Thr Gly Val Val Pro Ile Leu Val Glu Leu Asp Gly Asp
        115                 120                 125

Val Asn Gly His Lys Phe Ser Val Ser Gly Glu Gly Glu Gly Asp Ala
    130                 135                 140

Thr Tyr Gly Lys Leu Thr Leu Lys Phe Ile Cys Thr Thr Gly Lys Leu
145                 150                 155                 160

Pro Val Pro Trp Pro Thr Leu Val Thr Thr Leu Thr Tyr Gly Val Gln
                165                 170                 175

Cys Phe Ser Arg Tyr Pro Asp His Met Lys Gln His Asp Phe Phe Lys
            180                 185                 190

Ser Ala Met Pro Glu Gly Tyr Val Gln Glu Arg Thr Ile Phe Phe Lys
        195                 200                 205

Asp Asp Gly Asn Tyr Lys Thr Arg Ala Glu Val Lys Phe Glu Gly Asp
    210                 215                 220

Thr Leu Val Asn Arg Ile Glu Leu Lys Gly Ile Asp Phe Lys Glu Asp
225                 230                 235                 240

Gly Asn Ile Leu Gly His Lys Leu Glu Tyr Asn Tyr Asn Ser His Asn
                245                 250                 255

Val Tyr Ile Met Ala Asp Lys Gln Lys Asn Gly Ile Lys Val Asn Phe
            260                 265                 270

Lys Ile Arg His Asn Ile Glu Asp Gly Ser Val Gln Leu Ala Asp His
        275                 280                 285

Tyr Gln Gln Asn Thr Pro Ile Gly Asp Gly Pro Val Leu Leu Pro Asp
    290                 295                 300

Asn His Tyr Leu Ser Thr Gln Ser Ala Leu Ser Lys Asp Pro Asn Glu
305                 310                 315                 320

Lys Arg Asp His Met Val Leu Leu Glu Phe Val Thr Ala Ala Gly Ile
                325                 330                 335

Thr Leu Gly Met Asp Glu Leu Tyr Lys
            340                 345
```

<210> SEQ ID NO 6
<211> LENGTH: 1047
<212> TYPE: DNA
<213> ORGANISM: Artificial Sequence
<220> FEATURE:
<223> OTHER INFORMATION: Synthetic Sequence

<400> SEQUENCE: 6

```
ccatgggtca tcaccatcat catcacgggt cggactcaga agtcaatcaa gaagctaagc     60
cagaggtcaa gccagaagtc aagcctgaga ctcacatcaa tttaaaggtg tccgatggat    120
cttcagagat cttcttcaag atcaaaaaga ccactccttt aagaaggctg atggaagcgt    180
tcgctaaaag acagggtaag gaaatggact ccttaagatt cttgtacgac ggtattagaa    240
ttcaagctga tcaggcccct gaagatttgg acatggagga taacgatatt attgaggctc    300
accgcgaaca gattggaggt atggtgagca agggcgagga gctgttcacc ggggtggtgc    360
ccatcctggt cgagctggac ggcgacgtaa acggccacaa gttcagcgtg tccggcgagg    420
gcgagggcga tgccacctac ggcaagctga ccctgaagtt catctgcacc accggcaagc    480
tgcccgtgcc ctggcccacc ctcgtgacca ccctgaccta cggcgtgcag tgcttcagcc    540
gctaccccga ccacatgaag cagcacgact tcttcaagtc cgccatgccc gaaggctacg    600
tccaggagcg caccatcttc ttcaaggacg acggcaacta caagacccgc gccgaggtga    660
```

-continued

```
agttcgaggg cgacaccctg gtgaaccgca tcgagctgaa gggcatcgac ttcaaggagg    720

acggcaacat cctggggcac aagctggagt acaactacaa cagccacaac gtctatatca    780

tggccgacaa gcagaagaac ggcatcaagg tgaacttcaa gatccgccac aacatcgagg    840

acggcagcgt gcagctcgcc gaccactacc agcagaacac ccccatcggc gacggccccg    900

tgctgctgcc cgacaaccac tacctgagca cccagtccgc cctgagcaaa gaccccaacg    960

agaagcgcga tcacatggtc ctgctggagt tcgtgaccgc cgccgggatc actctcggca   1020

tggacgagct gtacaagtaa taagctt                                        1047
```

```
<210> SEQ ID NO 7
<211> LENGTH: 323
<212> TYPE: PRT
<213> ORGANISM: Artificial Sequence
<220> FEATURE:
<223> OTHER INFORMATION: Synthetic Sequence

<400> SEQUENCE: 7

Met Gly His His His His His His Gly Gln Ile Phe Val Lys Thr Leu
1               5                   10                  15

Thr Gly Lys Thr Ile Thr Leu Glu Val Glu Pro Ser Asp Thr Ile Glu
            20                  25                  30

Asn Val Lys Ala Lys Ile Gln Asp Lys Glu Gly Ile Pro Pro Asp Gln
        35                  40                  45

Gln Arg Leu Ile Phe Ala Gly Lys Gln Leu Glu Asp Gly Arg Thr Leu
    50                  55                  60

Ser Asp Tyr Asn Ile Gln Lys Glu Ser Thr Leu His Leu Val Leu Arg
65                  70                  75                  80

Leu Arg Gly Gly Met Val Ser Lys Gly Glu Glu Leu Phe Thr Gly Val
                85                  90                  95

Val Pro Ile Leu Val Glu Leu Asp Gly Asp Val Asn Gly His Lys Phe
            100                 105                 110

Ser Val Ser Gly Glu Gly Glu Gly Asp Ala Thr Tyr Gly Lys Leu Thr
        115                 120                 125

Leu Lys Phe Ile Cys Thr Thr Gly Lys Leu Pro Val Pro Trp Pro Thr
    130                 135                 140

Leu Val Thr Thr Leu Thr Tyr Gly Val Gln Cys Phe Ser Arg Tyr Pro
145                 150                 155                 160

Asp His Met Lys Gln His Asp Phe Phe Lys Ser Ala Met Pro Glu Gly
                165                 170                 175

Tyr Val Gln Glu Arg Thr Ile Phe Phe Lys Asp Asp Gly Asn Tyr Lys
            180                 185                 190

Thr Arg Ala Glu Val Lys Phe Glu Gly Asp Thr Leu Val Asn Arg Ile
        195                 200                 205

Glu Leu Lys Gly Ile Asp Phe Lys Glu Asp Gly Asn Ile Leu Gly His
    210                 215                 220

Lys Leu Glu Tyr Asn Tyr Asn Ser His Asn Val Tyr Ile Met Ala Asp
225                 230                 235                 240

Lys Gln Lys Asn Gly Ile Lys Val Asn Phe Lys Ile Arg His Asn Ile
                245                 250                 255

Glu Asp Gly Ser Val Gln Leu Ala Asp His Tyr Gln Gln Asn Thr Pro
            260                 265                 270

Ile Gly Asp Gly Pro Val Leu Leu Pro Asp Asn His Tyr Leu Ser Thr
        275                 280                 285
```

-continued

```
Gln Ser Ala Leu Ser Lys Asp Pro Asn Glu Lys Arg Asp His Met Val
    290                 295                 300

Leu Leu Glu Phe Val Thr Ala Ala Gly Ile Thr Leu Gly Met Asp Glu
305                 310                 315                 320

Leu Tyr Lys

<210> SEQ ID NO 8
<211> LENGTH: 981
<212> TYPE: DNA
<213> ORGANISM: Artificial Sequence
<220> FEATURE:
<223> OTHER INFORMATION: Synthetic Sequence

<400> SEQUENCE: 8
ccatgggtca tcaccatcat catcacgggc agatcttcgt caagacgtta accggtaaaa     60
ccataactct agaagttgaa ccatccgata ccatcgaaaa cgttaaggct aaaattcaag    120
acaaggaagg cattccacct gatcaacaaa gattgatctt tgccggtaag cagctcgagg    180
acggtagaac gctgtctgat tacaacattc agaaggagtc gaccttacat cttgtcttac    240
gcctacgtgg aggtatggtg agcaagggcg aggagctgtt caccggggtg gtgcccatcc    300
tggtcgagct ggacggcgac gtaaacggcc acaagttcag cgtgtccggc gagggcgagg    360
gcgatgccac ctacggcaag ctgaccctga agttcatctg caccaccggc aagctgcccg    420
tgccctggcc caccctcgtg accaccctga cctacggcgt gcagtgcttc agccgctacc    480
ccgaccacat gaagcagcac gacttcttca agtccgccat gcccgaaggc tacgtccagg    540
agcgcaccat cttcttcaag gacgacggca actacaagac ccgcgccgag gtgaagttcg    600
agggcgacac cctggtgaac cgcatcgagc tgaagggcat cgacttcaag gaggacggca    660
acatcctggg gcacaagctg gagtacaact acaacagcca caacgtctat atcatggccg    720
acaagcagaa gaacggcatc aaggtgaact tcaagatccg ccacaacatc gaggacggca    780
gcgtgcagct cgccgaccac taccagcaga acacccccat cggcgacggc cccgtgctgc    840
tgcccgacaa ccactacctg agcacccagt ccgccctgag caaagacccc aacgagaagc    900
gcgatcacat ggtcctgctg gagttcgtga ccgccgccgg gatcactctc ggcatggacg    960
agctgtacaa gtaataagct t                                              981

<210> SEQ ID NO 9
<211> LENGTH: 346
<212> TYPE: PRT
<213> ORGANISM: Artificial Sequence
<220> FEATURE:
<223> OTHER INFORMATION: Synthetic Sequence

<400> SEQUENCE: 9

Met Gly His His His His His His Gly Val Asn Val Lys Val Glu Phe
1               5                   10                  15

Leu Gly Gly Leu Asp Ala Ile Phe Gly Lys Gln Arg Val His Lys Ile
            20                  25                  30

Lys Met Asp Lys Glu Asp Pro Val Thr Val Gly Asp Leu Ile Asp His
        35                  40                  45

Ile Val Ser Thr Met Ile Asn Asn Pro Asn Asp Val Ser Ile Phe Ile
    50                  55                  60

Glu Asp Asp Ser Ile Arg Pro Gly Ile Ile Thr Leu Ile Asn Asp Thr
65                  70                  75                  80

Asp Trp Glu Leu Glu Gly Glu Lys Asp Tyr Ile Leu Glu Asp Gly Asp
                85                  90                  95
```

-continued

```
Ile Ile Ser Phe Thr Ser Thr Leu His Gly Gly Met Val Ser Lys Gly
            100                 105                 110

Glu Glu Leu Phe Thr Gly Val Val Pro Ile Leu Val Glu Leu Asp Gly
        115                 120                 125

Asp Val Asn Gly His Lys Phe Ser Val Ser Gly Glu Gly Glu Gly Asp
    130                 135                 140

Ala Thr Tyr Gly Lys Leu Thr Leu Lys Phe Ile Cys Thr Thr Gly Lys
145                 150                 155                 160

Leu Pro Val Pro Trp Pro Thr Leu Val Thr Thr Leu Thr Tyr Gly Val
                165                 170                 175

Gln Cys Phe Ser Arg Tyr Pro Asp His Met Lys Gln His Asp Phe Phe
            180                 185                 190

Lys Ser Ala Met Pro Glu Gly Tyr Val Gln Glu Arg Thr Ile Phe Phe
        195                 200                 205

Lys Asp Asp Gly Asn Tyr Lys Thr Arg Ala Glu Val Lys Phe Glu Gly
    210                 215                 220

Asp Thr Leu Val Asn Arg Ile Glu Leu Lys Gly Ile Asp Phe Lys Glu
225                 230                 235                 240

Asp Gly Asn Ile Leu Gly His Lys Leu Glu Tyr Asn Tyr Asn Ser His
                245                 250                 255

Asn Val Tyr Ile Met Ala Asp Lys Gln Lys Asn Gly Ile Lys Val Asn
            260                 265                 270

Phe Lys Ile Arg His Asn Ile Glu Asp Gly Ser Val Gln Leu Ala Asp
        275                 280                 285

His Tyr Gln Gln Asn Thr Pro Ile Gly Asp Gly Pro Val Leu Leu Pro
    290                 295                 300

Asp Asn His Tyr Leu Ser Thr Gln Ser Ala Leu Ser Lys Asp Pro Asn
305                 310                 315                 320

Glu Lys Arg Asp His Met Val Leu Leu Glu Phe Val Thr Ala Ala Gly
                325                 330                 335

Ile Thr Leu Gly Met Asp Glu Leu Tyr Lys
            340                 345
```

<210> SEQ ID NO 10
<211> LENGTH: 1050
<212> TYPE: DNA
<213> ORGANISM: Artificial Sequence
<220> FEATURE:
<223> OTHER INFORMATION: Synthetic Sequence

<400> SEQUENCE: 10

```
ccatgggtca tcaccatcat catcacgggg taaacgtgaa agtggagttt ctaggtggac     60
ttgatgctat ttttggaaaa caaagagtac ataaaattaa gatggacaaa gaagatcctg    120
tcacagtggg cgatttgatt gaccacattg tatctactat gatcaataac cctaatgacg    180
ttagtatctt catcgaagat gattctataa gacccggtat catcacatta atcaacgaca    240
ccgactggga gctcgaaggc gaaaaagact acatattgga agacggtgac atcatctctt    300
ttacttcaac attacatgga ggtatggtga gcaagggcga ggagctgttc accggggtgg    360
tgcccatcct ggtcgagctg gacggcgacg taaacggcca caagttcagc gtgtccggcg    420
agggcgaggg cgatgccacc tacggcaagc tgaccctgaa gttcatctgc accaccggca    480
agctgcccgt gccctggccc accctcgtga ccaccctgac ctacggcgtg cagtgcttca    540
gccgctaccc cgaccacatg aagcagcacg acttcttcaa gtccgccatg cccgaaggct    600
```

-continued

```
acgtccagga gcgcaccatc ttcttcaagg acgacggcaa ctacaagacc cgcgccgagg    660

tgaagttcga gggcgacacc ctggtgaacc gcatcgagct gaagggcatc gacttcaagg    720

aggacggcaa catcctgggg cacaagctgg agtacaacta caacagccac aacgtctata    780

tcatggccga caagcagaag aacggcatca aggtgaactt caagatccgc cacaacatcg    840

aggacggcag cgtgcagctc gccgaccact accagcagaa cacccccatc ggcgacggcc    900

ccgtgctgct gcccgacaac cactacctga gcacccagtc cgccctgagc aaagacccca    960

acgagaagcg cgatcacatg gtcctgctgg agttcgtgac cgccgccggg atcactctcg   1020

gcatggacga gctgtacaag taataagctt                                    1050
```

<210> SEQ ID NO 11
<211> LENGTH: 320
<212> TYPE: PRT
<213> ORGANISM: Artificial Sequence
<220> FEATURE:
<223> OTHER INFORMATION: Synthetic Sequence

<400> SEQUENCE: 11

```
Met Gly His His Tyr His His His Gly Met Ile Glu Val Val Val Asn
1               5                   10                  15

Asp Arg Leu Gly Lys Lys Val Arg Val Lys Cys Leu Ala Glu Asp Ser
            20                  25                  30

Val Gly Asp Phe Lys Lys Val Leu Ser Leu Gln Ile Gly Thr Gln Pro
        35                  40                  45

Asn Lys Ile Val Leu Gln Lys Gly Gly Ser Val Leu Lys Asp His Ile
    50                  55                  60

Ser Leu Glu Asp Tyr Glu Val His Asp Gln Thr Asn Leu Glu Leu Tyr
65                  70                  75                  80

Tyr Met Val Ser Lys Gly Glu Glu Leu Phe Thr Gly Val Val Pro Ile
                85                  90                  95

Leu Val Glu Leu Asp Gly Asp Val Asn Gly His Lys Phe Ser Val Ser
            100                 105                 110

Gly Glu Gly Glu Gly Asp Ala Thr Tyr Gly Lys Leu Thr Leu Lys Phe
        115                 120                 125

Ile Cys Thr Thr Gly Lys Leu Pro Val Pro Trp Pro Thr Leu Val Thr
    130                 135                 140

Thr Leu Thr Tyr Gly Val Gln Cys Phe Ser Arg Tyr Pro Asp His Met
145                 150                 155                 160

Lys Gln His Asp Phe Phe Lys Ser Ala Met Pro Glu Gly Tyr Val Gln
                165                 170                 175

Glu Arg Thr Ile Phe Phe Lys Asp Asp Gly Asn Tyr Lys Thr Arg Ala
            180                 185                 190

Glu Val Lys Phe Glu Gly Asp Thr Leu Val Asn Arg Ile Glu Leu Lys
        195                 200                 205

Gly Ile Asp Phe Lys Glu Asp Gly Asn Ile Leu Gly His Lys Leu Glu
    210                 215                 220

Tyr Asn Tyr Asn Ser His Asn Val Tyr Ile Met Ala Asp Lys Gln Lys
225                 230                 235                 240

Asn Gly Ile Lys Val Asn Phe Lys Ile Arg His Asn Ile Glu Asp Gly
                245                 250                 255

Ser Val Gln Leu Ala Asp His Tyr Gln Gln Asn Thr Pro Ile Gly Asp
            260                 265                 270

Gly Pro Val Leu Leu Pro Asp Asn His Tyr Leu Ser Thr Gln Ser Ala
        275                 280                 285
```

-continued

```
Leu Ser Lys Asp Pro Asn Glu Lys Arg Asp His Met Val Leu Leu Glu
    290                 295                 300

Phe Val Thr Ala Ala Gly Ile Thr Leu Gly Met Asp Glu Leu Tyr Lys
305                 310                 315                 320
```

<210> SEQ ID NO 12
<211> LENGTH: 972
<212> TYPE: DNA
<213> ORGANISM: Artificial Sequence
<220> FEATURE:
<223> OTHER INFORMATION: Synthetic Sequence

<400> SEQUENCE: 12

```
ccatgggtca tcactatcat catcacggga tgattgaggt agttgtgaat gaccgattag     60

gcaaaaaagt cagagtgaag tgccttgctg aagatagtgt aggtgatttc aaaaaagtat    120

tgtccttgca aattggcacc caaccaaaca aaattgtgtt gcagaagggt ggaagtgttt    180

taaaagacca tatctctctg gaagattatg aggtacatga tcagacaaat ttggagctgt    240

attacatggt gagcaagggc gaggagctgt tcaccggggt ggtgcccatc ctggtcgagc    300

tggacggcga cgtaaacggc cacaagttca gcgtgtccgg cgagggcgag ggcgatgcca    360

cctacggcaa gctgaccctg aagttcatct gcaccaccgg caagctgccc gtgccctggc    420

ccaccctcgt gaccaccctg acctacggcg tgcagtgctt cagccgctac cccgaccaca    480

tgaagcagca cgacttcttc aagtccgcca tgcccgaagg ctacgtccag gagcgcacca    540

tcttcttcaa ggacgacggc aactacaaga cccgcgccga ggtgaagttc gagggcgaca    600

ccctggtgaa ccgcatcgag ctgaagggca tcgacttcaa ggaggacggc aacatcctgg    660

ggcacaagct ggagtacaac tacaacagcc acaacgtcta tatcatggcc gacaagcaga    720

agaacggcat caaggtgaac ttcaagatcc gccacaacat cgaggacggc agcgtgcagc    780

tcgccgacca ctaccagcag aacaccccca tcggcgacgg ccccgtgctg ctgcccgaca    840

accactacct gagcacccag tccgccctga gcaaagaccc caacgagaag cgcgatcaca    900

tggtcctgct ggagttcgtg accgccgccg ggatcactct cggcatggac gagctgtaca    960

agtaataagc tt                                                        972
```

<210> SEQ ID NO 13
<211> LENGTH: 323
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (0)...(0)
<223> OTHER INFORMATION: Xaa = unknown

<400> SEQUENCE: 13

```
Met Gly His His His His His His Gly Ile Val Lys Xaa Lys Thr Leu
1               5                   10                  15

Thr Gly Lys Glu Ile Ser Val Glu Leu Lys Glu Ser Asp Leu Val Tyr
            20                  25                  30

His Ile Lys Glu Leu Leu Glu Glu Lys Glu Gly Ile Pro Pro Ser Gln
        35                  40                  45

Gln Arg Leu Ile Phe Gln Gly Lys Gln Ile Asp Asp Lys Leu Thr Val
    50                  55                  60

Thr Asp Ala His Xaa Val Glu Gly Met Gln Leu His Leu Val Leu Thr
65                  70                  75                  80
```

-continued

```
Leu Arg Gly Gly Met Val Ser Lys Gly Glu Glu Leu Phe Thr Gly Val
                85                  90                  95

Val Pro Ile Leu Val Glu Leu Asp Gly Asp Val Asn Gly His Lys Phe
            100                 105                 110

Ser Val Ser Gly Glu Gly Glu Gly Asp Ala Thr Tyr Gly Lys Leu Thr
        115                 120                 125

Leu Lys Phe Ile Cys Thr Thr Gly Lys Leu Pro Val Pro Trp Pro Thr
    130                 135                 140

Leu Val Thr Thr Leu Thr Tyr Gly Val Gln Cys Phe Ser Arg Tyr Pro
145                 150                 155                 160

Asp His Met Lys Gln His Asp Phe Phe Lys Ser Ala Met Pro Glu Gly
                165                 170                 175

Tyr Val Gln Glu Arg Thr Ile Phe Phe Lys Asp Asp Gly Asn Tyr Lys
            180                 185                 190

Thr Arg Ala Glu Val Lys Phe Glu Gly Asp Thr Leu Val Asn Arg Ile
        195                 200                 205

Glu Leu Lys Gly Ile Asp Phe Lys Glu Asp Gly Asn Ile Leu Gly His
    210                 215                 220

Lys Leu Glu Tyr Asn Tyr Asn Ser His Asn Val Tyr Ile Met Ala Asp
225                 230                 235                 240

Lys Gln Lys Asn Gly Ile Lys Val Asn Phe Lys Ile Arg His Asn Ile
                245                 250                 255

Glu Asp Gly Ser Val Gln Leu Ala Asp His Tyr Gln Gln Asn Thr Pro
            260                 265                 270

Ile Gly Asp Gly Pro Val Leu Leu Pro Asp Asn His Tyr Leu Ser Thr
        275                 280                 285

Gln Ser Ala Leu Ser Lys Asp Pro Asn Glu Lys Arg Asp His Met Val
    290                 295                 300

Leu Leu Glu Phe Val Thr Ala Ala Gly Ile Thr Leu Gly Met Asp Glu
305                 310                 315                 320

Leu Tyr Lys
```

<210> SEQ ID NO 14
<211> LENGTH: 981
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (0)...(0)
<223> OTHER INFORMATION: n = a, c, g, or t

<400> SEQUENCE: 14

```
ccatgggtca tcaccatcat catcacggga ttgttaaagn gaagacactg actgggaagg     60
agatctctgt tgagctgaag gaatcagatc tcgtatatca catcaaggaa cttttggagg    120
aaaaagaagg gattccacca tctcaacaaa gacttatatt ccagggaaaa caaattgatg    180
ataaattaac agtaacggat gcacatntag tagagggaat gcaactccac ttggtattaa    240
cactacgcgg aggtatggtg agcaagggcg aggagctgtt caccggggtg gtgcccatcc    300
tggtcgagct ggacggcgac gtaaacggcc acaagttcag cgtgtccggc gagggcgagg    360
gcgatgccac ctacggcaag ctgaccctga agttcatctg caccaccggc aagctgcccg    420
tgccctggcc caccctcgtg accaccctga cctacggcgt gcagtgcttc agccgctacc    480
ccgaccacat gaagcagcac gacttcttca agtccgccat gcccgaaggc tacgtccagg    540
```

-continued

```
agcgcaccat cttcttcaag gacgacggca actacaagac ccgcgccgag gtgaagttcg    600

agggcgacac cctggtgaac cgcatcgagc tgaagggcat cgacttcaag gaggacggca    660

acatcctggg gcacaagctg gagtacaact acaacagcca caacgtctat atcatggccg    720

acaagcagaa gaacggcatc aaggtgaact tcaagatccg ccacaacatc gaggacggca    780

gcgtgcagct cgccgaccac taccagcaga acacccccat cggcgacggc cccgtgctgc    840

tgcccgacaa ccactacctg agcacccagt ccgccctgag caaagacccc aacgagaagc    900

gcgatcacat ggtcctgctg gagttcgtga ccgccgccgg gatcactctc ggcatggacg    960

agctgtacaa gtaataagct t                                              981
```

<210> SEQ ID NO 15
<211> LENGTH: 363
<212> TYPE: PRT
<213> ORGANISM: Artificial Sequence
<220> FEATURE:
<223> OTHER INFORMATION: Synthetic Sequence

<400> SEQUENCE: 15

```
Met Gly His His His His His His Gly Lys Ser Thr Phe Lys Ser Glu
1               5                   10                  15

Tyr Pro Phe Glu Lys Arg Lys Ala Glu Ser Glu Arg Ile Ala Asp Arg
            20                  25                  30

Phe Lys Asn Arg Ile Pro Val Ile Cys Glu Lys Ala Glu Lys Ser Asp
        35                  40                  45

Ile Pro Glu Ile Asp Lys Arg Lys Tyr Leu Val Pro Ala Asp Leu Thr
    50                  55                  60

Val Gly Gln Phe Val Tyr Val Ile Arg Lys Arg Ile Met Leu Pro Pro
65                  70                  75                  80

Glu Lys Ala Ile Phe Ile Phe Val Asn Asp Thr Leu Pro Pro Thr Ala
                85                  90                  95

Ala Leu Met Ser Ala Ile Tyr Gln Glu His Lys Asp Lys Asp Gly Phe
            100                 105                 110

Leu Tyr Val Thr Tyr Ser Gly Glu Asn Thr Phe Gly Met Val Ser Lys
        115                 120                 125

Gly Glu Glu Leu Phe Thr Gly Val Val Pro Ile Leu Val Glu Leu Asp
    130                 135                 140

Gly Asp Val Asn Gly His Lys Phe Ser Val Ser Gly Glu Gly Glu Gly
145                 150                 155                 160

Asp Ala Thr Tyr Gly Lys Leu Thr Leu Lys Phe Ile Cys Thr Thr Gly
                165                 170                 175

Lys Leu Pro Val Pro Trp Pro Thr Leu Val Thr Thr Leu Thr Tyr Gly
            180                 185                 190

Val Gln Cys Phe Ser Arg Tyr Pro Asp His Met Lys Gln His Asp Phe
        195                 200                 205

Phe Lys Ser Ala Met Pro Glu Gly Tyr Val Gln Glu Arg Thr Ile Phe
    210                 215                 220

Phe Lys Asp Asp Gly Asn Tyr Lys Thr Arg Ala Glu Val Lys Phe Glu
225                 230                 235                 240

Gly Asp Thr Leu Val Asn Arg Ile Glu Leu Lys Gly Ile Asp Phe Lys
                245                 250                 255

Glu Asp Gly Asn Ile Leu Gly His Lys Leu Glu Tyr Asn Tyr Asn Ser
            260                 265                 270

His Asn Val Tyr Ile Met Ala Asp Lys Gln Lys Asn Gly Ile Lys Val
```

-continued

```
        275                 280                 285

Asn Phe Lys Ile Arg His Asn Ile Glu Asp Gly Ser Val Gln Leu Ala
    290                 295                 300

Asp His Tyr Gln Gln Asn Thr Pro Ile Gly Asp Gly Pro Val Leu Leu
305                 310                 315                 320

Pro Asp Asn His Tyr Leu Ser Thr Gln Ser Ala Leu Ser Lys Asp Pro
                325                 330                 335

Asn Glu Lys Arg Asp His Met Val Leu Leu Glu Phe Val Thr Ala Ala
            340                 345                 350

Gly Ile Thr Leu Gly Met Asp Glu Leu Tyr Lys
        355                 360
```

<210> SEQ ID NO 16
<211> LENGTH: 1099
<212> TYPE: DNA
<213> ORGANISM: Artificial Sequence
<220> FEATURE:
<223> OTHER INFORMATION: Synthetic Sequence

<400> SEQUENCE: 16

```
atgggtcatc accatcatca tcacgggaag tctacattta agtctgaata tccatttgaa     60

aaaaggaagg cggagtcgga gaggattgct gacaggttca agaataggat acctgtgatt    120

tgcgaaaaag ctgaaaagtc agatattcca gagattgata agcgtaaata tctagttcct    180

gctgacctta ccgtagggca atttgtttat gttataagaa agaggattat gctacccccct    240

gagaaggcca tcttcatttt tgtcaatgat actttgccac ctactgcggc gttgatgtct    300

gccatatatc aagaacacaa ggataaggac gggtttttgt atgtcactta ctcaggagaa    360

aatacatttg gtatggtgag caagggcgag gagctgttca ccggggtggt gcccatcctg    420

gtcgagctgg acggcgacgt aaacggccac aagttcagcg tgtccggcga gggcgagggc    480

gatgccacct acggcaagct gaccctgaag ttcatctgca ccaccggcaa gctgcccgtg    540

ccctggccca ccctcgtgac caccctgacc tacggcgtgc agtgcttcag ccgctacccc    600

gaccacatga agcagcacga cttcttcaag tccgccatgc ccgaaggcta cgtccaggag    660

cgcaccatct tcttcaagga cgacggcaac tacaagaccc gcgccgaggt gaagttcgag    720

ggcgacaccc tggtgaaccg catcgagctg aagggcatcg acttcaagga ggacggcaac    780

atcctggggc acaagctgga gtacaactac aacagccaca acgtctatat catggccgac    840

aagcagaaga acggcatcaa ggtgaacttc aagatccgcc acaacatcga ggacggcagc    900

gtgcagctcg ccgaccacta ccagcagaac acccccatcg gcgacggccc cgtgctgctg    960

cccgacaacc actacctgag cacccagtcc gccctgagca aagaccccaa cgagaagcgc   1020

gatcacatgg tcctgctgga gttcgtgacc gccgccggga tcactctcgg catggacgag   1080

ctgtacaagt aataagctt                                                1099
```

<210> SEQ ID NO 17
<211> LENGTH: 433
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (0)...(0)
<223> OTHER INFORMATION: Xaa = unknown

<400> SEQUENCE: 17

-continued

Met Gly His His His His His His Gly Ser Arg Ile Leu Glu Ser Glu
1               5                   10                  15

Asn Glu Thr Glu Ser Asp Glu Ser Ser Ile Ile Ser Thr Asn Asn Gly
            20                  25                  30

Thr Ala Met Glu Arg Ser Arg Asn Asn Gln Glu Leu Arg Ser Ser Pro
        35                  40                  45

His Thr Val Gln Asn Arg Leu Glu Leu Phe Ser Arg Arg Leu Ser Gln
    50                  55                  60

Leu Gly Leu Ala Ser Asp Ile Ser Val Asp Gln Gln Val Glu Asp Ser
65                  70                  75                  80

Ser Ser Gly Thr Tyr Glu Gln Glu Glu Thr Ile Lys Thr Asn Ala Gln
                85                  90                  95

Thr Ser Lys Gln Lys Ser His Lys Asp Glu Lys Asn Ile Gln Lys Ile
            100                 105                 110

Gln Ile Lys Phe Gln Pro Ile Gly Ser Ile Gly Gln Leu Lys Pro Ser
        115                 120                 125

Val Cys Lys Ile Ser Met Ser Gln Ser Phe Ala Met Val Ile Leu Phe
    130                 135                 140

Leu Lys Arg Arg Leu Lys Met Asp His Val Tyr Cys Tyr Ile Asn Asn
145                 150                 155                 160

Ser Phe Ala Pro Ser Pro Gln Gln Asn Ile Gly Glu Leu Trp Met Xaa
                165                 170                 175

Phe Lys Thr Asn Asp Glu Leu Ile Val Ser Tyr Cys Ala Ser Val Ala
            180                 185                 190

Phe Gly Met Val Ser Lys Gly Glu Glu Leu Phe Thr Gly Val Val Pro
        195                 200                 205

Ile Leu Val Glu Leu Asp Gly Asp Val Asn Gly His Lys Phe Ser Val
    210                 215                 220

Ser Gly Glu Gly Glu Gly Asp Ala Thr Tyr Gly Lys Leu Thr Leu Lys
225                 230                 235                 240

Phe Ile Cys Thr Thr Gly Lys Leu Pro Val Pro Trp Pro Thr Leu Val
                245                 250                 255

Thr Thr Leu Thr Tyr Gly Val Gln Cys Phe Ser Arg Tyr Pro Asp His
            260                 265                 270

Met Lys Gln His Asp Phe Phe Lys Ser Ala Met Pro Glu Gly Tyr Val
        275                 280                 285

Gln Glu Arg Thr Ile Phe Phe Lys Asp Asp Gly Asn Tyr Lys Thr Arg
    290                 295                 300

Ala Glu Val Lys Phe Glu Gly Asp Thr Leu Val Asn Arg Ile Glu Leu
305                 310                 315                 320

Lys Gly Ile Asp Phe Lys Glu Asp Gly Asn Ile Leu Gly His Lys Leu
                325                 330                 335

Glu Tyr Asn Tyr Asn Ser His Asn Val Tyr Ile Met Ala Asp Lys Gln
            340                 345                 350

Lys Asn Gly Ile Lys Val Asn Phe Lys Ile Arg His Asn Ile Glu Asp
        355                 360                 365

Gly Ser Val Gln Leu Ala Asp His Tyr Gln Gln Asn Thr Pro Ile Gly
    370                 375                 380

Asp Gly Pro Val Leu Leu Pro Asp Asn His Tyr Leu Ser Thr Gln Ser
385                 390                 395                 400

Ala Leu Ser Lys Asp Pro Asn Glu Lys Arg Asp His Met Val Leu Leu
                405                 410                 415

Glu Phe Val Thr Ala Ala Gly Ile Thr Leu Gly Met Asp Glu Leu Tyr

-continued

```
            420                 425                 430

Lys

<210> SEQ ID NO 18
<211> LENGTH: 1311
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (0)...(0)
<223> OTHER INFORMATION: n = a, c, g, or t

<400> SEQUENCE: 18
ccatgggtca tcaccatcat catcacggga gtaggatcct agagagcgaa aatgaaacag      60
aaagtgacga aagctccatc atatccacaa ataatggaac ggcaatggaa agatccagaa     120
ataatcaaga attaagatca tctcctcata ccgttcaaaa tagattggaa ctttttagca     180
ggagattgtc tcagcttggt ttggcgagtg acatttctgt cgaccagcaa gttgaagatt     240
cctctagtgg cacttatgaa caggaagaga caatcaaaac gaatgcacaa acaagcaaac     300
aaaaaagcca taaagacgaa aaaaacatac aaaagataca gataaaattt cagcccattg     360
gttctattgg gcagttaaaa ccatctgttt gtaaaatatc natgtcacag tcttttgcaa     420
tggttatttt atttcttaag agacggctga aaatggacca tgtttattgt tatataaata     480
attcgtttgc gccaagtccg cagcaaaata ttggtgaact ttggatgcna ttcaagacta     540
atgatgagct tattgtaagt tattgtgcat ccgtagcgtt tggtatggtg agcaagggcg     600
aggagctgtt caccggggtg gtgcccatcc tggtcgagct ggacggcgac gtaaacggcc     660
acaagttcag cgtgtccggc gagggcgagg gcgatgccac ctacggcaag ctgaccctga     720
agttcatctg caccaccggc aagctgcccg tgccctggcc caccctcgtg accaccctga     780
cctacggcgt gcagtgcttc agccgctacc ccgaccacat gaagcagcac gacttcttca     840
agtccgccat gcccgaaggc tacgtccagg agcgcaccat cttcttcaag gacgacggca     900
actacaagac ccgcgccgag gtgaagttcg agggcgacac cctggtgaac cgcatcgagc     960
tgaagggcat cgacttcaag gaggacggca acatcctggg gcacaagctg gagtacaact    1020
acaacagcca caacgtctat atcatggccg acaagcagaa gaacggcatc aaggtgaact    1080
tcaagatccg ccacaacatc gaggacggca gcgtgcagct cgccgaccac taccagcaga    1140
acacccccat cggcgacggc cccgtgctgc tgcccgacaa ccactacctg agcacccagt    1200
ccgccctgag caaagacccc aacgagaagc gcgatcacat ggtcctgctg gagttcgtga    1260
ccgccgccgg gatcactctc ggcatggacg agctgtacaa gtaataagct t             1311

<210> SEQ ID NO 19
<211> LENGTH: 410
<212> TYPE: PRT
<213> ORGANISM: Artificial Sequence
<220> FEATURE:
<223> OTHER INFORMATION: Synthetic Sequence

<400> SEQUENCE: 19

Met Gly His His His His His His Gly Gly Trp Asp Leu Thr Val Lys
1               5                   10                  15

Met Leu Ala Gly Asn Glu Phe Gln Val Ser Leu Ser Ser Ser Met Ser
            20                  25                  30

Val Ser Glu Leu Lys Ala Gln Ile Thr Gln Lys Ile Gly Val His Ala
```

-continued

```
        35                  40                  45

Phe Gln Gln Arg Leu Ala Val His Pro Ser Gly Val Ala Leu Gln Asp
    50                  55                  60

Arg Val Pro Leu Ala Ser Gln Gly Leu Gly Pro Gly Ser Thr Val Leu
65                  70                  75                  80

Leu Val Val Asp Lys Cys Asp Glu Pro Leu Ser Ile Leu Val Arg Asn
                85                  90                  95

Asn Lys Gly Arg Ser Ser Thr Tyr Glu Val Arg Leu Thr Gln Thr Val
            100                 105                 110

Ala His Leu Lys Gln Gln Val Ser Gly Leu Glu Gly Val Gln Asp Asp
        115                 120                 125

Leu Phe Trp Leu Thr Phe Glu Gly Lys Pro Leu Glu Asp Gln Leu Pro
    130                 135                 140

Leu Gly Glu Tyr Gly Leu Lys Pro Leu Ser Thr Val Phe Met Asn Leu
145                 150                 155                 160

Arg Leu Arg Gly Gly Gly Thr Glu Pro Gly Gly Met Val Ser Lys Gly
                165                 170                 175

Glu Glu Leu Phe Thr Gly Val Val Pro Ile Leu Val Glu Leu Asp Gly
            180                 185                 190

Asp Val Asn Gly His Lys Phe Ser Val Ser Gly Glu Gly Glu Gly Asp
        195                 200                 205

Ala Thr Tyr Gly Lys Leu Thr Leu Lys Phe Ile Cys Thr Thr Gly Lys
    210                 215                 220

Leu Pro Val Pro Trp Pro Thr Leu Val Thr Thr Leu Thr Tyr Gly Val
225                 230                 235                 240

Gln Cys Phe Ser Arg Tyr Pro Asp His Met Lys Gln His Asp Phe Phe
                245                 250                 255

Lys Ser Ala Met Pro Glu Gly Tyr Val Gln Glu Arg Thr Ile Phe Phe
            260                 265                 270

Lys Asp Asp Gly Asn Tyr Lys Thr Arg Ala Glu Val Lys Phe Glu Gly
        275                 280                 285

Asp Thr Leu Val Asn Arg Ile Glu Leu Lys Gly Ile Asp Phe Lys Glu
    290                 295                 300

Asp Gly Asn Ile Leu Gly His Lys Leu Glu Tyr Asn Tyr Asn Ser His
305                 310                 315                 320

Asn Val Tyr Ile Met Ala Asp Lys Gln Lys Asn Gly Ile Lys Val Asn
                325                 330                 335

Phe Lys Ile Arg His Asn Ile Glu Asp Gly Ser Val Gln Leu Ala Asp
            340                 345                 350

His Tyr Gln Gln Asn Thr Pro Ile Gly Asp Gly Pro Val Leu Leu Pro
        355                 360                 365

Asp Asn His Tyr Leu Ser Thr Gln Ser Ala Leu Ser Lys Asp Pro Asn
    370                 375                 380

Glu Lys Arg Asp His Met Val Leu Leu Glu Phe Val Thr Ala Ala Gly
385                 390                 395                 400

Ile Thr Leu Gly Met Asp Glu Leu Tyr Lys
                405                 410
```

<210> SEQ ID NO 20
<211> LENGTH: 1242
<212> TYPE: DNA
<213> ORGANISM: Artificial Sequence
<220> FEATURE:
<223> OTHER INFORMATION: Synthetic Sequence -continued

<400> SEQUENCE: 20

```
ccatgggtca tcaccatcat catcacgggg gctgggacct gacggtgaag atgctggcgg     60
gcaacgaatt ccaggtgtcc ctgagcagct ccatgtcggt gtcagagctg aaggcgcaga    120
tcacccagaa gattggcgtg cacgccttcc agcagcgtct ggctgtccac ccgagcggtg    180
tggcgctgca ggacagggtc cccttgcca gccagggcct gggccctggc agcacggtcc    240
tgctggtggt ggacaaatgc gacgaacctc tgagcatcct ggtgaggaat aacaagggcc    300
gcagcagcac ctacgaggtc cggctgacgc agaccgtggc ccacctgaag cagcaagtga    360
gcgggctgga gggtgtgcag gacgacctgt tctggctgac cttcgagggg aagcccctgg    420
aggaccagct cccgctgggg gagtacggcc tcaagcccct gagcaccgtg ttcatgaatc    480
tgcgcctgcg gggaggcggc acagagcctg gaggtatggt gagcaagggc gaggagctgt    540
tcaccggggt ggtgcccatc ctggtcgagc tggacggcga cgtaaacggc cacaagttca    600
gcgtgtccgg cgagggcgag ggcgatgcca cctacggcaa gctgaccctg aagttcatct    660
gcaccaccgg caagctgccc gtgccctggc ccaccctcgt gaccaccctg acctacggcg    720
tgcagtgctt cagccgctac cccgaccaca tgaagcagca cgacttcttc aagtccgcca    780
tgcccgaagg ctacgtccag gagcgcacca tcttcttcaa ggacgacggc aactacaaga    840
cccgcgccga ggtgaagttc gagggcgaca ccctggtgaa ccgcatcgag ctgaagggca    900
tcgacttcaa ggaggacggc aacatcctgg ggcacaagct ggagtacaac tacaacagcc    960
acaacgtcta tatcatggcc gacaagcaga agaacggcat caaggtgaac ttcaagatcc   1020
gccacaacat cgaggacggc agcgtgcagc tcgccgacca ctaccagcag aacaccccca   1080
tcggcgacgg ccccgtgctg ctgcccgaca accactacct gagcacccag tccgccctga   1140
gcaaagaccc caacgagaag cgcgatcaca tggtcctgct ggagttcgtg accgccgccg   1200
ggatcactct cggcatggac gagctgtaca agtaataagc tt                      1242
```

<210> SEQ ID NO 21
<211> LENGTH: 166
<212> TYPE: PRT
<213> ORGANISM: Artificial Sequence
<220> FEATURE:
<223> OTHER INFORMATION: Synthetic Sequence

<400> SEQUENCE: 21

```
Met Gly His His His His His His Gly Ser Asp Ser Glu Val Asn Gln
1               5                   10                  15

Glu Ala Lys Pro Glu Val Lys Pro Glu Val Lys Pro Glu Thr His Ile
            20                  25                  30

Asn Leu Lys Val Ser Asp Gly Ser Ser Glu Ile Phe Phe Lys Ile Lys
        35                  40                  45

Lys Thr Thr Pro Leu Arg Arg Leu Met Glu Ala Phe Ala Lys Arg Gln
    50                  55                  60

Gly Lys Glu Met Asp Ser Leu Arg Phe Leu Tyr Asp Gly Ile Arg Ile
65                  70                  75                  80

Gln Ala Asp Gln Thr Pro Glu Asp Leu Asp Met Glu Asp Asn Asp Ile
                85                  90                  95

Ile Glu Ala His Arg Glu Gln Ile Gly Gly Thr Pro Ala Val Thr Thr
            100                 105                 110

Tyr Lys Leu Val Ile Asn Gly Lys Thr Leu Lys Gly Glu Thr Thr Thr
        115                 120                 125

Lys Ala Val Asp Ala Glu Thr Ala Glu Lys Ala Phe Lys Gln Tyr Ala
```

-continued

```
    130                 135                 140

Asn Asp Asn Gly Val Asp Gly Val Trp Thr Tyr Asp Asp Ala Thr Lys
145                 150                 155                 160

Thr Phe Thr Val Thr Glu
                165

<210> SEQ ID NO 22
<211> LENGTH: 510
<212> TYPE: DNA
<213> ORGANISM: Artificial Sequence
<220> FEATURE:
<223> OTHER INFORMATION: Synthetic Sequence

<400> SEQUENCE: 22
ccatgggtca tcaccatcat catcacgggt cggactcaga agtcaatcaa gaagctaagc     60
cagaggtcaa gccagaagtc aagcctgaga ctcacatcaa tttaaaggtg tccgatggat    120
cttcagagat cttcttcaag atcaaaaaga ccactccttt aagaaggctg atggaagcgt    180
tcgctaaaag acagggtaag gaaatggact ccttaagatt cttgtacgac ggtattagaa    240
ttcaagctga tcagacccct gaagatttgg acatggagga taacgatatt attgaggctc    300
accgcgaaca gattggaggt acgccggcgg tgaccaccta taaactggtg attaacggca    360
aaaccctgaa aggcgaaacc accaccaaag cggtggatgc ggaaaccgcg gaaaaagcgt    420
ttaaacagta tgcgaacgat aacggcgtgg atggcgtgtg gacctatgat gatgcgacca    480
aaacctttac cgtgaccgaa taataagctt                                     510

<210> SEQ ID NO 23
<211> LENGTH: 711
<212> TYPE: PRT
<213> ORGANISM: Artificial Sequence
<220> FEATURE:
<223> OTHER INFORMATION: Synthetic Sequence

<400> SEQUENCE: 23

Met Gly His His His His His His Gly Ser Asp Ser Glu Val Asn Gln
1               5                   10                  15

Glu Ala Lys Pro Glu Val Lys Pro Glu Val Lys Pro Glu Thr His Ile
            20                  25                  30

Asn Leu Lys Val Ser Asp Gly Ser Ser Glu Ile Phe Phe Lys Ile Lys
        35                  40                  45

Lys Thr Thr Pro Leu Arg Arg Leu Met Glu Ala Phe Ala Lys Arg Gln
    50                  55                  60

Gly Lys Glu Met Asp Ser Leu Arg Phe Leu Tyr Asp Gly Ile Arg Ile
65                  70                  75                  80

Gln Ala Asp Gln Thr Pro Glu Asp Leu Asp Met Glu Asp Asn Asp Ile
                85                  90                  95

Ile Glu Ala His Arg Glu Gln Ile Gly Gly Met Glu Phe Met Leu Arg
            100                 105                 110

Pro Val Glu Thr Pro Thr Arg Glu Ile Lys Lys Leu Asp Gly Leu Trp
        115                 120                 125

Ala Phe Ser Leu Asp Arg Glu Asn Cys Gly Ile Asp Gln Arg Trp Trp
    130                 135                 140

Glu Ser Ala Leu Gln Glu Ser Arg Ala Ile Ala Val Pro Gly Ser Phe
145                 150                 155                 160

Asn Asp Gln Phe Ala Asp Ala Asp Ile Arg Asn Tyr Ala Gly Asn Val
                165                 170                 175
```

-continued

```
Trp Tyr Gln Arg Glu Val Phe Ile Pro Lys Gly Trp Ala Gly Gln Arg
            180                 185                 190

Ile Val Leu Arg Phe Asp Ala Val Thr His Tyr Gly Lys Val Trp Val
        195                 200                 205

Asn Asn Gln Glu Val Met Glu His Gln Gly Gly Tyr Thr Pro Phe Glu
    210                 215                 220

Ala Asp Val Thr Pro Tyr Val Ile Ala Gly Lys Ser Val Arg Ile Thr
225                 230                 235                 240

Val Cys Val Asn Asn Glu Leu Asn Trp Gln Thr Ile Pro Pro Gly Met
                245                 250                 255

Val Ile Thr Asp Glu Asn Gly Lys Lys Lys Gln Ser Tyr Phe His Asp
            260                 265                 270

Phe Phe Asn Tyr Ala Gly Ile His Arg Ser Val Met Leu Tyr Thr Thr
        275                 280                 285

Pro Asn Thr Trp Val Asp Asp Ile Thr Val Val Thr His Val Ala Gln
    290                 295                 300

Asp Cys Asn His Ala Ser Val Asp Trp Gln Val Val Ala Asn Gly Asp
305                 310                 315                 320

Val Ser Val Glu Leu Arg Asp Ala Asp Gln Gln Val Val Ala Thr Gly
                325                 330                 335

Gln Gly Thr Ser Gly Thr Leu Gln Val Val Asn Pro His Leu Trp Gln
            340                 345                 350

Pro Gly Glu Gly Tyr Leu Tyr Glu Leu Cys Val Thr Ala Lys Ser Gln
        355                 360                 365

Thr Glu Cys Asp Ile Tyr Pro Leu Arg Val Gly Ile Arg Ser Val Ala
    370                 375                 380

Val Lys Gly Gln Gln Phe Leu Ile Asn His Lys Pro Phe Tyr Phe Thr
385                 390                 395                 400

Gly Phe Gly Arg His Glu Asp Ala Asp Leu Arg Gly Lys Gly Phe Asp
                405                 410                 415

Asn Val Leu Met Val His Asp His Ala Leu Met Asp Trp Ile Gly Ala
            420                 425                 430

Asn Ser Tyr Arg Thr Ser His Tyr Pro Tyr Ala Glu Glu Met Leu Asp
        435                 440                 445

Trp Ala Asp Glu His Gly Ile Val Val Ile Asp Glu Thr Ala Ala Val
    450                 455                 460

Gly Phe Asn Leu Ser Leu Gly Ile Gly Phe Glu Ala Gly Asn Lys Pro
465                 470                 475                 480

Lys Glu Leu Tyr Ser Glu Glu Ala Val Asn Gly Glu Thr Gln Gln Ala
                485                 490                 495

His Leu Gln Ala Ile Lys Glu Leu Ile Ala Arg Asp Lys Asn His Pro
            500                 505                 510

Ser Val Val Met Trp Ser Ile Ala Asn Glu Pro Asp Thr Arg Pro Gln
        515                 520                 525

Val His Gly Asn Ile Ser Pro Leu Ala Glu Ala Thr Arg Lys Leu Asp
    530                 535                 540

Pro Thr Arg Pro Ile Thr Cys Val Asn Val Met Phe Cys Asp Ala His
545                 550                 555                 560

Thr Asp Thr Ile Ser Asp Leu Phe Asp Val Leu Cys Leu Asn Arg Tyr
                565                 570                 575

Tyr Gly Trp Tyr Val Gln Ser Gly Asp Leu Glu Thr Ala Glu Lys Val
            580                 585                 590

Leu Glu Lys Glu Leu Leu Ala Trp Gln Glu Lys Leu His Gln Pro Ile
```

-continued

```
        595                 600                 605

Ile Ile Thr Glu Tyr Gly Val Asp Thr Leu Ala Gly Leu His Ser Met
    610                 615                 620

Tyr Thr Asp Met Trp Ser Glu Glu Tyr Gln Cys Ala Trp Leu Asp Met
625                 630                 635                 640

Tyr His Arg Val Phe Asp Arg Val Ser Ala Val Val Gly Glu Gln Val
                645                 650                 655

Trp Asn Phe Ala Asp Phe Ala Thr Ser Gln Gly Ile Leu Arg Val Gly
            660                 665                 670

Gly Asn Lys Lys Gly Ile Phe Thr Arg Asp Arg Lys Pro Lys Ser Ala
        675                 680                 685

Ala Phe Leu Leu Gln Lys Arg Trp Thr Gly Met Asn Phe Gly Glu Lys
    690                 695                 700

Pro Gln Gln Gly Gly Lys Gln
705                 710

<210> SEQ ID NO 24
<211> LENGTH: 2133
<212> TYPE: DNA
<213> ORGANISM: Artificial Sequence
<220> FEATURE:
<223> OTHER INFORMATION: Synthetic Sequence

<400> SEQUENCE: 24
atgggtcatc accatcatca tcacgggtcg gactcagaag tcaatcaaga agctaagcca      60
gaggtcaagc cagaagtcaa gcctgagact cacatcaatt taaaggtgtc cgatggatct     120
tcagagatct tcttcaagat caaaaagacc actcctttaa gaaggctgat ggaagcgttc     180
gctaaaagac agggtaagga aatggactcc ttaagattct tgtacgacgg tattagaatt     240
caagctgatc agacccctga agatttggac atggaggata acgatattat tgaggctcac     300
cgcgaacaga ttggaggtat ggaattcatg ttacgtcctg tagaaacccc aacccgtgaa     360
atcaaaaaac tcgacggcct gtgggcattc agtctggatc gcgaaaactg tggaattgat     420
cagcgttggt gggaaagcgc gttacaagaa agccgggcaa ttgctgtgcc aggcagtttt     480
aacgatcagt tcgccgatgc agatattcgt aattatgcgg gcaacgtctg gtatcagcgc     540
gaagtcttta taccgaaagg ttgggcaggc cagcgtatcg tgctgcgttt cgatgcggtc     600
actcattacg gcaaagtgtg ggtcaataat caggaagtga tggagcatca gggcggctat     660
acgccatttg aagccgatgt cacgccgtat gttattgccg ggaaaagtgt acgtatcacc     720
gtttgtgtga acaacgaact gaactggcag actatcccgc cgggaatggt gattaccgac     780
gaaaacggca agaaaaagca gtcttacttc catgatttct ttaactatgc cggaatccat     840
cgcagcgtaa tgctctacac cacgccgaac acctgggtgg acgatatcac cgtggtgacg     900
catgtcgcgc aagactgtaa ccacgcgtct gttgactggc aggtggtggc caatggtgat     960
gtcagcgttg aactgcgtga tgcggatcaa caggtggttg caactggaca aggcactagc    1020
gggactttgc aagtggtgaa tccgcacctc tggcaaccgg gtgaaggtta tctctatgaa    1080
ctgtgcgtca cagccaaaag ccagacagag tgtgatatct acccgcttcg cgtcggcatc    1140
cggtcagtgg cagtgaaggg ccaacagttc ctgattaacc acaaaccgtt ctactttact    1200
ggctttggtc gtcatgaaga tgcggactta cgtggcaaag gattcgataa cgtgctgatg    1260
gtgcacgacc acgcattaat ggactggatt ggggccaact cctaccgtac ctcgcattac    1320
ccttacgctg aagagatgct cgactgggca gatgaacatg gcatcgtggt gattgatgaa    1380
```

-continued

```
actgctgctg tcggctttaa cctctcttta ggcattggtt tcgaagcggg caacaagccg   1440

aaagaactgt acagcgaaga ggcagtcaac ggggaaactc agcaagcgca cttacaggcg   1500

attaaagagc tgatagcgcg tgacaaaaac cacccaagcg tggtgatgtg gagtattgcc   1560

aacgaaccgg atacccgtcc gcaagtgcac gggaatattt cgccactggc ggaagcaacg   1620

cgtaaactcg acccgacgcg tccgatcacc tgcgtcaatg taatgttctg cgacgctcac   1680

accgatacca tcagcgatct ctttgatgtg ctgtgcctga accgttatta cggatggtat   1740

gtccaaagcg gcgatttgga aacggcagag aaggtactgg aaaaagaact tctggcctgg   1800

caggagaaac tgcatcagcc gattatcatc accgaatacg gcgtggatac gttagccggg   1860

ctgcactcaa tgtacaccga catgtggagt gaagagtatc agtgtgcatg gctggatatg   1920

tatcaccgcg tctttgatcg cgtcagcgcc gtcgtcggtg aacaggtatg gaatttcgcc   1980

gattttgcga cctcgcaagg catattgcgc gttggcggta acaagaaagg gatcttcact   2040

cgcgaccgca aaccgaagtc ggcggctttt ctgctgcaaa aacgctggac tggcatgaac   2100

ttcggtgaaa aaccgcagca gggaggcaaa caa                                2133
```

<210> SEQ ID NO 25
<211> LENGTH: 553
<212> TYPE: PRT
<213> ORGANISM: Artificial Sequence
<220> FEATURE:
<223> OTHER INFORMATION: Synthetic Sequence

<400> SEQUENCE: 25

```
Met Gly His His His His His His Gly Ser Asp Ser Glu Val Asn Gln
1               5                   10                  15

Glu Ala Lys Pro Glu Val Lys Pro Glu Val Lys Pro Glu Thr His Ile
            20                  25                  30

Asn Leu Lys Val Ser Asp Gly Ser Ser Glu Ile Phe Phe Lys Ile Lys
        35                  40                  45

Lys Thr Thr Pro Leu Arg Arg Leu Met Glu Ala Phe Ala Lys Arg Gln
    50                  55                  60

Gly Lys Glu Met Asp Ser Leu Arg Phe Leu Tyr Asp Gly Ile Arg Ile
65                  70                  75                  80

Gln Ala Asp Gln Thr Pro Glu Asp Leu Asp Met Glu Asp Asn Asp Ile
                85                  90                  95

Ile Glu Ala His Arg Glu Gln Ile Gly Gly Met Ser Leu Trp Leu Gly
            100                 105                 110

Ala Pro Val Pro Asp Ile Pro Pro Asp Ser Ala Val Glu Leu Trp Lys
        115                 120                 125

Pro Gly Ala Gln Asp Ala Ser Ser Gln Ala Gln Gly Gly Ser Ser Cys
    130                 135                 140

Ile Leu Arg Glu Glu Ala Arg Met Pro His Ser Ala Gly Gly Thr Ala
145                 150                 155                 160

Gly Val Gly Leu Glu Ala Ala Glu Pro Thr Ala Leu Leu Thr Arg Ala
                165                 170                 175

Glu Pro Pro Ser Glu Pro Thr Glu Ile Arg Pro Gln Lys Arg Lys Lys
            180                 185                 190

Gly Pro Ala Pro Lys Met Leu Gly Asn Glu Leu Cys Ser Val Cys Gly
        195                 200                 205

Asp Lys Ala Ser Gly Phe His Tyr Asn Val Leu Ser Cys Glu Gly Cys
    210                 215                 220

Lys Gly Phe Phe Arg Arg Ser Val Ile Lys Gly Ala His Tyr Ile Cys
```

-continued

```
225                 230                 235                 240

His Ser Gly Gly His Cys Pro Met Asp Thr Tyr Met Arg Arg Lys Cys
                245                 250                 255

Gln Glu Cys Arg Leu Arg Lys Cys Arg Gln Ala Gly Met Arg Glu Glu
            260                 265                 270

Cys Val Leu Ser Glu Glu Gln Ile Arg Leu Lys Lys Leu Lys Arg Gln
        275                 280                 285

Glu Glu Glu Gln Ala His Ala Thr Ser Leu Pro Pro Arg Arg Ser Ser
    290                 295                 300

Pro Pro Gln Ile Leu Pro Gln Leu Ser Pro Glu Gln Leu Gly Met Ile
305                 310                 315                 320

Glu Lys Leu Val Ala Ala Gln Gln Gln Cys Asn Arg Arg Ser Phe Ser
                325                 330                 335

Asp Arg Leu Arg Val Thr Pro Trp Pro Met Ala Pro Asp Pro His Ser
            340                 345                 350

Arg Glu Ala Arg Gln Gln Arg Phe Ala His Phe Thr Glu Leu Ala Ile
        355                 360                 365

Val Ser Val Gln Glu Ile Val Asp Phe Ala Lys Gln Leu Pro Gly Phe
    370                 375                 380

Leu Gln Leu Ser Arg Glu Asp Gln Ile Ala Leu Leu Lys Thr Ser Ala
385                 390                 395                 400

Ile Glu Val Met Leu Leu Glu Thr Ser Arg Arg Tyr Asn Pro Gly Ser
                405                 410                 415

Glu Ser Ile Thr Phe Leu Lys Asp Phe Ser Tyr Asn Arg Glu Asp Phe
            420                 425                 430

Ala Lys Ala Gly Leu Gln Val Glu Phe Ile Asn Pro Ile Phe Glu Phe
        435                 440                 445

Ser Arg Ala Met Asn Glu Leu Gln Leu Asn Asp Ala Glu Phe Ala Leu
    450                 455                 460

Leu Ile Ala Ile Ser Ile Phe Ser Ala Asp Arg Pro Asn Val Gln Asp
465                 470                 475                 480

Gln Leu Gln Val Glu Arg Leu Gln His Thr Tyr Val Glu Ala Leu His
                485                 490                 495

Ala Tyr Val Ser Ile His His Pro His Asp Arg Leu Met Phe Pro Arg
            500                 505                 510

Met Leu Met Lys Leu Val Ser Leu Arg Thr Leu Ser Ser Val His Ser
        515                 520                 525

Glu Gln Val Phe Ala Leu Arg Leu Gln Asp Lys Lys Leu Pro Pro Leu
    530                 535                 540

Leu Ser Glu Ile Trp Asp Val His Glu
545                 550
```

<210> SEQ ID NO 26
<211> LENGTH: 1662
<212> TYPE: DNA
<213> ORGANISM: Artificial Sequence
<220> FEATURE:
<223> OTHER INFORMATION: Synthetic Sequence

<400> SEQUENCE: 26

```
atgggtcatc accatcatca tcacgggtcg gactcagaag tcaatcaaga agctaagcca     60
gaggtcaagc cagaagtcaa gcctgagact cacatcaatt taaaggtgtc cgatggatct    120
tcagagatct tcttcaagat caaaaagacc actcctttaa gaaggctgat ggaagcgttc    180
gctaaaagac agggtaagga aatggactcc ttaagattct tgtacgacgg tattagaatt    240
```

-continued

```
caagctgatc agaccccctga agatttggac atggaggata acgatattat tgaggctcac    300

cgcgaacaga ttggaggtat gtccttgtgg ctgggggccc ctgtgcctga cattcctcct    360

gactctgcgg tggagctgtg gaagccaggc gcacaggatg caagcagcca ggcccaggga    420

ggcagcagct gcatcctcag agaggaagcc aggatgcccc actctgctgg gggtactgca    480

ggggtggggc tggaggctgc agagcccaca gccctgctca ccagggcaga gcccccttca    540

gaacccacag agatccgtcc acaaaagcgg aaaaaggggc cagcccccaa aatgctgggg    600

aacgagctat gcagcgtgtg tggggacaag gcctcgggct tccactacaa tgttctgagc    660

tgcgagggct gcaagggatt cttccgccgc agcgtcatca agggagcgca ctacatctgc    720

cacagtggcg gccactgccc catggacacc tacatgcgtc gcaagtgcca ggagtgtcgg    780

cttcgcaaat gccgtcaggc tggcatgcgg gaggagtgtg tcctgtcaga agaacagatc    840

cgcctgaaga aactgaagcg gcaagaggag gaacaggctc atgccacatc cttgcccccc    900

aggcgttcct caccccccca aatcctgccc cagctcagcc cggaacaact gggcatgatc    960

gagaagctcg tcgctgccca gcaacagtgt aaccggcgct ccttttctga ccggcttcga   1020

gtcacgcctt ggcccatggc accagatccc catagccggg aggcccgtca gcagcgcttt   1080

gcccacttca ctgagctggc catcgtctct gtgcaggaga tagttgactt tgctaaacag   1140

ctacccggct tcctgcagct cagccgggag gaccagattg ccctgctgaa gacctctgcg   1200

atcgaggtga tgcttctgga gacatctcgg aggtacaacc ctgggagtga gagtatcacc   1260

ttcctcaagg atttcagtta taaccgggaa gactttgcca aagcagggct gcaagtggaa   1320

ttcatcaacc ccatcttcga gttctccagg gccatgaatg agctgcaact caatgatgcc   1380

gagtttgcct tgctcattgc tatcagcatc ttctctgcag accggcccaa cgtgcaggac   1440

cagctccagg tggagaggct gcagcacaca tatgtggaag ccctgcatgc ctacgtctcc   1500

atccaccatc cccatgaccg actgatgttc ccacggatgc taatgaaact ggtgagcctc   1560

cggaccctga gcagcgtcca ctcagagcaa gtgtttgcac tgcgtctgca ggacaaaaag   1620

ctcccaccgc tgctctctga gatctgggat gtgcacgaat ga                       1662
```

<210> SEQ ID NO 27
<211> LENGTH: 473
<212> TYPE: PRT
<213> ORGANISM: Artificial Sequence
<220> FEATURE:
<223> OTHER INFORMATION: Synthetic Sequence

<400> SEQUENCE: 27

```
Met Gly His His His His His His Gly Ser Asp Ser Glu Val Asn Gln
1               5                   10                  15

Glu Ala Lys Pro Glu Val Lys Pro Glu Val Lys Pro Glu Thr His Ile
            20                  25                  30

Asn Leu Lys Val Ser Asp Gly Ser Ser Glu Ile Phe Phe Lys Ile Lys
        35                  40                  45

Lys Thr Thr Pro Leu Arg Arg Leu Met Glu Ala Phe Ala Lys Arg Gln
    50                  55                  60

Gly Lys Glu Met Asp Ser Leu Arg Phe Leu Tyr Asp Gly Ile Arg Ile
65                  70                  75                  80

Gln Ala Asp Gln Thr Pro Glu Asp Leu Asp Met Glu Asp Asn Asp Ile
                85                  90                  95

Ile Glu Ala His Arg Glu Gln Ile Gly Gly Met Cys Pro Asn Ser Ser
            100                 105                 110
```

-continued

```
Ala Ser Asn Ala Ser Gly Ala Ala Ala Pro Thr Leu Pro Ala His Pro
        115                 120                 125

Ser Thr Leu Thr His Pro Gln Arg Arg Ile Asp Thr Leu Asn Ser Asp
    130                 135                 140

Gly Tyr Thr Pro Glu Pro Ala Arg Ile Thr Ser Pro Asp Lys Pro Arg
145                 150                 155                 160

Pro Met Pro Met Asp Thr Ser Val Tyr Glu Ser Pro Tyr Ser Asp Pro
                165                 170                 175

Glu Glu Leu Lys Asp Lys Lys Leu Phe Leu Lys Arg Asp Asn Leu Leu
            180                 185                 190

Ile Ala Asp Ile Glu Leu Gly Cys Gly Asn Phe Gly Ser Val Arg Gln
        195                 200                 205

Gly Val Tyr Arg Met Arg Lys Lys Gln Ile Asp Val Ala Ile Lys Val
    210                 215                 220

Leu Lys Gln Gly Thr Glu Lys Ala Asp Thr Glu Glu Met Met Arg Glu
225                 230                 235                 240

Ala Gln Ile Met His Gln Leu Asp Asn Pro Tyr Ile Val Arg Leu Ile
                245                 250                 255

Gly Val Cys Gln Ala Glu Ala Leu Met Leu Val Met Glu Met Ala Gly
            260                 265                 270

Gly Gly Pro Leu His Lys Phe Leu Val Gly Lys Arg Glu Glu Ile Pro
        275                 280                 285

Val Ser Asn Val Ala Glu Leu Leu His Gln Val Ser Met Gly Met Lys
    290                 295                 300

Tyr Leu Glu Glu Lys Asn Phe Val His Arg Asp Leu Ala Ala Arg Asn
305                 310                 315                 320

Val Leu Leu Val Asn Arg His Tyr Ala Lys Ile Ser Asp Phe Gly Leu
                325                 330                 335

Ser Lys Ala Leu Gly Ala Asp Asp Ser Tyr Tyr Thr Ala Arg Ser Ala
            340                 345                 350

Gly Lys Trp Pro Leu Lys Trp Tyr Ala Pro Glu Cys Ile Asn Phe Arg
        355                 360                 365

Lys Phe Ser Ser Arg Ser Asp Val Trp Ser Tyr Gly Val Thr Met Trp
    370                 375                 380

Glu Ala Leu Ser Tyr Gly Gln Lys Pro Tyr Lys Lys Met Lys Gly Pro
385                 390                 395                 400

Glu Val Met Ala Phe Ile Glu Gln Gly Lys Arg Met Glu Cys Pro Pro
                405                 410                 415

Glu Cys Pro Pro Glu Leu Tyr Ala Leu Met Ser Asp Cys Trp Ile Tyr
            420                 425                 430

Lys Trp Glu Asp Arg Pro Asp Phe Leu Thr Val Glu Gln Arg Met Arg
        435                 440                 445

Ala Cys Tyr Tyr Ser Leu Ala Ser Lys Val Glu Gly Pro Pro Gly Ser
    450                 455                 460

Thr Gln Lys Ala Glu Ala Ala Cys Ala
465                 470
```

<210> SEQ ID NO 28
<211> LENGTH: 1422
<212> TYPE: DNA
<213> ORGANISM: Artificial Sequence
<220> FEATURE:
<223> OTHER INFORMATION: Synthetic Sequence

<400> SEQUENCE: 28

-continued

```
atgggtcatc accatcatca tcacgggtcg gactcagaag tcaatcaaga agctaagcca     60
gaggtcaagc cagaagtcaa gcctgagact cacatcaatt taaaggtgtc cgatggatct    120
tcagagatct tcttcaagat caaaaagacc actcctttaa gaaggctgat ggaagcgttc    180
gctaaaagac agggtaagga aatggactcc ttaagattct tgtacgacgg tattagaatt    240
caagctgatc agacccctga agatttggac atggaggata acgatattat tgaggctcac    300
cgcgaacaga ttggaggtat gtgccccaac agcagtgcca gcaacgcctc aggggctgct    360
gctcccacac tcccagccca cccatccacg ttgactcatc ctcagagacg aatcgacacc    420
ctcaactcag atggatacac ccctgagcca gcacgcataa cgtccccaga caaaccgcgg    480
ccgatgccca tggacacgag cgtgtatgag agcccctaca gcgacccaga ggagctcaag    540
gacaagaagc tcttcctgaa gcgcgataac ctcctcatag ctgacattga acttggctgc    600
ggcaactttg gctcagtgcg ccagggcgtg taccgcatgc gcaagaagca gatcgacgtg    660
gccatcaagg tgctgaagca gggcacggag aaggcagaca cggaagagat gatgcgcgag    720
gcgcagatca tgcaccagct ggacaacccc tacatcgtgc ggctcattgg cgtctgccag    780
gccgaggccc tcatgctggt catggagatg gctgggggcg ggccgctgca caagttcctg    840
gtcggcaaga gggaggagat ccctgtgagc aatgtggccg agctgctgca ccaggtgtcc    900
atggggatga agtacctgga ggagaagaac tttgtgcacc gtgacctggc ggcccgcaac    960
gtcctgctgg ttaaccggca ctacgccaag atcagcgact ttggcctctc caaagcactg   1020
ggtgccgacg acagctacta cactgcccgc tcagcaggga agtggccgct caagtggtac   1080
gcacccgaat gcatcaactt ccgcaagttc tccagccgca gcgatgtctg gagctatggg   1140
gtcaccatgt gggaggcctt gtcctacggc cagaagccct acaagaagat gaaagggccg   1200
gaggtcatgg ccttcatcga gcagggcaag cggatggagt gcccaccaga gtgtccaccc   1260
gaactgtacg cactcatgag tgactgctgg atctacaagt gggaggatcg ccccgacttc   1320
ctgaccgtgg agcagcgcat gcgagcctgt tactacagcc tggccagcaa ggtggaaggg   1380
cccccaggca gcacacagaa ggctgaggct gcctgtgcct ga                      1422
```

```
<210> SEQ ID NO 29
<211> LENGTH: 434
<212> TYPE: PRT
<213> ORGANISM: Artificial Sequence
<220> FEATURE:
<223> OTHER INFORMATION: Synthetic Sequence

<400> SEQUENCE: 29

Met Gly His His His His His His Gly Ser Asp Ser Glu Val Asn Gln
1               5                   10                  15

Glu Ala Lys Pro Glu Val Lys Pro Glu Val Lys Pro Glu Thr His Ile
            20                  25                  30

Asn Leu Lys Val Ser Asp Gly Ser Ser Glu Ile Phe Phe Lys Ile Lys
        35                  40                  45

Lys Thr Thr Pro Leu Arg Arg Leu Met Glu Ala Phe Ala Lys Arg Gln
    50                  55                  60

Gly Lys Glu Met Asp Ser Leu Arg Phe Leu Tyr Asp Gly Ile Arg Ile
65                  70                  75                  80

Gln Ala Asp Gln Thr Pro Glu Asp Leu Asp Met Glu Asp Asn Asp Ile
                85                  90                  95

Ile Glu Ala His Arg Glu Gln Ile Gly Gly Met Gln Phe His Val Lys
            100                 105                 110
```

-continued

```
Ser Gly Leu Gln Ile Lys Lys Asn Ala Ile Ile Asp Asp Tyr Lys Val
        115                 120                 125

Thr Ser Gln Val Leu Gly Leu Gly Ile Asn Gly Lys Val Leu Gln Ile
    130                 135                 140

Phe Asn Lys Arg Thr Gln Glu Lys Phe Ala Leu Lys Met Leu Gln Asp
145                 150                 155                 160

Cys Pro Lys Ala Arg Arg Glu Val Glu Leu His Trp Arg Ala Ser Gln
                165                 170                 175

Cys Pro His Ile Val Arg Ile Val Asp Val Tyr Glu Asn Leu Tyr Ala
            180                 185                 190

Gly Arg Lys Cys Leu Leu Ile Val Met Glu Cys Leu Asp Gly Gly Glu
        195                 200                 205

Leu Phe Ser Arg Ile Gln Asp Arg Gly Asp Gln Ala Phe Thr Glu Arg
    210                 215                 220

Glu Ala Ser Glu Ile Met Lys Ser Ile Gly Glu Ala Ile Gln Tyr Leu
225                 230                 235                 240

His Ser Ile Asn Ile Ala His Arg Asp Val Lys Pro Glu Asn Leu Leu
                245                 250                 255

Tyr Thr Ser Lys Arg Pro Asn Ala Ile Leu Lys Leu Thr Asp Phe Gly
            260                 265                 270

Phe Ala Lys Glu Thr Thr Ser His Asn Ser Leu Thr Thr Pro Cys Tyr
        275                 280                 285

Thr Pro Tyr Tyr Val Ala Pro Glu Val Leu Gly Pro Glu Lys Tyr Asp
    290                 295                 300

Lys Ser Cys Asp Met Trp Ser Leu Gly Val Ile Met Tyr Ile Leu Leu
305                 310                 315                 320

Cys Gly Tyr Pro Pro Phe Tyr Ser Asn His Gly Leu Ala Ile Ser Pro
                325                 330                 335

Gly Met Lys Thr Arg Ile Arg Met Gly Gln Tyr Glu Phe Pro Asn Pro
            340                 345                 350

Glu Trp Ser Glu Val Ser Glu Glu Val Lys Met Leu Ile Arg Asn Leu
        355                 360                 365

Leu Lys Thr Glu Pro Thr Gln Arg Met Thr Ile Thr Glu Phe Met Asn
    370                 375                 380

His Pro Trp Ile Met Gln Ser Thr Lys Val Pro Gln Thr Pro Leu His
385                 390                 395                 400

Thr Ser Arg Val Leu Lys Glu Asp Lys Glu Arg Trp Glu Asp Val Lys
                405                 410                 415

Glu Glu Met Thr Ser Ala Leu Ala Thr Met Arg Val Asp Tyr Glu Gln
            420                 425                 430

Ile Lys
```

<210> SEQ ID NO 30
<211> LENGTH: 1305
<212> TYPE: DNA
<213> ORGANISM: Artificial Sequence
<220> FEATURE:
<223> OTHER INFORMATION: Synthetic Sequence

<400> SEQUENCE: 30

```
atgggtcatc accatcatca tcacgggtcg gactcagaag tcaatcaaga agctaagcca      60
gaggtcaagc cagaagtcaa gcctgagact cacatcaatt taaaggtgtc cgatggatct     120
tcagagatct tcttcaagat caaaaagacc actcctttaa gaaggctgat ggaagcgttc     180
```

-continued gctaaaagac agggtaagga aatggactcc ttaagattct tgtacgacgg tattagaatt 240
caagctgatc agacccctga agatttggac atggaggata acgatattat tgaggctcac 300
cgcgaacaga ttggaggtat gcagttccac gtcaagtccg gcctgcagat caagaagaac 360
gccatcatcg atgactacaa ggtcaccagc caggtcctgg ggctgggcat caacggcaaa 420
gttttgcaga tcttcaacaa gaggacccag gagaaattcg ccctcaaaat gcttcaggac 480
tgccccaagg cccgcaggga ggtggagctg cactggcggg cctcccagtg cccgcacatc 540
gtacggatcg tggatgtgta cgagaatctg tacgcaggga ggaagtgcct gctgattgtc 600
atggaatgtt tggacggtgg agaactcttt agccgaatcc aggatcgagg agaccaggca 660
ttcacagaaa gagaagcatc cgaaatcatg aagagcatcg gtgaggccat ccagtatctg 720
cattcaatca acattgccca tcgggatgtc aagcctgaga atctcttata cacctccaaa 780
aggcccaacg ccatcctgaa actcactgac tttggctttg ccaaggaaac caccagccac 840
aactctttga ccactccttg ttatacaccg tactatgtgg ctccagaagt gctgggtcca 900
gagaagtatg acaagtcctg tgacatgtgg tccctgggtg tcatcatgta catcctgctg 960
tgtgggtatc ccccttcta ctccaaccac ggccttgcca tctctccggg catgaagact 1020
cgcatccgaa tgggccagta tgaatttccc aacccagaat ggtcagaagt atcagaggaa 1080
gtgaagatgc tcattcggaa tctgctgaaa acagagccca cccagagaat gaccatcacc 1140
gagtttatga accacccttg gatcatgcaa tcaacaaagg tccctcaaac cccactgcac 1200
accagccggg tcctgaagga ggacaaggag cggtgggagg atgtcaagga ggagatgacc 1260
agtgccttgg ccacaatgcg cgttgactac gagcagatca agtaa 1305

<210> SEQ ID NO 31
<211> LENGTH: 1130
<212> TYPE: PRT
<213> ORGANISM: Artificial Sequence
<220> FEATURE:
<223> OTHER INFORMATION: Synthetic Sequence

<400> SEQUENCE: 31

Met Gly His His His His His His Gly Ser Asp Ser Glu Val Asn Gln
1 5 10 15

Glu Ala Lys Pro Glu Val Lys Pro Glu Val Lys Pro Glu Thr His Ile
20 25 30

Asn Leu Lys Val Ser Asp Gly Ser Ser Glu Ile Phe Phe Lys Ile Lys
35 40 45

Lys Thr Thr Pro Leu Arg Arg Leu Met Glu Ala Phe Ala Lys Arg Gln
50 55 60

Gly Lys Glu Met Asp Ser Leu Arg Phe Leu Tyr Asp Gly Ile Arg Ile
65 70 75 80

Gln Ala Asp Gln Thr Pro Glu Asp Leu Asp Met Glu Asp Asn Asp Ile
85 90 95

Ile Glu Ala His Arg Glu Gln Ile Gly Gly Met Thr Met Ile Thr Asp
100 105 110

Ser Leu Ala Val Val Leu Gln Arg Arg Asp Trp Glu Asn Pro Gly Val
115 120 125

Thr Gln Leu Asn Arg Leu Ala Ala His Pro Pro Phe Ala Ser Trp Arg
130 135 140

Asn Ser Glu Glu Ala Arg Thr Asp Arg Pro Ser Gln Gln Leu Arg Ser
145 150 155 160

Leu Asn Gly Glu Trp Arg Phe Ala Trp Phe Pro Ala Pro Glu Ala Val

-continued

```
                165                 170                 175

Pro Glu Ser Trp Leu Glu Cys Asp Leu Pro Glu Ala Asp Thr Val Val
            180                 185                 190

Val Pro Ser Asn Trp Gln Met His Gly Tyr Asp Ala Pro Ile Tyr Thr
        195                 200                 205

Asn Val Thr Tyr Pro Ile Thr Val Asn Pro Pro Phe Val Pro Thr Glu
    210                 215                 220

Asn Pro Thr Gly Cys Tyr Ser Leu Thr Phe Asn Val Asp Glu Ser Trp
225                 230                 235                 240

Leu Gln Glu Gly Gln Thr Arg Ile Ile Phe Asp Gly Val Asn Ser Ala
                245                 250                 255

Phe His Leu Trp Cys Asn Gly Arg Trp Val Gly Tyr Gly Gln Asp Ser
            260                 265                 270

Arg Leu Pro Ser Glu Phe Asp Leu Ser Ala Phe Leu Arg Ala Gly Glu
        275                 280                 285

Asn Arg Leu Ala Val Met Val Leu Arg Trp Ser Asp Gly Ser Tyr Leu
    290                 295                 300

Glu Asp Gln Asp Met Trp Arg Met Ser Gly Ile Phe Arg Asp Val Ser
305                 310                 315                 320

Leu Leu His Lys Pro Thr Thr Gln Ile Ser Asp Phe His Val Ala Thr
                325                 330                 335

Arg Phe Asn Asp Asp Phe Ser Arg Ala Val Leu Glu Ala Glu Val Gln
            340                 345                 350

Met Cys Gly Glu Leu Arg Asp Tyr Leu Arg Val Thr Val Ser Leu Trp
        355                 360                 365

Gln Gly Glu Thr Gln Val Ala Ser Gly Thr Ala Pro Phe Gly Gly Glu
    370                 375                 380

Ile Ile Asp Glu Arg Gly Gly Tyr Ala Asp Arg Val Thr Leu Arg Leu
385                 390                 395                 400

Asn Val Glu Asn Pro Lys Leu Trp Ser Ala Glu Ile Pro Asn Leu Tyr
                405                 410                 415

Arg Ala Val Val Glu Leu His Thr Ala Asp Gly Thr Leu Ile Glu Ala
            420                 425                 430

Glu Ala Cys Asp Val Gly Phe Arg Glu Val Arg Ile Glu Asn Gly Leu
        435                 440                 445

Leu Leu Leu Asn Gly Lys Pro Leu Leu Ile Arg Gly Val Asn Arg His
    450                 455                 460

Glu His His Pro Leu His Gly Gln Val Met Asp Glu Gln Thr Met Val
465                 470                 475                 480

Gln Asp Ile Leu Leu Met Lys Gln Asn Asn Phe Asn Ala Val Arg Cys
                485                 490                 495

Ser His Tyr Pro Asn His Pro Leu Trp Tyr Thr Leu Cys Asp Arg Tyr
            500                 505                 510

Gly Leu Tyr Val Val Asp Glu Ala Asn Ile Glu Thr His Gly Met Val
        515                 520                 525

Pro Met Asn Arg Leu Thr Asp Asp Pro Arg Trp Leu Pro Ala Met Ser
    530                 535                 540

Glu Arg Val Thr Arg Met Val Gln Arg Asp Arg Asn His Pro Ser Val
545                 550                 555                 560

Ile Ile Trp Ser Leu Gly Asn Glu Ser Gly His Gly Ala Asn His Asp
                565                 570                 575

Ala Leu Tyr Arg Trp Ile Lys Ser Val Asp Pro Ser Arg Pro Val Gln
            580                 585                 590
```

-continued

Tyr Glu Gly Gly Gly Ala Asp Thr Thr Ala Thr Asp Ile Ile Cys Pro
595 600 605

Met Tyr Ala Arg Val Asp Glu Asp Gln Pro Phe Pro Ala Val Pro Lys
610 615 620

Trp Ser Ile Lys Lys Trp Leu Ser Leu Pro Gly Glu Thr Arg Pro Leu
625 630 635 640

Ile Leu Cys Glu Tyr Ala His Ala Met Gly Asn Ser Leu Gly Gly Phe
645 650 655

Ala Lys Tyr Trp Gln Ala Phe Arg Gln Tyr Pro Arg Leu Gln Gly Gly
660 665 670

Phe Val Trp Asp Trp Val Asp Gln Ser Leu Ile Lys Tyr Asp Glu Asn
675 680 685

Gly Asn Pro Trp Ser Ala Tyr Gly Gly Asp Phe Gly Asp Thr Pro Asn
690 695 700

Asp Arg Gln Phe Cys Met Asn Gly Leu Val Phe Ala Asp Arg Thr Pro
705 710 715 720

His Pro Ala Leu Thr Glu Ala Lys His Gln Gln Gln Phe Phe Gln Phe
725 730 735

Arg Leu Ser Gly Gln Thr Ile Glu Val Thr Ser Glu Tyr Leu Phe Arg
740 745 750

His Ser Asp Asn Glu Leu Leu His Trp Met Val Ala Leu Asp Gly Lys
755 760 765

Pro Leu Ala Ser Gly Glu Val Pro Leu Asp Val Ala Pro Gln Gly Lys
770 775 780

Gln Leu Ile Glu Leu Pro Glu Leu Pro Gln Pro Glu Ser Ala Gly Gln
785 790 795 800

Leu Trp Leu Thr Val Arg Val Val Gln Pro Asn Ala Thr Ala Trp Ser
805 810 815

Glu Ala Gly His Ile Ser Ala Trp Gln Gln Trp Arg Leu Ala Glu Asn
820 825 830

Leu Ser Val Thr Leu Pro Ala Ala Ser His Ala Ile Pro His Leu Thr
835 840 845

Thr Ser Glu Met Asp Phe Cys Ile Glu Leu Gly Asn Lys Arg Trp Gln
850 855 860

Phe Asn Arg Gln Ser Gly Phe Leu Ser Gln Met Trp Ile Gly Asp Lys
865 870 875 880

Lys Gln Leu Leu Thr Pro Leu Arg Asp Gln Phe Thr Arg Ala Pro Leu
885 890 895

Asp Asn Asp Ile Gly Val Ser Glu Ala Thr Arg Ile Asp Pro Asn Ala
900 905 910

Trp Val Glu Arg Trp Lys Ala Ala Gly His Tyr Gln Ala Glu Ala Ala
915 920 925

Leu Leu Gln Cys Thr Ala Asp Thr Leu Ala Asp Ala Val Leu Ile Thr
930 935 940

Thr Ala His Ala Trp Gln His Gln Gly Lys Thr Leu Phe Ile Ser Arg
945 950 955 960

Lys Thr Tyr Arg Ile Asp Gly Ser Gly Gln Met Ala Ile Thr Val Asp
965 970 975

Val Glu Val Ala Ser Asp Thr Pro His Pro Ala Arg Ile Gly Leu Asn
980 985 990

Cys Gln Leu Ala Gln Val Ala Glu Arg Val Asn Trp Leu Gly Leu Gly
995 1000 1005

-continued

```
Pro Gln Glu Asn Tyr Pro Asp Arg Leu Thr Ala Ala Cys Phe Asp Arg
    1010                1015                1020

Trp Asp Leu Pro Leu Ser Asp Met Tyr Thr Pro Tyr Val Phe Pro Ser
1025                1030                1035                1040

Glu Asn Gly Leu Arg Cys Gly Thr Arg Glu Leu Asn Tyr Gly Pro His
                1045                1050                1055

Gln Trp Arg Gly Asp Phe Gln Phe Asn Ile Ser Arg Tyr Ser Gln Gln
            1060                1065                1070

Gln Leu Met Glu Thr Ser His Arg His Leu Leu His Ala Glu Glu Gly
        1075                1080                1085

Thr Trp Leu Asn Ile Asp Gly Phe His Met Gly Ile Gly Gly Asp Asp
    1090                1095                1100

Ser Trp Ser Pro Ser Val Ser Ala Glu Phe Gln Leu Ser Ala Gly Arg
1105                1110                1115                1120

Tyr His Tyr Gln Leu Val Trp Cys Gln Lys
                1125                1130
```

<210> SEQ ID NO 32
<211> LENGTH: 3396
<212> TYPE: DNA
<213> ORGANISM: Artificial Sequence
<220> FEATURE:
<223> OTHER INFORMATION: Synthetic Sequence

<400> SEQUENCE: 32

```
atgggtcatc accatcatca tcacgggtcg gactcagaag tcaatcaaga agctaagcca      60
gaggtcaagc cagaagtcaa gcctgagact cacatcaatt taaaggtgtc cgatggatct     120
tcagagatct tcttcaagat caaaaagacc actcctttaa gaaggctgat ggaagcgttc     180
gctaaaagac agggtaagga aatggactcc ttaagattct tgtacgacgg tattagaatt     240
caagctgatc agacccctga agatttggac atggaggata acgatattat tgaggctcac     300
cgcgaacaga ttggaggtat gaccatgatt acggattcac tggccgtcgt tttacaacgt     360
cgtgactggg aaaaccctgg cgttacccaa cttaatcgcc ttgcagcaca tccccctttc     420
gccagctggc gtaatagcga agaggcccgc accgatcgcc cttcccaaca gttgcgcagc     480
ctgaatggcg aatggcgctt tgcctggttt ccggcaccag aagcggtgcc ggaaagctgg     540
ctggagtgcg atcttcctga ggccgatact gtcgtcgtcc cctcaaactg gcagatgcac     600
ggttacgatg cgcccatcta caccaacgta acctatccca ttacggtcaa tccgccgttt     660
gttcccacgg agaatccgac gggttgttac tcgctcacat ttaatgttga tgaaagctgg     720
ctacaggaag gccagacgcg aattattttt gatggcgtta actcggcgtt tcatctgtgg     780
tgcaacgggc gctgggtcgg ttacggccag gacagtcgtt tgccgtctga atttgacctg     840
agcgcatttt tacgcgccgg agaaaaccgc ctcgcggtga tggtgctgcg ttggagtgac     900
ggcagttatc tggaagatca ggatatgtgg cggatgagcg gcattttccg tgacgtctcg     960
ttgctgcata aaccgactac acaaatcagc gatttccatg ttgccactcg ctttaatgat    1020
gatttcagcc gcgctgtact ggaggctgaa gttcagatgt gcggcgagtt gcgtgactac    1080
ctacgggtaa cagtttcttt atggcagggt gaaacgcagg tcgccagcgg caccgcgcct    1140
ttcggcggtg aaattatcga tgagcgtggt ggttatgccg atcgcgtcac actacgtctg    1200
aacgtcgaaa acccgaaact gtggagcgcc gaaatcccga atctctatcg tgcggtggtt    1260
gaactgcaca ccgccgacgg cacgctgatt gaagcagaag cctgcgatgt cggtttccgc    1320
gaggtgcgga ttgaaaatgg tctgctgctg ctgaacggca agccgttgct gattcgaggc    1380
```

-continued

```
gttaaccgtc acgagcatca tcctctgcat ggtcaggtca tggatgagca gacgatggtg   1440
caggatatcc tgctgatgaa gcagaacaac tttaacgccg tgcgctgttc gcattatccg   1500
aaccatccgc tgtggtacac gctgtgcgac cgctacggcc tgtatgtggt ggatgaagcc   1560
aatattgaaa cccacggcat ggtgccaatg aatcgtctga ccgatgatcc gcgctggcta   1620
ccggcgatga gcgaacgcgt aacgcgaatg gtgcagcgcg atcgtaatca cccgagtgtg   1680
atcatctggt cgctggggaa tgaatcaggc cacggcgcta atcacgacgc gctgtatcgc   1740
tggatcaaat ctgtcgatcc ttcccgcccg gtgcagtatg aaggcggcgg agccgacacc   1800
acggccaccg atattatttg cccgatgtac gcgcgcgtgg atgaagacca gcccttcccg   1860
gctgtgccga aatggtccat caaaaaatgg ctttcgctac ctggagagac gcgcccgctg   1920
atcctttgcg aatacgccca cgcgatgggt aacagtcttg gcggtttcgc taaatactgg   1980
caggcgtttc gtcagtatcc ccgtttacag ggcggcttcg tctgggactg ggtggatcag   2040
tcgctgatta aatatgatga aaacggcaac ccgtggtcgg cttacggcgg tgattttggc   2100
gatacgccga acgatcgcca gttctgtatg aacggtctgg tctttgccga ccgcacgccg   2160
catccagcgc tgacggaagc aaaacaccag cagcagtttt tccagttccg tttatccggg   2220
caaaccatcg aagtgaccag cgaatacctg ttccgtcata gcgataacga gctcctgcac   2280
tggatggtgg cgctggatgg taagccgctg gcaagcggtg aagtgcctct ggatgtcgct   2340
ccacaaggta aacagttgat tgaactgcct gaactaccgc agccggagag cgccgggcaa   2400
ctctggctca cagtacgcgt agtgcaaccg aacgcgaccg catggtcaga agccgggcac   2460
atcagcgcct ggcagcagtg gcgtctggcg gaaaacctca gtgtgacgct ccccgccgcg   2520
tcccacgcca tcccgcatct gaccaccagc gaaatggatt tttgcatcga gctgggtaat   2580
aagcgttggc aatttaaccg ccagtcaggc tttctttcac agatgtggat tggcgataaa   2640
aaacaactgc tgacgccgct gcgcgatcag ttcacccgtg caccgctgga taacgacatt   2700
ggcgtaagtg aagcgacccg cattgaccct aacgcctggg tcgaacgctg gaaggcggcg   2760
ggccattacc aggccgaagc agcgttgttg cagtgcacgg cagatacact tgctgatgcg   2820
gtgctgatta cgaccgctca cgcgtggcag catcagggga aaaccttatt tatcagccgg   2880
aaaacctacc ggattgatgg tagtggtcaa atggcgatta ccgttgatgt tgaagtggcg   2940
agcgatacac cgcatccggc gcggattggc ctgaactgcc agctggcgca ggtagcagag   3000
cgggtaaact ggctcggatt agggccgcaa gaaaactatc ccgaccgcct tactgccgcc   3060
tgttttgacc gctgggatct gccattgtca gacatgtata ccccgtacgt cttcccgagc   3120
gaaaacggtc tgcgctgcgg gacgcgcgaa ttgaattatg gcccacacca gtggcgcggc   3180
gacttccagt tcaacatcag ccgctacagt caacagcaac tgatggaaac cagccatcgc   3240
catctgctgc acgcggaaga aggcacatgg ctgaatatcg acggtttcca tatggggatt   3300
ggtggcgacg actcctggag cccgtcagta tcggcggaat tccagctgag cgccggtcgc   3360
taccattacc agttggtctg gtgtcaaaaa taataa                             3396
```

<210> SEQ ID NO 33
<211> LENGTH: 6865
<212> TYPE: DNA
<213> ORGANISM: Artificial Sequence
<220> FEATURE:
<223> OTHER INFORMATION: Synthetic Sequence

<400> SEQUENCE: 33

-continued

```
cgccttgtta ctagttagaa aaagacattt ttgctgtcag tcactgtcaa gagattcttt     60
tgctggcatt tcttctagaa gcaaaaagag cgatgcgtct tttccgctga accgttccag    120
caaaaaagac taccaacgca atatggattg tcagaatcat ataaaagaga agcaaataac    180
tccttgtctt gtatcaattg cattataata tcttcttgtt agtgcaatat catatagaag    240
tcatcgaaat agatattaag aaaaacaaac tgtacaatcc atgggtcatc accatcatca    300
tcacgggtcg gactcagaag tcaatcaaga agctaagcca gaggtcaagc cagaagtcaa    360
gcctgagact cacatcaatt taaaggtgtc cgatggatct tcagagatct tcttcaagat    420
caaaaagacc actcctttaa gaaggctgat ggaagcgttc gctaaaagac agggtaagga    480
aatggactcc ttaagattct tgtacgacgg tattagaatt caagctgatc agacccctga    540
agatttggac atggaggata acgatattat tgaggctcac cgcgaacaga ttggaggtat    600
ggtgagcaag ggcgaggagc tgttcaccgg ggtggtgccc atcctggtcg agctggacgg    660
cgacgtaaac ggccacaagt tcagcgtgtc cggcgagggc gagggcgatg ccacctacgg    720
caagctgacc ctgaagttca tctgcaccac cggcaagctg cccgtgccct ggcccaccct    780
cgtgaccacc ctgacctacg gcgtgcagtg cttcagccgc taccccgacc acatgaagca    840
gcacgacttc ttcaagtccg ccatgcccga aggctacgtc caggagcgca ccatcttctt    900
caaggacgac ggcaactaca agacccgcgc cgaggtgaag ttcgagggcg acaccctggt    960
gaaccgcatc gagctgaagg gcatcgactt caaggaggac ggcaacatcc tggggcacaa   1020
gctggagtac aactacaaca gccacaacgt ctatatcatg gccgacaagc agaagaacgg   1080
catcaaggtg aacttcaaga tccgccacaa catcgaggac ggcagcgtgc agctcgccga   1140
ccactaccag cagaacaccc ccatcggcga cggccccgtg ctgctgcccg acaaccacta   1200
cctgagcacc cagtccgccc tgagcaaaga ccccaacgag aagcgcgatc acatggtcct   1260
gctggagttc gtgaccgccg ccgggatcac tctcggcatg gacgagctgt acaagtaata   1320
agcttgcggc cgcactcgag gagctccctg gcgaattgta ccaagatggc ctttggtggg   1380
ttgaagaagg aaaaagacag aaacgactta attacctact tgaaaaaagc ctgtgagtaa   1440
acaggcccct tttcctttgt cgatatcatg taattagtta tgtcacgctt acattcacgc   1500
cctcccccca catccgctct aaccgaaaag gaaggagtta gacaacctga agtctaggtc   1560
cctatttatt tttttatagt tatgttagta ttaagaacgt tatttatatt tcaaattttt   1620
cttttttttc tgtacagacg cgtgtacgca tgtaacatta tactgaaaac cttgcttgag   1680
aaggttttgg gacgctcgaa ggctttaatt tgcaagctta tcgatgataa gctgtcaaac   1740
atgagaattc ggtcgaaaaa agaaaaggag agggccaaga gggagggcat tggtgactat   1800
tgagcacgtg agtatacgtg attaagcaca caaaggcagc ttggagtatg tctgttatta   1860
atttcacagg tagttctggt ccattggtga aagtttgcgg cttgcagagc acagaggccg   1920
cagaatgtgc tctagattcc gatgctgact tgctgggtat tatatgtgtg cccaatagaa   1980
agagaacaat tgacccggtt attgcaagga aaatttcaag tcttgtaaaa gcatataaaa   2040
atagttcagg cactccgaaa tacttggttg gcgtgtttcg taatcaacct aaggaggatg   2100
ttttggctct ggtcaatgat tacggcattg atatcgtcca actgcatgga gatgagtcgt   2160
ggcaagaata ccaagagttc ctcggtttgc cagttattaa aagactcgta tttccaaaag   2220
actgcaacat actactcagt gcagcttcac agaaacctca ttcgtttatt cccttgtttg   2280
attcagaagc aggtgggaca ggtgaacttt tggattggaa ctcgatttct gactgggttg   2340
gaaggcaaga gagccccgaa agcttacatt ttatgttagc tggtggactg acgccagaaa   2400
```

-continued

```
atgttggtga tgcgcttaga ttaaatggcg ttattggtgt tgatgtaagc ggaggtgtgg   2460
agacaaatgg tgtaaaagac tctaacaaaa tagcaaattt cgtcaaaaat gctaagaaat   2520
aggttattac tgagtagtat ttatttaagt attgtttgtg cacttgcctg cagcttctca   2580
atgatattcg aatacgcttt gaggagatac agcctaatat ccgacaaact gttttacaga   2640
tttacgatcg tacttgttac ccatcattga attttgaaca tccgaacctg ggagttttcc   2700
ctgaaacaga tagtatattt gaacctgtat aataatatat agtctagcgc tttacggaag   2760
acaatgtatg tatttcggtt cctggagaaa ctattgcatc tattgcatag gtaatcttgc   2820
acgtcgcatc cccggttcat tttctgcgtt tccatcttgc acttcaatag catatctttg   2880
ttaacgaagc atctgtgctt cattttgtag aacaaaaatg caacgcgaga gcgctaattt   2940
ttcaaacaaa gaatctgagc tgcattttta cagaacagaa atgcaacgcg aaagcgctat   3000
tttaccaacg aagaatctgt gcttcatttt tgtaaaacaa aaatgcaacg cgagagcgct   3060
aatttttcaa acaaagaatc tgagctgcat ttttacagaa cagaaatgca acgcgagagc   3120
gctattttac caacaaagaa tctatacttc tttttgttc tacaaaaatg catcccgaga    3180
gcgctatttt tctaacaaag catcttagat tactttttt ctcctttgtg cgctctataa    3240
tgcagtctct tgataacttt ttgcactgta ggtccgttaa ggttagaaga aggctacttt   3300
ggtgtctatt ttctcttcca taaaaaaagc ctgactccac ttcccgcgtt tactgattac   3360
tagcgaagct gcgggtgcat tttttcaaga taaaggcatc cccgattata ttctataccg   3420
atgtggattg cgcatacttt gtgaacagaa agtgatagcg ttgatgattc ttcattggtc   3480
agaaaattat gaacggtttc ttctattttg tctctatata ctacgtatag gaaatgttta   3540
cattttcgta ttgttttcga ttcactctat gaatagttct tactacaatt tttttgtcta   3600
aagagtaata ctagagataa acataaaaaa tgtagaggtc gagtttagat gcaagttcaa   3660
ggagcgaaag gtggatgggt aggttatata gggatatagc acagagatat atagcaaaga   3720
gatacttttg agcaatgttt gtggaagcgg tattcgcaat attttagtag ctcgttacag   3780
tccggtgcgt ttttggtttt ttgaaagtgc gtcttcagag cgcttttggt tttcaaaagc   3840
gctctgaagt tcctatactt tctagagaat aggaacttcg gaataggaac ttcaaagcgt   3900
ttccgaaaac gagcgcttcc gaaaatgcaa cgcgagctgc gcacatacag ctcactgttc   3960
acgtcgcacc tatatctgcg tgttgcctgt atatatatat acatgagaag aacggcatag   4020
tgcgtgttta tgcttaaatg cgtacttata tgcgtctatt tatgtaggat gaaaggtagt   4080
ctagtacctc ctgtgatatt atcccattcc atgcggggta tcgtatgctt ccttcagcac   4140
taccctttag ctgttctata tgctgccact cctcaattgg attagtctca tccttcaatg   4200
ctatcatttc ctttgatatt ggatcatatg catagtaccg agaaactagt gcgaagtagt   4260
gatcaggtat tgctgttatc tgatgagtat acgttgtcct ggccacggca gaagcacgct   4320
tatcgctcca atttcccaca acattagtca actccgttag gcccttcatt gaaagaaatg   4380
aggtcatcaa atgtcttcca atgtgagatt ttgggccatt ttttatagca aagattgaat   4440
aaggcgcatt tttcttcaaa gctttattgt acgatctgac taagttatct tttaataatt   4500
ggtattcctg tttattgctt gaagaattgc cggtcctatt tactcgtttt aggactggtt   4560
cagaattctt gaagacgaaa gggcctcgtg atacgcctat ttttataggt taatgtcatg   4620
ataataatgg tttcttagac gtcaggtggc acttttcggg gaaatgtgcg cggaacccct   4680
atttgtttat ttttctaaat acattcaaat atgtatccgc tcatgagaca ataaccctga   4740
```

-continued taaatgcttc aataatattg aaaaaggaag agtatgagta ttcaacattt ccgtgtcgcc 4800
cttattccct tttttgcggc attttgcctt cctgtttttg ctcacccaga aacgctggtg 4860
aaagtaaaag atgctgaaga tcagttgggt gcacgagtgg gttacatcga actggatctc 4920
aacagcggta agatccttga gagttttcgc cccgaagaac gttttccaat gatgagcact 4980
tttaaagttc tgctatgtgg cgcggtatta tcccgtgttg acgccgggca agagcaactc 5040
ggtcgccgca tacactattc tcagaatgac ttggttgagt actcaccagt cacagaaaag 5100
catcttacgg atggcatgac agtaagagaa ttatgcagtg ctgccataac catgagtgat 5160
aacactgcgg ccaacttact tctgacaacg atcggaggac cgaaggagct aaccgctttt 5220
ttgcacaaca tgggggatca tgtaactcgc cttgatcgtt gggaaccgga gctgaatgaa 5280
gccataccaa acgacgagcg tgacaccacg atgcctgcag caatggcaac aacgttgcgc 5340
aaactattaa ctggcgaact acttactcta gcttcccggc aacaattaat agactggatg 5400
gaggcggata aagttgcagg accacttctg cgctcggccc ttccggctgg ctggtttatt 5460
gctgataaat ctggagccgg tgagcgtggg tctcgcggta tcattgcagc actggggcca 5520
gatggtaagc cctcccgtat cgtagttatc tacacgacgg ggagtcaggc aactatggat 5580
gaacgaaata gacagatcgc tgagataggt gcctcactga ttaagcattg gtaactgtca 5640
gaccaagttt actcatatat actttagatt gatttaaaac ttcattttta atttaaaagg 5700
atctaggtga agatcctttt tgataatctc atgaccaaaa tcccttaacg tgagttttcg 5760
ttccactgag cgtcagaccc cgtagaaaag atcaaaggat cttcttgaga tccttttttt 5820
ctgcgcgtaa tctgctgctt gcaaacaaaa aaaccaccgc taccagcggt ggtttgtttg 5880
ccggatcaag agctaccaac tctttttccg aaggtaactg gcttcagcag agcgcagata 5940
ccaaatactg tccttctagt gtagccgtag ttaggccacc acttcaagaa ctctgtagca 6000
ccgcctacat acctcgctct gctaatcctg ttaccagtgg ctgctgccag tggcgataag 6060
tcgtgtctta ccgggttgga ctcaagacga tagttaccgg ataaggcgca gcggtcgggc 6120
tgaacggggg gttcgtgcac acagcccagc ttggagcgaa cgacctacac cgaactgaga 6180
tacctacagc gtgagctatg agaaagcgcc acgcttcccg aagggagaaa ggcggacagg 6240
tatccggtaa gcggcagggt cggaacagga gagcgcacga gggagcttcc agggggaaac 6300
gcctggtatc tttatagtcc tgtcgggttt cgccacctct gacttgagcg tcgatttttg 6360
tgatgctcgt caggggggcg gagcctatgg aaaaacgcca gcaacgcggc ctttttacgg 6420
ttcctggcct tttgctggcc ttttgctcac atgttctttc ctgcgttatc ccctgattct 6480
gtggataacc gtattaccgc ctttgagtga gctgataccg ctcgccgcag ccgaacgacc 6540
gagcgcagcg agtcagtgag cgaggaagcg gaagagcgcc tgatgcggta ttttctcctt 6600
acgcatctgt gcggtatttc acaccgcata tggtgcactc tcagtacaat ctgctctgat 6660
gccgcatagt taagccagta tacactccgc tatcgctacg tgactgggtc atggctgcgc 6720
cccgacaccc gccaacaccc gctgacgcgc cctgacgggc ttgtctgctc ccggcatccg 6780
cttacagaca agctgtgacc gtctccggga gctgcatgtg tcagaggttt tcaccgtcat 6840
caccgaaacg cgcgaggcag ggatc 6865

<210> SEQ ID NO 34
<211> LENGTH: 7894
<212> TYPE: DNA
<213> ORGANISM: Artificial Sequence
<220> FEATURE:
<223> OTHER INFORMATION: Synthetic Sequence -continued

<400> SEQUENCE: 34
ccttgttact agttagaaaa agacattttt gctgtcagtc actgtcaaga gattcttttg 60
ctggcatttc ttctagaagc aaaaagagcg atgcgtcttt tccgctgaac cgttccagca 120
aaaaagacta ccaacgcaat atggattgtc agaatcatat aaaagagaag caaataactc 180
cttgtcttgt atcaattgca ttataatatc ttcttgttag tgcaatatca tatagaagtc 240
atcgaaatag atattaagaa aaacaaactg tacaatccat gggtcatcac catcatcatc 300
acgggcagat cttcgtcaag acgttaaccg gtaaaaccat aactctagaa gttgaaccat 360
ccgataccat cgaaaacgtt aaggctaaaa ttcaagacaa ggaaggcatt ccacctgatc 420
aacaaagatt gatctttgcc ggtaagcagc tcgaggacgg tagaacgctg tctgattaca 480
acattcagaa ggagtcgacc ttacatcttg tcttacgcct acgtggaggt atggaattca 540
tgttacgtcc tgtagaaacc ccaacccgtg aaatcaaaaa actcgacggc ctgtgggcat 600
tcagtctgga tcgcgaaaac tgtggaattg atcagcgttg gtgggaaagc gcgttacaag 660
aaagccgggc aattgctgtg ccaggcagtt ttaacgatca gttcgccgat gcagatattc 720
gtaattatgc gggcaacgtc tggtatcagc gcgaagtctt tataccgaaa ggttgggcag 780
gccagcgtat cgtgctgcgt ttcgatgcgg tcactcatta cggcaaagtg tgggtcaata 840
atcaggaagt gatggagcat cagggcggct atacgccatt tgaagccgat gtcacgccgt 900
atgttattgc cgggaaaagt gtacgtatca ccgtttgtgt gaacaacgaa ctgaactggc 960
agactatccc gccgggaatg gtgattaccg acgaaaacgg caagaaaaag cagtcttact 1020
tccatgattt ctttaactat gccggaatcc atcgcagcgt aatgctctac accacgccga 1080
acacctgggt ggacgatatc accgtggtga cgcatgtcgc gcaagactgt aaccacgcgt 1140
ctgttgactg gcaggtggtg gccaatggtg atgtcagcgt tgaactgcgt gatgcggatc 1200
aacaggtggt tgcaactgga caaggcacta gcgggacttt gcaagtggtg aatccgcacc 1260
tctggcaacc gggtgaaggt tatctctatg aactgtgcgt cacagccaaa agccagacag 1320
agtgtgatat ctacccgctt cgcgtcggca tccggtcagt ggcagtgaag ggccaacagt 1380
tcctgattaa ccacaaaccg ttctacttta ctggctttgg tcgtcatgaa gatgcggact 1440
tacgtggcaa aggattcgat aacgtgctga tggtgcacga ccacgcatta atggactgga 1500
ttggggccaa ctcctaccgt acctcgcatt acccttacgc tgaagagatg ctcgactggg 1560
cagatgaaca tggcatcgtg gtgattgatg aaactgctgc tgtcggcttt aacctctctt 1620
taggcattgg tttcgaagcg ggcaacaagc cgaaagaact gtacagcgaa gaggcagtca 1680
acggggaaac tcagcaagcg cacttacagg cgattaaaga gctgatagcg cgtgacaaaa 1740
accacccaag cgtggtgatg tggagtattg ccaacgaacc ggatacccgt ccgcaagtgc 1800
acgggaatat ttcgccactg gcggaagcaa cgcgtaaact cgacccgacg cgtccgatca 1860
cctgcgtcaa tgtaatgttc tgcgacgctc acaccgatac catcagcgat ctctttgatg 1920
tgctgtgcct gaaccgttat tacggatggt atgtccaaag cggcgatttg gaaacggcag 1980
agaaggtact ggaaaaagaa cttctggcct ggcaggagaa actgcatcag ccgattatca 2040
tcaccgaata cggcgtggat acgttagccg ggctgcactc aatgtacacc gacatgtgga 2100
gtgaagagta tcagtgtgca tggctggata tgtatcaccg cgtctttgat cgcgtcagcg 2160
ccgtcgtcgg tgaacaggta tggaatttcg ccgattttgc gacctcgcaa ggcatattgc 2220
gcgttggcgg taacaagaaa gggatcttca ctcgcgaccg caaaccgaag tcggcggctt 2280

-continued

```
ttctgctgca aaaacgctgg actggcatga acttcggtga aaaaccgcag cagggaggca   2340
aacaataagc ttgcggccgc actcgaggag ctccctggcg aattgtacca agatggcctt   2400
tggtgggttg aagaaggaaa aagacagaaa cgacttaatt acctacttga aaaaagcctg   2460
tgagtaaaca ggcccctttt cctttgtcga tatcatgtaa ttagttatgt cacgcttaca   2520
ttcacgccct ccccccacat ccgctctaac cgaaaaggaa ggagttagac aacctgaagt   2580
ctaggtccct atttattttt ttatagttat gttagtatta agaacgttat ttatatttca   2640
aatttttctt ttttttctgt acagacgcgt gtacgcatgt aacattatac tgaaaacctt   2700
gcttgagaag gttttgggac gctcgaaggc tttaatttgc aagcttatcg atgataagct   2760
gtcaaacatg agaattcggt cgaaaaaaga aaaggagagg gccaagaggg agggcattgg   2820
tgactattga gcacgtgagt atacgtgatt aagcacacaa aggcagcttg gagtatgtct   2880
gttattaatt tcacaggtag ttctggtcca ttggtgaaag tttgcggctt gcagagcaca   2940
gaggccgcag aatgtgctct agattccgat gctgacttgc tgggtattat atgtgtgccc   3000
aatagaaaga gaacaattga cccggttatt gcaaggaaaa tttcaagtct tgtaaaagca   3060
tataaaaata gttcaggcac tccgaaatac ttggttggcg tgtttcgtaa tcaacctaag   3120
gaggatgttt tggctctggt caatgattac ggcattgata tcgtccaact gcatggagat   3180
gagtcgtggc aagaatacca agagttcctc ggtttgccag ttattaaaag actcgtattt   3240
ccaaaagact gcaacatact actcagtgca gcttcacaga aacctcattc gtttattccc   3300
ttgtttgatt cagaagcagg tgggacaggt gaacttttgg attggaactc gatttctgac   3360
tgggttggaa ggcaagagag ccccgaaagc ttacatttta tgttagctgg tggactgacg   3420
ccagaaaatg ttggtgatgc gcttagatta aatggcgtta ttggtgttga tgtaagcgga   3480
ggtgtggaga caaatggtgt aaaagactct aacaaaatag caaatttcgt caaaaatgct   3540
aagaaatagg ttattactga gtagtattta tttaagtatt gtttgtgcac ttgcctgcag   3600
cttctcaatg atattcgaat acgctttgag gagatacagc ctaatatccg acaaactgtt   3660
ttacagattt acgatcgtac ttgttaccca tcattgaatt ttgaacatcc gaacctggga   3720
gttttccctg aaacagatag tatatttgaa cctgtataat aatatatagt ctagcgcttt   3780
acggaagaca atgtatgtat ttcggttcct ggagaaacta ttgcatctat tgcataggta   3840
atcttgcacg tcgcatcccc ggttcatttt ctgcgtttcc atcttgcact tcaatagcat   3900
atctttgtta acgaagcatc tgtgcttcat tttgtagaac aaaaatgcaa cgcgagagcg   3960
ctaatttttc aaacaaagaa tctgagctgc atttttacag aacagaaatg caacgcgaaa   4020
gcgctatttt accaacgaag aatctgtgct tcatttttgt aaaacaaaaa tgcaacgcga   4080
gagcgctaat ttttcaaaca aagaatctga gctgcatttt tacagaacag aaatgcaacg   4140
cgagagcgct attttaccaa caaagaatct atacttcttt tttgttctac aaaaatgcat   4200
cccgagagcg ctatttttct aacaaagcat cttagattac tttttttctc ctttgtgcgc   4260
tctataatgc agtctcttga taacttttttg cactgtaggt ccgttaaggt tagaagaagg   4320
ctactttggt gtctattttc tcttccataa aaaaagcctg actccacttc ccgcgtttac   4380
tgattactag cgaagctgcg ggtgcatttt ttcaagataa aggcatcccc gattatattc   4440
tataccgatg tggattgcgc atactttgtg aacagaaagt gatagcgttg atgattcttc   4500
attggtcaga aaattatgaa cggtttcttc tattttgtct ctatatacta cgtataggaa   4560
atgtttacat tttcgtattg ttttcgattc actctatgaa tagttcttac tacaattttt   4620
ttgtctaaag agtaatacta gagataaaca taaaaaatgt agaggtcgag tttagatgca   4680
```

-continued agttcaagga gcgaaaggtg gatgggtagg ttatataggg atatagcaca gagatatata 4740
gcaaagagat acttttgagc aatgtttgtg gaagcggtat tcgcaatatt ttagtagctc 4800
gttacagtcc ggtgcgtttt tggttttttg aaagtgcgtc ttcagagcgc ttttggtttt 4860
caaaagcgct ctgaagttcc tatactttct agagaatagg aacttcggaa taggaacttc 4920
aaagcgtttc cgaaaacgag cgcttccgaa aatgcaacgc gagctgcgca catacagctc 4980
actgttcacg tcgcacctat atctgcgtgt tgcctgtata tatatataca tgagaagaac 5040
ggcatagtgc gtgtttatgc ttaaatgcgt acttatatgc gtctatttat gtaggatgaa 5100
aggtagtcta gtacctcctg tgatattatc ccattccatg cggggtatcg tatgcttcct 5160
tcagcactac cctttagctg ttctatatgc tgccactcct caattggatt agtctcatcc 5220
ttcaatgcta tcatttcctt tgatattgga tcatatgcat agtaccgaga aactagtgcg 5280
aagtagtgat caggtattgc tgttatctga tgagtatacg ttgtcctggc cacggcagaa 5340
gcacgcttat cgctccaatt tcccacaaca ttagtcaact ccgttaggcc cttcattgaa 5400
agaaatgagg tcatcaaatg tcttccaatg tgagattttg ggccattttt tatagcaaag 5460
attgaataag gcgcattttt cttcaaagct ttattgtacg atctgactaa gttatctttt 5520
aataattggt attcctgttt attgcttgaa gaattgccgg tcctatttac tcgttttagg 5580
actggttcag aattcttgaa gacgaaaggg cctcgtgata cgcctatttt tataggttaa 5640
tgtcatgata ataatggttt cttagacgtc aggtggcact tttcggggaa atgtgcgcgg 5700
aacccctatt tgtttatttt tctaaataca ttcaaatatg tatccgctca tgagacaata 5760
accctgataa atgcttcaat aatattgaaa aaggaagagt atgagtattc aacatttccg 5820
tgtcgccctt attccctttt ttgcggcatt ttgccttcct gtttttgctc acccagaaac 5880
gctggtgaaa gtaaaagatg ctgaagatca gttgggtgca cgagtgggtt acatcgaact 5940
ggatctcaac agcggtaaga tccttgagag ttttcgcccc gaagaacgtt ttccaatgat 6000
gagcactttt aaagttctgc tatgtggcgc ggtattatcc cgtgttgacg ccgggcaaga 6060
gcaactcggt cgccgcatac actattctca gaatgacttg gttgagtact caccagtcac 6120
agaaaagcat cttacggatg gcatgacagt aagagaatta tgcagtgctg ccataaccat 6180
gagtgataac actgcggcca acttacttct gacaacgatc ggaggaccga aggagctaac 6240
cgcttttttg cacaacatgg gggatcatgt aactcgcctt gatcgttggg aaccggagct 6300
gaatgaagcc ataccaaacg acgagcgtga caccacgatg cctgcagcaa tggcaacaac 6360
gttgcgcaaa ctattaactg gcgaactact tactctagct tcccggcaac aattaataga 6420
ctggatggag gcggataaag ttgcaggacc acttctgcgc tcggcccttc cggctggctg 6480
gtttattgct gataaatctg gagccggtga gcgtgggtct cgcggtatca ttgcagcact 6540
ggggccagat ggtaagccct cccgtatcgt agttatctac acgacgggga gtcaggcaac 6600
tatggatgaa cgaaatagac agatcgctga gataggtgcc tcactgatta agcattggta 6660
actgtcagac caagtttact catatatact ttagattgat ttaaaacttc atttttaatt 6720
taaaaggatc taggtgaaga tcctttttga taatctcatg accaaaatcc cttaacgtga 6780
gttttcgttc cactgagcgt cagaccccgt agaaaagatc aaaggatctt cttgagatcc 6840
tttttttctg cgcgtaatct gctgcttgca aacaaaaaaa ccaccgctac cagcggtggt 6900
ttgtttgccg gatcaagagc taccaactct ttttccgaag gtaactggct tcagcagagc 6960
gcagatacca aatactgtcc ttctagtgta gccgtagtta ggccaccact tcaagaactc 7020

-continued tgtagcaccg cctacatacc tcgctctgct aatcctgtta ccagtggctg ctgccagtgg 7080
cgataagtcg tgtcttaccg ggttggactc aagacgatag ttaccggata aggcgcagcg 7140
gtcgggctga acggggggtt cgtgcacaca gcccagcttg gagcgaacga cctacaccga 7200
actgagatac ctacagcgtg agctatgaga aagcgccacg cttcccgaag ggagaaaggc 7260
ggacaggtat ccggtaagcg gcagggtcgg aacaggagag cgcacgaggg agcttccagg 7320
gggaaacgcc tggtatcttt atagtcctgt cgggtttcgc cacctctgac ttgagcgtcg 7380
atttttgtga tgctcgtcag gggggcggag cctatggaaa aacgccagca acgcggcctt 7440
tttacggttc ctggcctttt gctggccttt tgctcacatg ttctttcctg cgttatcccc 7500
tgattctgtg gataaccgta ttaccgcctt tgagtgagct gataccgctc gccgcagccg 7560
aacgaccgag cgcagcgagt cagtgagcga ggaagcggaa gagcgcctga tgcggtattt 7620
tctccttacg catctgtgcg gtatttcaca ccgcatatgg tgcactctca gtacaatctg 7680
ctctgatgcc gcatagttaa gccagtatac actccgctat cgctacgtga ctgggtcatg 7740
gctgcgcccc gacacccgcc aacacccgct gacgcgccct gacgggcttg tctgctcccg 7800
gcatccgctt acagacaagc tgtgaccgtc tccgggagct gcatgtgtca gaggttttca 7860
ccgtcatcac cgaaacgcgc gaggcaggga tccg 7894

<210> SEQ ID NO 35
<211> LENGTH: 5800
<212> TYPE: DNA
<213> ORGANISM: Artificial Sequence
<220> FEATURE:
<223> OTHER INFORMATION: Synthetic Sequence

<400> SEQUENCE: 35
atcatggaga taattaaaat gataaccatc tcgcaaataa ataagtattt tactgttttc 60
gtaacagttt tgtaataaaa aaacctataa atattccgga ttattcatac cgtcccacca 120
tcgggcgcga tgggtcatca ccatcatcat cacgggtcgg actcagaagt caatcaagaa 180
gctaagccag aggtcaagcc agaagtcaag cctgagactc acatcaattt aaaggtgtcc 240
gatggatctt cagagatctt cttcaagatc aaaaagacca ctcctttaag aaggctgatg 300
gaagcgttcg ctaaaagaca gggtaaggaa atggactcct taagattctt gtacgacggt 360
attagaattc aagctgatca gacccctgaa gatttggaca tggaggataa cgatattatt 420
gaggctcacc gcgaacagat tggaggtatg gtgagcaagg gcgaggagct gttcaccggg 480
gtggtgccca tcctggtcga gctggacggc gacgtaaacg gccacaagtt cagcgtgtcc 540
ggcgagggcg agggcgatgc cacctacggc aagctgaccc tgaagttcat ctgcaccacc 600
ggcaagctgc ccgtgccctg gcccaccctc gtgaccaccc tgacctacgg cgtgcagtgc 660
ttcagccgct accccgacca catgaagcag cacgacttct tcaagtccgc catgcccgaa 720
ggctacgtcc aggagcgcac catcttcttc aaggacgacg gcaactacaa gacccgcgcc 780
gaggtgaagt tcgagggcga caccctggtg aaccgcatcg agctgaaggg catcgacttc 840
aaggaggacg gcaacatcct ggggcacaag ctggagtaca actacaacag ccacaacgtc 900
tatatcatgg ccgacaagca gaagaacggc atcaaggtga acttcaagat ccgccacaac 960
atcgaggacg gcagcgtgca gctcgccgac cactaccagc agaacacccc catcggcgac 1020
ggccccgtgc tgctgcccga caaccactac ctgagcaccc agtccgccct gagcaaagac 1080
cccaacgaga agcgcgatca catggtcctg ctggagttcg tgaccgccgc cgggatcact 1140
ctcggcatgg acgagctgta caagtaatga gacggaattc aaaggcctac gtcgacgagc 1200

-continued

```
tcactagtcg cggccgcttt cgaatctaga gcctgcagtc tcgaggcatg cggtaccaag   1260
cttgtcgaga agtactagag gatcataatc agccatacca catttgtaga ggttttactt   1320
gctttaaaaa acctcccaca cctccccctg aacctgaaac ataaaatgaa tgcaattgtt   1380
gttgttaact tgtttattgc agcttataat ggttacaaat aaagcaatag catcacaaat   1440
ttcacaaata aagcattttt ttcactgcat tctagttgtg gtttgtccaa actcatcaat   1500
gtatcttatc atgtctggat ctgatcactg cttgagccta ggagatccga accagataag   1560
tgaaatctag ttccaaacta ttttgtcatt tttaattttc gtattagctt acgacgctac   1620
acccagttcc catctatttt gtcactcttc cctaaataat ccttaaaaac tccatttcca   1680
cccctcccag ttcccaacta ttttgtccgc ccacagcggg gcatttttct tcctgttatg   1740
tttttaatca aacatcctgc caactccatg tgacaaaccg tcatcttcgg ctactttttc   1800
tctgtcacag aatgaaaatt tttctgtcat ctcttcgtta ttaatgtttg taattgactg   1860
aatatcaacg cttatttgca gcctgaatgg cgaatgggac gcgccctgta gcggcgcatt   1920
aagcgcggcg ggtgtggtgg ttacgcgcag cgtgaccgct acacttgcca gcgccctagc   1980
gcccgctcct ttcgctttct tcccttcctt tctcgccacg ttcgccggct ttccccgtca   2040
agctctaaat cgggggctcc ctttagggtt ccgatttagt gctttacggc acctcgaccc   2100
caaaaaactt gattagggtg atggttcacg tagtgggcca tcgccctgat agacggtttt   2160
tcgccctttg acgttggagt ccacgttctt taatagtgga ctcttgttcc aaactggaac   2220
aacactcaac cctatctcgg tctattcttt tgatttataa gggattttgc cgatttcggc   2280
ctattggtta aaaaatgagc tgatttaaca aaaatttaac gcgaatttta acaaaatatt   2340
aacgtttaca atttcaggtg gcacttttcg gggaaatgtg cgcggaaccc ctatttgttt   2400
atttttctaa atacattcaa atatgtatcc gctcatgaga caataaccct gataaatgct   2460
tcaataatat tgaaaaagga agagtatgag tattcaacat ttccgtgtcg cccttattcc   2520
cttttttgcg gcattttgcc ttcctgtttt tgctcaccca gaaacgctgg tgaaagtaaa   2580
agatgctgaa gatcagttgg gtgcacgagt gggttacatc gaactggatc tcaacagcgg   2640
taagatcctt gagagttttc gccccgaaga acgttttcca atgatgagca cttttaaagt   2700
tctgctatgt ggcgcggtat tatcccgtat tgacgccggg caagagcaac tcggtcgccg   2760
catacactat tctcagaatg acttggttga gtactcacca gtcacagaaa agcatcttac   2820
ggatggcatg acagtaagag aattatgcag tgctgccata accatgagtg ataacactgc   2880
ggccaactta cttctgacaa cgatcggagg accgaaggag ctaaccgctt ttttgcacaa   2940
catgggggat catgtaactc gccttgatcg ttgggaaccg gagctgaatg aagccatacc   3000
aaacgacgag cgtgacacca cgatgcctgt agcaatggca acaacgttgc gcaaactatt   3060
aactggcgaa ctacttactc tagcttcccg gcaacaatta atagactgga tggaggcgga   3120
taaagttgca ggaccacttc tgcgctcggc ccttccggct ggctggttta ttgctgataa   3180
atctggagcc ggtgagcgtg ggtctcgcgg tatcattgca gcactggggc cagatggtaa   3240
gccctcccgt atcgtagtta tctacacgac ggggagtcag gcaactatgg atgaacgaaa   3300
tagacagatc gctgagatag gtgcctcact gattaagcat tggtaactgt cagaccaagt   3360
ttactcatat atactttaga ttgatttaaa acttcatttt taatttaaaa ggatctaggt   3420
gaagatcctt tttgataatc tcatgaccaa aatcccttaa cgtgagtttt cgttccactg   3480
agcgtcagac cccgtagaaa agatcaaagg atcttcttga gatccttttt ttctgcgcgt   3540
```

-continued

```
aatctgctgc ttgcaaacaa aaaaaccacc gctaccagcg gtggtttgtt tgccggatca   3600
agagctacca actctttttc cgaaggtaac tggcttcagc agagcgcaga taccaaatac   3660
tgtccttcta gtgtagccgt agttaggcca ccacttcaag aactctgtag caccgcctac   3720
atacctcgct ctgctaatcc tgttaccagt ggctgctgcc agtggcgata agtcgtgtct   3780
taccgggttg gactcaagac gatagttacc ggataaggcg cagcggtcgg gctgaacggg   3840
gggttcgtgc acacagccca gcttggagcg aacgacctac accgaactga gatacctaca   3900
gcgtgagcat tgagaaagcg ccacgcttcc cgaagggaga aaggcggaca ggtatccggt   3960
aagcggcagg gtcggaacag gagagcgcac gagggagctt ccagggggaa acgcctggta   4020
tctttatagt cctgtcgggt ttcgccacct ctgacttgag cgtcgatttt tgtgatgctc   4080
gtcagggggg cggagcctat ggaaaaacgc cagcaacgcg gcctttttac ggttcctggc   4140
cttttgctgg ccttttgctc acatgttctt tcctgcgtta tcccctgatt ctgtggataa   4200
ccgtattacc gcctttgagt gagctgatac cgctcgccgc agccgaacga ccgagcgcag   4260
cgagtcagtg agcgaggaag cggaagagcg cctgatgcgg tattttctcc ttacgcatct   4320
gtgcggtatt tcacaccgca gaccagccgc gtaacctggc aaaatcggtt acggttgagt   4380
aataaatgga tgccctgcgt aagcgggtgt gggcggacaa taaagtctta aactgaacaa   4440
aatagatcta aactatgaca ataaagtctt aaactagaca gaatagttgt aaactgaaat   4500
cagtccagtt atgctgtgaa aaagcatact ggacttttgt tatggctaaa gcaaactctt   4560
cattttctga agtgcaaatt gcccgtcgta ttaaagaggg gcgtggccaa gggcatggta   4620
aagactatat tcgcggcgtt gtgacaattt accgaacaac tccgcggccg ggaagccgat   4680
ctcggcttga acgaattgtt aggtggcggt acttgggtcg atatcaaagt gcatcacttc   4740
ttcccgtatg cccaactttg tatagagagc cactgcggga tcgtcaccgt aatctgcttg   4800
cacgtagatc acataagcac caagcgcgtt ggcctcatgc ttgaggagat tgatgagcgc   4860
ggtggcaatg ccctgcctcc ggtgctcgcc ggagactgcg agatcataga tatagatctc   4920
actacgcggc tgctcaaacc tgggcagaac gtaagccgcg agagcgccaa caaccgcttc   4980
ttggtcgaag gcagcaagcg cgatgaatgt cttactacgg agcaagttcc cgaggtaatc   5040
ggagtccggc tgatgttggg agtaggtggc tacgtctccg aactcacgac cgaaaagatc   5100
aagagcagcc cgcatggatt tgacttggtc agggccgagc ctacatgtgc gaatgatgcc   5160
catacttgag ccacctaact ttgttttagg gcgactgccc tgctgcgtaa catcgttgct   5220
gctgcgtaac atcgttgctg ctccataaca tcaaacatcg acccacggcg taacgcgctt   5280
gctgcttgga tgcccgaggc atagactgta caaaaaaaca gtcataacaa gccatgaaaa   5340
ccgccactgc gccgttacca ccgctgcgtt cggtcaaggt tctggaccag ttgcgtgagc   5400
gcatacgcta cttgcattac agtttacgaa ccgaacaggc ttatgtcaac tgggttcgtg   5460
ccttcatccg tttccacggt gtgcgtcacc cggcaacctt gggcagcagc gaagtcgagg   5520
catttctgtc ctggctggcg aacgagcgca aggtttcggt ctccacgcat cgtcaggcat   5580
tggcggcctt gctgttcttc tacggcaagg tgctgtgcac ggatctgccc tggcttcagg   5640
agatcggaag acctcggccg tcgcggcgct tgccggtggt gctgaccccg gatgaagtgg   5700
ttcgcatcct cggttttctg gaaggcgagc atcgtttgtt cgcccaggac tctagctata   5760
gttctagtgg ttggctacgt atactccgga atattaatag                         5800
```

<210> SEQ ID NO 36
<211> LENGTH: 5598

-continued

<212> TYPE: DNA
<213> ORGANISM: Artificial Sequence
<220> FEATURE:
<223> OTHER INFORMATION: Synthetic Sequence

<400> SEQUENCE: 36
atccggatat agttcctcct ttcagcaaaa aacccctcaa gacccgttta gaggccccaa 60
ggggttatgc tagttattgc tcagcggtgg cagcagccaa ctcagcttcc tttcgggctt 120
tgttagcagc cggatctcag tggtggtggt ggtggtgctc gagtgcggcc gcaagcttgt 180
cgacggagct cgaattcgga tccggtctca acctccaatc tgttcgcggt gagcctcaat 240
aatatcgtta tcctccatgt ccaaatcttc aggggtctga tcagcttgaa ttctaatacc 300
gtcgtacaag aatcttaagg agtccatttc cttaccctgt cttttagcga acgcttccat 360
cagccttctt aaaggagtgg tctttttgat cttgaagaag atctctgaag atccatcgga 420
cacctttaaa ttgatgtgag tctcaggctt gacttctggc ttgacctctg gcttagcttc 480
ttgattgact tctgagtccg acccgtgatg atgatggtga tgacccatgg tatatctcct 540
tcttaaagtt aaacaaaatt atttctagag gggaattgtt atccgctcac aattccccta 600
tagtgagtcg tattaatttc gcgggatcga gatctcgatc ctctacgccg gacgcatcgt 660
ggccggcatc accggcgcca caggtgcggt tgctggcgcc tatatcgccg acatcaccga 720
tggggaagat cgggctcgcc acttcgggct catgagcgct tgtttcggcg tgggtatggt 780
ggcaggcccc gtggccgggg gactgttggg cgccatctcc ttgcatgcac cattccttgc 840
ggcggcggtg ctcaacggcc tcaacctact actgggctgc ttcctaatgc aggagtcgca 900
taagggagag cgtcgagatc ccggacacca tcgaatggcg caaaaccttt cgcggtatgg 960
catgatagcg cccggaagag agtcaattca gggtggtgaa tgtgaaacca gtaacgttat 1020
acgatgtcgc agagtatgcc ggtgtctctt atcagaccgt ttcccgcgtg gtgaaccagg 1080
ccagccacgt ttctgcgaaa acgcgggaaa aagtggaagc ggcgatggcg gagctgaatt 1140
acattcccaa ccgcgtggca caacaactgg cgggcaaaca gtcgttgctg attggcgttg 1200
ccacctccag tctggccctg cacgcgccgt cgcaaattgt cgcggcgatt aaatctcgcg 1260
ccgatcaact gggtgccagc gtggtggtgt cgatggtaga acgaagcggc gtcgaagcct 1320
gtaaagcggc ggtgcacaat cttctcgcgc aacgcgtcag tgggctgatc attaactatc 1380
cgctggatga ccaggatgcc attgctgtgg aagctgcctg cactaatgtt ccggcgttat 1440
ttcttgatgt ctctgaccag acacccatca acagtattat tttctcccat gaagacggta 1500
cgcgactggg cgtggagcat ctggtcgcat tgggtcacca gcaaatcgcg ctgttagcgg 1560
gcccattaag ttctgtctcg gcgcgtctgc gtctggctgg ctggcataaa tatctcactc 1620
gcaatcaaat tcagccgata gcggaacggg aaggcgactg gagtgccatg tccggttttc 1680
aacaaaccat gcaaatgctg aatgagggca tcgttcccac tgcgatgctg gttgccaacg 1740
atcagatggc gctgggcgca atgcgcgcca ttaccgagtc cgggctgcgc gttggtgcgg 1800
atatctcggt agtgggatac gacgataccg aagacagctc atgttatatc ccgccgttaa 1860
ccaccatcaa acaggatttt cgcctgctgg ggcaaaccag cgtggaccgc ttgctgcaac 1920
tctctcaggg ccaggcggtg aagggcaatc agctgttgcc cgtctcactg gtgaaaagaa 1980
aaaccaccct ggcgcccaat acgcaaaccg cctctccccg cgcgttggcc gattcattaa 2040
tgcagctggc acgacaggtt tcccgactgg aaagcgggca gtgagcgcaa cgcaattaat 2100
gtaagttagc tcactcatta ggcaccggga tctcgaccga tgcccttgag agccttcaac 2160

-continued

```
ccagtcagct ccttccggtg ggcgcggggc atgactatcg tcgccgcact tatgactgtc   2220
ttctttatca tgcaactcgt aggacaggtg ccggcagcgc tctgggtcat tttcggcgag   2280
gaccgctttc gctggagcgc gacgatgatc ggcctgtcgc ttgcggtatt cggaatcttg   2340
cacgccctcg ctcaagcctt cgtcactggt cccgccacca aacgtttcgg cgagaagcag   2400
gccattatcg ccggcatggc ggccccacgg gtgcgcatga tcgtgctcct gtcgttgagg   2460
acccggctag gctggcgggg ttgccttact ggttagcaga atgaatcacc gatacgcgag   2520
cgaacgtgaa gcgactgctg ctgcaaaacg tctgcgacct gagcaacaac atgaatggtc   2580
ttcggtttcc gtgtttcgta aagtctggaa acgcggaagt cagcgccctg caccattatg   2640
ttccggatct gcatcgcagg atgctgctgg ctaccctgtg gaacacctac atctgtatta   2700
acgaagcgct ggcattgacc ctgagtgatt tttctctggt cccgccgcat ccataccgcc   2760
agttgtttac cctcacaacg ttccagtaac cgggcatgtt catcatcagt aacccgtatc   2820
gtgagcatcc tctctcgttt catcggtatc attaccccca tgaacagaaa tcccccttac   2880
acggaggcat cagtgaccaa acaggaaaaa accgccctta acatggcccg ctttatcaga   2940
agccagacat taacgcttct ggagaaactc aacgagctgg acgcggatga acaggcagac   3000
atctgtgaat cgcttcacga ccacgctgat gagctttacc gcagctgcct cgcgcgtttc   3060
ggtgatgacg gtgaaaacct ctgacacatg cagctcccgg agacggtcac agcttgtctg   3120
taagcggatg ccgggagcag acaagcccgt cagggcgcgt cagcgggtgt tggcgggtgt   3180
cggggcgcag ccatgaccca gtcacgtagc gatagcggag tgtatactgg cttaactatg   3240
cggcatcaga gcagattgta ctgagagtgc accatatatg cggtgtgaaa taccgcacag   3300
atgcgtaagg agaaaatacc gcatcaggcg ctcttccgct tcctcgctca ctgactcgct   3360
gcgctcggtc gttcggctgc ggcgagcggt atcagctcac tcaaaggcgg taatacggtt   3420
atccacagaa tcaggggata acgcaggaaa gaacatgtga gcaaaaggcc agcaaaaggc   3480
caggaaccgt aaaaaggccg cgttgctggc gtttttccat aggctccgcc cccctgacga   3540
gcatcacaaa aatcgacgct caagtcagag gtggcgaaac ccgacaggac tataaagata   3600
ccaggcgttt ccccctggaa gctccctcgt gcgctctcct gttccgaccc tgccgcttac   3660
cggatacctg tccgcctttc tcccttcggg aagcgtggcg ctttctcata gctcacgctg   3720
taggtatctc agttcggtgt aggtcgttcg ctccaagctg ggctgtgtgc acgaaccccc   3780
cgttcagccc gaccgctgcg ccttatccgg taactatcgt cttgagtcca acccggtaag   3840
acacgactta tcgccactgg cagcagccac tggtaacagg attagcagag cgaggtatgt   3900
aggcggtgct acagagttct tgaagtggtg gcctaactac ggctacacta gaaggacagt   3960
atttggtatc tgcgctctgc tgaagccagt taccttcgga aaaagagttg gtagctcttg   4020
atccggcaaa caaaccaccg ctggtagcgg tggttttttt gtttgcaagc agcagattac   4080
gcgcagaaaa aaaggatctc aagaagatcc tttgatcttt tctacggggt ctgacgctca   4140
gtggaacgaa aactcacgtt aagggatttt ggtcatgaac aataaaactg tctgcttaca   4200
taaacagtaa tacaaggggt gttatgagcc atattcaacg ggaaacgtct tgctctaggc   4260
cgcgattaaa ttccaacatg gatgctgatt tatatgggta taaatgggct cgcgataatg   4320
tcgggcaatc aggtgcgaca atctatcgat tgtatgggaa gcccgatgcg ccagagttgt   4380
ttctgaaaca tggcaaaggt agcgttgcca atgatgttac agatgagatg gtcagactaa   4440
actggctgac ggaatttatg cctcttccga ccatcaagca ttttatccgt actcctgatg   4500
atgcatggtt actcaccact gcgatccccg ggaaaacagc attccaggta ttagaagaat   4560
```

-continued

```
atcctgattc aggtgaaaat attgttgatg cgctggcagt gttcctgcgc cggttgcatt   4620

cgattcctgt ttgtaattgt ccttttaaca gcgatcgcgt atttcgtctc gctcaggcgc   4680

aatcacgaat gaataacggt ttggttgatg cgagtgattt tgatgacgag cgtaatggct   4740

ggcctgttga acaagtctgg aaagaaatgc ataaactttt gccattctca ccggattcag   4800

tcgtcactca tggtgatttc tcacttgata accttatttt tgacgagggg aaattaatag   4860

gttgtattga tgttggacga gtcggaatcg cagaccgata ccaggatctt gccatcctat   4920

ggaactgcct cggtgagttt tctccttcat tacagaaacg gctttttcaa aaatatggta   4980

ttgataatcc tgatatgaat aaattgcagt ttcatttgat gctcgatgag tttttctaag   5040

aattaattca tgagcggata catatttgaa tgtatttaga aaaataaaca aataggggtt   5100

ccgcgcacat ttccccgaaa agtgccacct gaaattgtaa acgttaatat tttgttaaaa   5160

ttcgcgttaa atttttgtta aatcagctca ttttttaacc aataggccga aatcggcaaa   5220

atcccttata aatcaaaaga atagaccgag atagggttga gtgttgttcc agtttggaac   5280

aagagtccac tattaaagaa cgtggactcc aacgtcaaag ggcgaaaaac cgtctatcag   5340

ggcgatggcc cactacgtga accatcaccc taatcaagtt ttttggggtc gaggtgccgt   5400

aaagcactaa atcggaaccc taaagggagc ccccgattta gagcttgacg gggaaagccg   5460

gcgaacgtgg cgagaaagga agggaagaaa gcgaaaggag cgggcgctag ggcgctggca   5520

agtgtagcgg tcacgctgcg cgtaaccacc acacccgccg cgcttaatgc gccgctacag   5580

ggcgcgtccc attcgcca                                                  5598
```

```
<210> SEQ ID NO 37
<211> LENGTH: 478
<212> TYPE: DNA
<213> ORGANISM: Artificial Sequence
<220> FEATURE:
<223> OTHER INFORMATION: Synthetic Sequence

<400> SEQUENCE: 37

agatctcgat cccgcgaaat taatacgact cactataggg gaattgtgag cggataacaa     60

ttcccctcta gaaataattt tgtttaactt taagaaggag atataccatg ggtcatcacc    120

atcatcatca cgggtcggac tcagaagtca atcaagaagc taagccagag gtcaagccag    180

aagtcaagcc tgagactcac atcaatttaa aggtgtccga tggatcttca gagatcttct    240

tcaagatcaa aaagaccact cctttaagaa ggctgatgga agcgttcgct aaaagacagg    300

gtaaggaaat ggactcctta agattcttgt acgacggtat tagaattcaa gctgatcaga    360

cccctgaaga tttggacatg gaggataacg atattattga ggctcaccgc gaacagattg    420

gaggttgaga ccggatccga attcgagctc cgtcgacaag cttgcggccg cactcgag      478
```

```
<210> SEQ ID NO 38
<211> LENGTH: 106
<212> TYPE: PRT
<213> ORGANISM: Saccharomtces cerevisiae

<400> SEQUENCE: 38

Met Gly His His His His His His Gly Ser Asp Ser Glu Val Asn Gln
1               5                   10                  15

Glu Ala Lys Pro Glu Val Lys Pro Glu Val Lys Pro Glu Thr His Ile
            20                  25                  30

Asn Leu Lys Val Ser Asp Gly Ser Ser Glu Ile Phe Phe Lys Ile Lys
        35                  40                  45
```

-continued

```
Lys Thr Thr Pro Leu Arg Arg Leu Met Glu Ala Phe Ala Lys Arg Gln
    50                  55                  60

Gly Lys Glu Met Asp Ser Leu Arg Phe Leu Tyr Asp Gly Ile Arg Ile
65                  70                  75                  80

Gln Ala Asp Gln Thr Pro Glu Asp Leu Asp Met Glu Asp Asn Asp Ile
                85                  90                  95

Ile Glu Ala His Arg Glu Gln Ile Gly Gly
            100                 105

<210> SEQ ID NO 39
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 39

Leu Arg Leu Arg Gly Gly
1               5

<210> SEQ ID NO 40
<211> LENGTH: 50
<212> TYPE: DNA
<213> ORGANISM: Artificial Sequence
<220> FEATURE:
<223> OTHER INFORMATION: primer

<400> SEQUENCE: 40
ccatgggtca tcaccatcat catcacgggt cggactcaga agtcaatcaa                50

<210> SEQ ID NO 41
<211> LENGTH: 36
<212> TYPE: DNA
<213> ORGANISM: Artificial Sequence
<220> FEATURE:
<223> OTHER INFORMATION: primer

<400> SEQUENCE: 41
ggatccggtc tcaacctcca atctgttcgc ggtgag                               36

<210> SEQ ID NO 42
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (0)...(0)
<223> OTHER INFORMATION: n = a, c, g, or t

<400> SEQUENCE: 42
ggtctcaagg tnnngtgagc aagggcgagg agc                                  33

<210> SEQ ID NO 43
<211> LENGTH: 31
<212> TYPE: DNA
<213> ORGANISM: Artificial Sequence
<220> FEATURE:
<223> OTHER INFORMATION: primer

<400> SEQUENCE: 43
aagcttatta cttgtacagc tcgtccatgc c                                    31
```

-continued

<210> SEQ ID NO 44
<211> LENGTH: 14
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (0)...(0)
<223> OTHER INFORMATION: n = a, c, g, or t

<400> SEQUENCE: 44
ggtctcaagg tnnn 14

<210> SEQ ID NO 45
<211> LENGTH: 18
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (0)...(0)
<223> OTHER INFORMATION: n = a, c, g, or t

<400> SEQUENCE: 45
ggtctcctcg agttannn 18

<210> SEQ ID NO 46
<211> LENGTH: 84
<212> TYPE: DNA
<213> ORGANISM: Artificial Sequence
<220> FEATURE:
<223> OTHER INFORMATION: Synthetic Sequence

<400> SEQUENCE: 46
gtcttaagac taagaggtgg cacgccggcg gtgaccacct ataaactggt gattaacggc 60
aaaaccctga aaggcgaaac cacc 84

<210> SEQ ID NO 47
<211> LENGTH: 78
<212> TYPE: DNA
<213> ORGANISM: Artificial Sequence
<220> FEATURE:
<223> OTHER INFORMATION: Synthetic Sequence

<400> SEQUENCE: 47
gccgttatcg ttcgcatact gtttaaacgc tttttccgcg gtttccgcat ccaccgcttt 60
ggtggtttcg cctttcag 78

<210> SEQ ID NO 48
<211> LENGTH: 86
<212> TYPE: DNA
<213> ORGANISM: Artificial Sequence
<220> FEATURE:
<223> OTHER INFORMATION: Synthetic Sequence

<400> SEQUENCE: 48
cagtatgcga acgataacgg cgtggatggc gtgtggacct atgatgatgc gaccaaaacc 60
tttaccgtga ccgaataagg taccccc 86

<210> SEQ ID NO 49
<211> LENGTH: 15
<212> TYPE: DNA
<213> ORGANISM: Artificial Sequence
<220> FEATURE:

-continued

<223> OTHER INFORMATION: primer

<400> SEQUENCE: 49
cttgtcttaa gaggt 15

<210> SEQ ID NO 50
<211> LENGTH: 21
<212> TYPE: DNA
<213> ORGANISM: Artificial Sequence
<220> FEATURE:
<223> OTHER INFORMATION: primer

<400> SEQUENCE: 50
gctgggtacc ttattcggtc a 21

<210> SEQ ID NO 51
<211> LENGTH: 30
<212> TYPE: DNA
<213> ORGANISM: Artificial Sequence
<220> FEATURE:
<223> OTHER INFORMATION: primer

<400> SEQUENCE: 51
ggtctcaagg tacgccggcg gtgaccacct 30

<210> SEQ ID NO 52
<211> LENGTH: 30
<212> TYPE: DNA
<213> ORGANISM: Artificial Sequence
<220> FEATURE:
<223> OTHER INFORMATION: primer

<400> SEQUENCE: 52
aagcttatta ttcggtcacg gtaaaggttt 30

<210> SEQ ID NO 53
<211> LENGTH: 34
<212> TYPE: DNA
<213> ORGANISM: Artificial Sequence
<220> FEATURE:
<223> OTHER INFORMATION: primer

<400> SEQUENCE: 53
ggtctcaagg tatgaccatg attacggatt cact 34

<210> SEQ ID NO 54
<211> LENGTH: 32
<212> TYPE: DNA
<213> ORGANISM: Artificial Sequence
<220> FEATURE:
<223> OTHER INFORMATION: primer

<400> SEQUENCE: 54
aagcttatta ttattatttt tgacaccaga cc 32

<210> SEQ ID NO 55
<211> LENGTH: 34
<212> TYPE: DNA
<213> ORGANISM: Artificial Sequence
<220> FEATURE:
<223> OTHER INFORMATION: primer

<400> SEQUENCE: 55
ggtctcaagg tatgcagatc ttcgtcaaga cgtt 34

-continued

<210> SEQ ID NO 56
<211> LENGTH: 30
<212> TYPE: DNA
<213> ORGANISM: Artificial Sequence
<220> FEATURE:
<223> OTHER INFORMATION: primer

<400> SEQUENCE: 56
aagcttatta ttgtttgcct ccctgctgcg 30

<210> SEQ ID NO 57
<211> LENGTH: 25
<212> TYPE: DNA
<213> ORGANISM: Artificial Sequence
<220> FEATURE:
<223> OTHER INFORMATION: primer

<400> SEQUENCE: 57
gctcgagagc acagatgctt cgttg 25

<210> SEQ ID NO 58
<211> LENGTH: 25
<212> TYPE: DNA
<213> ORGANISM: Artificial Sequence
<220> FEATURE:
<223> OTHER INFORMATION: primer

<400> SEQUENCE: 58
gcaaagcttg gagttgattg tatgc 25

<210> SEQ ID NO 59
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 59

Gly Gly Ala Thr Tyr
1 5

<210> SEQ ID NO 60
<211> LENGTH: 18
<212> TYPE: DNA
<213> ORGANISM: Artificial Sequence
<220> FEATURE:
<223> OTHER INFORMATION: primer

<400> SEQUENCE: 60
ttttggtctc caggttgt 18

<210> SEQ ID NO 61
<211> LENGTH: 18
<212> TYPE: DNA
<213> ORGANISM: Artificial Sequence
<220> FEATURE:
<223> OTHER INFORMATION: primer

<400> SEQUENCE: 61
acaacctgga gaccaaaa 18

<210> SEQ ID NO 62
<211> LENGTH: 13
<212> TYPE: DNA
<213> ORGANISM: Artificial Sequence
<220> FEATURE:
<223> OTHER INFORMATION: primer -continued

<400> SEQUENCE: 62
ggaggttgag acc 13

<210> SEQ ID NO 63
<211> LENGTH: 13
<212> TYPE: DNA
<213> ORGANISM: Artificial Sequence
<220> FEATURE:
<223> OTHER INFORMATION: primer

<400> SEQUENCE: 63
ggtctcaacc tcc 13

<210> SEQ ID NO 64
<211> LENGTH: 294
<212> TYPE: DNA
<213> ORGANISM: Artificial Sequence
<220> FEATURE:
<223> OTHER INFORMATION: Synthetic Sequence

<400> SEQUENCE: 64
atgtcggact cagaagtcaa tcaagaagct aagccagagg tcaagccaga agtcaagcct 60
gagactcaca tcaatttaaa ggtgtccgat ggatcttcag agatcttctt caagatcaaa 120
aagaccactc ctttaagaag gctgatggaa gcgttcgcta aaagacaggg taaggaaatg 180
gactccttaa gattcttgta cgacggtatt agaattcaag ctgatcaggc ccctgaagat 240
ttggacatgg aggataacga tattattgag gctcaccgcg aacagattgg aggt 294

<210> SEQ ID NO 65
<211> LENGTH: 98
<212> TYPE: PRT
<213> ORGANISM: Artificial Sequence
<220> FEATURE:
<223> OTHER INFORMATION: Synthetic Sequence

<400> SEQUENCE: 65

Met Ser Asp Ser Glu Val Asn Gln Glu Ala Lys Pro Glu Val Lys Pro
1 5 10 15

Glu Val Lys Pro Glu Thr His Ile Asn Leu Lys Val Ser Asp Gly Ser
20 25 30

Ser Glu Ile Phe Phe Lys Ile Lys Lys Thr Thr Pro Leu Arg Arg Leu
35 40 45

Met Glu Ala Phe Ala Lys Arg Gln Gly Lys Glu Met Asp Ser Leu Arg
50 55 60

Phe Leu Tyr Asp Gly Ile Arg Ile Gln Ala Asp Gln Ala Pro Glu Asp
65 70 75 80

Leu Asp Met Glu Asp Asn Asp Ile Ile Glu Ala His Arg Glu Gln Ile
85 90 95

Gly Gly